US012448462B2

(12) United States Patent
Marasco et al.

(10) Patent No.: US 12,448,462 B2
(45) Date of Patent: Oct. 21, 2025

(54) ANTIBODIES AGAINST MUC1

(71) Applicant: Dana-Farber Cancer Institute, Inc., Boston, MA (US)

(72) Inventors: Wayne A. Marasco, Wellesley, MA (US); Elizabeth Baez, Ashburn, VA (US); Matthew Chang, Brookline, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 849 days.

(21) Appl. No.: 17/618,363

(22) PCT Filed: Jun. 15, 2020

(86) PCT No.: PCT/US2020/037783

§ 371 (c)(1),
(2) Date: Dec. 10, 2021

(87) PCT Pub. No.: WO2020/252472

PCT Pub. Date: Dec. 17, 2020

(65) Prior Publication Data

US 2022/0289863 A1 Sep. 15, 2022

Related U.S. Application Data

(60) Provisional application No. 62/861,619, filed on Jun. 14, 2019.

(51) Int. Cl.

| | |
|---|---|
| ***C07K 16/30*** | (2006.01) |
| ***A61K 40/11*** | (2025.01) |
| ***A61K 40/31*** | (2025.01) |
| ***A61K 40/42*** | (2025.01) |
| ***A61P 35/00*** | (2006.01) |
| ***C07K 14/725*** | (2006.01) |

(52) U.S. Cl.

CPC .......... *C07K 16/3092* (2013.01); *A61K 40/11* (2025.01); *A61K 40/31* (2025.01); *A61K 40/4257* (2025.01); *A61P 35/00* (2018.01); *C07K 14/7051* (2013.01); *A61K 2239/13* (2023.05); *C07K 2317/21* (2013.01); *C07K 2317/565* (2013.01); *C07K 2317/622* (2013.01); *C07K 2319/03* (2013.01)

(58) Field of Classification Search

CPC ............ C07K 16/3092; C07K 14/7051; C07K 2317/21; C07K 2317/565; C07K 2317/622; C07K 2319/03; C07K 2317/34; C07K 2317/92; A61K 40/11; A61K 40/31; A61K 40/4257; A61K 2239/13; A61P 35/00

See application file for complete search history.

(56) References Cited

U.S. PATENT DOCUMENTS

| | | | |
|---|---|---|---|
| 3,773,919 | A | 11/1973 | Boswell et al. |
| 4,485,045 | A | 11/1984 | Regen |
| 4,522,811 | A | 6/1985 | Eppstein et al. |
| 4,544,545 | A | 10/1985 | Ryan et al. |
| 4,816,567 | A | 3/1989 | Cabilly et al. |
| 4,946,778 | A | 8/1990 | Ladner et al. |
| 5,013,556 | A | 5/1991 | Woodle et al. |
| 5,030,719 | A | 7/1991 | Umemoto et al. |
| 5,132,405 | A | 7/1992 | Huston et al. |
| 5,202,238 | A | 4/1993 | Fell, Jr. et al. |
| 5,202,244 | A | 4/1993 | Hiramitsu et al. |
| 5,545,806 | A | 8/1996 | Lonberg et al. |
| 5,545,807 | A | 8/1996 | Surani et al. |
| 5,569,825 | A | 10/1996 | Lonberg et al. |
| 5,625,126 | A | 4/1997 | Lonberg et al. |
| 5,633,425 | A | 5/1997 | Lonberg et al. |
| 5,661,016 | A | 8/1997 | Lonberg et al. |
| 5,916,771 | A | 6/1999 | Hori et al. |
| 5,939,598 | A | 8/1999 | Kucherlapati et al. |
| 2006/0134663 | A1 | 6/2006 | Harkin et al. |
| 2009/0074660 | A1 | 3/2009 | Korman et al. |
| 2012/0058906 | A1 | 3/2012 | Smider et al. |
| 2013/0101664 | A1 | 4/2013 | Kufe et al. |
| 2017/0362297 | A1 | 12/2017 | Marasco |
| 2018/0036441 | A1 | 2/2018 | Kufe et al. |
| 2018/0118822 | A1 | 5/2018 | Brentjens et al. |

FOREIGN PATENT DOCUMENTS

| | | | |
|---|---|---|---|
| CA | 3056582 | C | 5/2022 |
| WO | WO1991000360 | A1 | 1/1991 |
| WO | WO1992020373 | A1 | 11/1992 |
| WO | WO1994002602 | A1 | 2/1994 |
| WO | WO1994011026 | A2 | 5/1994 |
| WO | WO1995022618 | A1 | 8/1995 |

(Continued)

OTHER PUBLICATIONS

Pichinuk et al. Antibody Targeting of Cell-Bound MUC1 SEA Domain Kills Tumor Cells. Cancer Res. 2012, 72 (13): 3324-36 (Year: 2012).*
International Search Report for PCT/US20/037783 mailed Dec. 7, 2020.
Levitin, Fiana, et al. "The MUC1 SEA module is a self-cleaving domain." Journal of Biological Chemistry 280.39 (2005): 33374-33386.
Panchamoorthy, Govind, et al. "Targeting the human MUC1-C oncoprotein with an antibody-drug conjugate." JCI insight 3.12 (2018).
Pichinuk, Edward, et al. "Antibody targeting of cell-bound MUC1 SEA domain kills tumor cells." Cancer research 72.13 (2012): 3324-3336.

(Continued)

*Primary Examiner* — Misook Yu
*Assistant Examiner* — Grace H Lunde
(74) *Attorney, Agent, or Firm* — Baker Donelson

(57) ABSTRACT

MUC1 is overexpressed in many cancers, including those of the lung, colon, breast, ovary, and pancreas. Aspects of the invention are directed towards the discovery of monoclonal antibodies and fragments thereof, such as a human single chain variable fragment (scFv), that recognizes human MUC1-SEA.

21 Claims, 99 Drawing Sheets

Specification includes a Sequence Listing.

(56) References Cited

FOREIGN PATENT DOCUMENTS

| | | | |
|---|---|---|---|
| WO | WO1996033735 | A1 | 10/1996 |
| WO | WO1996034096 | A1 | 10/1996 |
| WO | WO1999053049 | A1 | 10/1999 |
| WO | WO2005018572 | A2 | 3/2005 |
| WO | WO2005047327 | A2 | 5/2005 |
| WO | WO2009086514 | A1 | 7/2009 |
| WO | WO2013166500 | A1 | 11/2013 |
| WO | WO2014134165 | A1 | 9/2014 |
| WO | WO2015116753 | A1 | 8/2015 |
| WO | WO2016057488 | A1 | 4/2016 |
| WO | WO2016100985 | A2 | 6/2016 |
| WO | WO2016178779 | A1 | 11/2016 |
| WO | WO2018174544 | A2 | 9/2018 |
| WO | WO2019178356 | A1 | 9/2019 |

OTHER PUBLICATIONS

Written Opinion for PCT/US20/037783 mailed Dec. 7, 2020.
"Conjugate Vaccines", Contributions to Microbiology and Immunology, J. M. Cruse and R. E. Lewis, Jr (eds), Carger Press, New York, (1989).
"ELISA: Theory and Practice: Methods in Molecular Biology", vol. 42, J. R. Crowther (Ed.) Human Press, Totowa, NJ, 1995.
"Immunoassay", E. Diamandis and T. Christopoulus, Academic Press, Inc., San Diego, CA, 1996.
Antibodies: A Laboratory Manual, Harlow E, and Lane D, 1988.
Barbas 3rd, C. F., et al. "Recombinant human Fab fragments neutralize human type 1 immunodeficiency virus in vitro." Proceedings of the National Academy of Sciences 89.19 (1992): 9339-9343.
Bobo, R. Hunt, et al. "Convection-enhanced delivery of macromolecules in the brain." Proceedings of the National Academy of Sciences 91.6 (1994): 2076-2080.
Boerner, Paula, et al. "Production of antigen-specific human monoclonal antibodies from in vitro-primed human splenocytes." Journal of immunology (Baltimore, Md.: 1950) 147.1 (1991): 86-95.
Brodeur, Bernard R., et al. "Monoclonal idiotypic and anti-idiotypic antibodies to human immunodeficiency virus type 1 envelope glycoprotein." Journal of general virology 72.1 (1991): Abstract.
Caron et al, J. Exp Med., 176: 1 191-1 195 (1992).
Cole, et al, 1985 In: Monoclonal Antibodies and Cancer Therapy, Alan R. Liss, Inc., pp. 77-96.
Cote, Richard J., et al. "Generation of human monoclonal antibodies reactive with cellular antigens." Proceedings of the National Academy of Sciences 80.7 (1983): 2026-2030.
Davidson, Beverly L., et al. "A model system for in vivo gene transfer into the central nervous system using an adenoviral vector." Nature genetics 3.3 (1993): 219-223.
Davies, David R., Eduardo A. Padlan, and Steven Sheriff. "Antibody-antigen complexes." Annual review of biochemistry 59.1 (1990): 439-473.
Drug Absorption Enhancement: Concepts, Possibilities, Limitations, And Trends, Harwood Academic Publishers, Langhorne, Pa., 1994.
Epstein et al, Proc. Natl. Acad. Sci. USA, 82: 3688 (1985).
Fishwild, Dianne M., et al. "High-avidity human IgGκ monoclonal antibodies from a novel strain of minilocus transgenic mice." Nature biotechnology 14.7 (1996): 845-851.
Geller, A. I., et al. "An efficient deletion mutant packaging system for defective HSV-1 vectors; potential applications to neuronal physiology and human gene therapy." Proc. Natl. Acad. Sci. USA 87 (1990): 8950-8954.
Geller, Alfred I., et al. "An HSV-1 Vector Expressing Tyrosine Hydroxylase Causes Production and Release of I-DOPA from Cultured Rat Striatal Cells." Journal of neurochemistry 64.2 (1995): 487-496.
Geller, Alfred I., et al. "Long-term increases in neurotransmitter release from neuronal cells expressing a constitutively active adenylate cyclase from a herpes simplex virus type 1 vector." Proceedings of the National Academy of Sciences 90.16 (1993): 7603-7607.
Goding, Monoclonal Antibodies: Principles and Practice, Academic Press, (1986) pp. 59-103.
Hassan, Raffit, et al. "Mesothelin immunotherapy for cancer: ready for prime time?." Journal of Clinical Oncology 34.34 (2016): 4171-4179.
Hoogenboom, Hennie R., and Greg Winter. "By-passing immunisation: human antibodies from synthetic repertoires of germline VH gene segments rearranged in vitro." Journal of molecular biology 227.2 (1992): 381-388.
Horm, Teresa M., and Joyce A. Schroeder. "MUC1 and metastatic cancer: expression, function and therapeutic targeting." Cell adhesion & migration 7.2 (2013): 187-198.
Huse, et al, 1989 Science 246: 1275-1281.
Huston, James S., et al. "Protein engineering of antibody binding sites: recovery of specific activity in an anti-digoxin single-chain Fv analogue produced in *Escherichia coli*." Proceedings of the National Academy of Sciences 85.16 (1988): 5879-5883.
Hwang, Karl J., K. F. Luk, and Paul L. Beaumier. "Hepatic uptake and degradation of unilamellar sphingomyelin/ cholesterol liposomes: a kinetic study." Proceedings of the National Academy of Sciences 77.7 (1980): 4030-4034.
Jakobovits, Aya, et al. "Analysis of homozygous mutant chimeric mice: deletion of the immunoglobulin heavy-chain joining region blocks B-cell development and antibody production." Proceedings of the National Academy of Sciences 90.6 (1993): 2551-2555.
Jansen, F. K., H. E. Blythman, and D. Carriere. "Casellas, o." Gros, P. Gros, JC Laurent, F. Paolucci, B. Pau, P. Ponce let, G. Richer, H. Vidal, and GA Voison, Immunotoxins: hybrid molecules combining high specificity and potent cytotoxicity, Immunol. Rev 62 (1982): 185.
Kaplitt, Michael G., et al. "Long-term gene expression and phenotypic correction using adeno-associated virus vectors in the mammalian brain." Nature genetics 8.2 (1994): 148-154.
Killen and Lindstrom, Jour. Immun. 133 : 1335-2549 (1984).
Köhler, Georges, and Cesar Milstein. "Continuous cultures of fused cells secreting antibody of predefined specificity." nature 256.5517 (1975): 495-497.
Kozbor, Danuta, and John C. Roder. "The production of monoclonal antibodies from human lymphocytes." Immunology Today 4.3 (1983): 72-79.
Kozbor, Danuta, et al. "A human hybrid myeloma for production of human monoclonal antibodies." Journal of immunology (Baltimore, Md.: 1950) 133.6 (1984): 3001-3005.
Kufe, Donald W. "Targeting the human MUC1 oncoprotein: a tale of two proteins." Cancer biology & therapy 7.1 (2008): 81-84.
Labrijn, Aran F., et al. "Species-specific determinants in the IgG CH3 domain enable Fab-arm exchange by affecting the noncovalent CH3—CH3 interaction strength." The Journal of Immunology 187.6 (2011): 3238-3246.
Lam, Kit S. "Mini-review. Application of combinatorial library methods in cancer research and drug discovery." Anti-cancer drug design 12.3 (1997): 145-167.
Lazar, Greg A., et al. "Engineered antibody Fc variants with enhanced effector function." Proceedings of the National Academy of Sciences 103.11 (2006): 4005-4010.
LeGal LaSalle et al, Science, 259:988 (1993).
Lim, F., et al, in DNA Cloning: Mammalian Systems, D. Glover, Ed. (Oxford Univ. Press, Oxford England) (1995).
Lonberg, Nils, and Dennis Huszar. "Human antibodies from transgenic mice." International reviews of immunology 13.1 (1995): 65-93.
Lonberg, Nils, et al. "Antigen-specific human antibodies from mice comprising four distinct genetic modifications." Nature 368.6474 (1994): 856-859.
Malmqvist, Magnus. "Biospecific interaction analysis using biosensor technology." Nature 361.6408 (1993): 186-187.
Marasco, Wayne A., William A. Haseltine, and SiYi Chen. "Design, intracellular expression, and activity of a human anti-human immunodeficiency virus type 1 gp120 single-chain antibody." Proceedings of the National Academy of Sciences 90.16 (1993): 7889-7893.
Marks, James D., et al. "By-passing immunization: human antibodies from V-gene libraries displayed on phage." Journal of molecular biology 222.3 (1991): 581-597.

(56) References Cited

OTHER PUBLICATIONS

Martin, Francis J., and Demetrios Papahadjopoulos. "Irreversible coupling of immunoglobulin fragments to preformed vesicles. An improved method for liposome targeting." Journal of Biological Chemistry 257.1 (1982): 286-288.
Morrison et al, Am. J. Physiol. 266:292-305 (1994).
Morrison, Nature 368, 812-13 (1994).
Morrison, Sherie L., et al. "Chimeric human antibody molecules: mouse antigen-binding domains with human constant region domains." Proceedings of the National Academy of Sciences 81.21 (1984): 6851-6855.
Munson, Peter J., and David Rodbard. "Ligand: a versatile computerized approach for characterization of ligand-binding systems." Analytical biochemistry 107.1 (1980): 220-239.
Nath, Sritama, and Pinku Mukherjee. "MUC1: a multifaceted oncoprotein with a key role in cancer progression." Trends in molecular medicine 20.6 (2014): 332-342.
Neuberger, Michael. "Generating high-avidity human Mabs in mice." Nature biotechnology 14.7 (1996): 826-826.
Peptide And Protein Drug Delivery (Advances In Parenteral Sciences, vol. 4), 1991, M. Dekker, New York.
Ramakrishnan, S., and L. L. Houston. "Comparison of the selective cytotoxic effects of immunotoxins containing ricin A chain or pokeweed antiviral protein and anti-Thy 1.1 monoclonal antibodies." Cancer research 44.1 (1984): 201-208.
Remington: The Science And Practice Of Pharmacy 19th ed. (Alfonso R. Gennaro, et al., editors) Mack Pub. Co., Easton, Pa., 1995.
Richards, John O., et al. "Optimization of antibody binding to FcγRIIa enhances macrophage phagocytosis of tumor cells." Molecular cancer therapeutics 7.8 (2008): 2517-2527.
Ridgway et al, Protein Eng 7:617-621 (1996).
Shields, Robert L., et al. "High resolution mapping of the binding site on human IgG1 for FcγRI, FcγRII, FcγRIII, and FcRn and design of IgG1 variants with improved binding to the FcγR." Journal of Biological Chemistry 276.9 (2001): 6591-6604.
Shopes, Bob. "A genetically engineered human IgG mutant with enhanced cytolytic activity." Journal of immunology (Baltimore, Md.: 1950) 148.9 (1992): 2918-2922.
Stevenson, G. T., A. Pindar, and C. J. Slade. "A chimeric antibody with dual Fc regions (bisFabFc) prepared by manipulations at the IgG hinge." Anti-cancer drug design 3.4 (1989): 219-230.
Stewart, Ross, et al. "A variant human IgG1-Fc mediates improved ADCC." Protein Engineering, Design & Selection 24.9 (2011): 671-678.
The Scientist, published by The Scientist, Inc., Philadelphia PA, vol. 14, No. 8 (Apr. 17, 2000), pp. 25-28).
Van Der Neut Kolfschoten, Marijn, et al. "Anti-inflammatory activity of human IgG4 antibodies by dynamic Fab arm exchange." Science 317.5844 (2007): 1554-1557.
Van Dijk, Marc A., and Jan GJ Van De Winkel. "Human antibodies as next generation therapeutics." Current Opinion in Chemical Biology 5.4 (2001): 368-374.
Vitetta, Ellen S., et al. "Redesigning nature's poisons to create anti-tumor reagents." Science 238.4830 (1987): 1098-1104.
Woo, Edward Y., et al. "Regulatory CD4+ CD25+ T cells in tumors from patients with early-stage non-small cell lung cancer and late-stage ovarian cancer." Cancer research 61.12 (2001): 4766-4772.
Wood, Kathryn J., and Shimon Sakaguchi. "Regulatory T cells in transplantation tolerance." Nature Reviews Immunology 3.3 (2003): 199-210.
Yang, Yiping, et al. "Cellular and humoral immune responses to viral antigens create barriers to lung-directed gene therapy with recombinant adenoviruses." Journal of virology 69.4 (1995): 2004-2015.
Zebedee, Suzanne L., et al. "Human combinatorial antibody libraries to hepatitis B surface antigen." Proceedings of the National Academy of Sciences 89.8 (1992): 3175-3179.

* cited by examiner

| **Construct** | [Live] (M /mL) | [Total] (M/ mL) | [Live + Transduced] M / mL | Total # of cells | Viability (%) | Transduction (% ZsGreen) |
|---|---|---|---|---|---|---|
| Untransduced | 1.57 | 1.81 | 1.57 | 1.56 M | 86.7 | 0 |
| G36-ZsG | 0.95 | 2.18 | 0.20 | 400 K | 86.7 | 21 |
| 3D1-ZsG | 1.11 | 1.39 | 0.4329 | 432 K | 79.9 | 39 |
| X48-ZsG | 0.68 | 1.01 | 0.437 | 437 K | 67.6 | 64 |
| T4E3-ZsG | 0.39 | 0.520 | 0.111 | 111 K | 74.7 | 28 |

FIG. 3

10:1

| | | 1 | 2 | 3 | 4 | 5 | 6 | 7 | 8 | 9 | 10 | 11 | 12 |
|---|---|---|---|---|---|---|---|---|---|---|---|---|---|
| | | | HCT116-v | | | HCT116-MUC1 | | | COV362 | | | | |
| A | | | | | | | | | | | | | |
| B | Untransduced | | X | X | X | X | X | X | X | X | X | | |
| C | G36-ZsGreen | | X | X | X | X | X | X | X | X | X | | |
| D | X48-ZsGreen | | X | X | X | X | X | X | X | X | X | | |
| E | 3D1-ZsGreen | | X | X | X | X | X | X | X | X | X | | |
| F | T4E3-ZsGreen | | | X | | | | | X | X | | | |
| G | | | HCT116-v only | | | HCT116-MUC1 only | | | COV362 only | | | | |
| H | | | | | | | | | | | | | |

FIG. 3 CON'T

2:1

| | | 1 | 2 | 3 | 4 | 5 | 6 | 7 | 8 | 9 | 10 | 11 | 12 |
|---|---|---|---|---|---|---|---|---|---|---|---|---|---|
| | | | HCT116-v | | | HCT116-MUC1 | | | COV362 | | | | |
| A | | | | | | | | | | | | | |
| B | Untransduced | | X | X | X | X | X | X | X | X | X | | |
| C | G36-ZsGreen | | X | X | X | X | X | X | X | X | X | | |
| D | X48-ZsGreen | | X | X | X | X | X | X | X | X | X | | |
| E | 3D1-ZsGreen | | X | X | X | X | X | X | X | X | X | | |
| F | T4E3-ZsGreen | | | X | | | | | X | X | | | |
| G | | | HCT116-v only | | | HCT116-MUC1 only | | | COV362 only | | | | |
| H | | | | | | | | | | | | | |

FIG. 3 CON'T

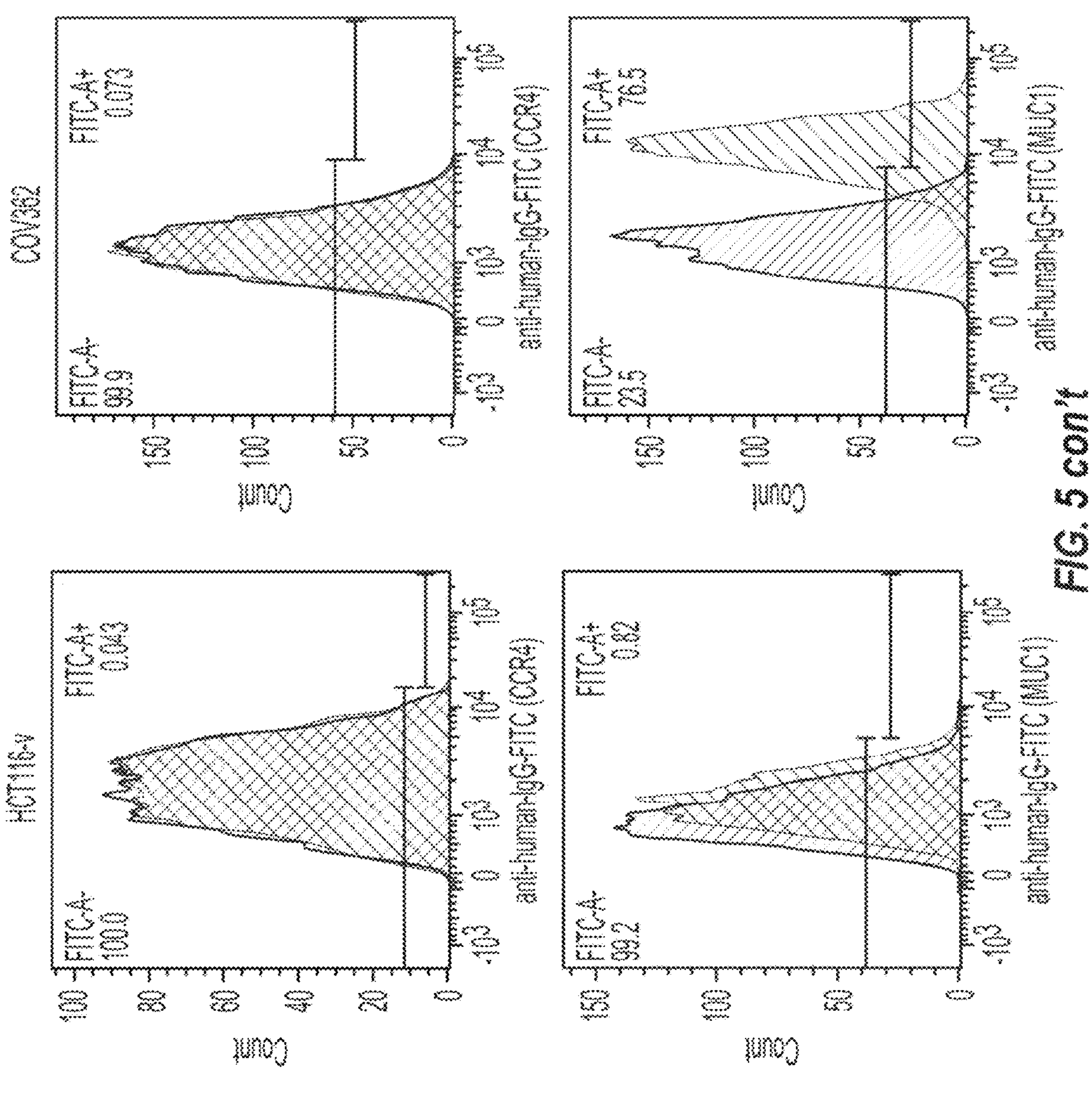
*FIG. 5 con't*

| | |
|---|---|
| | |
| | % FACS Positive in scFv-Fc format (@ [ ] in nM) |
| T4E3 | 75.7 (182) |
| G2-2-F8 | 46.8 (910) |
| G1-3-A3 | 20.1 (910) |
| G1-2-B10 | 31.0 (910) |
| G1-1-A1 | 47.5 (910) |
| h3D1 | 64.4 (182) |

FIG. 7

| | *Light Chain* | |
|---|---|---|
| | V-GENE and allele | J-GENE and allele |
| T4E3 | Homsap IGLV3-19*01 F | Homsap IGLJ2*01 F, or Homsap IGLJ3*01 F |
| G2-2-F8 | Homsap IGLV3-19*01 F | Homsap IGLJ3*02 F |
| G1-3-A3 | Homsap IGKV3-20*01 F | Homsap IGKJ1*01 F |
| G1-2-B10 | Homsap IGLV3-19*01 F | Homsap IGLJ2*01 F, or Homsap IGLJ3*01 F |
| G1-1-A1 | Homsap IGLV3-19*01 F | Homsap IGLJ2*01 F, or Homsap IGLJ3*01 F |
| h3D1 | Homsap IGKV6-21*02 F | Homsap IGKJ1*01 F, or Homsap IGKJ4*01 F or Homsap IGKJ4*02 F |

FIG. 7 con't

| | V-GENE and allele | J-GENE and allele | D-GENE and allele |
|---|---|---|---|
| T4E3 | Homsap IGHV3-9*01 F | Homsap IGHJ6*02 F | Homsap IGHD3-10*01 F |
| G2-2-F8 | Homsap IGHV3-9*01 F | Homsap IGHJ6*02 F | Homsap IGHD5-12*01 F |
| G1-3-A3 | Homsap IGHV3-9*01 F | Homsap IGHJ3*02 F | Homsap IGHD3-22*01 F |
| G1-2-B10 | Homsap IGHV3-9*01 F | Homsap IGHJ3*02 F | Homsap IGHD6-19*01 F |
| G1-1-A1 | Homsap IGHV1-18*01 F | Homsap IGHJ6*02 F | Homsap IGHD6-19*01 F |
| h3D1 | Homsap IGHV1-46*01 F, or Homsap IGHV1-46*02 F or Homsap IGHV1-46*03 F | Homsap IGHJ5*01 F | Homsap IGHD1-1*01 F |

FIG. 7 con't

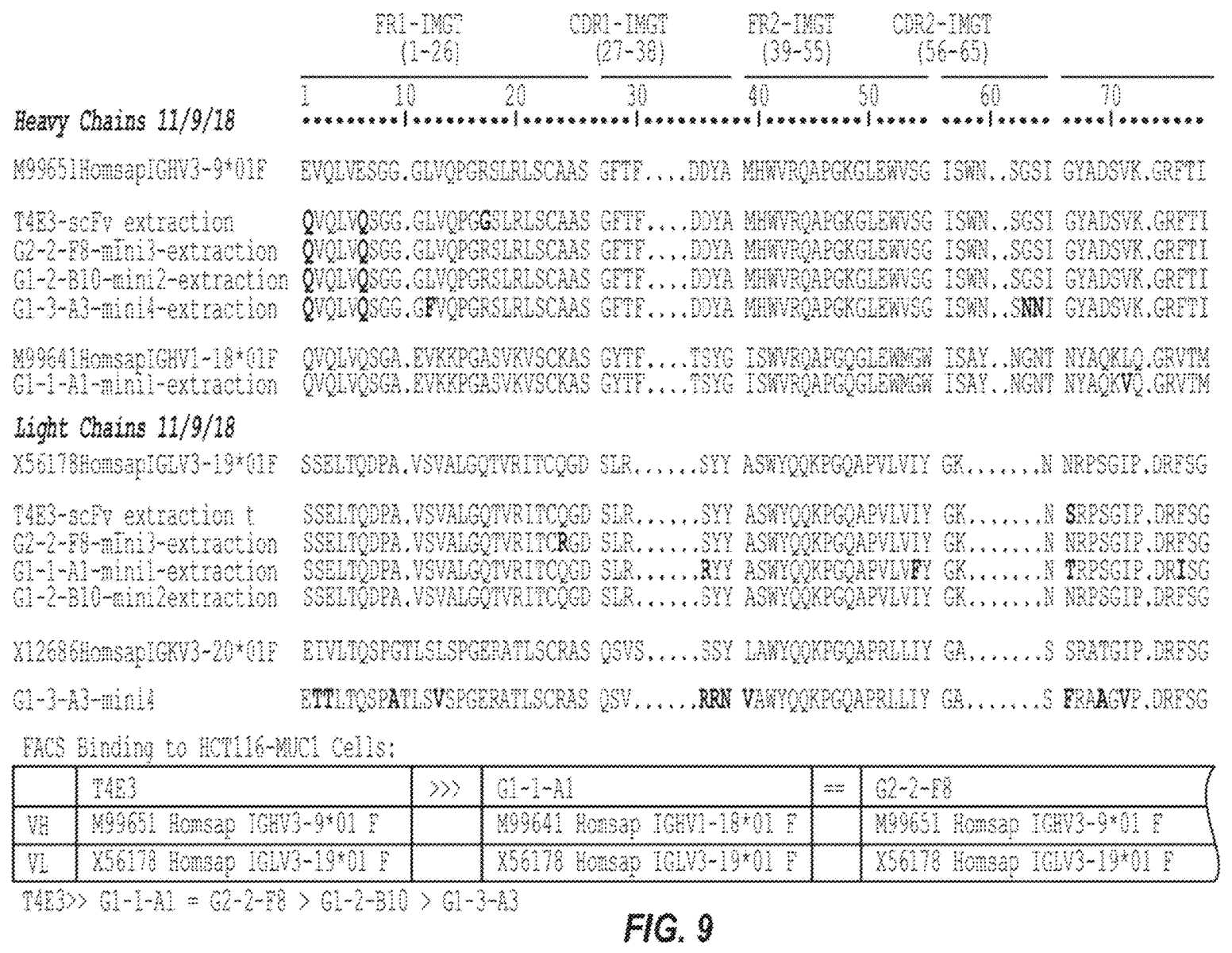

Heavy Chains 11/9/18

| | FR1-IMGT (1-26) | CDR1-IMGT (27-38) | FR2-IMGT (39-55) | CDR2-IMGT (56-65) | |
|---|---|---|---|---|---|
| M99651HomsapIGHV3-9*01F | EVQLVESGG.GLVQPGRSLRLSCAAS | GFTF....DDYA | MHWVRQAPGKGLEWVSG | ISWN..SGSI | GYADSVK.GRFTI |
| T4E3-scFv extraction | **Q**VQLV**Q**SGG.GLVQPG**G**SLRLSCAAS | GFTF....DDYA | MHWVRQAPGKGLEWVSG | ISWN..SGSI | GYADSVK.GRFTI |
| G2-2-F8-mIni3-extraction | **Q**VQLV**Q**SGG.GLVQPGRSLRLSCAAS | GFTF....DDYA | MHWVRQAPGKGLEWVSG | ISWN..SGSI | GYADSVK.GRFTI |
| G1-2-B10-mini2-extraction | **Q**VQLV**Q**SGG.GLVQPGRSLRLSCAAS | GFTF....DDYA | MHWVRQAPGKGLEWVSG | ISWN..SGSI | GYADSVK.GRFTI |
| G1-3-A3-mini4-extraction | **Q**VQLV**Q**SGG.G**F**VQPGRSLRLSCAAS | GFTF....DDYA | MHWVRQAPGKGLEWVSG | ISWN..S**NN**I | GYADSVK.GRFTI |
| M99641HomsapIGHV1-18*01F | QVQLVQSGA.EVKKPGASVKVSCKAS | GYTF....TSYG | ISWVRQAPGQGLEWMGW | ISAY..NGNT | NYAQKLQ.GRVTM |
| G1-1-A1-mini1-extraction | QVQLVQSGA.EVKKPGASVKVSCKAS | GYTF....TSYG | ISWVRQAPGQGLEWMGW | ISAY..NGNT | NYAQK**V**Q.GRVTM |

Light Chains 11/9/18

| | FR1-IMGT (1-26) | CDR1-IMGT (27-38) | FR2-IMGT (39-55) | CDR2-IMGT (56-65) | |
|---|---|---|---|---|---|
| X56178HomsapIGLV3-19*01F | SSELTQDPA.VSVALGQTVRITCQGD | SLR......SYY | ASWYQQKPGQAPVLVIY | GK.......N | NRPSGIP.DRFSG |
| T4E3-scFv extraction t | SSELTQDPA.VSVALGQTVRITCQGD | SLR......SYY | ASWYQQKPGQAPVLVIY | GK.......N | **S**RPSGIP.DRFSG |
| G2-2-F8-mIni3-extraction | SSELTQDPA.VSVALGQTVRITC**R**GD | SLR......SYY | ASWYQQKPGQAPVLVIY | GK.......N | NRPSGIP.DRFSG |
| G1-1-A1-mini1-extraction | SSELTQDPA.VSVALGQTVRITCQGD | SLR......**R**YY | ASWYQQKPGQAPVLV**F**Y | GK.......N | **T**RPSGIP.DR**I**SG |
| G1-2-B10-mini2extraction | SSELTQDPA.VSVALGQTVRITCQGD | SLR......SYY | ASWYQQKPGQAPVLVIY | GK.......N | NRPSGIP.DRFSG |
| X12686HomsapIGKV3-20*01F | EIVLTQSPGTLSLSPGERATLSCRAS | QSVS.....SSY | LAWYQQKPGQAPRLLIY | GA.......S | SRATGIP.DRFSG |
| G1-3-A3-mini4 | E**TT**LTQSP**A**TLS**V**SPGERATLSCRAS | QSV......**RRN** | **V**AWYQQKPGQAPRLLIY | GA.......S | **F**RA**A**GVP.DRFSG |

FACS Binding to HCT116-MUC1 Cells:

| | T4E3 | >>> | G1-1-A1 | == | G2-2-F8 |
|---|---|---|---|---|---|
| VH | M99651 Homsap IGHV3-9*01 F | | M99641 Homsap IGHV1-18*01 F | | M99651 Homsap IGHV3-9*01 F |
| VL | X56178 Homsap IGLV3-19*01 F | | X56178 Homsap IGLV3-19*01 F | | X56178 Homsap IGLV3-19*01 F |

T4E3>> G1-1-A1 = G2-2-F8 > G1-2-B10 > G1-3-A3

*FIG. 9*

```
FR3-IMGT                          CDR3              FR4
(66-104)
 80         90         100
 *|.........|.........|....

SRDNAKNSLYLQMNSLRAEDTALYYC AKD GSGSYYYYYYGMDV   WGQGTTVTVSS

SRDNAKNSLYLQMNSLRAEDTALYYC AKDIGSGSYYNYYYGMDV   WGQGTTATISS
SRDNAKNSLYLQMNSLRAEDTALYYC AKDMGSG YDWYYYGMDV   WGQGTTVTVSS
SRDNAKNSLYLQMNSLRAEDTALYYC AKDISSGWYP.     DAFDIWGQGTLVTVSS
SRENAKNSLYLQMNSLRAEDTAVYYC AR VSPGYYDSSGQGTDAFDIWGQGTTVTVSS

TTDTSTSTAYMELRSLRSDDTAVYYC AR PHLSSDYYYYYGMDVWGQGTTVTVSS
TTDTSTSTAYMELRSLRSDDTAVYYC ARDPHLSSGWYKGNGMDVWGQGTLVTVSS


SS..SGNTASLTITGAQAEDEADYYC NSRDSSGNH VIFGGGTKLTVL

SN..SGSTASLTITGAQAEDEADYYC NSRDRYGNSLVIFGGGTKLTVL
SS..SGNTASLTITGAQAEDEADYYC NSRDSSGNH LVFGGGTKLTVL
SS..SGNTASLTITGAQAEDEADYYC NSRDSSGN PVVFGGGTKLTVL
SN..SGNTASLTITGAQAEDEADYYC NSRDFSGLQ LVFGGGTRLTVL

SG..SGTDFTLTISRLEPEDFAVYYC QQYGSSP TFGQGTKVEIK

GSG..SGTDFTLTITRLEPEDFAVYYC QQYGSSPRTFGQGTKVEIK
```

| | | | |
|---|---|---|---|
| > | G1-2-B10 | > | G1-3-A3 |
| | M99651 Homsap IGHV3-9*01 F | | M99651 Homsap IGHV3-9*01 F |
| | X56178 Homsap IGLV3-19*01 F | | X12686 Homsap IGKV3-20*01 F |

*FIG. 9 con't*

Additional embodiments:

VH:

```
KC713938 Homsap IGHV1-18*04 F           QVQLVQSGA.EVKKPGASVKVSCKAS GYTF....TSYG ISWVRQAPGQGLEWMGW ISAY..
G3-1-D6-mini7-extraction_extraction     QVQLVQSGA.EVKRPGASVKVSCKAS GYTF....STYA INWVRQAPGQGPEWMGW ISGY..

X92343 Homsap IGHV1-46*01 F             QVQLVQSGA.EVKKPGASVKVSCKAS GYTF....TSYY MHWVRQAPGQGLEWMGI INPS..
3D1-VH-VL_Genewiz_extraction_Genewi     QVQLVQSGA.EVKKPGASVKVSCKAS GYAF....SNFW MNWVRQAPGQGLEWMGQ IYPG..
```

VL:

```
M23090 Homsap IGKV3-15*01 F              EIVMTQSPATLSVSPGERATLSCRAS QSV......SSN LAWYQQKPGQAPRLLIY GA....

G3-1-D6-mini7-extraction_extraction     ETTLTQSPATLSVSPGERATLSCRAS QSV......GSN LAWYQQKPGQAPRLLIY GA....


KM455568 Homsap IGKV6-21*02 F           EIVLTQSPDFQSVTPKEKVTITCRAS QSI......GSS LHWYQQKPDQSPKLLIK YA....

3D1-VH-VL_Genewiz_extraction_Genewi     EIVLTQSPDFQSVTPKEKVTITCRAS QSI......GTS IHWYQQKPDQSPKLLIK YA....
```

*FIG. 9 con't*

```
NGNT NYAQKLQ.GRVTMTTDTSTSTAYMELRSLRSDDTAVYYC AR  GVGDYFDYW GQGTLVTVSS
NGNT KYAQKVQ.GRVIMTTDTSTTTAYMELRSLTSDDTAVYYC AR DGVGAAFDYW GQGTLVTVSS

GGST SYAQKFQ.GRVTMTRDTSTSTVYMELSSLRSEDTAVYYC ARSYYRNNWFDSWGQGTLVTVSS
DGDT NYNGKFK.GRVTMTRDTSTSTVYMELSSLRSEDTAVYYC ARSYYRSAWFAYWGQGTLVTVSS


...S TRATGIP.ARFSGSG..SGTEFTLTISS LQSEDFAVYYCQQYNNWP

...S TRATGIP.ARFSGSG..SGTEFTLTISS


...S QSISGVP.SRFSGSG..SGTDFTLTINSLEAEDAATYYC HQSSSLPWTFGQGTKVEIK

...S ESISGVP.SRFSGSG..SGTDFTLTINSLEAEDAATYYC QQSNNWPLTFGQGTKVEIK
```

*FIG. 9 con't*

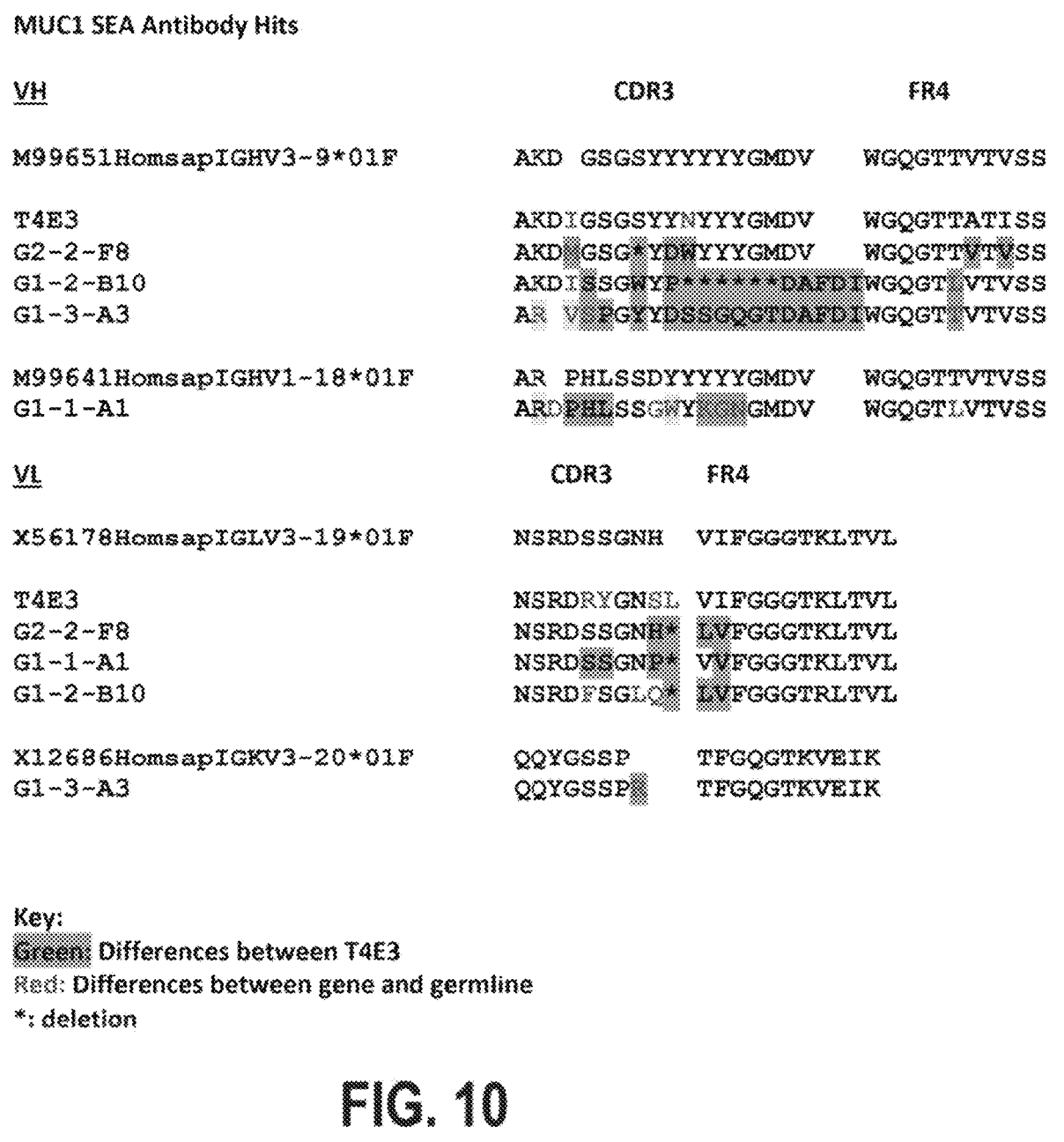

MUC1 SEA Antibody Hits

| VH | CDR3 | FR4 |
|---|---|---|
| M99651HomsapIGHV3-9*01F | AKD GSGSYYYYYYGMDV | WGQGTTVTVSS |
| T4E3 | AKDIGSGSYYNYYYGMDV | WGQGTTATISS |
| G2-2-F8 | AKD GSG*YDWYYYGMDV | WGQGTTVTVSS |
| G1-2-B10 | AKDISSGWYP******DAFDI | WGQGT VTVSS |
| G1-3-A3 | AR VSPGYYDSSGQGTDAFDI | WGQGT VTVSS |
| M99641HomsapIGHV1-18*01F | AR PHLSSDYYYYYGMDV | WGQGTTVTVSS |
| G1-1-A1 | ARDPHLSSGWY GMDV | WGQGTLVTVSS |

| VL | CDR3 | FR4 |
|---|---|---|
| X56178HomsapIGLV3-19*01F | NSRDSSGNH | VIFGGGTKLTVL |
| T4E3 | NSRDRYGNSL | VIFGGGTKLTVL |
| G2-2-F8 | NSRDSSGNH* | LVFGGGTKLTVL |
| G1-1-A1 | NSRDSSGNP* | VVFGGGTKLTVL |
| G1-2-B10 | NSRDFSGLQ* | LVFGGGTRLTVL |
| X12686HomsapIGKV3-20*01F | QQYGSSP | TFGQGTKVEIK |
| G1-3-A3 | QQYGSSP | TFGQGTKVEIK |

Key:
Green: Differences between T4E3
Red: Differences between gene and germline
*: deletion

FIG. 10

| | % FACS Positive in scFv-Fc format (@ [ ] in nM) |
|---|---|
| T4E3 | 75.7 (182) |
| G2-2-F8 | 46.8 (910) |
| G1-3-A3 | 20.1 (910) |
| G1-2-B10 | 31.0 (910) |
| G1-1-A1 | 47.5 (910) |

FIG. 10 con't

*Survival based on stage at diagnosis*

| | All subtypes | Serous | Endometroid | Mucinous | Clear Cell |
|---|---|---|---|---|---|
| All stages | 47 | 44 | 82 | 69 | 67 |
| Localized | 93 | 90 | 98 | 93 | 90 |
| Regional | 74 | 75 | 87 | 81 | 74 |
| Distant | 30 | 35 | 48 | 18 | 26 |

FIG. 11 con't

Conventional treatments: Surgery and chemotherapy
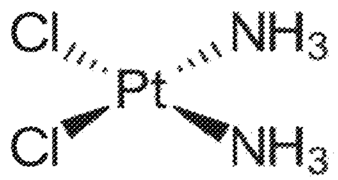
Cisplatin
**(*DNA replication inhibitor*)**
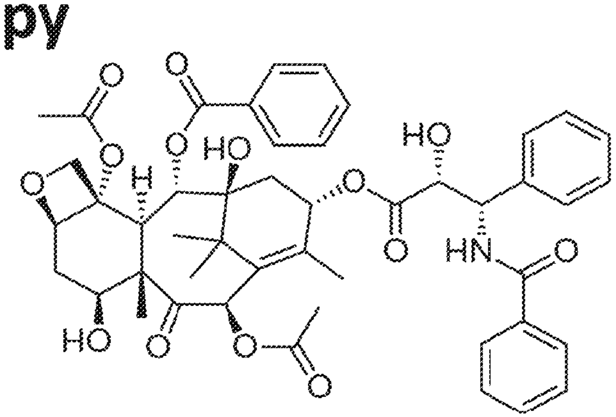
Paclitaxel
**(*blocks mitosis*)**
Bevacizumab (VEGF)
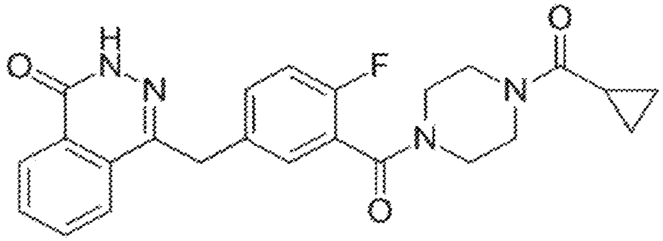
**Olaparib (*DNA repair inhibitor)***
Benefit in progression free survival but not overall survival
FIG. 12

Checkpoint inhibitors

Nivolumab (PD-1)

Pembrolizumab (PD-1)

Ipilimumab (CTLA-4)

Tremelimumab (CTLA-4)

Durvalumab (PD-L1)

Atezolizumab (PD-L1)

Single agents: 10-15 % response

CAR T cells

Folate receptor alpha CAR T cells (Phase 1)

Mesothelin CAR T cells (Phase 1,2)

MUC16 CAR T cells (Phase 1)

WT-1 CAR T cells (Phase 1)

Combination therapy for success!

FIG. 12 con't

Scarlett, U. K., & Conejo-Garcia, J. R. (2012). Modulating the tumor immune microenvironment as an ovarian cancer treatment strategy. *Expert Review of Obstetrics & Gynecology, 7*(5), 413–419. http://doi.org/10.1586/eog.12.41

Heterogeneous tumor microenvironment composed of cells which inhibit cancer cell killing and cells which promote cancer cell killing

Clinical Observations

CD8 T cells are correlated with increased prognosis in epithelial ovarian cancer

Tregs are associated with decreased survival in epithelial ovarian cancer

Many cells/molecules lead to Treg production and recruitment at the tumor site

FIG. 13 con't

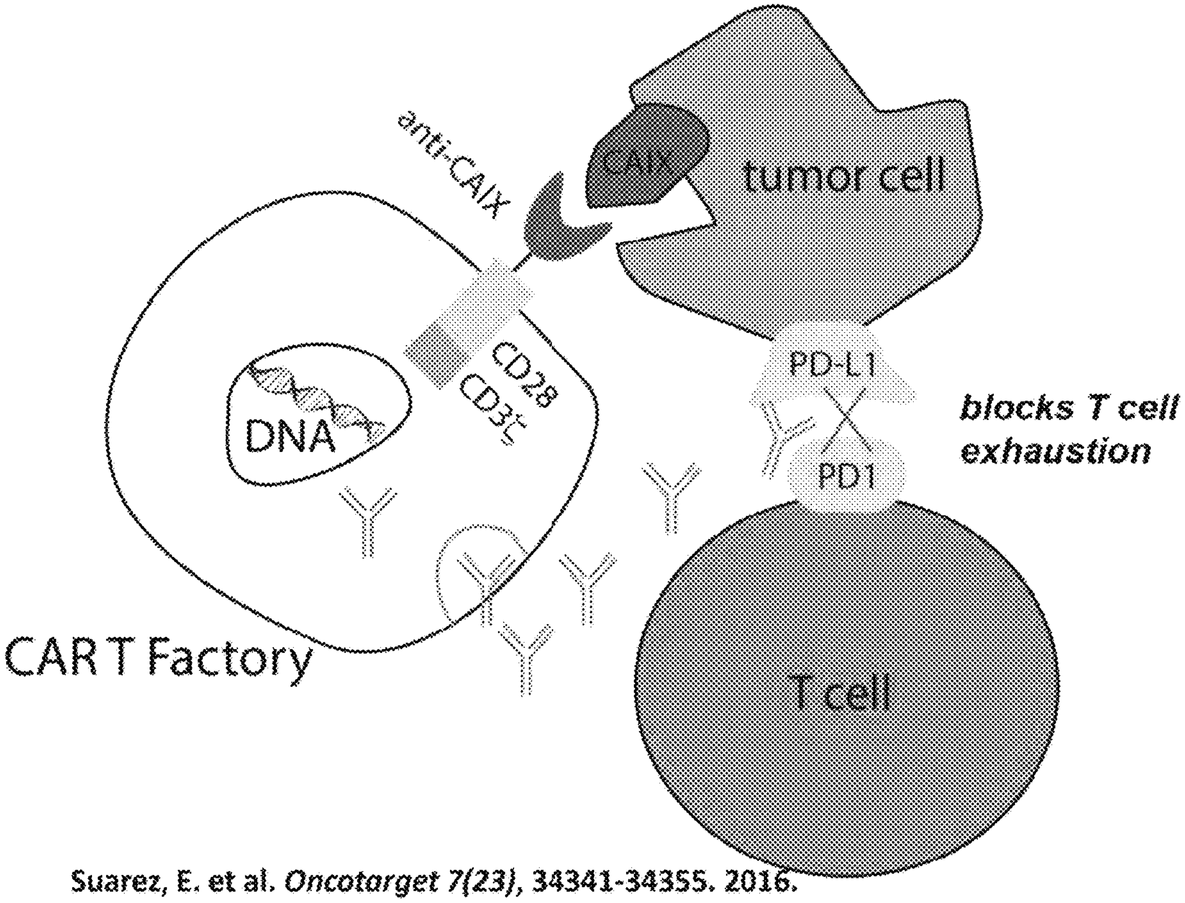
Suarez, E. et al. *Oncotarget 7(23)*, 34341-34355. 2016.
Components:
- chimeric antigen receptor (CAR) directed against antigen overexpressed on tumor cells aka target
- Immunomodulatory scFv-Fc which overcomes immunosuppressive solid tumor microenvironment aka payload
FIG. 15 con't

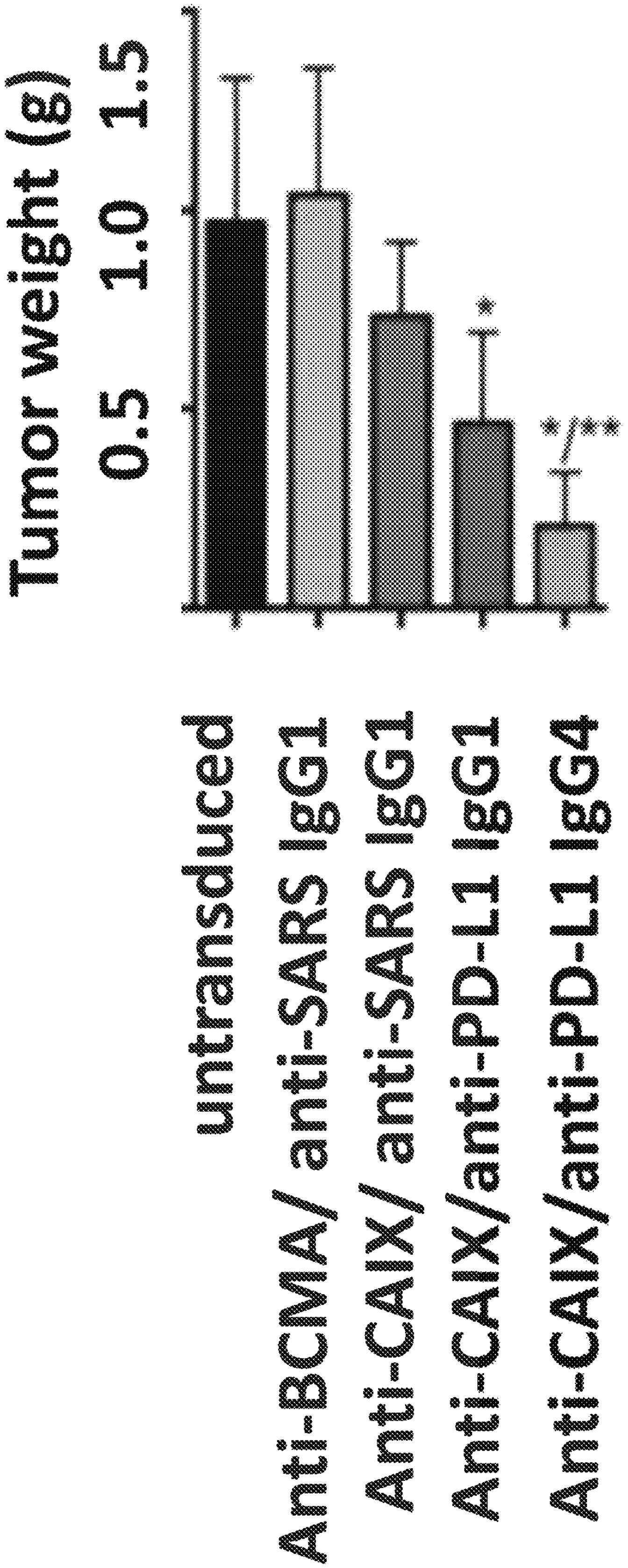
Enhanced tumor killing with addition of payload
FIG. 15 con't

Target: MUC1-C

Payload: anti-CCR4

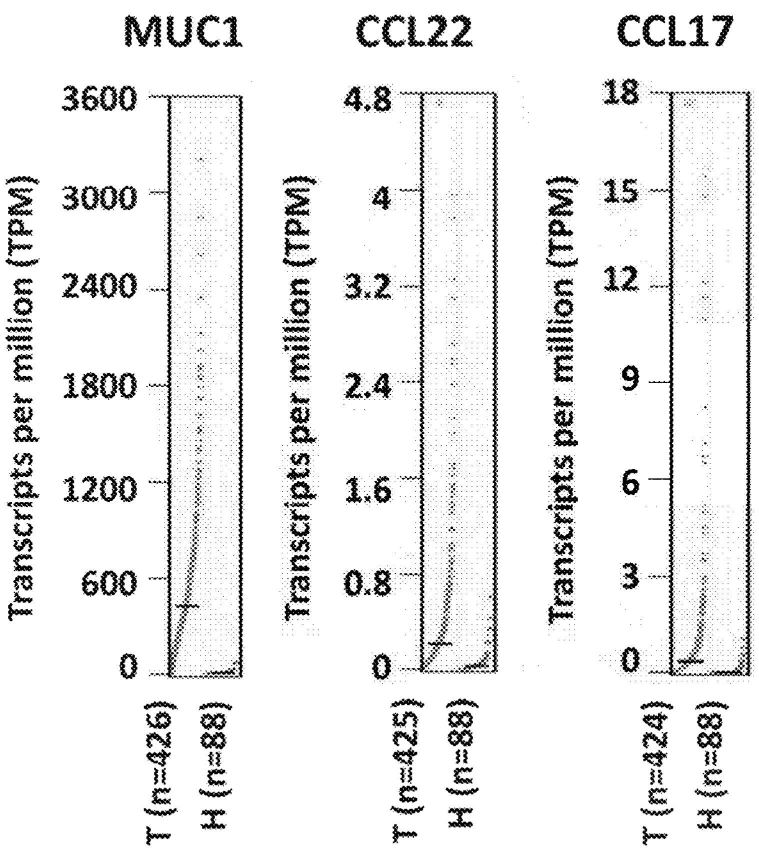
Overexpression of MUC1, CCL22, and CCL17 in tumor (T) tissue relative to healthy tissue (H)
*Gene expression data plots generated using GEPIA*
FIG. 16 con't

Depletion of Tregs through CAR T cell therapy

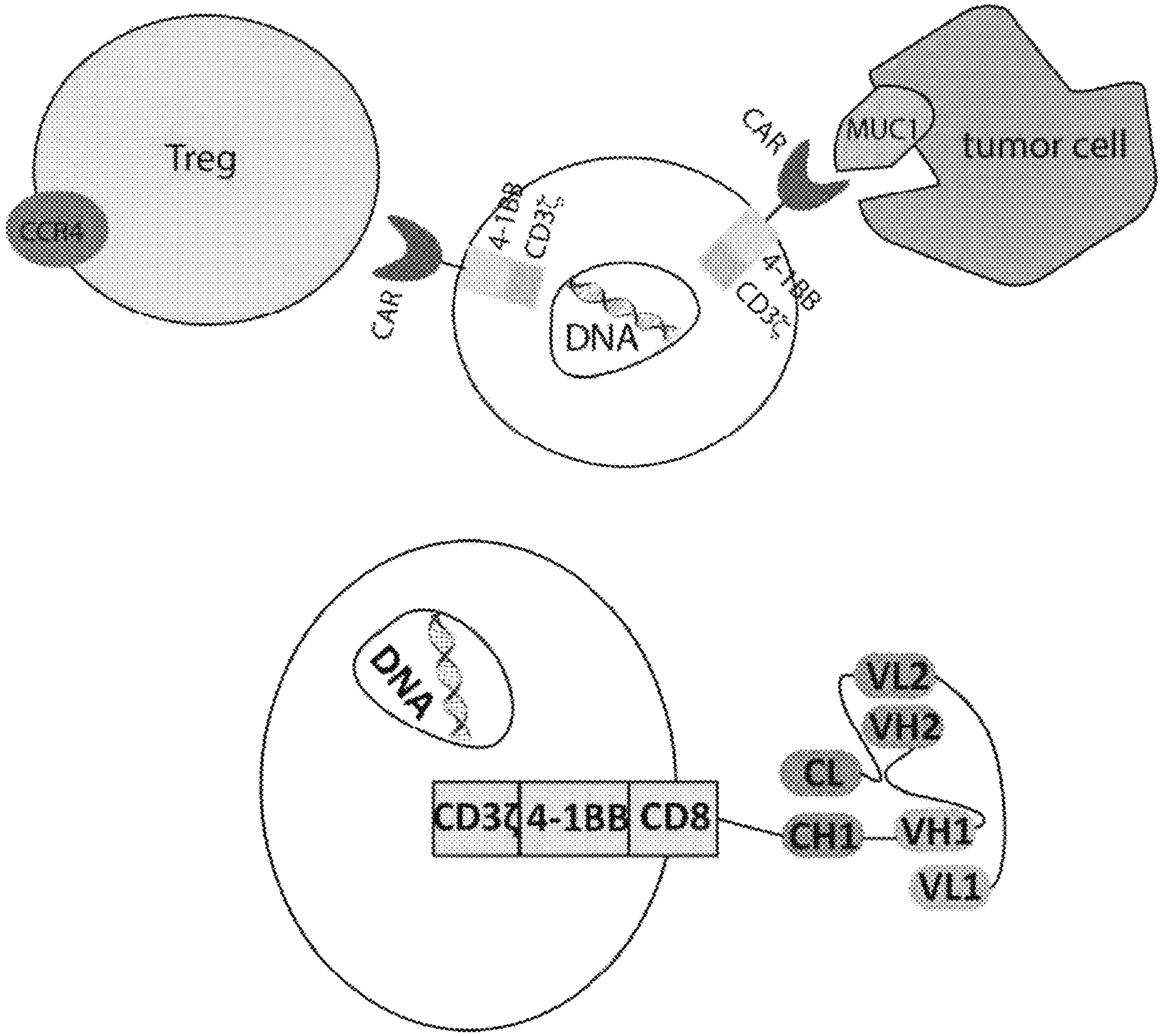
Used in conjunction with MUC1-C CAR T cell therapy by contransducing T cells with anti-MUC1-C and anti-CCR4 or delivering therapy in a bispecific format
FIG. 17 con't 3D1-MMAE antibody drug conjugates regress tumor growth of MUC1-C+ tumors but not MUC1-C - tumors

MUC1-C Terminal Domain
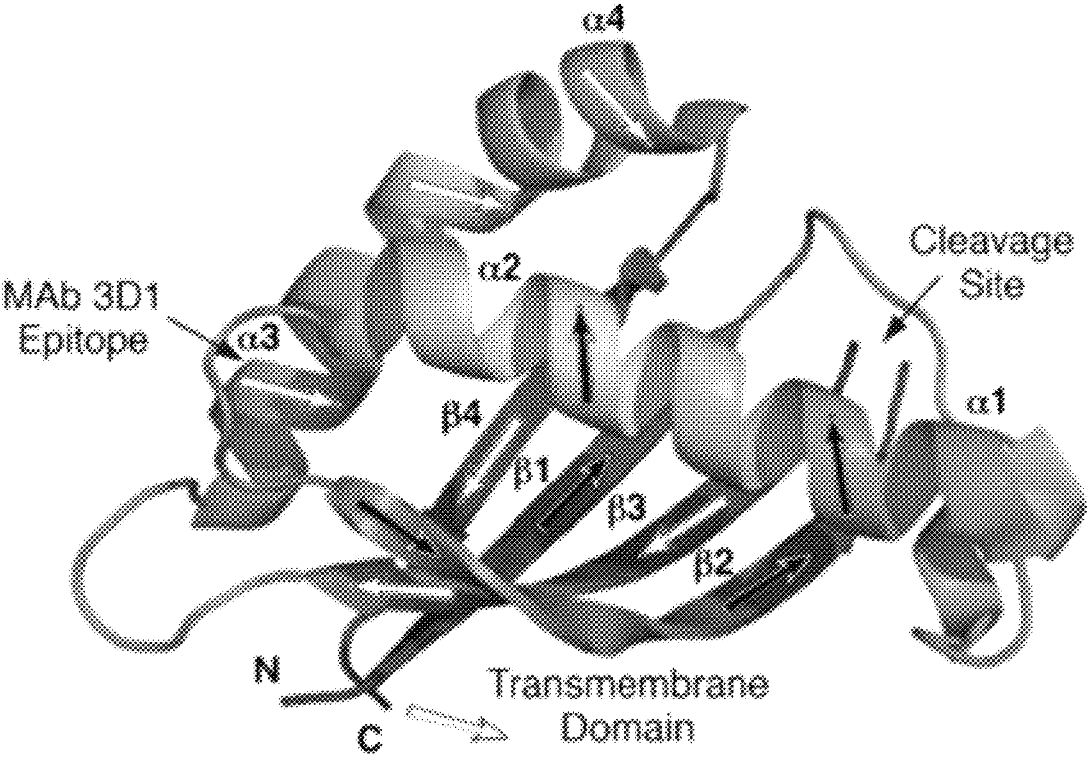
PDB: 2ACM
Panchamoorthy, G. *et al. JCI Insight* 3, 12: e99880. 2018.
FIG. 18 CON'T

Effect of CAR affinity

T cell activation of ICAM-1 directed CARS

*ICAM-1 directed CARS of varying affinity*

*20 μM CAR eradicated tumors in vivo and exhibited the least on-target off tumor toxicity*

Adapted from Park, S. *et al. Nature Scientific Reports 7*, 14366:1-15. 2017.

Effect of the CAR's epitope
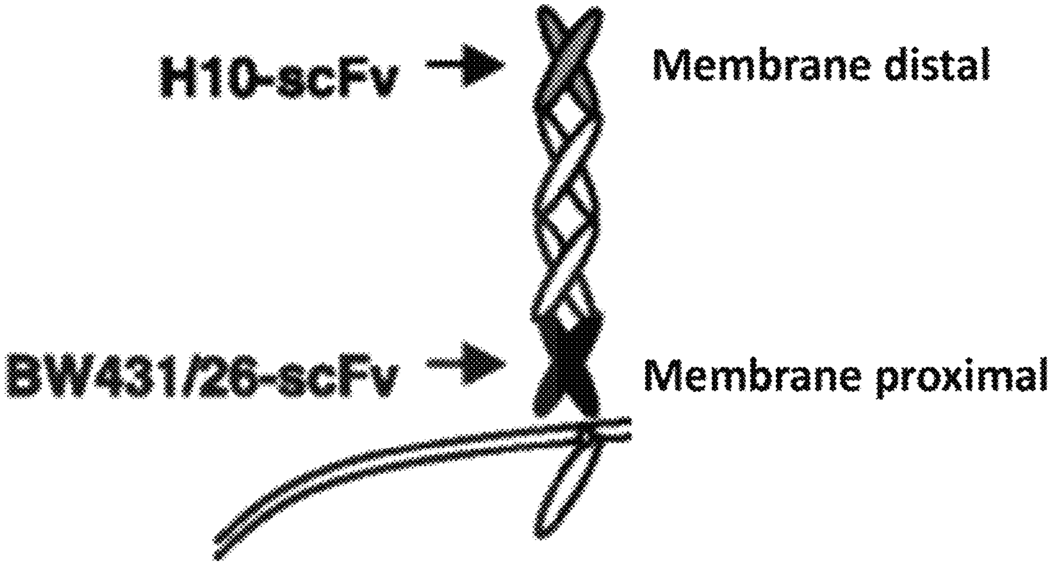
CEA: antigen
Hombach A *et al. J Immunology 17, 7: 4650-4657.* 2007.
FIG. 19 con't

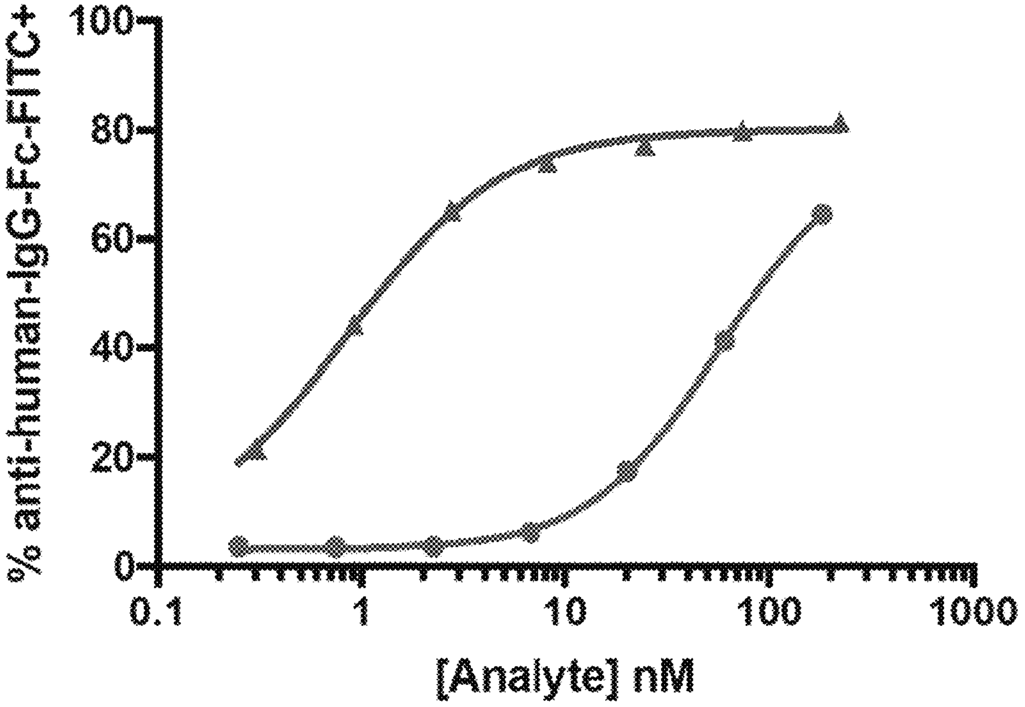
| Analyte | EC50 (nM) |
|---|---|
| 3D1 scFv-Fc | 57.02 |
| 3D1 IgG | 0.8347 |
Differences between scFv-Fc and IgG:
- $(GGGGS)_3$ linker in scFv-Fc conformation
- CH1/ CL domains
FIG. 20 con't Nath S. *et al. Trends in Molecular Medicine 20*, 6: 332-342. 2014. doi:10.1038/nsmb1035
Macao B. *et al. Nature Structural and Molecular Biology 13*, 71-76. 2006. doi:10.1038/nsmb1035

MUC1-SEA (PDB ID: 2ACM)
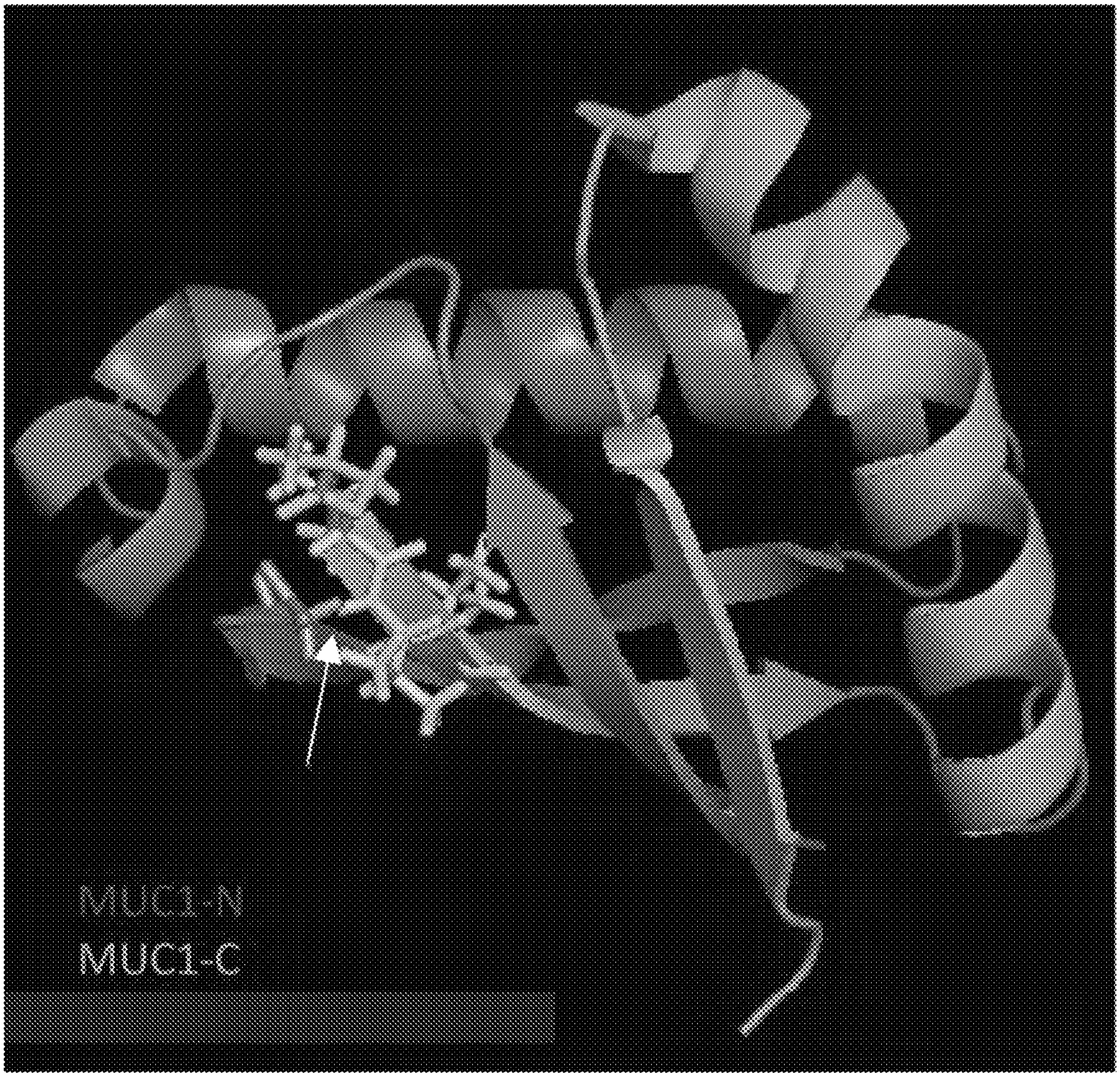
MUC1-SEA Domain: undergoes autoproteolytic self cleavage at the conserved GVVVS sequence
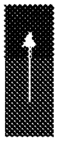
FIG. 22 con't

Panning with soluble MUC1-SEA

| Round 1 (01/17/2018) | | |
|---|---|---|
| 10ug/ml antigen, 1ml total volume | | |
| I | Target | O |
| 3.33E+12 | Muc1(SEA)-his | 2.27E+05 |
| 3.33E+12 | CD70-hFc (ACRO) | 4.63E+04 |
| 3.33E+12 | CD70-His (Sino) | 9.81E+05 |

| Round 3 (01/22/18) | | |
|---|---|---|
| 1 ug/ml antigen, 1ml total volume | | |
| I | Target | O |
| 1.00E+12 | Muc1(SEA)-his | 3.25E+07 |
| 1.00E+12 | CD70-hFc (ACRO) | 2.70E+04 |
| 1.00E+12 | CD70-His (Sino) | 3.60E+05 |

| Round 2 (01/20/2018) | | |
|---|---|---|
| 5ug/ml antigen, 1ml total volume | | |
| I | Target | O |
| 1.50E+12 | Muc1(SEA)-his | 2.60E+03 |
| 1.50E+12 | CD70-hFc (ACRO) | 2.40E+03 |
| 1.50E+12 | CD70-His (Sino) | 2.00E+02 |

| Round 3.2 (01/22/18) | | |
|---|---|---|
| 1 ug/ml antigen, 1ml total volume | | |
| I | Target | O |
| 1.00E+12 | Muc1(SEA)-his | 2.50E+03 |
| 1.00E+12 | CD70-hFc (ACRO) | 4.50E+03 |
| 1.00E+12 | CD70-His (Sino) | 3.48E+04 |

| Round 2.2 (01/22/18) | | |
|---|---|---|
| 5ug/ml antigen, 1ml total volume | | |
| I | Target | O |
| 1.00E+12 | Muc1(SEA)-his | 1.15E+04 |
| 1.00E+12 | CD70-hFc (ACRO) | 2.67E+04 |
| 1.00E+12 | CD70-His (Sino) | 1.07E+04 |

| Round 3.3 (02/26/18) | | |
|---|---|---|
| 1 ug/ml antigen, 1ml total volume | | |
| I | Target | O |
| 2.00E+12 | Muc1(SEA)-his | 3.13E+05 |
| 2.00E+12 | CD70-hFc (ACRO) | 7.48E+04 |
| 2.00E+12 | CD70-His (Sino) | 6.93E+04 |

One high affinity anti-MUC1-SEA hit found in round 3.3

FIG. 26

Panning with MUC1+ HCT116-MUC1 cells

| | | |
|---|---|---|
| | Round 3.5 (06/28/18)<br>Muc1+ or CD70+ cells | |
| | Muc1 | |
| 3.00E+12 | Gly Wash 1 | 2.76E+05 |
| | Gly Wash 2 | 2.45E+04 |
| | Gly Wash 3 | 2.00E+03 |
| | TEA Lysis | 3.70E+04 |

| | | |
|---|---|---|
| | Round 3.6 (06/28/18)<br>Muc1+ or CD70+ cells | |
| | Muc1 | |
| 3.00E+12 | Gly Wash 1 | 9.37E+04 |
| | Gly Wash 2 | 1.29E+05 |
| | Gly Wash 3 | 1.73E+04 |
| | TEA Lysis | 4.27E+05 |

Four lower affinity anti-MUC1-SEA hits found whole cell panning round 3.5

FIG. 26 con't

| % MUC1+ at 1 µM scFv-Fc | | FR1-IMGT (1-26) | CDR1-IMGT (27-38) | FR2-IMGT (39-55) | CDR2-IMGT (56-65) |
|---|---|---|---|---|---|
| | | 1 10 20 | 30 | 40 50 | 60 |
| | *Heavy Chains 11/9/18* | | | | |
| | M99651HomsapIGHV3-9*01F | EVQLVESGG.GLVQPGRSLRLSCAAS | GFTF....DDYA | MHWVRQAPGKGLEWVSG | ISWN..SGSI |
| G2-2-F8: 48 | T4E3-scFv_extraction | QVQLVQSGG.GLVQPGGSLRLSCAAS | GFTF....DDYA | MHWVRQAPGKGLEWVSG | ISWN..SGSI |
| G1-2-B10: 30 | G2-2-F8-mini3-extraction | QVQLVQSGG.GLVQPGRSLRLSCAAS | GFTF....DDYA | MHWVRQAPGKGLEWVSG | ISWN..SGSI |
| G1-3-A3: 20 | G1-2-B10-mini2-extractio | QVQLVQSGG.GLVQPGRSLRLSCAAS | GFTF....DDYA | MHWVRQAPGKGLEWVSG | ISWN..SGSI |
| | G1-3-A3-mini4-extraction | QVQLVQSGG.GFVQPGRSLRLSCAAS | GFTF....DDYA | MHWVRQAPGKGLEWVSG | ISWN..SNNI |
| | M99641HomsapIGHV1-18*01F | QVQLVQSGA.EVKKPGASVKVSCKAS | GYTF....TSYG | ISWVRQAPGQGLEWMGW | ISAY..NGNT |
| G1-1-A1: 48 | G1-1-A1-mini1-extraction | QVQLVQSGA.EVKKPGASVKVSCKAS | GYTF....TSYG | ISWVRQAPGQGLEWMGW | ISAY..NGNT |
| | *Light Chains 11/9/18* | | | | |
| | X56178HomsapIGLV3-19*01F | SSELTQDPA.VSVALGQTVRITCQGD | SLR......SYY | ASWYQQKPGQAPVLVIY | GK.......N |
| G2-2-F8: 48 | T4E3-scFv_extraction | SSELTQDPA.VSVALGQTVRITCQGD | SLR......SYY | ASWYQQKPGQAPVLVIY | GK.......N |
| G1-1-A1: 48 | G2-2-F8-mini3-extraction | SSELTQDPA.VSVALGQTVRITCRGD | SLR......SYY | ASWYQQKPGQAPVLVIY | GK.......N |
| G1-2-B10: 30 | G1-1-A1-mini1-extraction | SSELTQDPA.VSVALGQTVRITCQGD | SLR......RYY | ASWYQQKPGQAPVLVFY | GK.......N |
| | G1-2-B10-mini2extraction | SSELTQDPA.VSVALGQTVRITCQGD | SLR......SYY | ASWYQQKPGQAPVLVIY | GK.......N |
| | X12686HomsapIGKV3-20*01F | EIVLTQSPGTLSLSPGERATLSCRAS | QSVS......SSY | LAWYQQKPGQAPRLLIY | GA.......S |
| G1-3-A3: 20 | G1-3-A3-mini4 | ETTLTQSPATLSVSPGERATLSCRAS | QSV......RRN | VAWYQQKPGQAPRLLIY | GA.......S |

FIG. 29

```
                                                      FR3-IMGT                       CDR3          FR4
                                                      (66-104)
                                        ---------------------------------------- ----------------- ----------
                                           70        80        90        100
                                        ....|.........|.........|.........|....
% MUC1+ at 1
μM scFv-Fc      Heavy Chains 11/9/18/

                M99651HomsapIGHV3-9*01F  GYADSVK.GRFTISRDNAKNSLYLQMNSLRAEDTALYYC AKD GSGSYYYYYYGMDV   WGQGTTVTVSS

G2-2-F8: 48     T4E3-scFv extraction     GYADSVK.GRFTISRDNAKNSLYLQMNSLRAEDTALYYC AKDIGSGSYYNYYYGMDV   WGQGTTATISS
G1-2-B10: 30    G2-2-F8-mini3-extraction GYADSVK.GRFTISRDNAKNSLYLQMNSLRAEDTALYYC AKDMGSG YDWYYYGMDV   WGQGTTVTVSS
G1-3-A3: 20     G1-2-B10-mini2-extractio GYADSVK.GRFTISRDNAKNSLYLQMNSLRAEDTALYYC AKDISSGWYP.     DAFDIWGQGTLVTVSS
                G1-3-A3-mini4-extraction GYADSVK.GRFTISRENAKNSLYLQMNSLRAEDTAVYYC AR VSPGYYDSSGQGTDAFDIWGQGTTVTVSS

                M99641HomsapIGHV1-18*01F NYAQKLQ.GRVTMTTDTSTSTAYMELRSLRSDDTAVYYC AR PHLSSDYYYYYGMDVWGQGTTVTVSS
G1-1-A1: 48     G1-1-A1-mini1-extraction NYAQKVQ.GRVTMTTDTSTSTAYMELRSLRSDDTAVYYC ARDPHLSSGWYKGNGMDVWGQGTLVTVSS

                Light Chains 11/9/18

                X56178HomsapIGLV3-19*01F NRPSGIP.DRFSGSS..SGNTASLTITGAQAEDEADYYC NSRDSSGNH VIFGGGTKLTVL
G2-2-F8: 48     T4E3-scFv extraction     SRPSGIP.DRFSGSN..SGSTASLTITGAQAEDEADYYC NSRDRYGNSLVIFGGGTKLTVL
                G2-2-F8-mini3-extraction NRPSGIP.DRFSGSS..SGNTASLTITGAQAEDEADYYC NSRDSSGNH LVFGGGTKLTVL
G1-1-A1: 48     G1-1-A1-mini1-extraction TRPSGIP.DRISGSS..SGNTASLTITGAQAEDEADYYC NSRDSSGN PVVFGGGTKLTVL
G1-2-B10: 30    G1-2-B10-mini2extraction NRPSGIP.DRFSGSN..SGNTASLTITGAQAEDEADYYC NSRDFSGLQ LVFGGGTRLTVL

                X12686HomsapIGKV3-20*01F SRATGIP.DRFSGSG..SGTDFTLTISRLEPEDFAVYYC QQYGSSP TFGQGTKVEIK
G1-3-A3: 20     G1-3-A3-mini4            FRAAGVP.DRFSGSG..SGTDFTLTITRLEPEDFAVYYC QQYGSSPRTFGQGTKVEIK
```

FIG. 30

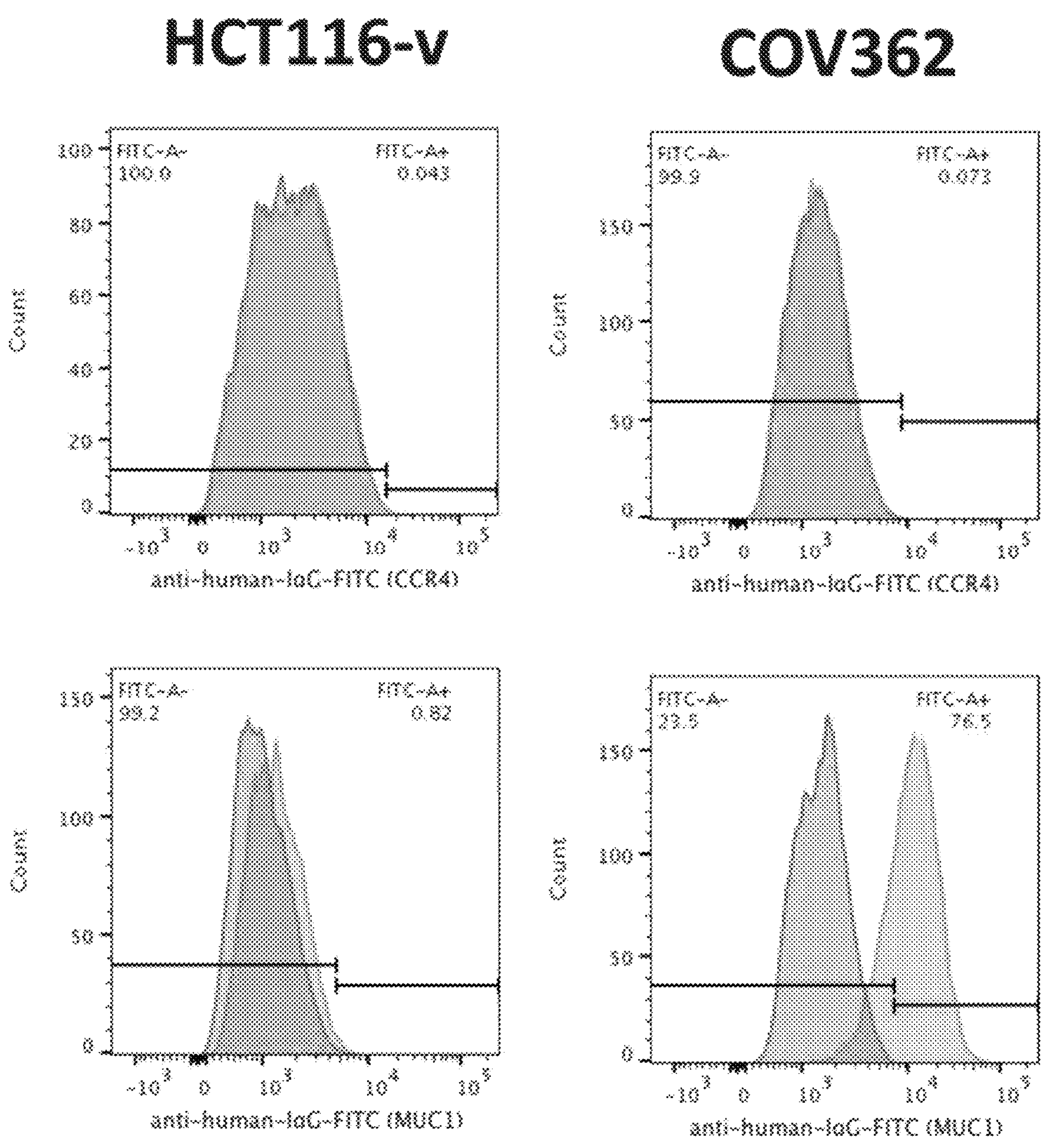
FIG. 31 con't pHAGE-ef1 alpha-T4E3-mAb23-Fab2a-CD8-CD137-CD3-IRES-ZsGreen-WPRE MRC
11,291 bp

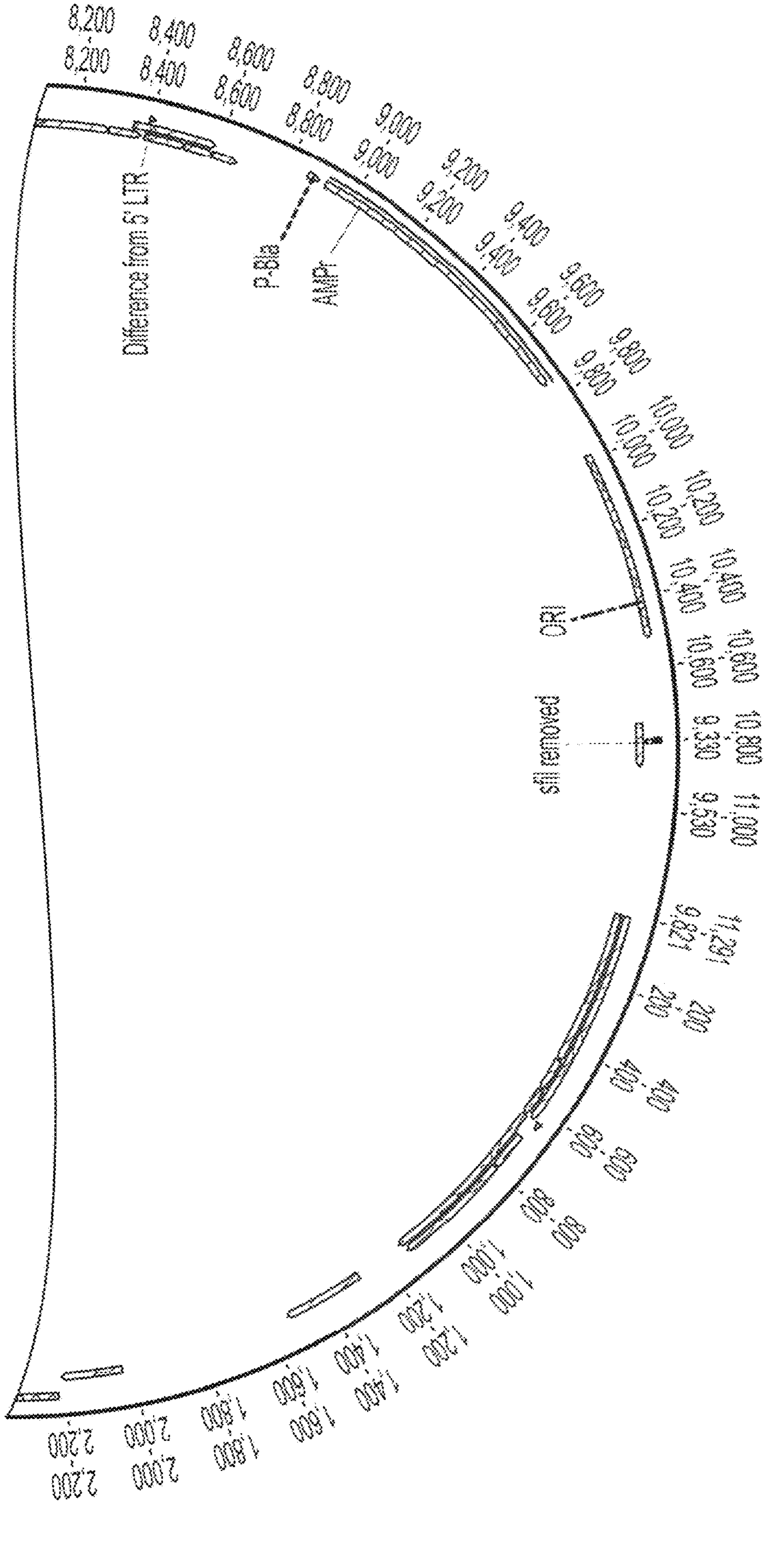
FIG. 35 con't

Nomenclature and amino acid sequences of different 2A peptides.

| 2A Mutant | Mutation Type | Amino Acid Sequence |
|---|---|---|
| F2A | Wild-type | QLLNFDLLKLAGDVESNPGP |
| F2A(−1) | 1aa N-terminal deletion | LLNFDLLKLAGDVESNPGP |
| F2A(−2) | 2aa N-terminal deletion | LNFDLLKLAGDVESNPGP |
| F2A(−3) | 3aa N-terminal deletion | NFDLLKLAGDVESNPGP |
| F2A(−4) | 4aa N-terminal deletion | FDLLKLAGDVESNPGP |
| F2A(−5) | 5aa N-terminal deletion | DLLKLAGDVESNPGP |
| F2A(−6) | 6aa N-terminal deletion | LLKLAGDVESNPGP |
| F2A(−7) | 7aa N-terminal deletion | LKLAGDVESNPGP |
| F2A(3) | Point mutation | QLLNFDLLKLAGDV**Q**SNPGP |
| F2A(11) | Point mutation | QLLNFDLLKLAGDVE**I**NPGP |
| F2A(14) | Point mutation | QLLNFDLLKLAGDVES**E**PGP |
| F2A(19) | Point mutation | QLLNFDLLKLAGDVESNP**A**P |

**Yu K. *et al. Plos One 7*, 11: e50438-342. 2012.**

FIG. 36 con't

B

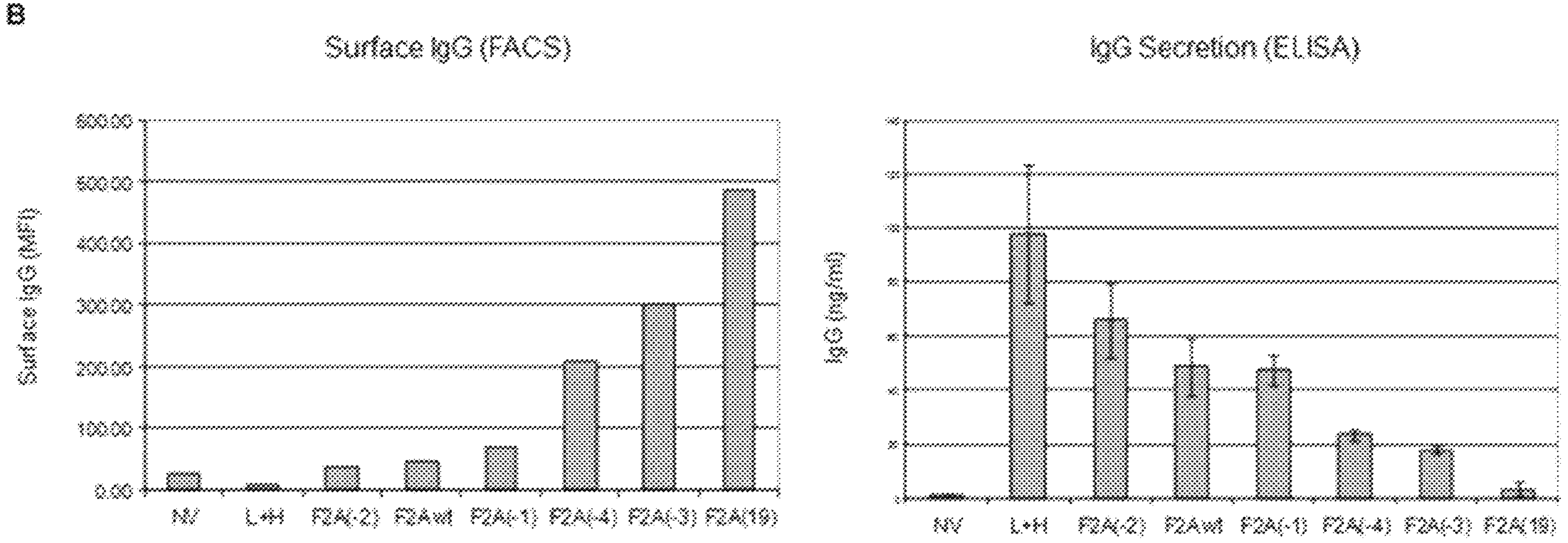

Inversely-related expression of b12 chimeric IgG/M BCR and secreted IgG mediated by mutant 2A peptides. (A) Experimental design for measuring the expression of surface to secreted immunoglobulins by IgG Molecular Rheostat constructs. To establish that it is possible to tune the ratio of surface to secreted immunoglobulins by making appropriate choice of mutations in the 2A peptide, select b12 IgG/M chimeric constructs (based on the experiment with the 293T cells in Figure 2) were modified to include an additional ZsGreen fluorescent protein gene driven by an IRES 3' of the heavy chain. OCI-Ly7 B cells were infected with at low MOI (~ 0.1) with this library of constructs and the cells that express the ZsGreen gene were sorted out by FACS. The cells were cultured for 24 hours post-sorting; the cells were analyzed by flow cytometry and supernatants were taken for IgG ELISA. (B) Inverse relationship between surface expression of chimeric b12 IgG/M Molecular Rheostat BCRs and secreted b12 IgG in the supernatants of sorted cells. NV: untransduced control. L+H: secretion only b12 control. The Molecular Rheostat constructs are denoted by the mutant 2A elements they contain.
doi:10.1371/journal.pone.0050438.g003

Choose F2a which has high surface IgG but low IgG secretion

FIG. 36 con't

Expression of 3D1

In the presence of 5 μg/mL MUC1-HIS

Fabs do not bind MUC1-SEA

Expression of Light Chain
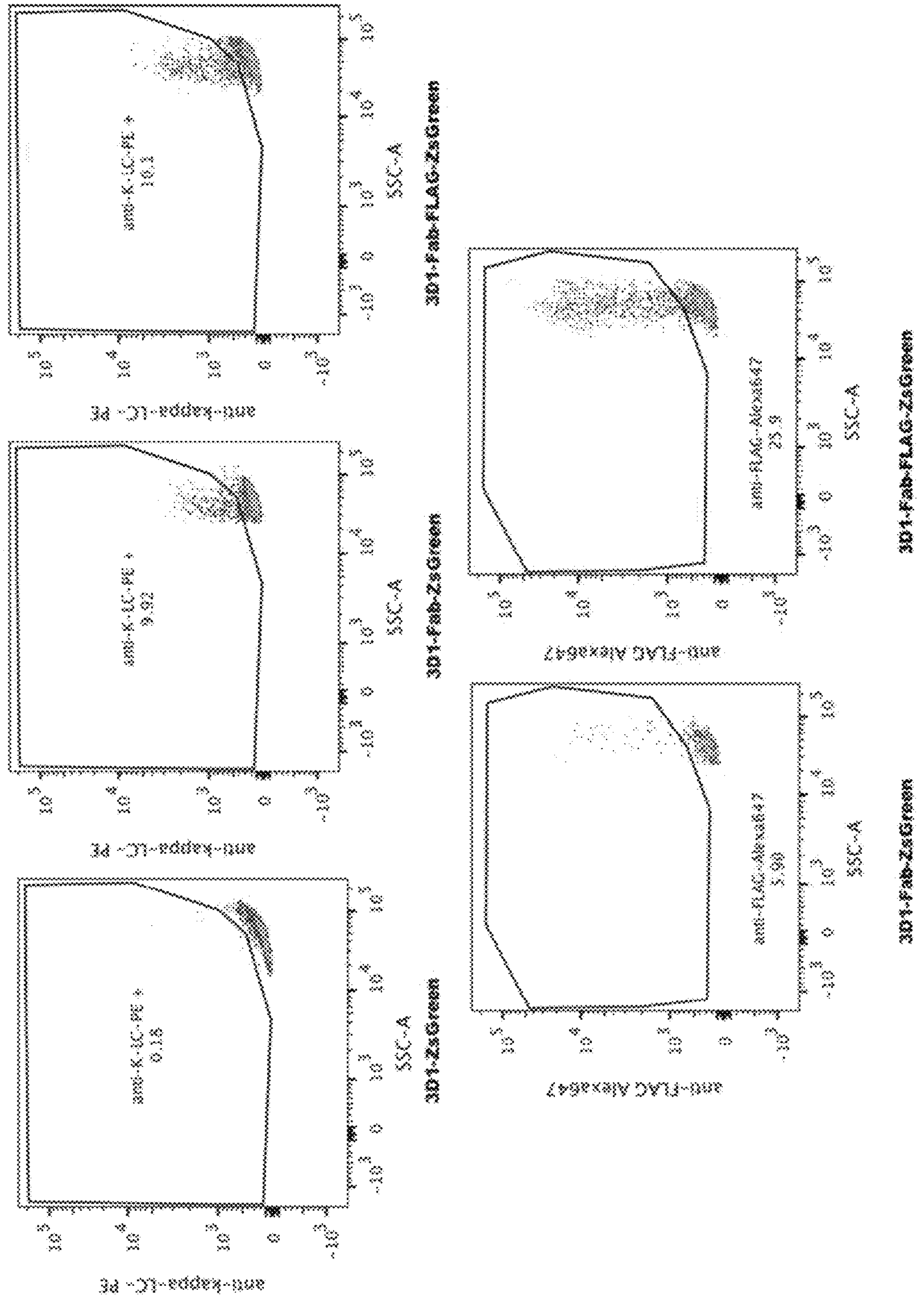
Fabs express light chain
FIG. 37 con't

HA-Stem: EC50 = 0.5958 nM
MUC1-SEA: EC50 N.D.

| | Expression (%) |
|---|---|
| ZsGreen | 45.9 |
| ZsGreen/ Kappa-Light Chain | 97.7 |
| ZsGreen/ CH1-APC | 98.5 |

| | ZsGreen (%) | ZsGreen/ Kappa Light Chain-PE (%) | ZsGreen/ CH1-APC(%) |
|---|---|---|---|
| **3D1-scFv-ZsGreen** | 66.3 | 2.2 | 2.3 |
| **3D1-Fab-ZsGreen** | 67.4 | 95.5 | 95.5 |
| **mAb2-3 scFv-ZsGreen** | 52.9 | 1.7 | 1.1 |
| **mAb2-3-Fab-ZsGreen** | 41.4 | 98.2 | 96.1 |

*FIG. 41*

EC50 = 7.483 nM (T4E3 scFv)
EC50= 15.96 nM (T4E3 Fab)

| | ZsGreen (%) | ZsGreen/ Lambda Light Chain-APC (%) | ZsGreen/ CH1-APC(%) |
|---|---|---|---|
| **T4E3-scFv-ZsGreen** | 70 | 0.673 | 1.2 |
| **T4E3-Fab-ZsGreen** | 73 | 93.9 | 93.7 |

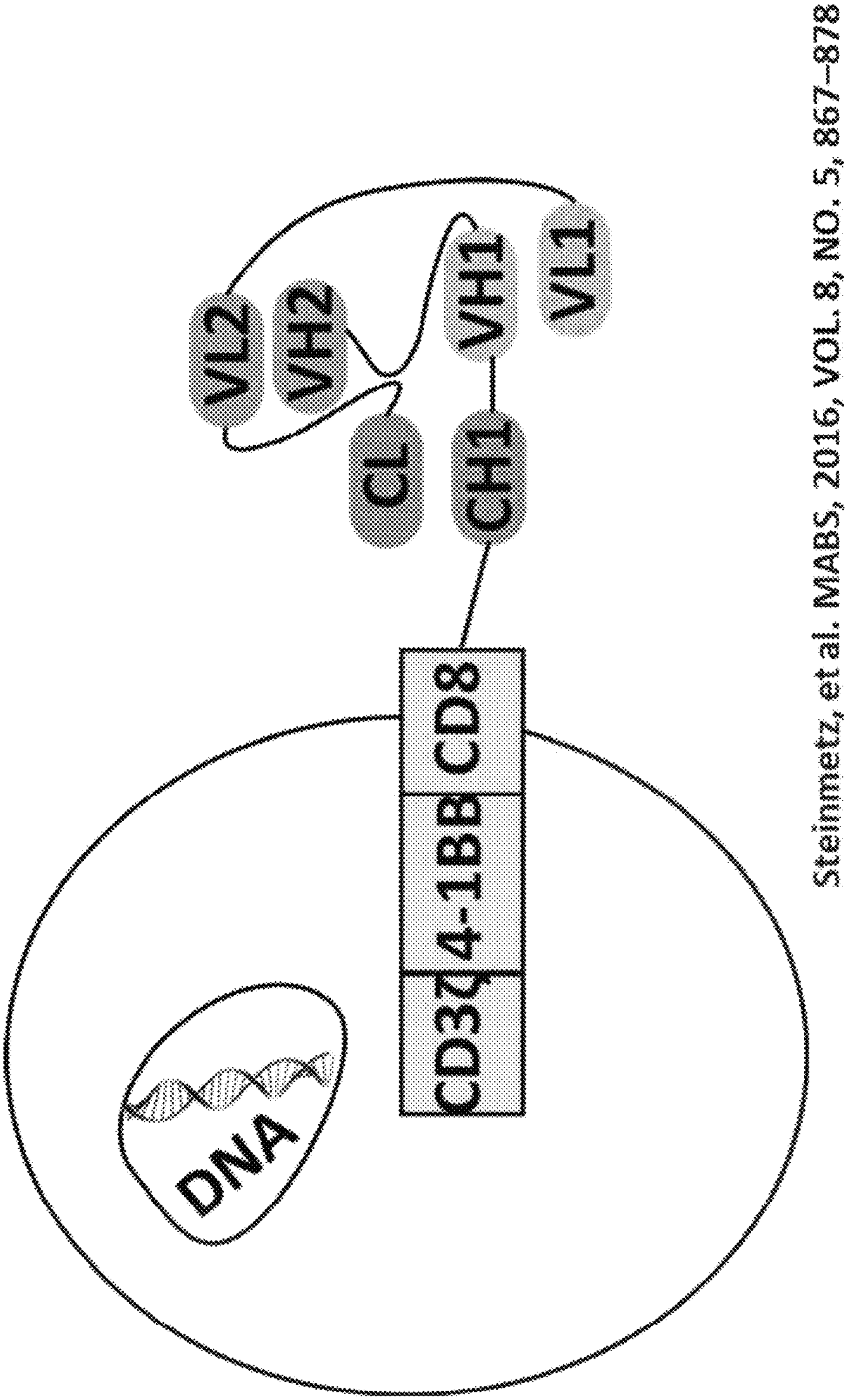
Steinmetz, et al. MABS, 2016, VOL. 8, NO. 5, 867–878
L1: $(Gly)_7$ L2: $(Gly)_5$ L3: Gly L4: Gly-Gly
FIG. 44 con't

| Construct | ZsGreen/CH1 | ZsGreen/anti-λ-light chain-APC | ZsGreen/anti-κ-light chain PE | ZsGreen |
|---|---|---|---|---|
| *3D1-scFv* | 2.2 | N/A | 2.3 | 66.3 |
| *3D1-Fab* | 95.5 | N/A | 95.5 | 67.4 |
| *T4E3-scFv* | 1.2 | 0.7 | N/A | 70.0 |
| *T4E3-Fab* | 93.7 | 93.9 | N/A | 73.0 |
| *mAb2-3 scFv* | 1.7 | N/A | 1.1 | 52.9 |
| *mAb2-3 Fab* | 98.2 | N/A | 96.1 | 41.4 |
| *T4E3-mAb2-3 Fab* | 10.6 | N/A | 11.9 | 61.0 |
| *mAb2-3-T4E3 Fab* | 3.6 | 25.0 | N/A | 54.4 |

*FIG. 45 CON'T*

| Construct | EC50 |
|---|---|
| mAb2-3 scFv | 8.949 nM |
| mAb2-3 Fab | 471.5 nM |
| 3D1-scFv | 2.524 nM |
| 3D1-Fab | 18.06 nM |
| T4E3-scFv | 7.483 nM |
| T4E3-Fab | 15.96 nM |

FIG. 46 CON'T

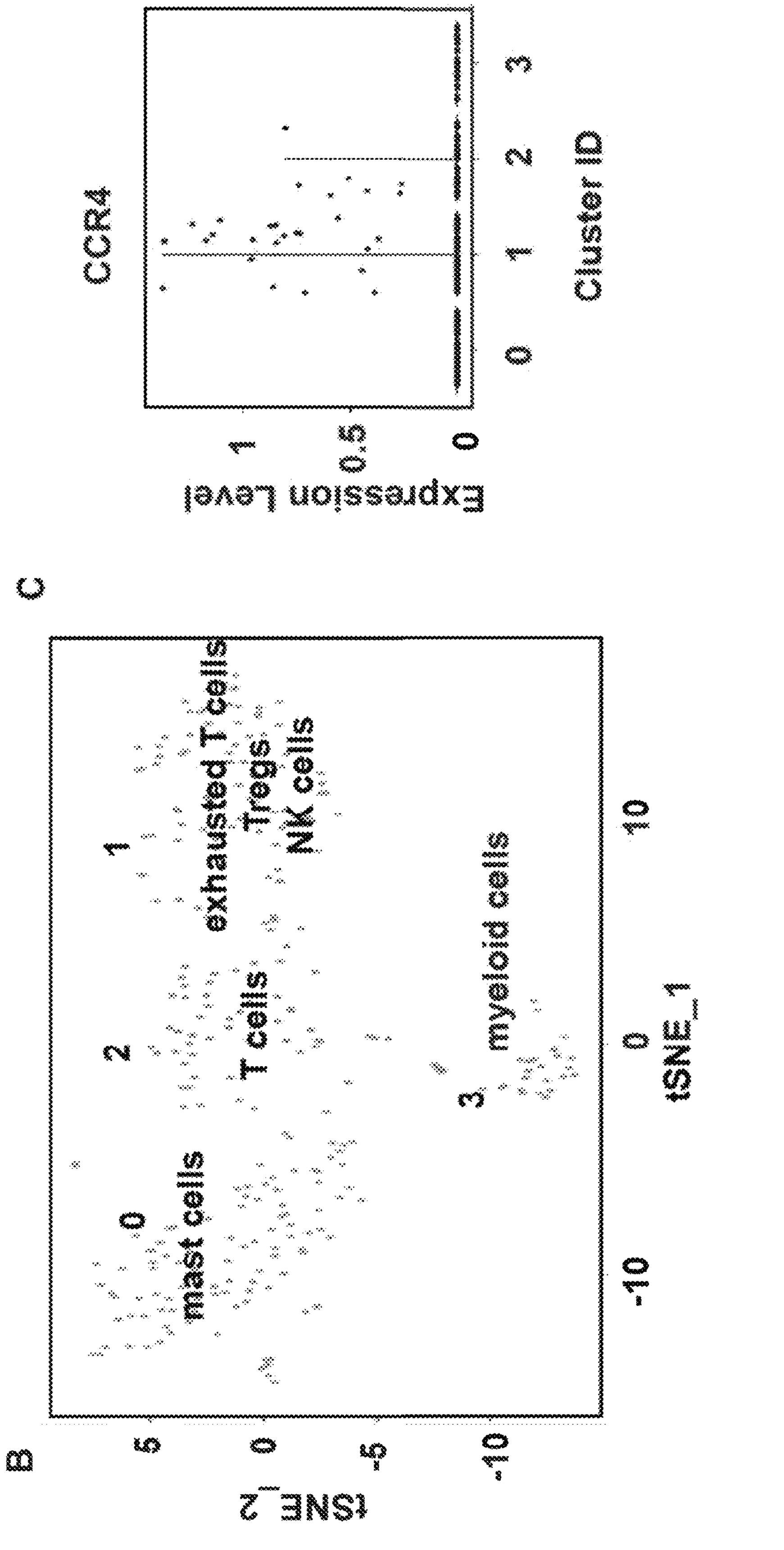
FIG. 50 CON'T

| Sequence ID | V-DOMAIN Functionality | V-GENE and allele | J-GENE and allele | D-GENE and allele |
|---|---|---|---|---|
| Muc1-R3-T4-D1 | productive | Homsap IGHV3-9*01 F | Homsap IGHJ6*02 F | Homsap IGHD3-10*01 F |
| Muc1-R3-T2-B1 | productive | Homsap IGHV3-9*01 F | Homsap IGHJ3*02 F | Homsap IGHD6-19*01 F |
| Muc1-R3-T4-B5 | productive | Homsap IGHV3-9*01 F | Homsap IGHJ6*02 F | Homsap IGHD5-12*01 F |
| Muc1-R3-E4-B12 | productive | Homsap IGHV1-18*04 F | Homsap IGHJ4*02 F | Homsap IGHD1-26*01 F |
| Muc1-R3-T3-H9 | productive | Homsap IGHV1-18*01 F | Homsap IGHJ6*02 F | Homsap IGHD6-19*01 F |
| Muc1-R3-T3-H3 | productive | Homsap IGHV1-18*01 F | Homsap IGHJ6*02 F | Homsap IGHD6-19*01 F |
| Muc1-R3-T4-D5 | productive | Homsap IGHV1-8*01 F | Homsap IGHJ3*02 F | Homsap IGHD1-7*01 F |
| Muc1-R3-T3-B9 | productive | Homsap IGHV1-8*01 F | Homsap IGHJ3*02 F | Homsap IGHD1-7*01 F |
| Muc1-R3-E4-G10 | productive | Homsap IGHV3-9*02 F | Homsap IGHJ3*02 F | Homsap IGHD3-22*01 F |
| Muc1-R3-T2-A3 | productive | Homsap IGHV3-30*03 F, or Homsap IGHV3-30*18 F or Homsap IGHV3-30-5*01 F or Homsap IGHV3-33*05 F | Homsap IGHJ3*01 F | Homsap IGHD2-15*01 F |
| Muc1-R3-T3-B6 | productive | Homsap IGHV1-8*01 F | Homsap IGHJ3*02 F | Homsap IGHD3-22*01 F |
| Muc1-R3-T4-E8 | productive | Homsap IGHV3-23*01 F, or Homsap IGHV3-23*04 F or Homsap IGHV3-23D*01 F | Homsap IGHJ6*02 F | Homsap IGHD1-26*01 F |
| Muc1-R3-E4-E1 | productive | Homsap IGHV3-7*03 F | Homsap IGHJ3*02 F | Homsap IGHD3-16*01 F |

| Sequence ID | V-DOMAIN Functionality | V-GENE and allele | J-GENE and allele | |
|---|---|---|---|---|
| Muc1-R3-T4-D1 | productive | Homsap IGLV3-19*01 F | Homsap IGLJ2*01 F, or Homsap IGLJ3*01 F | |

FIG. 51(A)

| FR1-IMGT | CDR1-IMGT |
|---|---|
| QVQLVQSGG.GLVQPGGSLRLSCAAS | GFTF....DDYA |
| QVQLVQSGG.GLVQPGGSLRLSCAAS | GFTF....DDYA |
| QVQLVQSGG.GLVQPGGSLRLSCAAS | GFTF....DDYA |
| QVQLVQSGA.EVKRPGASVKVSCKAS | GYTF....STYA |
| QEQLVQSGA.EVKKPGASVKVSCKAS | GYTF....TSYG |
| QVQLVQFGG.EVKKPGASVKVSCTAS | GYTY....TSYG |
| EVQLVQSGA.EVKKPGSSVKVSCKAS | GYTF....SNYD |
| DVQLVQSGG.EAKKPGSSVKVSCKAS | GYTF....CNYD |
| QLQLVQYGG.GFVQHGRSLRLFCAAS | GFTS....DDYD |
| QVQLVQSGG.GVVQPGRSLRLSCAAS | GFTF....SSYG |
| EVQLVQSGG.EAKKPGSSVKVSCKAS | GYTI....SNYD |
| QVQLQESGG.GLVQPGGSLRLSCAAS | GLSF....SKHA |
| PGALVQSGG.GLVQPGGSLRLSCAAS | GFTF....SDNW |

| FR1-IMGT | CDR1-IMGT |
|---|---|
| SSELTQDPA.VSVALGQTVRITCQGD | SLR......SYY |

FIG. 51(A) con't

| | | | | |
|---|---|---|---|---|
| Muc1-R3-T2-B1 | productive | Homsap IGLV3-19*01 F | Homsap IGLJ2*01 F, or Homsap IGLJ3*01 F | |
| Muc1-R3-T4-B5 | productive | Homsap IGLV3-19*01 F | Homsap IGLJ3*02 F | |
| Muc1-R3-E4-B12 | productive | Homsap IGKV3-11*01 F, or Homsap IGKV3-15*01 F or Homsap IGKV3D-11*02 F | Homsap IGKJ1*01 F | |
| Muc1-R3-T3-H9 | productive | Homsap IGLV3-19*01 F | Homsap IGLJ2*01 F, or Homsap IGLJ3*01 F | |
| Muc1-R3-T3-H3 | productive | Homsap IGLV3-19*01 F | Homsap IGLJ2*01 F, or Homsap IGLJ3*01 F | |
| Muc1-R3-T4-D5 | productive | Homsap IGLV2-18*02 F | Homsap IGLJ3*02 F | |
| Muc1-R3-T3-B9 | productive | Homsap IGLV2-18*02 F | Homsap IGLJ3*02 F | |
| Muc1-R3-E4-G10 | productive | Homsap IGKV3-20*01 F | Homsap IGKJ1*01 F | |
| Muc1-R3-T2-A3 | productive | Homsap IGLV6-57*01 F | Homsap IGLJ2*01 F, or Homsap IGLJ3*01 F | |
| Muc1-R3-T3-B6 | productive | Homsap IGLV2-18*02 F | Homsap IGLJ3*02 F | |
| Muc1-R3-T4-E8 | productive | Homsap IGLV3-21*02 F | Homsap IGLJ2*01 F, or Homsap IGLJ3*01 F, or Homsap IGLJ3*02 F | |
| Muc1-R3-E4-E1 | productive | Homsap IGLV6-57*01 F, or Homsap IGLV6-57*02 F | Homsap IGLJ1*01 F | |

FIG. 51(A) CONT

| | |
|---|---|
| SSELTQDPA.VSVALGQTVRITCQGD | SLR.....SYY |
| SSELTQDPA.VSVALGQTVRITCRGD | SLR.....SYY |
| ETTLTQSPATLSVSPGERATLSCRAS | QSV.....GSN |
| SSELTQDPA.VSVALGQTVRITCQGD | SLR.....RYY |
| SSELTQDPA.VSVALGQTVRITCQGD | SLR.....RYY |
| QSALTQPPS.VSGSPGQSVTISCTGT | SSDVG..GYNR |
| QSALTQPPS.VSGSPGQSVTISCTGT | SSDVG..GYNR |
| ETTLTQSSAAQWVSPGERATLSCRAS | QSV.....RRN |
| NFMLTQPHS.VSESPGKTVTISCTRS | SGSI....ANNY |
| QSALTQPPS.VSGSPGQSVTISCTGT | SSDVG..GYNR |
| SYELTQPPS.VSVAPGQTARITCGAN | NIG.....SKS |
| NFMLTQPHS.VSESPGKTVIISCTRS | SGSI....ANHR |

FIG. 51(A) CON'T

| FR2-IMGT | CDR2-IMGT | FR3-IMGT | CDR3-IMGT | FR4-IMGT |
|---|---|---|---|---|
| MHWVRQAPGKGLEWVSG | ISWN..SGSI | GYADSVK.GRFTISRDNAKNSLYLQMNSLRAEDTALYYC | AKDIGSGSYYNYYYGMDV | WGQGTTVTVSS |
| MHWVRQAPGKGLEWVSG | ISWN..SGSI | GYADSVK.GRFTISRDNAKNSLYLQMNSLRAEDTALYYC | AKDISSGWYPDAFDI | WGQGTLVTVSS |
| MHWVRQAPGKGLEWVSG | ISWN..SGSI | GYADSVK.GRFTISRDNAKNSLYLQMNSLRAEDTALYYC | AKDMGSGYDWYYYGMDV | WGQGTTVTVSS |
| INWVRQAPGQGPEWMGW | ISGY..NGNT | KYAQKVQ.GRVIMTTDTSTTTAYMELRSLTSDDYAVYYC | ARDGVGAAFDY | WGQGTLVTVSS |
| ISWVRQAPGQGLEWMGW | ISAY..NGNT | NYAQKVQ.GRVTMPTDTFTSTAYMELRSLRSDDTAVYYC | ARDPHLSSGWCKGNGMDV | WGQGTLVSVSS |
| ISWVRQAPGQGLEWMGW | ISAY..NGNT | NAYQKVQ.GRVTMTTDTSTSTAYMELRSLRSDDTAVYYC | ARDPHVSSGWYKGNGMDV | WGQGTLVTVSS |
| INWVRQATGHGLEWMGR | MNPN..SGNT | GYAEKFQ.GRVIMTSDTSIDTAYMDLSSLRSEDTAVYYC | AREIRGAFDI | WGQGTMVTVSS |
| INWVGQDTGHGLEWMGR | MNPY..SGNT | GYAEKFQ.GRVIMTSDTSIDTAYMDLSSLRYEDTAVYYC | AREIRGAFDM | WGQGPMVTVSS |
| MHWVRQAPGKSLEWVSG | ISWN..SNNI | GYAEYVK.GRFTISRETAKNSLYMQMNSLRAEDTAVYYC | ARVSPGYYDSSGQGSDAFDI | WGQGTTVAVSS |
| MHWVRQAPGKGLEWVAV | ISYD..GSNK | YYADSVK.GRFTISRDNSKNTLYQMNSLRVEDTAMYYC | ASGNPYYSYAMDV | WGQGTMVTVSS |
| INWVGQATGHGLEWMER | MNPN..SGNT | GYAEKLQ.GRVIMTSASSIDTAYMYVSSLRYEGAAVYYC | GREMCGGFDM | WVQGPMVTVSS |
| MNWVRQAPGKGLEWVST | ISGS..GTRT | YYADSVK.GRFTISRDNTRDLYLQMNRLRAEDTAIYYC | VKGEEGPYYYYYGLDV | WGQGTTVTVSS |
| MSWVRQAPVKGLEWVAN | IKQD..GSEK | YFVDSVK.GRFTISRDNAKKSLYQMNNLRAEDTAVYYC | VREFVGAYDI | WGQGTMVTVSS |

| FR2-IMGT | CDR2-IMGT | FR3-IMGT | CDR3-IMGT | FR4-IMGT |
|---|---|---|---|---|
| ASWYQQKPGQAPVLVIY | GK.......N | SRPSGIP.DRFSGSN..SGSTASLTITGAQAEDEADYYC | NSRDRYGNPLVI | FGGGTKLTVL |
| ASWYQQKPGQAPVLVIY | GK.......N | NRPSGIP.DRFSGSN..SGNTASLTITGAQAEDEADYYC | NSRDFSGLQLV | FGGGTRLTVL |

FIG. 51(B)

| | | | | |
|---|---|---|---|---|
| ASWYQQKPGQAPVLVIY | GK......N | NRPSGIP.DRFSGSS..SGNTASLTITGAQAEDEADYYC | NSRDSSGNHLV | FGGGTKLTVL |
| LAWYQQKPGQAPRLLIY | GA......S | TRATGIP.ARFSGSG..SGTEFTLTISSLEPEDFAVYYC | QQRSNWPPT | FGQGTKVESK |
| ASWYQQKPGQAPVLVFY | GK......N | SRPSGIP.DRISGSS..SGNTASLTITGGQAEDEADYYC | NSRDSSGNPVV | FGGGTKLTVL |
| ASWYQQKPGQAPVLVFY | GK......N | TRPSGIP.DRIFGSS..SGNTASLTITGAQAEDEADYYC | NSRDSSGNPVV | FGGGTKLTVL |
| VSWYQQPPGTAPKLMIH | DV......S | SRPSGVP.DRFSGSK..SGNTASLTISGLQADDEADYYC | SSYTSSSPRV | FGGGTKLTVL |
| VSWYQQPPGTAPKLMIH | DV......S | SRPSGVP.DRFSGSK..SGNTASLTIWGLQEDEEADYCC | SSYTSSSPRV | FGGGTKLTVL |
| VAWYQQKPGQAPRLLIY | GA......S | FRASGVP.DRFSGSG..SGTDFTLTITSLEPEDFAVYYC | QQYGSSPRT | FGQGTKVEIK |
| VQWYQQRPGSSPTTVIY | ED......N | QRPSGVP.DRFSGSIDSSSNSASLTISGLKTEDEADYYC | QSYDSINHHVV | FGGGTKLTVL |
| VSWYQQPPGTAPKLMIQ | KV......S | SRPSGVP.DRFSGSK..SGNTASLIIWGLQEDEEADYCC | SSYTSSSPRV | FGGGTKLTVL |
| VHWYQQKPGQAPVLVVY | DD......S | DRPSGIP.ERFSGSN..SGNTATLTISRVEAGDEADYYC | QVWDSSTDHQV | FGGGTKLTVL |
| VQWLQQRPGSAPLTVIY | EE......N | RRPSGVP.DRFSGSIDTSSNSASLTISGLKPEDEADYYC | QSLDGVTHYV | FGSGAKVTVL |

*FIG. 51(B) CON'T*

| Sequence ID | V-DOMAIN Functionality | V-GENE and allele | J-GENE and allele | D-GENE and allele |
|---|---|---|---|---|
| Muc1-R3-T4-D1 | productive | Homsap IGHV3-9*01 F | Homsap IGHJ6*02 F | Homsap IGHD3-10*01 F |
| Muc1-R3-T2-B1 | productive | Homsap IGHV3-9*01 F | Homsap IGHJ3*02 F | Homsap IGHD6-19*01 F |
| Muc1-R3-T4-B5 | productive | Homsap IGHV3-9*01 F | Homsap IGHJ6*02 F | Homsap IGHD5-12*01 F |
| Muc1-R3-E4-B12 | productive | Homsap IGHV1-18*04 F | Homsap IGHJ4*02 F | Homsap IGHD1-26*01 F |
| Muc1-R3-T3-H9 | productive | Homsap IGHV1-18*01 F | Homsap IGHJ6*02 F | Homsap IGHD6-19*01 F |
| Muc1-R3-T3-H3 | productive | Homsap IGHV1-18*01 F | Homsap IGHJ6*02 F | Homsap IGHD6-19*01 F |
| Muc1-R3-T4-D5 | productive | Homsap IGHV1-8*01 F | Homsap IGHJ3*02 F | Homsap IGHD1-7*01 F |
| Muc1-R3-T3-B9 | productive | Homsap IGHV1-8*01 F | Homsap IGHJ3*02 F | Homsap IGHD1-7*01 F |
| Muc1-R3-E4-G10 | productive | Homsap IGHV3-9*02 F | Homsap IGHJ3*02 F | Homsap IGHD3-22*01 F |
| Muc1-R3-T2-A3 | productive | Homsap IGHV3-30*03 F, or Homsap IGHV3-30*18 F or Homsap IGHV3-30-5*01 F or Homsap IGHV3-33*05 F | Homsap IGHJ3*01 F | Homsap IGHD2-15*01 F |
| Muc1-R3-T3-B6 | productive | Homsap IGHV1-8*01 F | Homsap IGHJ3*02 F | Homsap IGHD3-22*01 F |
| Muc1-R3-T4-E8 | productive | Homsap IGHV3-23*01 F, or Homsap IGHV3-23*04 F or Homsap IGHV3-23D*01 F | Homsap IGHJ6*02 F | Homsap IGHD1-26*01 F |
| Muc1-R3-E4-E1 | productive | Homsap IGHV3-7*03 F | Homsap IGHJ3*02 F | Homsap IGHD3-16*01 F |

| Sequence ID | V-DOMAIN Functionality | V-GENE and allele | J-GENE and allele | |
|---|---|---|---|---|
| Muc1-R3-T4-D1 | productive | Homsap IGLV3-19*01 F | Homsap IGLJ2*01 F, or Homsap IGLJ3*01 F | |

TO FIG 52(B)

FIG. 52(A)

| | | | | |
|---|---|---|---|---|
| Muc1-R3-T2-B1 | productive | Homsap IGLV3-19*01 F | Homsap IGLJ2*01 F, or Homsap IGLJ3*01 F | |
| Muc1-R3-T4-B5 | productive | Homsap IGLV3-19*01 F | Homsap IGLJ3*02 F | |
| Muc1-R3-E4-B12 | productive | Homsap IGKV3-11*01 F, or Homsap IGKV3-15*01 F or Homsap IGKV3D-11*02 F | Homsap IGKJ1*01 F | |
| Muc1-R3-T3-H9 | productive | Homsap IGLV3-19*01 F | Homsap IGLJ2*01 F, or Homsap IGLJ3*01 F | |
| Muc1-R3-T3-H3 | productive | Homsap IGLV3-19*01 F | Homsap IGLJ2*01 F, or Homsap IGLJ3*01 F | |
| Muc1-R3-T4-D5 | productive | Homsap IGLV2-18*02 F | Homsap IGLJ3*02 F | |
| Muc1-R3-T3-B9 | productive | Homsap IGLV2-18*02 F | Homsap IGLJ3*02 F | |
| Muc1-R3-E4-G10 | productive | Homsap IGKV3-20*01 F | Homsap IGKJ1*01 F | |
| Muc1-R3-T2-A3 | productive | Homsap IGLV6-57*01 F | Homsap IGLJ2*01 F, or Homsap IGLJ3*01 F | |
| Muc1-R3-T3-B6 | productive | Homsap IGLV2-18*02 F | Homsap IGLJ3*02 F | |
| Muc1-R3-T4-E8 | productive | Homsap IGLV3-21*02 F | Homsap IGLJ2*01 F, or Homsap IGLJ3*01 F, or Homsap IGLJ3*02 F | |
| Muc1-R3-E4-E1 | productive | Homsap IGLV6-57*01 F, or Homsap IGLV6-57*02 F | Homsap IGLJ1*01 F | |

FIG. 52(A) CON'T

| FR1-IMGT | CDR1-IMGT |
|---|---|
| caggtgcagctggtgcagtctgggga...ggcttggtccagcctggggggtccctgagactctcctgtgcagcctct | ggattcaccttt............gatgattatgcc |
| caggtgcagctggtgcagtctgggga...ggcttggtacagcctggcaggtccctgagactctcctgtgcagcctct | ggattcaccttt............gatgattatgcc |
| caggtgcagctggtgcagtctgggga...ggcttggtacagcctggcaggtccctgagactctcctgtgcagcctct | ggattcaccttt............gatgattatgcc |
| caggtgcagctggtgcagtctggagcc...gaggtgaagaggcccggggcctcagtgaaggtctcctgcaaggcttct | ggttacactttt............agcacctacgct |
| caggagcagctggtgcagtctggagct...gaggtgaagaagcctggggcctcagtgaaggtctcctgcaaggcttct | ggttacaccttt............accagctatggt |
| caggtgcagttggtgcagtttggaggt...gaggtgaagaagcctggggcctcagtgaaggtctcctgcacagcttct | ggttacacctat............accagctatggt |
| gaggtgcagctggtgcagtctggggct...gaggtgaagaagcctgggtcctcagtgaaggtctcctgcaaggcttct | ggatacaccttc............tccaattatgat |
| gatgtgcagctggtgcagtctgggggt...gaggcgaagaagcctgggtcctcagtgaaggtctcctgcaaggcttct | ggatacaccttc............tgcaattatgat |
| cagctgcagctggtgcagtatgggga...ggattcgtacagcatggcaggtccttgaggctcttctgtgcagcatct | ggattcacctct............gatgattatgac |
| caggtgcagctggtgcagtctgggga...ggcgtggtccagcctgggaggtccctgagactctcctgtgcagcctct | ggattcaccttc............agtagctatggc |
| gaggtgcagctggtgcagtgtgggggt...gaggcgaagaagcctgggtcctcagtgaaggtctcctgcaaggcttct | ggatacaccatc............tccaattatgat |
| caggtgcagctgcaggagtcgggggga...ggcttggtacagcctggggggtccctgagactctcctgtgcagcgtct | ggactcagtttt............agtaagcatgcc |
| ccaggtgcgctggtgcaatctgggga...ggcttggtccagcctgggggtcctgagactctcctgtgcagcctct | ggattcacattt............agtgacaattgg |
| FR1-IMGT | CDR1-IMGT |
| | |

FIG. 52(B)

| FR2-IMGT |
|---|
| atgcactgggtccggcaagctccagggaagggcctggagtgggtctcaggt |
| atgcactgggtccggcaagctccagggaagggcctggagtgggtctcaggt |
| atgcactgggtccggcaagctccagggaagggcctggagtgggtctcaggt |
| atcaactgggtgcgacaggcccctggacaagggcctgagtggatgggatgg |
| atcagctgggtgcgacaggcccctggacaagggcttgagtggatgggatgg |
| atcagctgggtgcgacaggcccctggacaagggcttgagtggatgggatgg |
| atcaactgggtgcgacaggccactggacacgggcttgagtggatggggaga |
| atcaactgggtgggacaggacactggacacgggcttgagtggatggggaga |
| atgcactgggtccggcaagctccagggaagagcctggagtgggtgtcaggt |
| atgcactgggtccgccaggctccaggcaaggggctggagtgggtggcagtt |
| atcaactgggtgggacaggccactggacacgggcttgagtggatggagaga |
| atgaactgggtccgccaggctccagggaaggggctggagtgggtctcaact |
| atgagctgggtccgccaggctccagtgaaggggctggagtgggtggccaac |
| FR2-IMGT |

FIG. 52(B) CON'T

| FR1-IMGT | CDR1-IMGT |
|---|---|
| tcttctgagctgactcaggaccctgct...gtgtctgtggccttgggacagacagtcaggatcacatgccaaggagac | agcctcaga.................agctattat |
| tctttctgagctgactcaggaccctgct...gtgtctgtggccttgggacagacagtcaggatcacatgccaaggagac | agcctcaga.................agctattat |
| tctttctgagctgactcaggaccctgct...gtgtctgtggccttgggacagacagtcaggatcacatgccaaggagac | agcctcaga.................agctattat |
| gaaacgacactcacgcagtctccagccaccctgtctgtgtctccaggggaaaagagccaccctctcctgcagggccagt | cagagtgtt.................ggcagcaac |
| tctttctgagctgactcaggaccctgct...gtgtctgtggccttgggacagacagtcaggatcacatgccaaggagac | agcctcaga.................aggtattat |
| tctttctgagctgactcaggaccctgct...gtgtctgtggccttgggacagacagtcaggatcacatgccaaggagac | agcctcaga.................aggtattat |
| cagtctgccctgactcagcctccctcc...gtgtccgggtctcctggacagtcagtcaccatctcctgcactggaacc | agcagtgacgctggt.........ggtttataaccgt |
| cagtctgccctgactcagcctccctcc...gtgtccgggtctcctggacagtcagtcaccatctcctgcactggaacc | agcagtgacgttggt.........ggtttataaccgt |
| gaaacgacactcacgcagtcttcagccgcccagtgggtgtctccaggggaagggccaccctctcctgcagggccagt | cagagtgtt.................cgccgcaac |
| aattttatgctgactcagccccactct...gtgtcggagtctccgggaagacggtaaccatctcctgcacccgcagc | agtggcagcatt...........gccaacaactat |
| cagtctgccctgactcagcctccctcc...gtgtccgggtctcctggacagtcagtcaccatctcctgcactggaacc | agcagtgacgttggt.........ggttataaccgt |
| tcctatgagctgactcagccaccctcg...gtgtcagtggccccaggacagacggccaggattacctgtgggcaaac | aacattgga.................agtaaagt |
| aattttatgctgactcagccccactct...gtgtcggagtctccgggaagacggtaaccatctcctgcacccgcagc | agcggcagcatt...........gccaaccaccgt |

FIG. 52(B) CON'T

| |
|---|
| gcaagctggtaccagcagaagccaggacaggcccctgtacttgtcatctat |
| gcaagctggtaccagcagaagccaggacaggcccctgtacttgtcatctat |
| gcaagctggtaccagcagaagccaggacaggcccctgtacttgtcatttat |
| ttagcctggtaccagcaaaaacctggccaggctcccaggctcctcatctac |
| gcaagttggtaccagcagaagccaggacaggcccctgtacttgtcttctat |
| gcaagttggtaccagcagaagccaggacaggcccctgtacttgtcttctat |
| gtctcctggtaccaacagcccccggcacagcccccaaactcatgattcat |
| gtctcctggtaccaacagcccccggcacagcccccaaactcatgattcat |
| gtagcctggtaccagcagaaacctggccaggctcccaggct cctcatuat |
| gtgcagtggtaccagcagcgcccgggcagttcccccaccactgtgatctat |
| gtgtcctggtaccaacagcccccggcacagcccccaaactcatgattcag |
| gtgcactggtaccagcagaagccaggccaggcccctgtgctggtcgtctat |
| gtgcagtggctccagcagcgcccgggcagtgccccctcactgtgatctat |

FIG. 52(B) CON'T

| CDR2-IMGT | FR3-IMGT |
|---|---|
| attagttggaat......agtggtagcata | ggctatgcggactctgtgaag...ggccgattcaccatctccagagacaacgccaagaactccctgtatctgcaaatgaacagtctgagagctgaggacacggccttgtcttactgt |
| attagttggaat......agtggtagcata | ggctatgcggactctgtgaag...ggccgattcaccatctccagagacaacgccaagaactccctgtatctgcaaatgaacagtctgagagctgaggacacggccttgtattactgt |
| attagttggaat......agtggtagcata | ggctatgcggactctgtgaag...ggccgattcaccatctccagagacaacgccaagaactccctgtatctgcaaatgaacagtctgagagctgacgacacggcttgtattactgt |
| atcagcggttac......aatggtaacaca | aaatatgcacagaaggtccag...ggtagagtcatcatgaccacagacacatccacgaccacagcctactggagttgaggagcctgacatatgacgacacggccgtgtattactgt |
| atcagcgcttac......aatggtaacaca | aattatgcacagaaggtccag...ggcagagtcaccatgcccacagacagattcacgagcacagcctacatggagctgaggagcctgagatctgacgacacggccgtgtattactgt |
| atcagcgcttac......aatggtaacaca | aactatgcacagaaggtccag...ggcagagtcaccatgaccacagacacatccacgagcacagcctacatggagctgaggagcctgagatctgacgacacggccgtgtattactgt |
| atcaatcctaac......agtggaaacaca | ggctatgcagagagagaagttccag...ggcagagtcatcatgaccagtgacacctccatagacacagcctacatggacctgagcagccttagatctgaggacacggccgtctattattgt |
| atgaatccttac......agtggaaacaca | ggctatgcagagaagttccag...ggcagagtcatcatgaccagtgacacctccatagacacgcctacatggacctgagcagccttagatatgaggacacggccgtctattattgt |
| attagttggaat......agtaataacata | gggtatgcggaatatgtgaag...ggccgattcaccatctccagagagacgcgaagaactccctgtatatgcaaatgaacagcctgagagccgaggacacggctgtgtattactgt |
| atacatatgat......ggaagtaataaa | tactatgcagactccgtgaag...ggccgattcaccatctccagagacaattccaagaacacgctgtatctgcaaatgaacagtctgagagtcgaggacacggctatgtattactgt |
| atgaatcctaac......agtggaaacaca | gggtatgcagagaagttgcag...ggcagagtcatcatgaccagtgcctcctccatagacacagcctacatgtacgtgagcagccttagatatgagggcgcggcggccgttattattgt |
| atcagtggcagt......ggtactagaaca | tactacgcagactccgtgaag...ggccggttcaccatctccagagacaataccagggacaccctctcatctgcaaatgaacagactgagagccgaagacacggccatatattactgt |
| ataaagcaagat......ggaagtgagaaa | tactttgtggactctgtgaag...ggccgattcaccatttccagagacaacgccaagaagtcactgtatctgcagatgaacaacctgagagccgaagacacggccgtgtattactgt |

| CDR2-IMGT | FR3-IMGT |
|---|---|
| ggtaaa.....................aat | agccggccctcggggatccca...gaccgattctctggctccaac......tcaggaagcacagcttccttgaccatcactggggctcaggcggaagatgaggctgactattactgt |

FIG. 52(C)

| | |
|---|---|
| ggtaaa.....................aac | aaccggccctcagggatccca...gaccgattctctggctccaac......tcaggaaacacagcttccttgaccatcactggggctcaggcggaagatgaggctgactattactgt |
| ggtaaa.....................aac | aaccggccctcagggatccca..gaccgattctctggctccagc......tcaggaaacacgcttccttgaccatcactggggctcaggcggaagatgaggctgactattagtct |
| ggtgca.....................tcc | accagggccactggtatccca...gccaggttcagtggcagtggg......tctgggacagaattcactctcaccatcagcagcctagagcctgaagattttgcagtttattactgt |
| ggggaa.....................aac | agtcggccctcagggatccca...gaccgaatctctggctccagc......tctggaaacacagcttccttgaccatcactggggtcaggcaggaagatgaggctgactattattgt |
| gggaaa.....................aac | acgcggccctcagggatccca...gaccgaatctttggctccagc......tctggaaacacagcttccttgaccatcactggggctcaggcggaagatgaggctgactattattgt |
| gacgtc.....................agt | agtcggccctcaggggtccct...gatcgcttctctgggtccaag......tctggcaacacggcctccctgaccatctctgggctccaggctgaccacgaggctgattattactgc |
| gcagtc.....................agt | agtcggccctcaggggtccct...gatcgcttctctgggtccaag......tctggcaacacggcctccctgaccatctggggctcaggaagacgaggaggctgattgttgc |
| ggtgca.....................tcc | ttcagggcctctggcgtccca...gacaggttcagtggaagtggg......tctgggacagacttcactctcaccatcaccagcctggcctgaagattttgcagtgtattactgt |
| gaggat.....................aac | caaagaccctctggggtccct...gatcggttctctggctccatcgacagctcctccaactctgcctccctcaccatctctggactgaagactgaggacgaggctgactactactgt |
| aaagtc.....................agt | agtcggccctcaggggtccct...gatcgcttctctgggtccaag......tctggcaacacggcctccctgatcatctggggctccaggaagacgaggaggctgattattgttgc |
| gatgat.....................agc | gaccggccctcagggatccct...gagcgattctctggctccaac......tctgggaacacggccaccctgaccatcagcaggtcgaagccggggatgaggccgactattactgt |
| gaggaa.....................aac | cgaagaccctctggggtccct...gatcggttctctggctccatcgacacgtcctccaactctgcctccctcaccatctctggactgaagcctgaggacgaggctgactactactgt |

FIG. 52(C) CON'T

| CDR3-IMGT | FR4-IMGT |
|---|---|
| gcaaaagatatcggttcagggagttattataactactactactacggtatggacgtc | tggggccaggggaccacggtcaccgtctcctca |
| gcaaaagatattagcagtggctggtaccctgatgcttttgatatc | tggggccaagggcaccctggtcaccgtctcctcag |
| gcaaaagatatgggaagtggctacgattggtactactacggtatggacgtc | tggggccaagggaccacggtcaccgtctcctca |
| gcgagagatggagtgggagctgcctttgactac | tggggccagggaaccctggtcaccgtctcctcag |
| gcgagagatccgcatcttagcagtggctggtgcaagggaaacggtatggacgtc | tggggccaaggaaccctggtctccgtctcctca |
| gcgagagatccgcatgttagcagtggctggtacaagggaaacggtatggacgtc | tggggccaaggaaccctggtcaccgtctcctca |
| gcgagggaaatacgtggtgcttttgatatc | tggggccaagggacaatggtcaccgtctcttcag |
| gcgagggaaatacgtggtgcttttgatatg | tggggccaagggccaatggtcaccgtctcttcag |
| gcgagagttagtccgggttactatgatagtagtggccaagggagtgatgcttttgatatc | tggggccaagggaccacggtcgccgtctcctcag |
| gcaagtggtaacccatactactcttatgctatggacgtc | tggggccaagggacaatggtcaccgtctcttcag |
| gggagggaaatgtgtggtggttttgatatg | tgggtccaagggccaatggtcaccgtctcttcag |
| gtaaaaggagaagagggaccttactactactactacggtttggacgtc | tggggccaagggaccacggtcaccgtctcctca |
| gtgcgcgagtttgtcggtgcttatgatatc | tggggccaagggacaatggtcaccgtctcttcag |

| CDR3-IMGT | FR4-IMGT |
|---|---|
| aactcccgggacaggtatggtaatccccttgtgata | ttcggcggagggaccaagctgaccgtcctag |

FIG. 52(D)

| | |
|---|---|
| aactcccgggacttcagtggtcttcagctggta | ttcggcggagggaccagactgaccgtcctgg |
| aactcccgggacagcagtggtaaccatctggtg | ttcggcggagggaccaagctgaccgtcctag |
| cagcagcgtagcaactggcctccgacg | ttcggccaagggaccaaggtggagagcaaac |
| aactcccgggacagcagtggtaaccctgtggta | ttcggcggagggaccaagctgaccgtcctag |
| aactcccgggacagcagtggtaaccctgtggta | ttcggcggagggaccaagctgaccgtcctag |
| agctcatatacaagcagcagccctcgggtg | ttcggcggagggaccaagctgaccgtcctag |
| agctcatatacaagcagcagccctcgggtg | ttcggcggagggaccaagctgaccgtcctag |
| cagcagtatggtagctcacctcggacg | ttcggccaagggaccaaggtggaaatcaaac |
| cagtcttatgatagcatcaatcatcatgtggtt | ttcggcggagggaccaagctgaccgtcctag |
| agctcatacacaagcagcagccctcgggtg | ttcggcggagggaccaagctgaccgtcctag |
| caggtgtgggatagtagtactgatcatcaggtt | ttcggcggagggaccaagctgaccgtcctag |
| cagtctttgga tggcg tea ctcatt atgtc | ttaggaagtggggccaaggtcaccgtcctag |

FIG. 52(D) con't

| Sequence ID | V-DOMAIN Functionality | V-GENE and allele | J-GENE and allele |
|---|---|---|---|
| Muc1-R3-E2-D12-PelB.ab1 | productive | Homsap IGHV1-18*01 F | Homsap IGHJ6*02 F |
| Muc1-R3-E2-F8-PelB.ab1 | unproductive | Homsap IGHV3-9*01 F | Homsap IGHJ3*02 F |
| Muc1-R3-E2-F11-PelB.ab1 | productive | Homsap IGHV1-18*01 F | Homsap IGHJ3*02 F |
| Muc1-R3-E2-B4-PelB.ab1 | productive | Homsap IGHV3-9*01 F | Homsap IGHJ3*02 F |
| Muc1-R3-E2-B2-PelB.ab1 | productive | Homsap IGHV1-18*04 F | Homsap IGHJ4*02 F |
| Muc1-R3-T1-F11-PelB.ab1 | productive | Homsap IGHV3-9*01 F | Homsap IGHJ3*02 F |
| Muc1-R3-T1-H8-PelB.ab1 | productive | Homsap IGHV1-18*01 F | Homsap IGHJ3*02 F |

| Sequence ID | V-DOMAIN Functionality | V-GENE and allele | J-GENE and allele |
|---|---|---|---|
| Muc1-R3-E2-D12-PelB.ab1 | productive | Homsap IGLV3-19*01 F | Homsap IGLJ2*01 F |
| Muc1-R3-E2-F8-PelB.ab1 | productive | Homsap IGLV10-54*01 F | Homsap IGLJ3*02 F |
| Muc1-R3-E2-F11-PelB.ab1 | productive | Homsap IGLV2-18*02 F | Homsap IGLJ3*02 F |
| Muc1-R3-E2-B4-PelB.ab1 | productive | Homsap IGLV3-20*01 F | Homsap IGKJ1*01 F |
| Muc1-R3-E2-B2-PelB.ab1 | productive | Homsap IGKV3-11*01 F, oe Homsap IGKV3-15*01 F or Homsap IGKV3D-11*02 F | Homspa IGKJ1*01 F |
| Muc1-R3-T1-F11-PelB.ab1 | unproductive | Homsap IGKV3-20*02 F | Homsap IGKJ1*01 F |
| Muc1-R3-T1-H8-PelB.ab1 | productive | Homsap IGLV2-14*01 F | Homsap IGLJ3*02 F |

FIG. 53(A)

| D-GENE and allele | FR1-IMGT | CDR1-IMGT | FR2-IMGT |
|---|---|---|---|
| Homsap IGHD6-19*01F | QVQLVQSGA.EVKKPGASVKVSCKAS | GYTF....TSYG | ISWVRQAPGQGLEWMGW |
| Homsap IGHD3-22*01F | QVQLVQSGG.GLVQPGRSLRLSCAAS | GFTF....DDYA | MHWVRQAPGKGLEWVSG |
| Homsap IGHD1-7*01 F | EVQLVQSGA.EVKKPGSSVKVSCKAS | GYTF....SNYD | INWVRQATGHGLEWMGR |
| Homsap IGHD3-22*01 F | QVQLVQSGG.GFVQPGRSLRLSCAAS | GFTF....DDYA | MHWVRQAPGKGLEWVSG |
| Homsap IGHD1-26*01 F | QVQLVQSGA.EVKRPGASVKVSCKAS | GYTF....STYA | INWVRQAPGQGFEWMGW |
| Homsap IGHD3-22*01 F | QVQLVQSGG.GFIQPGXSLXLSCAAS | GFTF....DDYA | MHWVRQAPGKGLEWVSC |
| Homsap IGHD5-12*01 F | QVQLVQSGA.EVKKPGASVKVSCKAS | GYTF....TSYG | ISWVRQAPGQGLEWMGW |
| | FR1-IMGT | CDR1-IMGT | FR2-IMGT |
| | SSELTQDPA.VSVALGQTVRITCQGD | SLR......RYY | ASWYQQKPGQAPVLVFY |
| | SYELTQPPS.VSKGLRQTATLTCSGN | SNNV....GHEG | AAWLQQHQGHPPKLLSY |
| | QSALTQPPS.VSGSPGQSVTISCTGT | SSDVG...GYNR | VSWYQQPPGTAPKLMIH |
| | ETTLTQSPATLSVSPGERATLSCRAS | QSV......RRN | VAWYQQKPGQAPRLLIY |
| | ETTLTQSPATLSVSPGERATLSCRAS | QSV......GSN | LAWYQQKPGQAPRLLIY |
| | KTTLTQSPATLSVSPGERATLSCXAX | XIV......RRN | VX*YQXKPGQAPSLLIY |
| | QSALTQPAS.VSGSPGQSITISCTGT | SSDFG...GYNY | VSWYQQHPGKAPKLMIY |

FIG. 53(B)

| CDR2-IMGT | FR3-IMGT | CDR3-IMGT | FR4-IMGT |
|---|---|---|---|
| ISAY..NGNT | NYAQKVQ.GRVTMTTDTSTSTAYMELRSLRSDDTAVYYC | ARDPHLSSGWYKGNGMDV | WGQGTLVTVSS |
| IS*N..SGSI | GYADSVK.GRFTISRDNTKNLLYLQMNSLRVEDTAVYYC | ARDGGYCDSTGCYDALDI | WGQGTTVTVSS |
| MNPN..SGNT | GYAEKFQ.GRVIMTSDTSIDTAYMDLSSLRSEDTAVYYC | AREIRGAFDI | WGQGTMVTVSS |
| ISWN..SNNI | GYADSVK.GRFTISRENAKNSLYLQMNSLRAEDTAVYYC | ARVSPGYYDSSGQGTDAFDI | WGQGTTVTVSS |
| ISGY..NGNT | KYAQKVQ.GRVIMTTDTSTTTAYMELRSLTSDDTAVYYC | ARDGVGAAFDY | WGQGTLVTVSS |
| ISWN..XNNI | GYADSVK.GQFTISRKNAKNSLYLQMNSLKAEDTAVYYC | AKVSPGYYDSSQGTDAFDI | WGQGTTVTVSS |
| ISTY..NGNT | KYAQKLQ.GRVTMTTDTSTSTAYMELRSLRSDDTAVYYC | ARDRATIDAFDI | WGQGTTVTVSS |

| CDR2-IMGT | FR3-IMGT | CDR3-IMGT | FR4-IMGT |
|---|---|---|---|
| GK.......N | TRPSGIP.DRISGSS..SGNTASLTITGAQAEDEADYYC | NSRDSSGNPVV | FGGGTKLTVL |
| RN.......N | NRPSGIS.ERFSASR..SGNTASLTITGLQPEDEADYYC | ATWDGSLRGWV | FGGGSKLTVL |
| DV.......S | SRPSGVP.DRFSGSK..SGNTASLTISGLQADDEADYYC | SSYTSSSTRV | FGGGTKLTVL |
| GA.......S | FRAAGVP.DRFSGSG..SGTDFTLTITRLEPEDFAVYYC | QQYGSSPRT | FGQGTKVEIK |
| GA.......S | TRATGIP.ARFSGSG..SGTEFTLTISSLEPEDFAVYYC | QQRSNWPPT | FGQGTKVESK |
| GA.......S | FXAAXVS.HXXSXSG..SGTYFSLTITXLXPXILQCITV | XSMVXHLX | FGXXTXVEIX |
| DV.......S | NRPSGIS.NRFSGSK..SGNTASLTITGLQSEDEADYYC | SGWDRSLSAWV | VGGXTKLTVL |

FIG. 53(C)

SEQUENCE LISTING

```
<160> NUMBER OF SEQ ID NOS: 177

<210> SEQ ID NO 1
<211> LENGTH: 158
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Met Gly Ser Ser His His His His His His Ser Ser Gly Leu Val Pro
1               5                   10                  15

Arg Gly Ser His Met Ala Ser Met Thr Gly Gly Gln Gln Met Gly Arg
            20                  25                  30

Asp Pro Leu Ser Thr Gly Val Ser Phe Phe Phe Leu Ser Phe His Ile
        35                  40                  45

Ser Asn Leu Gln Phe Asn Ser Ser Leu Glu Asp Pro Ser Thr Asp Tyr
    50                  55                  60

Tyr Gln Glu Leu Gln Arg Asp Ile Ser Glu Met Phe Leu Gln Ile Tyr
65                  70                  75                  80

Lys Gln Gly Gly Phe Leu Gly Leu Ser Asn Ile Lys Phe Arg Pro Gly
                85                  90                  95

Gly Gly Gly Gly Ser Val Val Val Gln Leu Thr Leu Ala Phe Arg Glu
            100                 105                 110

Gly Thr Ile Asn Val His Asp Val Glu Thr Gln Phe Asn Gln Tyr Lys
        115                 120                 125

Thr Glu Ala Ala Ser Arg Tyr Asn Leu Thr Ile Ser Asp Val Ser Val
    130                 135                 140

Ser Asp Val Pro Phe Pro Phe Ser Ala Gln Ser Gly Ala Gly
145                 150                 155


<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence: Synthetic
```

peptide

<400> SEQUENCE: 2

Gly Phe Thr Phe Asp Asp Tyr Ala
1 5

<210> SEQ ID NO 3

<400> SEQUENCE: 3

000

<210> SEQ ID NO 4

<400> SEQUENCE: 4

000

<210> SEQ ID NO 5

<400> SEQUENCE: 5

000

<210> SEQ ID NO 6
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 6

Gly Tyr Thr Phe Thr Ser Tyr Gly
1 5

<210> SEQ ID NO 7
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 7

Ser Leu Arg Ser Tyr Tyr
1 5

<210> SEQ ID NO 8

<400> SEQUENCE: 8

000

<210> SEQ ID NO 9
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 9

Gln Ser Val Arg Arg Asn
1 5

<210> SEQ ID NO 10

<400> SEQUENCE: 10

000

<210> SEQ ID NO 11
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 11

```
Ser Leu Arg Arg Tyr Tyr
1               5
```

<210> SEQ ID NO 12
<211> LENGTH: 125
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 12

```
Gln Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Ile Gly Ser Gly Ser Tyr Tyr Asn Tyr Tyr Tyr Gly Met
            100                 105                 110

Asp Val Trp Gly Gln Gly Thr Thr Ala Thr Ile Ser Ser
        115                 120                 125
```

<210> SEQ ID NO 13
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 13

```
Gln Val Gln Leu Val Gln Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80
```

```
Leu Gln Met Asn Ser Leu Arg Ala Glu Asp Thr Ala Leu Tyr Tyr Cys
                85                  90                  95

Ala Lys Asp Met Gly Ser Gly Tyr Asp Trp Tyr Tyr Tyr Gly Met Asp
            100                 105                 110

Val Trp Gly Gln Gly Thr Thr Val Thr Val Ser Ser
        115                 120


<210> SEQ ID NO 14
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Gln Val Gln Leu Val Gln Ser Gly Gly Gly Phe Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Asn Asn Ile Gly Tyr Ala Asp Ser Val
    50                  55                  60

Lys Gly Arg Phe Thr Ile Ser Arg Glu Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Val Ser Pro Gly Tyr Tyr Asp Ser Ser Gly Gln Gly Thr Asp
            100                 105                 110

Ala Phe Asp Ile Trp Gly Gln Gly Thr Thr Val Thr Val Ser Ser
        115                 120                 125


<210> SEQ ID NO 15
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Gln Val Gln Leu Val Gln Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Ile Ser Ser Gly Trp Tyr Pro Asp Ala Phe Asp Ile Trp
            100                 105                 110

Gly Gln Gly Thr Leu Val Thr Val Ser Ser
        115                 120
```

<210> SEQ ID NO 16
<211> LENGTH: 125
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 16

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Ser Tyr
20 25 30

Gly Ile Ser Trp Val Arg Gln Ala Pro Gly Gln Gly Leu Glu Trp Met
35 40 45

Gly Trp Ile Ser Ala Tyr Asn Gly Asn Thr Asn Tyr Ala Gln Lys Val
50 55 60

Gln Gly Arg Val Thr Met Thr Thr Asp Thr Ser Thr Ser Thr Ala Tyr
65 70 75 80

Met Glu Leu Arg Ser Leu Arg Ser Asp Asp Thr Ala Val Tyr Tyr Cys
85 90 95

Ala Arg Asp Pro His Leu Ser Ser Gly Trp Tyr Lys Gly Asn Gly Met
100 105 110

Asp Val Trp Gly Gln Gly Thr Leu Val Thr Val Ser Ser
115 120 125

<210> SEQ ID NO 17
<211> LENGTH: 109
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 17

Ser Ser Glu Leu Thr Gln Asp Pro Ala Val Ser Val Ala Leu Gly Gln
1 5 10 15

Thr Val Arg Ile Thr Cys Gln Gly Asp Ser Leu Arg Ser Tyr Tyr Ala
20 25 30

Ser Trp Tyr Gln Gln Lys Pro Gly Gln Ala Pro Val Leu Val Ile Tyr
35 40 45

Gly Lys Asn Ser Arg Pro Ser Gly Ile Pro Asp Arg Phe Ser Gly Ser
50 55 60

Asn Ser Gly Ser Thr Ala Ser Leu Thr Ile Thr Gly Ala Gln Ala Glu
65 70 75 80

Asp Glu Ala Asp Tyr Tyr Cys Asn Ser Arg Asp Arg Tyr Gly Asn Ser
85 90 95

Leu Val Ile Phe Gly Gly Gly Thr Lys Leu Thr Val Leu
100 105

<210> SEQ ID NO 18
<211> LENGTH: 108
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 18

```
Ser Ser Glu Leu Thr Gln Asp Pro Ala Val Ser Val Ala Leu Gly Gln
1               5                   10                  15

Thr Val Arg Ile Thr Cys Arg Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn His
                85                  90                  95

Leu Val Phe Gly Gly Gly Thr Lys Leu Thr Val Leu
            100                 105


<210> SEQ ID NO 19
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Glu Thr Thr Leu Thr Gln Ser Pro Ala Thr Leu Ser Val Ser Pro Gly
1               5                   10                  15

Glu Arg Ala Thr Leu Ser Cys Arg Ala Ser Gln Ser Val Arg Arg Asn
            20                  25                  30

Val Ala Trp Tyr Gln Gln Lys Pro Gly Gln Ala Pro Arg Leu Leu Ile
        35                  40                  45

Tyr Gly Ala Ser Phe Arg Ala Ala Gly Val Pro Asp Arg Phe Ser Gly
    50                  55                  60

Ser Gly Ser Gly Thr Asp Phe Thr Leu Thr Ile Thr Arg Leu Glu Pro
65                  70                  75                  80

Glu Asp Phe Ala Val Tyr Tyr Cys Gln Gln Tyr Gly Ser Ser Pro Arg
                85                  90                  95

Thr Phe Gly Gln Gly Thr Lys Val Glu Ile Lys
            100                 105


<210> SEQ ID NO 20
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Asn Ser Gly Asn Thr Ala Ser Leu Thr Ile Thr Gly Ala Gln Ala Glu
65                  70                  75                  80
```

Asp Glu Ala Asp Tyr Tyr Cys Asn Ser Arg Asp Phe Ser Gly Leu Gln
85 90 95

Leu Val Phe Gly Gly Gly Thr Arg Leu Thr Val Leu
100 105

<210> SEQ ID NO 21
<211> LENGTH: 108
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 21

Ser Ser Glu Leu Thr Gln Asp Pro Ala Val Ser Val Ala Leu Gly Gln
1 5 10 15

Thr Val Arg Ile Thr Cys Gln Gly Asp Ser Leu Arg Arg Tyr Tyr Ala
20 25 30

Ser Trp Tyr Gln Gln Lys Pro Gly Gln Ala Pro Val Leu Val Phe Tyr
35 40 45

Gly Lys Asn Thr Arg Pro Ser Gly Ile Pro Asp Arg Ile Ser Gly Ser
50 55 60

Ser Ser Gly Asn Thr Ala Ser Leu Thr Ile Thr Gly Ala Gln Ala Glu
65 70 75 80

Asp Glu Ala Asp Tyr Tyr Cys Asn Ser Arg Asp Ser Ser Gly Asn Pro
85 90 95

Val Val Phe Gly Gly Gly Thr Lys Leu Thr Val Leu
100 105

<210> SEQ ID NO 22
<211> LENGTH: 477
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: modified_base
<222> LOCATION: (139)..(139)
<223> OTHER INFORMATION: a, c, t, g, unknown or other

<400> SEQUENCE: 22
atgggcagca gccatcatca tcatcatcac agcagcggcc tggtgccgcg cggcagccat 60
atggctagca tgactggtgg acagcaaatg ggtcgggatc cgttgtctac tggggtctct 120
ttctttttcc tgtcttttna catttcaaac ctccagttta attcctctct ggaagatccc 180
agcaccgact actaccaaga gctgcagaga gacatttctg aaatgttttt gcagatttat 240
aaacaagggg gttttctggg cctctccaat attaagttca ggccaggagg aggaggagga 300
tctgtggtgg tacaattgac tctggccttc cgagaaggta ccatcaatgt ccacgacgtg 360
gagacacagt tcaatcagta taaaacggaa gcagcctctc gatataacct gacgatctca 420
gacgtcagcg tgagtgatgt gccatttcct ttctctgccc agtctggggc tgggtaa 477

<210> SEQ ID NO 23
<211> LENGTH: 375
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 23

```
caggtgcagc tggtgcagtc tgggggaggc ttggtccagc ctggggggtc cctgagactc     60

tcctgtgcag cctctggatt cacctttgat gattatgcca tgcactgggt ccggcaagct    120

ccagggaagg gcctggagtg ggtctcaggt attagttgga atagtggtag cataggctat    180

gcggactctg tgaagggccg attcaccatc tccagagaca acgccaagaa ctccctgtat    240

ctgcaaatga acagtctgag agctgaggac acggccttgt attactgtgc aaaagatatc    300

ggttcaggga gttattataa ctactactac ggtatggacg tctggggcca ggggaccacg    360

gccaccatct cctca                                                     375
```

```
<210> SEQ ID NO 24
<211> LENGTH: 372
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 24

caggtgcagc tggtgcagtc tgggggaggc ttggtacagc ctggcaggtc cctgagactc     60

tcctgtgcag cctctggatt cacctttgat gattatgcca tgcactgggt ccggcaagct    120

ccagggaagg gcctggagtg ggtctcaggt attagttgga atagtggtag cataggctat    180

gcggactctg tgaagggccg attcaccatc tccagagaca acgccaagaa ctccctgtat    240

ctgcaaatga acagtctgag agctgaggac acggccttgt attactgtgc aaaagatatg    300

ggaagtggct acgattggta ctactacggt atggacgtct ggggccaagg gaccacggtc    360

accgtctcct ca                                                        372
```

```
<210> SEQ ID NO 25
<211> LENGTH: 381
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 25

caggtgcagc tggtgcagtc tgggggaggc ttcgtacagc ctggcaggtc cctgagactc     60

tcctgtgcag cctctggatt cacctttgat gattatgcca tgcactgggt ccggcaagct    120

ccagggaagg gcctggagtg ggtctcaggt attagttgga atagtaataa cataggctat    180

gcggactctg tgaagggccg attcaccatc tccagagaga acgcgaagaa ctccctgtat    240

ctgcaaatga acagcctgag agccgaggac acggctgtgt attactgtgc gagagttagt    300

ccgggttact atgatagtag tggccaaggg actgatgctt ttgatatctg gggccaaggg    360

accacggtca ccgtctcctc a                                              381
```

```
<210> SEQ ID NO 26
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 26

caggtgcagc tggtgcagtc tgggggaggc ttggtacagc ctggcaggtc cctgagactc     60

tcctgtgcag cctctggatt cacctttgat gattatgcca tgcactgggt ccggcaagct    120
```

ccagggaagg gcctggagtg ggtctcaggt attagttgga atagtggtag cataggctat 180
gcggactctg tgaagggccg attcaccatc tccagagaca acgccaagaa ctccctgtat 240
ctgcaaatga acagtctgag agctgaggac acggccttgt attactgtgc aaaagatatt 300
agcagtggct ggtaccctga tgcttttgat atctggggcc aaggcaccct ggtcaccgtc 360
tcctca 366

<210> SEQ ID NO 27
<211> LENGTH: 375
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 27
caggtgcagc tggtgcagtc tggagctgag gtgaagaagc ctggggcctc agtgaaggtc 60
tcctgcaagg cttctggtta cacctttacc agctatggta tcagctgggt gcgacaggcc 120
cctggacaag ggcttgagtg gatgggatgg atcagcgctt acaatggtaa cacaaactat 180
gcacagaagg tccagggcag agtcaccatg accacagaca catccacgag cacagcctac 240
atggagctga ggagcctgag atctgacgac acggccgtgt attactgtgc gagagatccg 300
catcttagca gtggctggta caagggaaac ggtatggacg tctggggcca aggaaccctg 360
gtcaccgtct cctca 375

<210> SEQ ID NO 28
<211> LENGTH: 327
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 28
tcttctgagc tgactcagga ccctgctgtg tctgtggcct tgggacagac agtcaggatc 60
acatgccaag gagacagcct cagaagctat tatgcaagct ggtaccagca gaagccagga 120
caggcccctg tacttgtcat ctatggtaaa aatagccggc cctcggggat cccagaccga 180
ttctctggct ccaactcagg aagcacagct tccttgacca tcactggggc tcaggcggaa 240
gatgaggctg actattactg taactcccgg gacaggtatg gtaattccct tgtgatattc 300
ggcggaggga ccaagctgac cgtccta 327

<210> SEQ ID NO 29
<211> LENGTH: 324
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 29
tcttctgagc tgactcagga ccctgctgtg tctgtggcct tgggacagac agtcaggatc 60
acatgccgag gagacagcct cagaagctat tatgcaagct ggtaccagca gaagccagga 120
caggcccctg tacttgtcat ttatggtaaa aacaaccggc cctcagggat cccagaccga 180
ttctctggct ccagctcagg aaacacagct tccttgacca tcactggggc tcaggcggaa 240
gatgaggctg actattactg taactcccgg gacagcagtg gtaaccatct ggtgttcggc 300
ggagggacca agctgaccgt ccta 324

<210> SEQ ID NO 30
<211> LENGTH: 321
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 30
gaaacgacac tcacgcagtc tccagccacc ctgtctgtgt ctccagggga aagggccacc 60
ctctcctgca gggccagtca gagtgttcgc cgcaacgtag cctggtacca gcagaaacct 120
ggccaggctc ccaggctcct catctatggt gcatccttca gggccgctgg cgtcccagac 180
aggttcagtg gaagtgggtc tgggacagac ttcactctca ccatcaccag actggagcct 240
gaagattttg cagtgtatta ctgtcagcag tatggtagct cacctcggac gttcggccaa 300
gggaccaagg tggaaatcaa a 321

<210> SEQ ID NO 31
<211> LENGTH: 324
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 31
tcttctgagc tgactcagga ccctgctgtg tctgtggcct tgggacagac agtcaggatc 60
acatgccaag gagacagcct cagaagctat tatgcaagct ggtaccagca gaagccagga 120
caggcccctg tacttgtcat ctatggtaaa aacaaccggc cctcagggat cccagaccga 180
ttctctggct ccaactcagg aaacacagct tccttgacca tcactggggc tcaggcggaa 240
gatgaggctg actattactg taactcccgg gacttcagtg gtcttcagct ggtattcggc 300
ggagggacca gactgaccgt cctg 324

<210> SEQ ID NO 32
<211> LENGTH: 324
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 32
tcttctgagc tgactcagga ccctgctgtg tctgtggcct tgggacagac agtcaggatc 60
acatgccaag gagacagcct cagaaggtat tatgcaagtt ggtaccagca gaagccagga 120
caggcccctg tacttgtctt ctatgggaaa aacactcggc cctcagggat cccagaccga 180
atctctggct ccagctctgg aaacacagct tccttgacca tcactggggc tcaggcggaa 240
gatgaggctg actattattg taactcccgg gacagcagtg gtaaccctgt ggtattcggc 300
ggagggacca agctgaccgt ccta 324

<210> SEQ ID NO 33
<211> LENGTH: 4
<212> TYPE: PRT
<213> ORGANISM: Artificial Sequence
<220> FEATURE:
<223> OTHER INFORMATION: Description of Artificial Sequence: Synthetic peptide

<400> SEQUENCE: 33

Gly Val Val Ser
1

<210> SEQ ID NO 34
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 34

Gly Ser Val Val Val
1 5

<210> SEQ ID NO 35
<211> LENGTH: 375
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 35
caggtgcagc tggtgcagtc tgggggaggc ttggtccagc ctggggggtc cctgagactc 60
tcctgtgcag cctctggatt cacctttgat gattatgcca tgcactgggt ccggcaagct 120
ccagggaagg gcctggagtg ggtctcaggt attagttgga atagtggtag cataggctat 180
gcggactctg tgaagggccg attcaccatc tccagagaca acgccaagaa ctccctgtat 240
ctgcaaatga acagtctgag agctgaggac acggccttgt attactgtgc aaaagatatc 300
ggttcaggga gttattataa ctactactac ggtatggacg tctggggcca ggggaccacg 360
gtcaccgtct cctca 375

<210> SEQ ID NO 36
<211> LENGTH: 367
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 36
caggtgcagc tggtgcagtc tgggggaggc ttggtacagc ctggcaggtc cctgagactc 60
tcctgtgcag cctctggatt cacctttgat gattatgcca tgcactgggt ccggcaagct 120
ccagggaagg gcctggagtg ggtctcaggt attagttgga atagtggtag cataggctat 180
gcggactctg tgaagggccg attcaccatc tccagagaca acgccaagaa ctccctgtat 240
ctgcaaatga acagtctgag agctgaggac acggccttgt attactgtgc aaaagatatt 300
agcagtggct ggtaccctga tgcttttgat atctggggcc aaggcaccct ggtcaccgtc 360
tcctcag 367

<210> SEQ ID NO 37
<211> LENGTH: 355
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 37
caggtgcagc tggtgcagtc tggagccgag gtgaagaggc ccggggcctc agtgaaggtc 60
tcctgcaagg cttctggtta cacttttagc acctacgcta tcaactgggt gcgacaggcc 120
cctggacaag ggcctgagtg gatgggatgg atcagcggtt acaatggtaa cacaaaatat 180
gcacagaagg tccagggtag agtcatcatg accacagaca catccacgac cacagcctac 240
atggagttga ggagcctgac atctgacgac acggccgtgt attactgtgc gagagatgga 300
gtgggagctg cctttgacta ctggggccag ggaaccctgg tcaccgtctc ctcag 355

<210> SEQ ID NO 38
<211> LENGTH: 375
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 38
caggagcagc tggtgcagtc tggagctgag gtgaagaagc ctggggcctc agtgaaggtc 60
tcctgcaagg cttctggtta cacctttacc agctatggta tcagctgggt gcgacaggcc 120
cctggacaag ggcttgagtg gatgggatgg atcagcgctt acaatggtaa cacaaattat 180
gcacagaagg tccagggcag agtcaccatg cccacagaca cattcacgag cacagcctac 240
atggagctga ggagcctgag atctgacgac acggccgtgt attactgtgc gagagatccg 300
catcttagca gtggctggtg caagggaaac ggtatggacg tctggggcca aggaaccctg 360
gtctccgtct cctca 375

<210> SEQ ID NO 39
<211> LENGTH: 375
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 39
caggtgcagt tggtgcagtt tggaggtgag gtgaagaagc ctggggcctc agtgaaggtc 60
tcctgcacag cttctggtta cacctatacc agctatggta tcagctgggt gcgacaggcc 120
cctggacaag ggcttgagtg gatgggatgg atcagcgctt acaatggtaa cacaaactat 180
gcacagaagg tccagggcag agtcaccatg accacagaca catccacgag cacagcctac 240
atggagctga ggagcctgag atctgacgac acggccgtgt attactgtgc gagagatccg 300
catgttagca gtggctggta caagggaaac ggtatggacg tctggggcca aggaaccctg 360
gtcaccgtct cctca 375

<210> SEQ ID NO 40
<211> LENGTH: 352
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 40
gaggtgcagc tggtgcagtc tggggctgag gtgaagaagc ctgggtcctc agtgaaggtc 60
tcctgcaagg cttctggata caccttctcc aattatgata tcaactgggt gcgacaggcc 120
actggacacg ggcttgagtg gatggggaga atgaatccta acagtggaaa cacaggctat 180
gcagagaagt tccagggcag agtcatcatg accagtgaca cctccataga cacagcctac 240
atggacctga gcagccttag atctgaggac acggccgtct attattgtgc gagggaaata 300
cgtggtgctt ttgatatctg gggccaaggg acaatggtca ccgtctcttc ag 352

<210> SEQ ID NO 41
<211> LENGTH: 352
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 41
gatgtgcagc tggtgcagtc tggggggtgag gcgaagaagc ctgggtcctc agtgaaggtc 60
tcctgcaagg cttctggata caccttctgc aattatgata tcaactgggt gggacaggac 120
actggacacg ggcttgagtg gatggggaga atgaatcctt acagtggaaa cacaggctat 180
gcagagaagt tccagggcag agtcatcatg accagtgaca cctccataga cacagcctac 240
atggacctga gcagccttag atatgaggac acggccgtct attattgtgc gagggaaata 300
cgtggtgctt ttgatatgtg gggccaaggg ccaatggtca ccgtctcttc ag 352

<210> SEQ ID NO 42
<211> LENGTH: 382
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 42
cagctgcagc tggtgcagta tgggggagga ttcgtacagc atggcaggtc cttgaggctc 60
ttctgtgcag catctggatt cacctctgat gattatgaca tgcactgggt ccggcaagct 120
ccagggaaga gcctggagtg ggtgtcaggt attagttgga atagtaataa catagggtat 180
gcggaatatg tgaagggccg attcaccatc tccagagaga ccgcgaagaa ctccctgtat 240
atgcaaatga acagcctgag agccgaggac acggctgtgt attactgtgc gagagttagt 300
ccgggttact atgatagtag tggccaaggg agtgatgctt ttgatatctg gggccaaggg 360
accacggtcg ccgtctcctc ag 382

<210> SEQ ID NO 43
<211> LENGTH: 361
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 43
caggtgcagc tggtgcagtc tgggggaggc gtggtccagc ctgggaggtc cctgagactc 60
tcctgtgcag cctctggatt caccttcagt agctatggca tgcactgggt ccgccaggct 120
ccaggcaagg ggctggagtg ggtggcagtt atatcatatg atggaagtaa taaatactat 180
gcagactccg tgaagggccg attcaccatc tccagagaca attccaagaa cacgctgtat 240
ctgcaaatga acagtctgag agtcgaggac acggctatgt attactgtgc aagtggtaac 300
ccatactact cttatgctat ggacgtctgg ggccaaggga caatggtcac cgtctcttca 360
g 361

<210> SEQ ID NO 44
<211> LENGTH: 352
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 44
gaggtgcagc tggtgcagtc tgggggtgag gcgaagaagc ctgggtcctc agtgaaggtc 60
tcctgcaagg cttctggata caccatctcc aattatgata tcaactgggt gggacaggcc 120
actggacacg ggcttgagtg gatggagaga atgaatccta acagtggaaa cacagggtat 180
gcagagaagt tgcagggcag agtcatcatg accagtgcct cctccataga cacagcctac 240
atgtacgtga gcagccttag atatgagggc gcggccgttt attattgtgg gagggaaatg 300
tgtggtggtt ttgatatgtg ggtccaaggg ccaatggtca ccgtctcttc ag 352

<210> SEQ ID NO 45
<211> LENGTH: 369
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 45
caggtgcagc tgcaggagtc gggggaggc ttggtacagc ctgggggtc cctgagactc 60 tcctgtgcag cgtctggact cagttttagt aagcatgcca tgaactgggt ccgccaggct 120
ccagggaagg ggctggagtg ggtctcaact atcagtggca gtggtactag aacatactac 180
gcagactccg tgaagggccg gttcaccatc tccagagaca ataccaggga caccctctat 240
ctgcaaatga acagactgag agccgaagac acggccatat attactgtgt aaaaggagaa 300
gagggacctt actactacta ctacggtttg gacgtctggg gccaagggac cacggtcacc 360
gtctcctca 369

<210> SEQ ID NO 46
<211> LENGTH: 352
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 46
ccaggtgcgc tggtgcaatc tgggggaggc ttggtccagc ctgggggtc cctgagactc 60 tcctgtgcag cctctggatt cacatttagt gacaattgga tgagctgggt ccgccaggct 120
ccagtgaagg ggctggagtg ggtggccaac ataaagcaag atggaagtga gaaatacttt 180
gtggactctg tgaagggccg attcaccatt tccagagaca acgccaagaa gtcactgtat 240
ctgcagatga acaacctgag agccgaagac acggccgtgt attactgtgt gcgcgagttt 300
gtcggtgctt atgatatctg ggccaaggg acaatggtca ccgtctcttc ag 352

<210> SEQ ID NO 47
<211> LENGTH: 125
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 47

Gln Val Gln Leu Val Gln Ser Gly Gly Gly Leu Val Gln Pro Gly Gly
1 5 10 15

Ser Leu Arg Leu Ser Cys Ala Ala Ser Gly Phe Thr Phe Asp Asp Tyr
20 25 30

Ala Met His Trp Val Arg Gln Ala Pro Gly Lys Gly Leu Glu Trp Val
35 40 45

Ser Gly Ile Ser Trp Asn Ser Gly Ser Ile Gly Tyr Ala Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Leu Tyr Tyr Cys
85 90 95

Ala Lys Asp Ile Gly Ser Gly Ser Tyr Tyr Asn Tyr Tyr Tyr Gly Met
100 105 110

Asp Val Trp Gly Gln Gly Thr Thr Val Thr Val Ser Ser
115 120 125

<210> SEQ ID NO 48
<211> LENGTH: 118
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 48

Gln Val Gln Leu Val Gln Ser Gly Ala Glu Val Lys Arg Pro Gly Ala
1 5 10 15

Ser Val Lys Val Ser Cys Lys Ala Ser Gly Tyr Thr Phe Ser Thr Tyr
20 25 30

Ala Ile Asn Trp Val Arg Gln Ala Pro Gly Gln Gly Pro Glu Trp Met
35 40 45

Gly Trp Ile Ser Gly Tyr Asn Gly Asn Thr Lys Tyr Ala Gln Lys Val
50 55 60

Gln Gly Arg Val Ile Met Thr Thr Asp Thr Ser Thr Thr Thr Ala Tyr
65 70 75 80

Met Glu Leu Arg Ser Leu Thr Ser Asp Asp Thr Ala Val Tyr Tyr Cys
85 90 95

Ala Arg Asp Gly Val Gly Ala Ala Phe Asp Tyr Trp Gly Gln Gly Thr
100 105 110

Leu Val Thr Val Ser Ser
115

<210> SEQ ID NO 49
<211> LENGTH: 125
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 49

Gln Glu Gln Leu Val Gln Ser Gly Ala Glu Val Lys Lys Pro Gly Ala
1 5 10 15

```
Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Val
    50                  55                  60

Gln Gly Arg Val Thr Met Pro Thr Asp Thr Phe Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Pro His Leu Ser Ser Gly Trp Cys Lys Gly Asn Gly Met
            100                 105                 110

Asp Val Trp Gly Gln Gly Thr Leu Val Ser Val Ser Ser
        115                 120                 125


<210> SEQ ID NO 50
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Gln Val Gln Leu Val Gln Phe Gly Gly Glu Val Lys Lys Pro Gly Ala
1               5                   10                  15

Ser Val Lys Val Ser Cys Thr Ala Ser Gly Tyr Thr Tyr Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Val
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Pro His Val Ser Ser Gly Trp Tyr Lys Gly Asn Gly Met
            100                 105                 110

Asp Val Trp Gly Gln Gly Thr Leu Val Thr Val Ser Ser
        115                 120                 125


<210> SEQ ID NO 51
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Asn Tyr
            20                  25                  30

Asp Ile Asn Trp Val Arg Gln Ala Thr Gly His Gly Leu Glu Trp Met
        35                  40                  45

Gly Arg Met Asn Pro Asn Ser Gly Asn Thr Gly Tyr Ala Glu Lys Phe
    50                  55                  60
```

```
Gln Gly Arg Val Ile Met Thr Ser Asp Thr Ser Ile Asp Thr Ala Tyr
65                  70                  75                  80

Met Asp Leu Ser Ser Leu Arg Ser Glu Asp Thr Ala Val Tyr Tyr Cys
                85                  90                  95

Ala Arg Glu Ile Arg Gly Ala Phe Asp Ile Trp Gly Gln Gly Thr Met
            100                 105                 110

Val Thr Val Ser Ser
        115


<210> SEQ ID NO 52
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Asp Val Gln Leu Val Gln Ser Gly Gly Glu Ala Lys Lys Pro Gly Ser
1               5                   10                  15

Ser Val Lys Val Ser Cys Lys Ala Ser Gly Tyr Thr Phe Cys Asn Tyr
            20                  25                  30

Asp Ile Asn Trp Val Gly Gln Asp Thr Gly His Gly Leu Glu Trp Met
        35                  40                  45

Gly Arg Met Asn Pro Tyr Ser Gly Asn Thr Gly Tyr Ala Glu Lys Phe
    50                  55                  60

Gln Gly Arg Val Ile Met Thr Ser Asp Thr Ser Ile Asp Thr Ala Tyr
65                  70                  75                  80

Met Asp Leu Ser Ser Leu Arg Tyr Glu Asp Thr Ala Val Tyr Tyr Cys
                85                  90                  95

Ala Arg Glu Ile Arg Gly Ala Phe Asp Met Trp Gly Gln Gly Pro Met
            100                 105                 110

Val Thr Val Ser Ser
        115


<210> SEQ ID NO 53
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Gln Leu Gln Leu Val Gln Tyr Gly Gly Gly Phe Val Gln His Gly Arg
1               5                   10                  15

Ser Leu Arg Leu Phe Cys Ala Ala Ser Gly Phe Thr Ser Asp Asp Tyr
            20                  25                  30

Asp Met His Trp Val Arg Gln Ala Pro Gly Lys Ser Leu Glu Trp Val
        35                  40                  45

Ser Gly Ile Ser Trp Asn Ser Asn Asn Ile Gly Tyr Ala Glu Tyr Val
    50                  55                  60

Lys Gly Arg Phe Thr Ile Ser Arg Glu Thr Ala Lys Asn Ser Leu Tyr
65                  70                  75                  80

Met Gln Met Asn Ser Leu Arg Ala Glu Asp Thr Ala Val Tyr Tyr Cys
                85                  90                  95

Ala Arg Val Ser Pro Gly Tyr Tyr Asp Ser Ser Gly Gln Gly Ser Asp
            100                 105                 110
```

```
Ala Phe Asp Ile Trp Gly Gln Gly Thr Thr Val Ala Val Ser Ser
        115                 120                 125


<210> SEQ ID NO 54
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Val Glu Asp Thr Ala Met Tyr Tyr Cys
                85                  90                  95

Ala Ser Gly Asn Pro Tyr Tyr Ser Tyr Ala Met Asp Val Trp Gly Gln
            100                 105                 110

Gly Thr Met Val Thr Val Ser Ser
        115                 120


<210> SEQ ID NO 55
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Glu Val Gln Leu Val Gln Ser Gly Gly Glu Ala Lys Lys Pro Gly Ser
1               5                   10                  15

Ser Val Lys Val Ser Cys Lys Ala Ser Gly Tyr Thr Ile Ser Asn Tyr
            20                  25                  30

Asp Ile Asn Trp Val Gly Gln Ala Thr Gly His Gly Leu Glu Trp Met
        35                  40                  45

Glu Arg Met Asn Pro Asn Ser Gly Asn Thr Gly Tyr Ala Glu Lys Leu
    50                  55                  60

Gln Gly Arg Val Ile Met Thr Ser Ala Ser Ser Ile Asp Thr Ala Tyr
65                  70                  75                  80

Met Tyr Val Ser Ser Leu Arg Tyr Glu Gly Ala Ala Val Tyr Tyr Cys
                85                  90                  95

Gly Arg Glu Met Cys Gly Gly Phe Asp Met Trp Val Gln Gly Pro Met
            100                 105                 110

Val Thr Val Ser Ser
        115


<210> SEQ ID NO 56
<211> LENGTH: 123
<212> TYPE: PRT
<213> ORGANISM: Artificial Sequence
<220> FEATURE:
```

<223> OTHER INFORMATION: Description of Artificial Sequence: Synthetic
polypeptide

<400> SEQUENCE: 56

```
Gln Val Gln Leu Gln Glu Ser Gly Gly Gly Leu Val Gln Pro Gly Gly
1               5                   10                  15

Ser Leu Arg Leu Ser Cys Ala Ala Ser Gly Leu Ser Phe Ser Lys His
            20                  25                  30

Ala Met Asn Trp Val Arg Gln Ala Pro Gly Lys Gly Leu Glu Trp Val
        35                  40                  45

Ser Thr Ile Ser Gly Ser Gly Thr Arg Thr Tyr Tyr Ala Asp Ser Val
    50                  55                  60

Lys Gly Arg Phe Thr Ile Ser Arg Asp Asn Thr Arg Asp Thr Leu Tyr
65                  70                  75                  80

Leu Gln Met Asn Arg Leu Arg Ala Glu Asp Thr Ala Ile Tyr Tyr Cys
                85                  90                  95

Val Lys Gly Glu Glu Gly Pro Tyr Tyr Tyr Tyr Tyr Gly Leu Asp Val
            100                 105                 110

Trp Gly Gln Gly Thr Thr Val Thr Val Ser Ser
        115                 120
```

<210> SEQ ID NO 57
<211> LENGTH: 117
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 57

```
Pro Gly Ala Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser Asp Asn
            20                  25                  30

Trp Met Ser Trp Val Arg Gln Ala Pro Val Lys Gly Leu Glu Trp Val
        35                  40                  45

Ala Asn Ile Lys Gln Asp Gly Ser Glu Lys Tyr Phe Val Asp Ser Val
    50                  55                  60

Lys Gly Arg Phe Thr Ile Ser Arg Asp Asn Ala Lys Lys Ser Leu Tyr
65                  70                  75                  80

Leu Gln Met Asn Asn Leu Arg Ala Glu Asp Thr Ala Val Tyr Tyr Cys
                85                  90                  95

Val Arg Glu Phe Val Gly Ala Tyr Asp Ile Trp Gly Gln Gly Thr Met
            100                 105                 110

Val Thr Val Ser Ser
        115
```

<210> SEQ ID NO 58
<211> LENGTH: 125
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 58

```
Gln Val Gln Leu Val Gln Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
```

```
            20                  25                  30

Ala Met His Trp Val Arg Gln Ala Pro Gly Lys Gly Leu Glu Trp Val
        35                  40                  45

Ser Gly Ile Ser Gln Asn Ser Gly Ser Ile Gly Tyr Ala Asp Ser Val
    50                  55                  60

Lys Gly Arg Phe Thr Ile Ser Arg Asp Asn Thr Lys Asn Leu Leu Tyr
65                  70                  75                  80

Leu Gln Met Asn Ser Leu Arg Val Glu Asp Thr Ala Val Tyr Tyr Cys
                85                  90                  95

Ala Arg Asp Gly Gly Tyr Cys Asp Ser Thr Gly Cys Tyr Asp Ala Leu
            100                 105                 110

Asp Ile Trp Gly Gln Gly Thr Thr Val Thr Val Ser Ser
        115                 120                 125


<210> SEQ ID NO 59
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Thr Tyr Asn Gly Asn Thr Lys Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Arg Ala Thr Ile Asp Ala Phe Asp Ile Trp Gly Gln Gly
            100                 105                 110

Thr Thr Val Thr Val Ser Ser
        115


<210> SEQ ID NO 60
<211> LENGTH: 328
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 60

tcttctgagc tgactcagga ccctgctgtg tctgtggcct tgggacagac agtcaggatc      60

acatgccaag gagacagcct cagaagctat tatgcaagct ggtaccagca gaagccagga     120

caggcccctg tacttgtcat ctatggtaaa aatagccggc cctcggggat cccagaccga     180

ttctctggct ccaactcagg aagcacagct tccttgacca tcactggggc tcaggcggaa     240

gatgaggctg actattactg taactcccgg gacaggtatg gtaatcccct tgtgatattc     300

ggcggaggga ccaagctgac cgtcctag                                        328
```

<210> SEQ ID NO 61
<211> LENGTH: 325
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 61
tcttctgagc tgactcagga ccctgctgtg tctgtggcct tgggacagac agtcaggatc 60
acatgccaag gagacagcct cagaagctat tatgcaagct ggtaccagca gaagccagga 120
caggcccctg tacttgtcat ctatggtaaa aacaaccggc cctcagggat cccagaccga 180
ttctctggct ccaactcagg aaacacagct tccttgacca tcactggggc tcaggcggaa 240
gatgaggctg actattactg taactcccgg gacttcagtg gtcttcagct ggtattcggc 300
ggagggacca gactgaccgt cctgg 325

<210> SEQ ID NO 62
<211> LENGTH: 325
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 62
tcttctgagc tgactcagga ccctgctgtg tctgtggcct tgggacagac agtcaggatc 60
acatgccgag gagacagcct cagaagctat tatgcaagct ggtaccagca gaagccagga 120
caggcccctg tacttgtcat ttatggtaaa aacaaccggc cctcagggat cccagaccga 180
ttctctggct ccagctcagg aaacacagct tccttgacca tcactggggc tcaggcggaa 240
gatgaggctg actattactg taactcccgg gacagcagtg gtaaccatct ggtgttcggc 300
ggagggacca agctgaccgt cctag 325

<210> SEQ ID NO 63
<211> LENGTH: 322
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 63
gaaacgacac tcacgcagtc tccagccacc ctgtctgtgt ctccagggga aagagccacc 60
ctctcctgca gggccagtca gagtgttggc agcaacttag cctggtacca gcaaaaacct 120
ggccaggctc ccaggctcct catctacggt gcatccacca gggccactgg tatcccagcc 180
aggttcagtg gcagtgggtc tgggacagaa ttcactctca ccatcagcag cctagagcct 240
gaagattttg cagtttatta ctgtcagcag cgtagcaact ggcctccgac gttcggccaa 300
gggaccaagg tggagagcaa ac 322

<210> SEQ ID NO 64
<211> LENGTH: 325
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 64
tcttctgagc tgactcagga ccctgctgtg tctgtggcct tgggacagac agtcaggatc 60
acatgccaag gagacagcct cagaaggtat tatgcaagtt ggtaccagca gaagccagga 120
caggcccctg tacttgtctt ctatgggaaa aacagtcggc cctcagggat cccagaccga 180
atctctggct ccagctctgg aaacacagct tccttgacca tcactgggggg tcaggcggaa 240 gatgaggctg actattattg taactcccgg gacagcagtg gtaaccctgt ggtattcggc 300
ggagggacca agctgaccgt cctag 325

<210> SEQ ID NO 65
<211> LENGTH: 325
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 65
tcttctgagc tgactcagga ccctgctgtg tctgtggcct tgggacagac agtcaggatc 60
acatgccaag gagacagcct cagaaggtat tatgcaagtt ggtaccagca gaagccagga 120
caggcccctg tacttgtctt ctatgggaaa aacactcggc cctcagggat cccagaccga 180
atctttggct ccagctctgg aaacacagct tccttgacca tcactggggc tcaggcggaa 240
gatgaggctg actattattg taactcccgg gacagcagtg gtaaccctgt ggtattcggc 300
ggagggacca agctgaccgt cctag 325

<210> SEQ ID NO 66
<211> LENGTH: 331
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 66
cagtctgccc tgactcagcc tccctccgtg tccgggtctc ctggacagtc agtcaccatc 60
tcctgcactg gaaccagcag tgacgttggt ggttataacc gtgtctcctg gtaccaacag 120
ccccccggca cagcccccaa actcatgatt catgacgtca gtagtcggcc ctcaggggtc 180
cctgatcgct tctctgggtc caagtctggc aacacggcct ccctgaccat ctctgggctc 240
caggctgacg acgaggctga ttattactgc agctcatata caagcagcag ccctcgggtg 300
ttcggcggag ggaccaagct gaccgtccta g 331

<210> SEQ ID NO 67
<211> LENGTH: 331
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 67
cagtctgccc tgactcagcc tccctccgtg tccgggtctc ctggacagtc agtcaccatc 60
tcctgcactg gaaccagcag tgacgttggt ggttataacc gtgtctcctg gtaccaacag 120
ccccccggca cagcccccaa actcatgatt catgacgtca gtagtcggcc ctcaggggtc 180
cctgatcgct tctctgggtc caagtctggc aacacggcct ccctgaccat ctgggggctc 240
caggaagacg aggaggctga ttattgttgc agctcatata caagcagcag ccctcgggtg 300
ttcggcggag ggaccaagct gaccgtccta g 331

<210> SEQ ID NO 68
<211> LENGTH: 322
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 68
gaaacgacac tcacgcagtc ttcagccgcc cagtgggtgt ctccagggga aagggccacc 60
ctctcctgca gggccagtca gagtgttcgc cgcaacgtag cctggtacca gcagaaacct 120
ggccaggctc ccaggctcct catttatggt gcatccttca gggcctctgg cgtcccagac 180
aggttcagtg gaagtgggtc tgggacagac ttcactctca ccatcaccag cctggagcct 240
gaagattttg cagtgtatta ctgtcagcag tatggtagct cacctcggac gttcggccaa 300
gggaccaagg tggaaatcaa ac 322

<210> SEQ ID NO 69
<211> LENGTH: 337
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 69
aattttatgc tgactcagcc ccactctgtg tcggagtctc cggggaagac ggtaaccatc 60
tcctgcaccc gcagcagtgg cagcattgcc aacaactatg tgcagtggta ccagcagcgc 120
ccgggcagtt cccccaccac tgtgatctat gaggataacc aaagaccctc tggggtccct 180
gatcggttct ctggctccat cgacagctcc tccaactctg cctccctcac catctctgga 240
ctgaagactg aggacgaggc tgactactac tgtcagtctt atgatagcat caatcatcat 300
gtggttttcg gcggagggac caagctgacc gtcctag 337

<210> SEQ ID NO 70
<211> LENGTH: 331
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 70
cagtctgccc tgactcagcc tccctccgtg tccgggtctc ctggacagtc agtcaccatc 60
tcctgcactg gaaccagcag tgacgttggt ggttataacc gtgtgtcctg gtaccaacag 120
ccccccggca cagcccccaa actcatgatt cagaaagtca gtagtcggcc ctcaggggtc 180
cctgatcgct tctctgggtc caagtctggc aacacggcct ccctgatcat ctgggggctc 240
caggaagacg aggaggctga ttattgttgc agctcataca caagcagcag ccctcgggtg 300
ttcggcggag ggaccaagct gaccgtccta g 331

<210> SEQ ID NO 71
<211> LENGTH: 325
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 71

```
tcctatgagc tgactcagcc accctcggtg tcagtggccc caggacagac ggccaggatt     60

acctgtgggg caaacaacat tggaagtaaa agtgtgcact ggtaccagca gaagccaggc    120

caggcccctg tgctggtcgt ctatgatgat agcgaccggc cctcagggat ccctgagcga    180

ttctctggct ccaactctgg gaacacggcc accctgacca tcagcagggt cgaagccggg    240

gatgaggccg actattactg tcaggtgtgg gatagtagta ctgatcatca ggttttcggc    300

ggagggacca agctgaccgt cctag                                          325
```

<210> SEQ ID NO 72
<211> LENGTH: 334
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 72

```
aattttatgc tgactcagcc ccactctgtg tcggagtctc cggggaagac ggtaatcatc     60

tcctgcaccc gcagcagcgg cagcattgcc aaccaccgtg tgcagtggct ccagcagcgc    120

ccgggcagtg cccccctcac tgtgatctat gaggaaaacc gaagaccctc tggggtccct    180

gatcggttct ctggctccat cgacacgtcc tccaactctg cctccctcac catctctgga    240

ctgaagcctg aggacgaggc tgactactac tgtcagtctt tggatggcgt cactcattat    300

gtcttcggaa gtggggccaa ggtcaccgtc ctag                                334
```

<210> SEQ ID NO 73
<211> LENGTH: 109
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 73

```
Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Ser Arg Pro Ser Gly Ile Pro Asp Arg Phe Ser Gly Ser
    50                  55                  60

Asn Ser Gly Ser Thr Ala Ser Leu Thr Ile Thr Gly Ala Gln Ala Glu
65                  70                  75                  80

Asp Glu Ala Asp Tyr Tyr Cys Asn Ser Arg Asp Arg Tyr Gly Asn Pro
                85                  90                  95

Leu Val Ile Phe Gly Gly Gly Thr Lys Leu Thr Val Leu
            100                 105
```

<210> SEQ ID NO 74
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 74

```
Glu Thr Thr Leu Thr Gln Ser Pro Ala Thr Leu Ser Val Ser Pro Gly
1               5                   10                  15

Glu Arg Ala Thr Leu Ser Cys Arg Ala Ser Gln Ser Val Gly Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Thr Phe Gly Gln Gly Thr Lys Val Glu Ser Lys
            100                 105
```

<210> SEQ ID NO 75
<211> LENGTH: 108
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 75

```
Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Arg Tyr Tyr Ala
            20                  25                  30

Ser Trp Tyr Gln Gln Lys Pro Gly Gln Ala Pro Val Leu Val Phe Tyr
        35                  40                  45

Gly Lys Asn Ser Arg Pro Ser Gly Ile Pro Asp Arg Ile Ser Gly Ser
    50                  55                  60

Ser Ser Gly Asn Thr Ala Ser Leu Thr Ile Thr Gly Gly Gln Ala Glu
65                  70                  75                  80

Asp Glu Ala Asp Tyr Tyr Cys Asn Ser Arg Asp Ser Ser Gly Asn Pro
                85                  90                  95

Val Val Phe Gly Gly Gly Thr Lys Leu Thr Val Leu
            100                 105
```

<210> SEQ ID NO 76
<211> LENGTH: 108
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 76

```
Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Arg Tyr Tyr Ala
            20                  25                  30

Ser Trp Tyr Gln Gln Lys Pro Gly Gln Ala Pro Val Leu Val Phe Tyr
        35                  40                  45

Gly Lys Asn Thr Arg Pro Ser Gly Ile Pro Asp Arg Ile Phe Gly Ser
    50                  55                  60

Ser Ser Gly Asn Thr Ala Ser Leu Thr Ile Thr Gly Ala Gln Ala Glu
```

```
65                  70                  75                  80

Asp Glu Ala Asp Tyr Tyr Cys Asn Ser Arg Asp Ser Ser Gly Asn Pro
                85                  90                  95

Val Val Phe Gly Gly Gly Thr Lys Leu Thr Val Leu
            100                 105


<210> SEQ ID NO 77
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Gln Ser Ala Leu Thr Gln Pro Pro Ser Val Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Arg Val Ser Trp Tyr Gln Gln Pro Pro Gly Thr Ala Pro Lys Leu
        35                  40                  45

Met Ile His Asp Val Ser Ser Arg Pro Ser Gly Val Pro Asp Arg Phe
    50                  55                  60

Ser Gly Ser Lys Ser Gly Asn Thr Ala Ser Leu Thr Ile Ser Gly Leu
65                  70                  75                  80

Gln Ala Asp Asp Glu Ala Asp Tyr Tyr Cys Ser Ser Tyr Thr Ser Ser
                85                  90                  95

Ser Pro Arg Val Phe Gly Gly Gly Thr Lys Leu Thr Val Leu
            100                 105                 110


<210> SEQ ID NO 78
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Gln Ser Ala Leu Thr Gln Pro Pro Ser Val Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Arg Val Ser Trp Tyr Gln Gln Pro Pro Gly Thr Ala Pro Lys Leu
        35                  40                  45

Met Ile His Asp Val Ser Ser Arg Pro Ser Gly Val Pro Asp Arg Phe
    50                  55                  60

Ser Gly Ser Lys Ser Gly Asn Thr Ala Ser Leu Thr Ile Trp Gly Leu
65                  70                  75                  80

Gln Glu Asp Glu Glu Ala Asp Tyr Cys Cys Ser Ser Tyr Thr Ser Ser
                85                  90                  95

Ser Pro Arg Val Phe Gly Gly Gly Thr Lys Leu Thr Val Leu
            100                 105                 110


<210> SEQ ID NO 79
<211> LENGTH: 107
<212> TYPE: PRT
<213> ORGANISM: Artificial Sequence
<220> FEATURE:
<223> OTHER INFORMATION: Description of Artificial Sequence: Synthetic
```

polypeptide

<400> SEQUENCE: 79

Glu Thr Thr Leu Thr Gln Ser Ser Ala Ala Gln Trp Val Ser Pro Gly
1 5 10 15

Glu Arg Ala Thr Leu Ser Cys Arg Ala Ser Gln Ser Val Arg Arg Asn
20 25 30

Val Ala Trp Tyr Gln Gln Lys Pro Gly Gln Ala Pro Arg Leu Leu Ile
35 40 45

Tyr Gly Ala Ser Phe Arg Ala Ser Gly Val Pro Asp Arg Phe Ser Gly
50 55 60

Ser Gly Ser Gly Thr Asp Phe Thr Leu Thr Ile Thr Ser Leu Glu Pro
65 70 75 80

Glu Asp Phe Ala Val Tyr Tyr Cys Gln Gln Tyr Gly Ser Ser Pro Arg
85 90 95

Thr Phe Gly Gln Gly Thr Lys Val Glu Ile Lys
100 105

<210> SEQ ID NO 80
<211> LENGTH: 112
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 80

Asn Phe Met Leu Thr Gln Pro His Ser Val Ser Glu Ser Pro Gly Lys
1 5 10 15

Thr Val Thr Ile Ser Cys Thr Arg Ser Ser Gly Ser Ile Ala Asn Asn
20 25 30

Tyr Val Gln Trp Tyr Gln Gln Arg Pro Gly Ser Ser Pro Thr Thr Val
35 40 45

Ile Tyr Glu Asp Asn Gln Arg Pro Ser Gly Val Pro Asp Arg Phe Ser
50 55 60

Gly Ser Ile Asp Ser Ser Ser Asn Ser Ala Ser Leu Thr Ile Ser Gly
65 70 75 80

Leu Lys Thr Glu Asp Glu Ala Asp Tyr Tyr Cys Gln Ser Tyr Asp Ser
85 90 95

Ile Asn His His Val Val Phe Gly Gly Gly Thr Lys Leu Thr Val Leu
100 105 110

<210> SEQ ID NO 81
<211> LENGTH: 110
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 81

Gln Ser Ala Leu Thr Gln Pro Pro Ser Val Ser Gly Ser Pro Gly Gln
1 5 10 15

Ser Val Thr Ile Ser Cys Thr Gly Thr Ser Ser Asp Val Gly Gly Tyr
20 25 30

Asn Arg Val Ser Trp Tyr Gln Gln Pro Pro Gly Thr Ala Pro Lys Leu
35 40 45

Met Ile Gln Lys Val Ser Ser Arg Pro Ser Gly Val Pro Asp Arg Phe
50 55 60

Ser Gly Ser Lys Ser Gly Asn Thr Ala Ser Leu Ile Ile Trp Gly Leu
65 70 75 80

Gln Glu Asp Glu Glu Ala Asp Tyr Cys Cys Ser Ser Tyr Thr Ser Ser
85 90 95

Ser Pro Arg Val Phe Gly Gly Gly Thr Lys Leu Thr Val Leu
100 105 110

<210> SEQ ID NO 82
<211> LENGTH: 108
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 82

Ser Tyr Glu Leu Thr Gln Pro Pro Ser Val Ser Val Ala Pro Gly Gln
1 5 10 15

Thr Ala Arg Ile Thr Cys Gly Ala Asn Asn Ile Gly Ser Lys Ser Val
20 25 30

His Trp Tyr Gln Gln Lys Pro Gly Gln Ala Pro Val Leu Val Val Tyr
35 40 45

Asp Asp Ser Asp Arg Pro Ser Gly Ile Pro Glu Arg Phe Ser Gly Ser
50 55 60

Asn Ser Gly Asn Thr Ala Thr Leu Thr Ile Ser Arg Val Glu Ala Gly
65 70 75 80

Asp Glu Ala Asp Tyr Tyr Cys Gln Val Trp Asp Ser Ser Thr Asp His
85 90 95

Gln Val Phe Gly Gly Gly Thr Lys Leu Thr Val Leu
100 105

<210> SEQ ID NO 83
<211> LENGTH: 111
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 83

Asn Phe Met Leu Thr Gln Pro His Ser Val Ser Glu Ser Pro Gly Lys
1 5 10 15

Thr Val Ile Ile Ser Cys Thr Arg Ser Ser Gly Ser Ile Ala Asn His
20 25 30

Arg Val Gln Trp Leu Gln Gln Arg Pro Gly Ser Ala Pro Leu Thr Val
35 40 45

Ile Tyr Glu Glu Asn Arg Arg Pro Ser Gly Val Pro Asp Arg Phe Ser
50 55 60

Gly Ser Ile Asp Thr Ser Ser Asn Ser Ala Ser Leu Thr Ile Ser Gly
65 70 75 80

Leu Lys Pro Glu Asp Glu Ala Asp Tyr Tyr Cys Gln Ser Leu Asp Gly
85 90 95

Val Thr His Tyr Val Phe Gly Ser Gly Ala Lys Val Thr Val Leu
100 105 110

<210> SEQ ID NO 84
<211> LENGTH: 110
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 84

Ser Tyr Glu Leu Thr Gln Pro Pro Ser Val Ser Lys Gly Leu Arg Gln
1 5 10 15

Thr Ala Thr Leu Thr Cys Ser Gly Asn Ser Asn Asn Val Gly His Glu
20 25 30

Gly Ala Ala Trp Leu Gln Gln His Gln Gly His Pro Pro Lys Leu Leu
35 40 45

Ser Tyr Arg Asn Asn Asn Arg Pro Ser Gly Ile Ser Glu Arg Phe Ser
50 55 60

Ala Ser Arg Ser Gly Asn Thr Ala Ser Leu Thr Ile Thr Gly Leu Gln
65 70 75 80

Pro Glu Asp Glu Ala Asp Tyr Tyr Cys Ala Thr Trp Asp Gly Ser Leu
85 90 95

Arg Gly Trp Val Phe Gly Gly Gly Ser Lys Leu Thr Val Leu
100 105 110

<210> SEQ ID NO 85
<211> LENGTH: 110
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 85

Gln Ser Ala Leu Thr Gln Pro Pro Ser Val Ser Gly Ser Pro Gly Gln
1 5 10 15

Ser Val Thr Ile Ser Cys Thr Gly Thr Ser Ser Asp Val Gly Gly Tyr
20 25 30

Asn Arg Val Ser Trp Tyr Gln Gln Pro Pro Gly Thr Ala Pro Lys Leu
35 40 45

Met Ile His Asp Val Ser Ser Arg Pro Ser Gly Val Pro Asp Arg Phe
50 55 60

Ser Gly Ser Lys Ser Gly Asn Thr Ala Ser Leu Thr Ile Ser Gly Leu
65 70 75 80

Gln Ala Asp Asp Glu Ala Asp Tyr Tyr Cys Ser Ser Tyr Thr Ser Ser
85 90 95

Ser Thr Arg Val Phe Gly Gly Gly Thr Lys Leu Thr Val Leu
100 105 110

<210> SEQ ID NO 86
<211> LENGTH: 106
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<221> NAME/KEY: MOD_RES
<222> LOCATION: (24)..(24)
<223> OTHER INFORMATION: Any amino acid
<220> FEATURE:
<221> NAME/KEY: MOD_RES
<222> LOCATION: (26)..(27)
<223> OTHER INFORMATION: Any amino acid
<220> FEATURE:
<221> NAME/KEY: MOD_RES
<222> LOCATION: (34)..(34)
<223> OTHER INFORMATION: Any amino acid
<220> FEATURE:
<221> NAME/KEY: MOD_RES
<222> LOCATION: (38)..(38)
<223> OTHER INFORMATION: Any amino acid
<220> FEATURE:
<221> NAME/KEY: MOD_RES
<222> LOCATION: (54)..(54)
<223> OTHER INFORMATION: Any amino acid
<220> FEATURE:
<221> NAME/KEY: MOD_RES
<222> LOCATION: (57)..(57)
<223> OTHER INFORMATION: Any amino acid
<220> FEATURE:
<221> NAME/KEY: MOD_RES
<222> LOCATION: (61)..(62)
<223> OTHER INFORMATION: Any amino acid
<220> FEATURE:
<221> NAME/KEY: MOD_RES
<222> LOCATION: (64)..(64)
<223> OTHER INFORMATION: Any amino acid
<220> FEATURE:
<221> NAME/KEY: MOD_RES
<222> LOCATION: (77)..(77)
<223> OTHER INFORMATION: Any amino acid
<220> FEATURE:
<221> NAME/KEY: MOD_RES
<222> LOCATION: (79)..(79)
<223> OTHER INFORMATION: Any amino acid
<220> FEATURE:
<221> NAME/KEY: MOD_RES
<222> LOCATION: (81)..(81)
<223> OTHER INFORMATION: Any amino acid
<220> FEATURE:
<221> NAME/KEY: MOD_RES
<222> LOCATION: (89)..(89)
<223> OTHER INFORMATION: Any amino acid
<220> FEATURE:
<221> NAME/KEY: MOD_RES
<222> LOCATION: (93)..(93)
<223> OTHER INFORMATION: Any amino acid
<220> FEATURE:
<221> NAME/KEY: MOD_RES
<222> LOCATION: (96)..(96)
<223> OTHER INFORMATION: Any amino acid
<220> FEATURE:
<221> NAME/KEY: MOD_RES
<222> LOCATION: (99)..(100)
<223> OTHER INFORMATION: Any amino acid
<220> FEATURE:
<221> NAME/KEY: MOD_RES
<222> LOCATION: (102)..(102)
<223> OTHER INFORMATION: Any amino acid
<220> FEATURE:
<221> NAME/KEY: MOD_RES
<222> LOCATION: (106)..(106)
<223> OTHER INFORMATION: Any amino acid

<400> SEQUENCE: 86

```
Lys Thr Thr Leu Thr Gln Ser Pro Ala Thr Leu Ser Val Ser Pro Gly
1               5                   10                  15

Glu Arg Ala Thr Leu Ser Cys Xaa Ala Xaa Xaa Ile Val Arg Arg Asn
            20                  25                  30

Val Xaa Gln Tyr Gln Xaa Lys Pro Gly Gln Ala Pro Ser Leu Leu Ile
        35                  40                  45

Tyr Gly Ala Ser Phe Xaa Ala Ala Xaa Val Ser His Xaa Xaa Ser Xaa
    50                  55                  60

Ser Gly Ser Gly Thr Tyr Phe Ser Leu Thr Ile Thr Xaa Leu Xaa Pro
65                  70                  75                  80

Xaa Ile Leu Gln Cys Ile Thr Val Xaa Ser Met Val Xaa His Leu Xaa
                85                  90                  95

Phe Gly Xaa Xaa Thr Xaa Val Glu Ile Xaa
            100                 105
```

<210> SEQ ID NO 87
<211> LENGTH: 111
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (105)..(105)
<223> OTHER INFORMATION: Any amino acid

<400> SEQUENCE: 87

Gln Ser Ala Leu Thr Gln Pro Ala Ser Val Ser Gly Ser Pro Gly Gln
1 5 10 15

Ser Ile Thr Ile Ser Cys Thr Gly Thr Ser Ser Asp Phe Gly Gly Tyr
20 25 30

Asn Tyr Val Ser Trp Tyr Gln Gln His Pro Gly Lys Ala Pro Lys Leu
35 40 45

Met Ile Tyr Asp Val Ser Asn Arg Pro Ser Gly Ile Ser Asn Arg Phe
50 55 60

Ser Gly Ser Lys Ser Gly Asn Thr Ala Ser Leu Thr Ile Thr Gly Leu
65 70 75 80

Gln Ser Glu Asp Glu Ala Asp Tyr Tyr Cys Ser Gly Trp Asp Arg Ser
85 90 95

Leu Ser Ala Trp Val Val Gly Gly Xaa Thr Lys Leu Thr Val Leu
100 105 110

<210> SEQ ID NO 88
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 88

Gly Tyr Thr Phe Ser Thr Tyr Ala
1 5

<210> SEQ ID NO 89
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 89

Gly Tyr Thr Tyr Thr Ser Tyr Gly
1 5

<210> SEQ ID NO 90
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 90

Gly Tyr Thr Phe Ser Asn Tyr Asp
1 5

<210> SEQ ID NO 91
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 91

Gln Ser Val Gly Ser Asn
1 5

<210> SEQ ID NO 92
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 92

Ser Asn Asn Val Gly His Glu Gly
1 5

<210> SEQ ID NO 93
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 93

Ser Ser Asp Val Gly Gly Tyr Asn Arg
1 5

<210> SEQ ID NO 94
<211> LENGTH: 6
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (1)..(1)
<223> OTHER INFORMATION: Any amino acid

<400> SEQUENCE: 94

Xaa Ile Val Arg Arg Asn
1 5

<210> SEQ ID NO 95
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 95

Ser Ser Asp Phe Gly Gly Tyr Asn Tyr
1 5

<210> SEQ ID NO 96
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 96

Ile Ser Trp Asn Ser Gly Ser Ile
1 5

<210> SEQ ID NO 97
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 97

Ile Ser Trp Asn Ser Asn Asn Ile
1 5

<210> SEQ ID NO 98
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 98

Ile Ser Ala Tyr Asn Gly Asn Thr
1 5

<210> SEQ ID NO 99
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 99

Ile Ser Gly Tyr Asn Gly Asn Thr
1 5

<210> SEQ ID NO 100
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 100

Ile Ser Gln Asn Ser Gly Ser Ile
1 5

<210> SEQ ID NO 101
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 101

Met Asn Pro Asn Ser Gly Asn Thr
1 5

<210> SEQ ID NO 102
<211> LENGTH: 8
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (5)..(5)
<223> OTHER INFORMATION: Any amino acid

<400> SEQUENCE: 102

Ile Ser Trp Asn Xaa Asn Asn Ile
1               5

<210> SEQ ID NO 103
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 103

Ile Ser Thr Tyr Asn Gly Asn Thr
1               5

<210> SEQ ID NO 104
<211> LENGTH: 18
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 104

Ala Lys Asp Ile Gly Ser Gly Ser Tyr Tyr Asn Tyr Tyr Tyr Gly Met
1               5                   10                  15

Asp Val

<210> SEQ ID NO 105
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 105

Ala Lys Asp Met Gly Ser Gly Tyr Asp Trp Tyr Tyr Tyr Gly Met Asp
1               5                   10                  15

Val

<210> SEQ ID NO 106
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 106

Ala Arg Val Ser Pro Gly Tyr Tyr Asp Ser Ser Gly Gln Gly Thr Asp
1               5                   10                  15

Ala

<210> SEQ ID NO 107
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 107

Ala Lys Asp Ile Ser Ser Gly Trp Tyr Pro Asp Ala
1 5 10

<210> SEQ ID NO 108
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 108

Ala Arg Asp Pro His Leu Ser Ser Gly Trp Tyr Lys Gly Asn Gly Met
1 5 10 15

Asp Val

<210> SEQ ID NO 109
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 109

Ala Lys Asp Ile Ser Ser Gly Trp Tyr Pro Asp Ala Phe Asp Ile
1 5 10 15

<210> SEQ ID NO 110
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 110

Ala Arg Asp Gly Val Gly Ala Ala Phe Asp Tyr
1 5 10

<210> SEQ ID NO 111
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 111

Ala Arg Asp Pro His Leu Ser Ser Gly Trp Cys Lys Gly Asn Gly Met
1 5 10 15

Asp Val

<210> SEQ ID NO 112
<211> LENGTH: 18
<212> TYPE: PRT

<213> ORGANISM: Artificial Sequence
<220> FEATURE:
<223> OTHER INFORMATION: Description of Artificial Sequence: Synthetic
peptide

<400> SEQUENCE: 112

Ala Arg Asp Pro His Val Ser Ser Gly Trp Tyr Lys Gly Asn Gly Met
1 5 10 15

Asp Val

<210> SEQ ID NO 113
<211> LENGTH: 18
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 113

Ala Arg Asp Gly Gly Tyr Cys Asp Ser Thr Gly Cys Tyr Asp Ala Leu
1 5 10 15

Asp Ile

<210> SEQ ID NO 114
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 114

Ala Arg Glu Ile Arg Gly Ala Phe Asp Ile
1 5 10

<210> SEQ ID NO 115
<211> LENGTH: 20
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 115

Ala Arg Val Ser Pro Gly Tyr Tyr Asp Ser Ser Gly Gln Gly Thr Asp
1 5 10 15

Ala Phe Asp Ile
20

<210> SEQ ID NO 116
<211> LENGTH: 20
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 116

Ala Lys Val Ser Pro Gly Tyr Tyr Asp Ser Ser Gly Gln Gly Thr Asp
1 5 10 15

Ala Phe Asp Ile
20

<210> SEQ ID NO 117
<211> LENGTH: 12

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 117

Ala Arg Asp Arg Ala Thr Ile Asp Ala Phe Asp Ile
1 5 10

<210> SEQ ID NO 118
<211> LENGTH: 18
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 118

Asn Ser Arg Asp Arg Tyr Gly Asn Ser Leu Val Ile Phe Gly Gly Gly
1 5 10 15

Thr Lys

<210> SEQ ID NO 119
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 119

Asn Ser Arg Asp Ser Ser Gly Asn His Leu Val Phe Gly Gly Gly Thr
1 5 10 15

Lys

<210> SEQ ID NO 120
<211> LENGTH: 19
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 120

Gln Gln Tyr Gly Ser Ser Pro Arg Thr Phe Gly Gln Gly Thr Lys Val
1 5 10 15

Glu Ile Lys

<210> SEQ ID NO 121
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 121

Asn Ser Arg Asp Phe Ser Gly Leu Gln Leu Val Phe Gly Gly Gly Thr
1 5 10 15

Arg

<210> SEQ ID NO 122
<211> LENGTH: 17
<212> TYPE: PRT

<213> ORGANISM: Artificial Sequence
<220> FEATURE:
<223> OTHER INFORMATION: Description of Artificial Sequence: Synthetic
peptide

<400> SEQUENCE: 122

Asn Ser Arg Asp Ser Ser Gly Asn Pro Val Val Phe Gly Gly Gly Thr
1 5 10 15

Lys

<210> SEQ ID NO 123
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 123

Asn Ser Arg Asp Arg Tyr Gly Asn Pro Leu Val Ile
1 5 10

<210> SEQ ID NO 124
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 124

Asn Ser Arg Asp Phe Ser Gly Leu Gln Leu Val
1 5 10

<210> SEQ ID NO 125
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 125

Asn Ser Arg Asp Ser Ser Gly Asn His Leu Val
1 5 10

<210> SEQ ID NO 126
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 126

Gln Gln Arg Ser Asn Trp Pro Pro Thr
1 5

<210> SEQ ID NO 127
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 127

Asn Ser Arg Asp Ser Ser Gly Asn Pro Val Val
1 5 10

<210> SEQ ID NO 128
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 128

Ala Thr Trp Asp Gly Ser Leu Arg Gly Trp Val
1 5 10

<210> SEQ ID NO 129
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 129

Ser Ser Tyr Thr Ser Ser Ser Thr Arg Val
1 5 10

<210> SEQ ID NO 130
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 130

Gln Gln Tyr Gly Ser Ser Pro Arg Thr
1 5

<210> SEQ ID NO 131
<211> LENGTH: 8
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (8)..(8)
<223> OTHER INFORMATION: Any amino acid

<400> SEQUENCE: 131

Xaa Ser Met Val Xaa His Leu Xaa
1 5

<210> SEQ ID NO 132
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 132

Ser Gly Trp Asp Arg Ser Leu Ser Ala Trp Val
1 5 10

<210> SEQ ID NO 133
<211> LENGTH: 4
<212> TYPE: PRT
<213> ORGANISM: Homo sapiens

<400> SEQUENCE: 133

Cys Pro Ser Cys
1

<210> SEQ ID NO 134
<211> LENGTH: 4
<212> TYPE: PRT
<213> ORGANISM: Homo sapiens

<400> SEQUENCE: 134

Cys Pro Pro Cys
1

<210> SEQ ID NO 135
<211> LENGTH: 124
<212> TYPE: PRT
<213> ORGANISM: Homo sapiens

<400> SEQUENCE: 135

Glu Val Gln Leu Val Glu Ser Gly Gly Gly Leu Val Gln Pro Gly Arg
1 5 10 15

Ser Leu Arg Leu Ser Cys Ala Ala Ser Gly Phe Thr Phe Asp Asp Tyr
20 25 30

Ala Met His Trp Val Arg Gln Ala Pro Gly Lys Gly Leu Glu Trp Val
35 40 45

Ser Gly Ile Ser Trp Asn Ser Gly Ser Ile Gly Tyr Ala Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Leu Tyr Tyr Cys
85 90 95

Ala Lys Asp Gly Ser Gly Ser Tyr Tyr Tyr Tyr Tyr Tyr Gly Met Asp
100 105 110

Val Trp Gly Gln Gly Thr Thr Val Thr Val Ser Ser
115 120

<210> SEQ ID NO 136
<211> LENGTH: 124
<212> TYPE: PRT
<213> ORGANISM: Homo sapiens

<400> SEQUENCE: 136

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Ser Tyr
20 25 30

Gly Ile Ser Trp Val Arg Gln Ala Pro Gly Gln Gly Leu Glu Trp Met
35 40 45

Gly Trp Ile Ser Ala Tyr Asn Gly Asn Thr Asn Tyr Ala Gln Lys Leu
50 55 60

Gln Gly Arg Val Thr Met Thr Thr Asp Thr Ser Thr Ser Thr Ala Tyr
65 70 75 80

Met Glu Leu Arg Ser Leu Arg Ser Asp Asp Thr Ala Val Tyr Tyr Cys
85 90 95

Ala Arg Pro His Leu Ser Ser Asp Tyr Tyr Tyr Tyr Tyr Gly Met Asp
100 105 110

Val Trp Gly Gln Gly Thr Thr Val Thr Val Ser Ser
115 120

<210> SEQ ID NO 137
<211> LENGTH: 108
<212> TYPE: PRT
<213> ORGANISM: Homo sapiens

<400> SEQUENCE: 137

Ser Ser Glu Leu Thr Gln Asp Pro Ala Val Ser Val Ala Leu Gly Gln
1 5 10 15

Thr Val Arg Ile Thr Cys Gln Gly Asp Ser Leu Arg Ser Tyr Tyr Ala
20 25 30

Ser Trp Tyr Gln Gln Lys Pro Gly Gln Ala Pro Val Leu Val Ile Tyr
35 40 45

Gly Lys Asn Asn Arg Pro Ser Gly Ile Pro Asp Arg Phe Ser Gly Ser
50 55 60

Ser Ser Gly Asn Thr Ala Ser Leu Thr Ile Thr Gly Ala Gln Ala Glu
65 70 75 80

Asp Glu Ala Asp Tyr Tyr Cys Asn Ser Arg Asp Ser Ser Gly Asn His
85 90 95

Val Ile Phe Gly Gly Gly Thr Lys Leu Thr Val Leu
100 105

<210> SEQ ID NO 138
<211> LENGTH: 107
<212> TYPE: PRT
<213> ORGANISM: Homo sapiens

<400> SEQUENCE: 138

Glu Ile Val Leu Thr Gln Ser Pro Gly Thr Leu Ser Leu Ser Pro Gly
1 5 10 15

Glu Arg Ala Thr Leu Ser Cys Arg Ala Ser Gln Ser Val Ser Ser Ser
20 25 30

Tyr Leu Ala Trp Tyr Gln Gln Lys Pro Gly Gln Ala Pro Arg Leu Leu
35 40 45

Ile Tyr Gly Ala Ser Ser Arg Ala Thr Gly Ile Pro Asp Arg Phe Ser
50 55 60

Gly Ser Gly Ser Gly Thr Asp Phe Thr Leu Thr Ile Ser Arg Leu Glu
65 70 75 80

Pro Glu Asp Phe Ala Val Tyr Tyr Cys Gln Gln Tyr Gly Ser Ser Pro
85 90 95

Thr Phe Gly Gln Gly Thr Lys Val Glu Ile Lys
100 105

<210> SEQ ID NO 139
<211> LENGTH: 117
<212> TYPE: PRT
<213> ORGANISM: Homo sapiens

<400> SEQUENCE: 139

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Val Gly Asp Tyr Phe Asp Tyr Trp Gly Gln Gly Thr Leu
            100                 105                 110

Val Thr Val Ser Ser
        115


<210> SEQ ID NO 140
<211> LENGTH: 119
<212> TYPE: PRT
<213> ORGANISM: Homo sapiens

<400> SEQUENCE: 140

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Tyr Tyr Arg Asn Asn Trp Phe Asp Ser Trp Gly Gln Gly
            100                 105                 110

Thr Leu Val Thr Val Ser Ser
        115


<210> SEQ ID NO 141
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 141

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Ser Asn Phe
            20                  25                  30

Trp Met Asn Trp Val Arg Gln Ala Pro Gly Gln Gly Leu Glu Trp Met
        35                  40                  45

Gly Gln Ile Tyr Pro Gly Asp Gly Asp Thr Asn Tyr Asn Gly Lys Phe
    50                  55                  60
```

```
Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Tyr Tyr Arg Ser Ala Trp Phe Ala Tyr Trp Gly Gln Gly
            100                 105                 110

Thr Leu Val Thr Val Ser Ser
        115


<210> SEQ ID NO 142
<211> LENGTH: 95
<212> TYPE: PRT
<213> ORGANISM: Homo sapiens

<400> SEQUENCE: 142

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro
                85                  90                  95


<210> SEQ ID NO 143
<211> LENGTH: 77
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 143

Glu Thr Thr Leu Thr Gln Ser Pro Ala Thr Leu Ser Val Ser Pro Gly
1               5                   10                  15

Glu Arg Ala Thr Leu Ser Cys Arg Ala Ser Gln Ser Val Gly Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser
65                  70                  75


<210> SEQ ID NO 144
<211> LENGTH: 107
<212> TYPE: PRT
<213> ORGANISM: Homo sapiens

<400> SEQUENCE: 144

Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Gly Ser Ser
            20                  25                  30

Leu His Trp Tyr Gln Gln Lys Pro Asp Gln Ser Pro Lys Leu Leu Ile
```

```
        35                  40                  45

Lys Tyr Ala Ser Gln Ser Ile Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys His Gln Ser Ser Ser Leu Pro Trp
                85                  90                  95

Thr Phe Gly Gln Gly Thr Lys Val Glu Ile Lys
            100                 105


<210> SEQ ID NO 145
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 145

Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Gly Thr Ser
            20                  25                  30

Ile His Trp Tyr Gln Gln Lys Pro Asp Gln Ser Pro Lys Leu Leu Ile
        35                  40                  45

Lys Tyr Ala Ser Glu Ser Ile Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Ser Asn Asn Trp Pro Leu
                85                  90                  95

Thr Phe Gly Gln Gly Thr Lys Val Glu Ile Lys
            100                 105


<210> SEQ ID NO 146
<211> LENGTH: 28
<212> TYPE: PRT
<213> ORGANISM: Homo sapiens

<400> SEQUENCE: 146

Ala Lys Asp Gly Ser Gly Ser Tyr Tyr Tyr Tyr Tyr Tyr Gly Met Asp
1               5                   10                  15

Val Trp Gly Gln Gly Thr Thr Val Thr Val Ser Ser
            20                  25


<210> SEQ ID NO 147
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Ala Lys Asp Ile Gly Ser Gly Ser Tyr Tyr Asn Tyr Tyr Tyr Gly Met
1               5                   10                  15

Asp Val Trp Gly Gln Gly Thr Thr Ala Thr Ile Ser Ser
            20                  25


<210> SEQ ID NO 148
```

<211> LENGTH: 28
<212> TYPE: PRT
<213> ORGANISM: Artificial Sequence
<220> FEATURE:
<223> OTHER INFORMATION: Description of Artificial Sequence: Synthetic peptide

<400> SEQUENCE: 148

Ala Lys Asp Met Gly Ser Gly Tyr Asp Trp Tyr Tyr Tyr Gly Met Asp
1 5 10 15

Val Trp Gly Gln Gly Thr Thr Val Thr Val Ser Ser
20 25

<210> SEQ ID NO 149
<211> LENGTH: 26
<212> TYPE: PRT
<213> ORGANISM: Artificial Sequence
<220> FEATURE:
<223> OTHER INFORMATION: Description of Artificial Sequence: Synthetic peptide

<400> SEQUENCE: 149

Ala Lys Asp Ile Ser Ser Gly Trp Tyr Pro Asp Ala Phe Asp Ile Trp
1 5 10 15

Gly Gln Gly Thr Leu Val Thr Val Ser Ser
20 25

<210> SEQ ID NO 150
<211> LENGTH: 31
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 150

Ala Arg Val Ser Pro Gly Tyr Tyr Asp Ser Ser Gly Gln Gly Thr Asp
1 5 10 15

Ala Phe Asp Ile Trp Gly Gln Gly Thr Thr Val Thr Val Ser Ser
20 25 30

<210> SEQ ID NO 151
<211> LENGTH: 28
<212> TYPE: PRT
<213> ORGANISM: Homo sapiens

<400> SEQUENCE: 151

Ala Arg Pro His Leu Ser Ser Asp Tyr Tyr Tyr Tyr Tyr Gly Met Asp
1 5 10 15

Val Trp Gly Gln Gly Thr Thr Val Thr Val Ser Ser
20 25

<210> SEQ ID NO 152
<211> LENGTH: 29
<212> TYPE: PRT
<213> ORGANISM: Artificial Sequence
<220> FEATURE:
<223> OTHER INFORMATION: Description of Artificial Sequence: Synthetic peptide

<400> SEQUENCE: 152

Ala Arg Asp Pro His Leu Ser Ser Gly Trp Tyr Lys Gly Asn Gly Met
1 5 10 15

Asp Val Trp Gly Gln Gly Thr Leu Val Thr Val Ser Ser
20 25

<210> SEQ ID NO 153
<211> LENGTH: 21
<212> TYPE: PRT
<213> ORGANISM: Homo sapiens

<400> SEQUENCE: 153

Asn Ser Arg Asp Ser Ser Gly Asn His Val Ile Phe Gly Gly Gly Thr
1 5 10 15

Lys Leu Thr Val Leu
20

<210> SEQ ID NO 154
<211> LENGTH: 22
<212> TYPE: PRT
<213> ORGANISM: Artificial Sequence
<220> FEATURE:
<223> OTHER INFORMATION: Description of Artificial Sequence: Synthetic peptide

<400> SEQUENCE: 154

Asn Ser Arg Asp Arg Tyr Gly Asn Ser Leu Val Ile Phe Gly Gly Gly
1 5 10 15

Thr Lys Leu Thr Val Leu
20

<210> SEQ ID NO 155
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 155

Asn Ser Arg Asp Ser Ser Gly Asn His Leu Val Phe Gly Gly Gly Thr
1 5 10 15

Lys Leu Thr Val Leu
20

<210> SEQ ID NO 156
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 156

Asn Ser Arg Asp Ser Ser Gly Asn Pro Val Val Phe Gly Gly Gly Thr
1 5 10 15

Lys Leu Thr Val Leu
20

<210> SEQ ID NO 157
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 157

Asn Ser Arg Asp Phe Ser Gly Leu Gln Leu Val Phe Gly Gly Gly Thr
1 5 10 15

Arg Leu Thr Val Leu
20

<210> SEQ ID NO 158
<211> LENGTH: 18
<212> TYPE: PRT
<213> ORGANISM: Homo sapiens

<400> SEQUENCE: 158

Gln Gln Tyr Gly Ser Ser Pro Thr Phe Gly Gln Gly Thr Lys Val Glu
1 5 10 15

Ile Lys

<210> SEQ ID NO 159
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 159

Gly Gly Gly Gly Ser Gly Gly Gly Gly Ser Gly Gly Gly Gly Ser
1 5 10 15

<210> SEQ ID NO 160
<211> LENGTH: 20
<212> TYPE: PRT
<213> ORGANISM: Artificial Sequence
<220> FEATURE:
<223> OTHER INFORMATION: Description of Artificial Sequence: Synthetic peptide

<400> SEQUENCE: 160

Thr Ala Pro Pro Ala His Gly Val Thr Ser Ala Pro Asp Thr Arg Pro
1 5 10 15

Ala Pro Gly Ser
20

<210> SEQ ID NO 161
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 161

Gly Val Val Val Ser
1 5

<210> SEQ ID NO 162
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 162

Arg Ala Lys Arg Ser Gly Ser Gly
1 5

<210> SEQ ID NO 163
<211> LENGTH: 20

```
<212> TYPE: PRT
<213> ORGANISM: Foot-and-mouth disease virus

<400> SEQUENCE: 163

Gln Leu Leu Asn Phe Asp Leu Leu Lys Leu Ala Gly Asp Val Glu Ser
1               5                   10                  15

Asn Pro Gly Pro
            20


<210> SEQ ID NO 164
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Leu Leu Asn Phe Asp Leu Leu Lys Leu Ala Gly Asp Val Glu Ser Asn
1               5                   10                  15

Pro Gly Pro


<210> SEQ ID NO 165
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

Leu Asn Phe Asp Leu Leu Lys Leu Ala Gly Asp Val Glu Ser Asn Pro
1               5                   10                  15

Gly Pro


<210> SEQ ID NO 166
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Asn Phe Asp Leu Leu Lys Leu Ala Gly Asp Val Glu Ser Asn Pro Gly
1               5                   10                  15

Pro


<210> SEQ ID NO 167
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

Phe Asp Leu Leu Lys Leu Ala Gly Asp Val Glu Ser Asn Pro Gly Pro
1               5                   10                  15


<210> SEQ ID NO 168
<211> LENGTH: 15
<212> TYPE: PRT
<213> ORGANISM: Artificial Sequence
<220> FEATURE:
```

<223> OTHER INFORMATION: Description of Artificial Sequence: Synthetic peptide

<400> SEQUENCE: 168

Asp Leu Leu Lys Leu Ala Gly Asp Val Glu Ser Asn Pro Gly Pro
1 5 10 15

<210> SEQ ID NO 169
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 169

Leu Leu Lys Leu Ala Gly Asp Val Glu Ser Asn Pro Gly Pro
1 5 10

<210> SEQ ID NO 170
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 170

Leu Lys Leu Ala Gly Asp Val Glu Ser Asn Pro Gly Pro
1 5 10

<210> SEQ ID NO 171
<211> LENGTH: 20
<212> TYPE: PRT
<213> ORGANISM: Artificial Sequence
<220> FEATURE:
<223> OTHER INFORMATION: Description of Artificial Sequence: Synthetic peptide

<400> SEQUENCE: 171

Gln Leu Leu Asn Phe Asp Leu Leu Lys Leu Ala Gly Asp Val Gln Ser
1 5 10 15

Asn Pro Gly Pro
20

<210> SEQ ID NO 172
<211> LENGTH: 20
<212> TYPE: PRT
<213> ORGANISM: Artificial Sequence
<220> FEATURE:
<223> OTHER INFORMATION: Description of Artificial Sequence: Synthetic peptide

<400> SEQUENCE: 172

Gln Leu Leu Asn Phe Asp Leu Leu Lys Leu Ala Gly Asp Val Glu Ile
1 5 10 15

Asn Pro Gly Pro
20

<210> SEQ ID NO 173
<211> LENGTH: 20
<212> TYPE: PRT
<213> ORGANISM: Artificial Sequence
<220> FEATURE:
<223> OTHER INFORMATION: Description of Artificial Sequence: Synthetic peptide

<400> SEQUENCE: 173

Gln Leu Leu Asn Phe Asp Leu Leu Lys Leu Ala Gly Asp Val Glu Ser
1 5 10 15

Glu Pro Gly Pro
20

<210> SEQ ID NO 174
<211> LENGTH: 20
<212> TYPE: PRT
<213> ORGANISM: Artificial Sequence
<220> FEATURE:
<223> OTHER INFORMATION: Description of Artificial Sequence: Synthetic peptide

<400> SEQUENCE: 174

Gln Leu Leu Asn Phe Asp Leu Leu Lys Leu Ala Gly Asp Val Glu Ser
1 5 10 15

Asn Pro Ala Pro
20

<210> SEQ ID NO 175
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 175

Gly Gly Gly Gly Gly Gly Gly
1 5

<210> SEQ ID NO 176
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 176

Gly Gly Gly Gly Gly
1 5

<210> SEQ ID NO 177
<211> LENGTH: 127
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (16)..(16)
<223> OTHER INFORMATION: Any amino acid
<220> FEATURE:
<221> NAME/KEY: MOD_RES
<222> LOCATION: (19)..(19)
<223> OTHER INFORMATION: Any amino acid
<220> FEATURE:
<221> NAME/KEY: MOD_RES
<222> LOCATION: (55)..(55)
<223> OTHER INFORMATION: Any amino acid

<400> SEQUENCE: 177

Gln Val Gln Leu Val Gln Ser Gly Gly Gly Phe Ile Gln Pro Gly Xaa
1 5 10 15

-continued

```
Ser Leu Xaa Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Cys Ile Ser Trp Asn Xaa Asn Asn Ile Gly Tyr Ala Asp Ser Val
    50                  55                  60

Lys Gly Gln Phe Thr Ile Ser Arg Lys Asn Ala Lys Asn Ser Leu Tyr
65                  70                  75                  80

Leu Gln Met Asn Ser Leu Lys Ala Glu Asp Thr Ala Val Tyr Tyr Cys
                85                  90                  95

Ala Lys Val Ser Pro Gly Tyr Tyr Asp Ser Ser Gly Gln Gly Thr Asp
            100                 105                 110

Ala Phe Asp Ile Trp Gly Gln Gly Thr Thr Val Thr Val Ser Ser
        115                 120                 125
```

ANTIBODIES AGAINST MUC1

This application is a national stage application under 35 U.S.C. section 371 of PCT/US2020/037783 filed Jun. 15, 2020, which claims priority from U.S. Provisional Patent Application No. 62/861,619, filed on Jun. 14, 2019, the contents of which are incorporated herein by reference in their entireties.

GOVERNMENT INTERESTS

This invention was made with government support under Grant No. CA207201 awarded by the National Institutes of Health. The government has certain rights in the invention.

All patents, patent applications and publications cited herein are hereby incorporated by reference in their entirety. The disclosures of these publications in their entireties are hereby incorporated by reference into this application in order to more fully describe the state of the art as known to those skilled therein as of the date of the invention described and claimed herein.

This patent disclosure contains material that is subject to copyright protection. The copyright owner has no objection to the facsimile reproduction by anyone of the patent document or the patent disclosure as it appears in the U.S. Patent and Trademark Office patent file or records, but otherwise reserves any and all copyright rights.

SEQUENCE LISTING

The instant application contains a Sequence Listing which has been submitted electronically in ASCII format and is hereby incorporated by reference in its entirety. Said ASCII copy, created on Jun. 6, 2025, is named 5031461-047-US2 SL.txt and is 105,359 bytes in size.

FIELD OF THE INVENTION

This invention is directed to antibodies against MUC1 and methods of use thereof.

BACKGROUND OF THE INVENTION

Mucins line the apical surface of epithelial cells in the lungs, stomach, intestines, eyes, and several other organs, where they protect the body from infection by preventing the pathogen from reaching the cell surface. Mucin 1 (MUC1) is a glycoprotein encoded by the MUC1 gene that serves its protective function by binding to pathogens.

SUMMARY OF THE INVENTION

The present invention provides an isolated monoclonal antibody or antigen-binding fragment thereof that binds to a peptide corresponding to the MUC1-SEA domain (SEQ ID NO: 1) or an epitope thereon.

In embodiments, the antibody comprises a VH, wherein the VH corresponds to one or more amino acid sequences of SEQ ID NO: 12, 13, 14, 15, 16 or a portion thereof.

In embodiments, the antibody comprises a VL, wherein the VL corresponds to one or more amino acid sequence of SEQ ID NO: 17, 18, 19, 20, 21 or a portion(s).

In embodiments, the antibody comprises a VH and a VL, wherein the VH corresponds to one or more amino acid sequences of SEQ ID NO: 12, 13, 14, 15, 16 or a portion thereof, and wherein the VL corresponds to one or more amino acid sequence of SEQ ID NO: 17, 18, 19, 20, 21 or a portion(s), or any combination thereof.

In embodiments, the antibody comprises one or more of the amino acid sequences as described in Table 1. For example, the antibody comprises one or more of the CDRs described in Table 1. For example, the antibody can correspond to clone T4E3, G2-2-F8, G1-3-A3, G1-2-B10, G1-1-A1, or G3-1-D6.

In embodiments, the CDR3 of the antibody comprises one or more of: the amino acid sequence GMDV at the end of VH-CDR3, a VH-CDR3 that is 15-20 amino acids, has a single amino acid insertion at the 3' end of VL CDR3, or any combination thereof.

In embodiments, the antibody can be humanized or fully human.

In embodiments, the antibody can be monospecific, bispecific, trispecific, or multispecific.

In embodiments, the antibody can be a full chain antibody, a single chain antibody, or an Fab fragment antibody.

In embodiments, the antibody has a binding affinity within the range of 1 pM to 1 μM.

In embodiments, the antibody of according to any one of the preceding claims linked to a therapeutic agent. For example, the therapeutic agent can be a toxin, a radiolabel, a siRNA, a small molecule, or a cytokine. In a non-limiting example, the therapeutic agent is MMAE.

In embodiments, the antibody can be produced by a cell.

In embodiments, the antibody can be provided in a pharmaceutical composition comprising the antibody and a pharmaceutically acceptable excipient.

The present invention further provides a cell producing an antibody as described herein.

Still further, the present invention provides a pharmaceutical composition comprising an antibody described herein and a pharmaceutically acceptable excipient.

The present invention also provides a nucleic acid encoding an antibody described herein. For example, the nucleic acid encodes an isolated monoclonal antibody or antigen-binding fragment thereof that binds to a peptide corresponding to the MUC1-SEA domain (SEQ ID NO: 1) or an epitope thereon. For example, the nucleic acid comprises one or more nucleotide sequences according to SEQ ID NO: 23-32, a portion thereof, or any combination thereof.

In embodiments, the nucleic acid can be provided in a vector.

Also provided herein is a vector comprising a nucleic acid described herein.

In embodiments, the vector can be provided in a cell.

The present invention provides a cell comprising a vector described herein.

The cell can be provided in a pharmaceutical composition. For example, the pharmaceutical composition can comprise the cell and a pharmaceutically acceptable excipient.

Still further, the present invention provides a chimeric antigen receptor (CAR) comprising an antibody described herein or an antigen-binding fragment thereof. In embodiments, the antigen-binding fragment of the CAR comprises an scFv or a Fab.

In embodiments, the CAR comprises a bispecific CAR, a dual-targeted CAR, a tri-specific CAR, or a multi-specific CAR.

In embodiments, the CAR can be provided in an engineered cell, such as an engineered T cell.

In embodiments, the CAR is encoded by a nucleic acid.

Aspects of the invention are also drawn to a nucleic acid encoding a chimeric antigen receptor, such as a CAR described herein.

Aspects of the invention are also drawn to a cell comprising a chimeric antigen receptor, such as the chimeric antigen receptor described herein. In embodiments, the cell comprises a T cell.

In embodiments, the cell can be further engineered to secrete an antibody or fragment thereof. For example, the secreted antibody comprises a monoclonal antibody.

In embodiments, the secreted antibody comprises a monospecific antibody, a bispecific antibody, a trispecific antibody, or a multispecific antibody.

In embodiments, the secreted antibody comprises an immune checkpoint blockade antibody. For example, the secreted antibody can modulate the immune system of a subject.

Aspects of the invention are also drawn to a pharmaceutical composition a CAR T cell, such as a CAR T cell described herein, and a pharmaceutically acceptable excipient.

In embodiments, the engineered T-cell comprises a nucleic acid encoding a chimeric antigen receptor (CAR), wherein the chimeric antigen receptor is specific for MUC1-SEA domain.

In embodiments, the CAR of the engineered cell, such as an engineered T-cell, comprises an scFv or a Fab.

In embodiments, the CAR of the engineered cell, such as an engineered T-cell, comprises a mono-specific CAR, a bi-specific CAR, a tri-specific CAR, or a multi-specific CAR.

In embodiments, the engineered cell can comprise a nucleic acid that encodes the chimeric antigen receptor and, optionally, further encodes a polypeptide, wherein the polypeptide comprises an antibody of fragment thereof that can be secreted from the engineered cell.

The present invention is also drawn to a pharmaceutical composition comprising the engineered T-cell as described herein and a pharmaceutically acceptable excipient.

Aspects of the invention are also drawn towards methods for treating a subject afflicted with cancer. In embodiments, the method comprises administering to the subject afflicted with cancer a composition comprising an antibody or cell as described herein. In exemplary embodiments, the cancer comprises a cancer cell that expresses MUC1, mesothelin, and/or other tumor associated antigens. In embodiments, the antibody or cell induces apoptosis of the cancer cell, such as the MUC1-expressing cancer cell.

In embodiments, the cancer comprises an epithelial cancer. Non-limiting examples of an epithelial cancer that can be treated by aspects of the invention comprise breast cancer, basal cell carcinoma, adenocarcinoma, gastrointestinal cancer, lip cancer, mouth cancer, esophageal cancer, small bowel cancer and stomach cancer, colon cancer, liver cancer, bladder cancer, pancreas cancer, ovary cancer, cervical cancer, lung cancer, breast cancer and skin cancer, such as squamous cell and basal cell cancers, prostate cancer, renal cell carcinoma, and other known cancers that effect epithelial cells throughout the body.

In embodiments, the method can further comprise administering to said subject a chemotherapeutic agent.

In embodiments, the method can further comprise a step of selecting a subject with a MUC1-expressing cancer.

Still further, aspects of the invention are drawn towards a method for inducing apoptosis of a cancer cell. For example, the method comprises contacting the cancer cell with an antibody or a CAR as described herein.

In embodiments, the cancer cell contains on its surface MUC1-SEA.

Other objects and advantages of this invention will become readily apparent from the ensuing description.

BRIEF DESCRIPTION OF THE FIGURES

FIG. 3 shows T4E3 tumor cell killing experimental design. Cancer cells are plated at 3000 per well in 200 μL of RPMI-1640+10% FBS+20 mM HEPES. They are spun down for 5 minutes at 300 g and subsequently imaged on the Celigo imaging cytometer. 100 μL of media is removed from each of the wells, and T cells are added at E:T ratios of 10:1 or 2:1 according to the plate map below. Because of lack of T4E3 cells, T4E3 was only added to two wells of COV362 and one well of HCT116-v at the specified E:T ratios. IL-21 (30 ng/mL) was also added to the cultures to ensure T cell longevity. Immediately after addition of T cells, plates were imaged. Plates were also imaged 7 hours, 22 hours, and 42 hours after T cell addition. Included herein are plate maps where Xs indicate the wells that receive the indicated CAR T cells.

FIG. 7 shows genetic assignments.

FIG. 9 shows alignment of anti-MUC1 antibody amino acid sequences (SEQ ID NOS 135, 12, 13, 15, 14, 136, 16, 137, 17, 18, 21, 20, 138, 19, 139, 48, and 140-145, respectively, in order of appearance).

FIG. 10 shows analysis of anti-MUC1 antibody CDR3 regions. Figure discloses SEQ ID NOS 146-158, and 120, respectively, in order of appearance.

FIG. 12 shows treatments for epithelial ovarian cancer.

FIG. 26 shows MUC1 panning summary.

FIG. 29 shows alignment of FR1-CDR2. Figure discloses FR1-CDR2 of SEQ ID NOS 135, 12, 13, 15, 14, 136, 16, 137, 17, 18, 21, 20, 138, and 19, respectively, in order of appearance.

FIG. 30 shows alignment of FR3-FR4. Figure discloses FR3-FR4 of SEQ ID NOS 135, 12, 13, 15, 14, 136, 16, 137, 17, 18, 21, 20, 138, and 19, respectively, in order of appearance.

FIG. 41 shows mAb2-3 Fab and 3D1 Fabs cloned into Medi8852 Fab F105 construct and evaluated by flow cytometry for binding and expression. Each value represents the average of three replicates.

FIG. 51(A) and FIG. 51(B) show amino acid sequences of anti-MUC1 antibodies. Figures disclose SEQ ID NOS 47, 15, 13, 48-57, 73, 20, 18, and 74-83, respectively, in order of appearance.

FIG. 52(A) through FIG. 52(D) show nucleotide sequences of anti-MUC1 antibodies. Figure discloses SEQ ID NOS 35, 36, 24, 37-46, and 60-72, respectively, in order of appearance.

FIG. 53(A) through FIG. 53(C) show amino acid sequences of anti-MUC1 antibodies. Figure discloses SEQ ID NOS 16, 58, 51, 14, 48, 177, 59, 21, 84, 85, 19, 74, 86, and 87, respectively, in order of appearance.

DETAILED DESCRIPTION OF THE INVENTION

Figure 1:
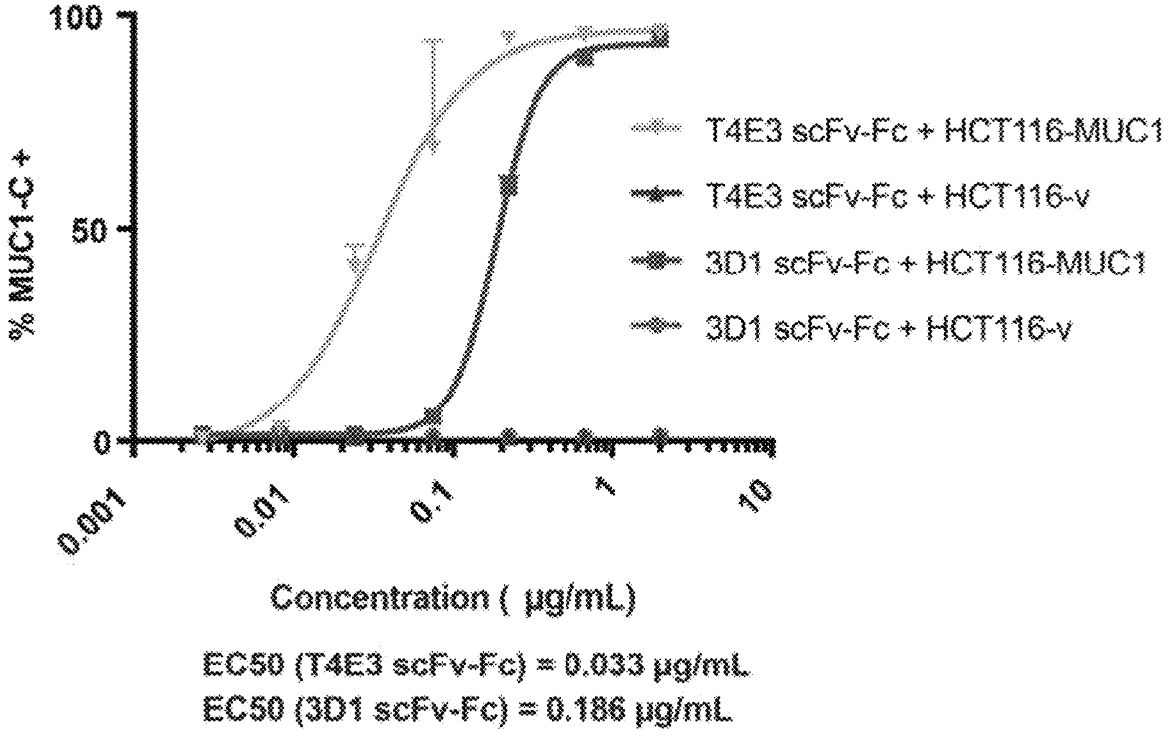
FIG. 1 shows dose response curves of two anti-MUC1-C scFv-Fcs. T4E3 scFv-Fc exhibits a 6-fold lower EC50 than 3D1 scFv-Fc. Dose response curves were generated by incubating serial dilutions of scFv-Fcs with HCT116-MUC1 (MUC1-C+) or HCT116-v (MUC1−) colon carcinoma cell lines followed by incubation with a secondary anti-human Fc-FITC antibody, and detecting binding by flow cytometry.

MUC1 is a member of the mucin family and encodes a membrane bound, glycosylated phosphoprotein. MUC1 is a heterodimeric protein complex that is encoded by a single transcript. MUC1 has a core protein mass of 120-225 kDa which increases to 250-500 kDa with glycosylation. It extends 200-500 nm beyond the surface of the cell. The protein is anchored to the apical surface of many epithelia by a transmembrane domain. Beyond the transmembrane domain is a SEA domain that contains a cleavage site for release of the large extracellular domain.

Following translation, the MUC1 polypeptide precursor undergoes autocleavage into two subunits that, in turn, form a stable noncovalent complex. The large MUC1 N-terminal subunit, designated MUC1-N, is the mucin component of the MUC1 dimer with the characteristic variable number of tandem repeats that are extensively decorated with O-linked glycans. MUC1-N extends well beyond the glycocalyx of the cell and is tethered to the cell surface through its association with the transmembrane MUC1 C-terminal subunit (MUC1-C). MUC1-N thereby contributes to a physical barrier that protects the epithelial cell layer from exposure to toxins, microorganisms and other forms of stress from the external environment. See Kufe, Donald W. "Targeting the human MUC1 oncoprotein: a tale of two proteins." *Cancer biology & therapy* 7.1 (2008): 81-84.

MUC1-C has a 58 amino acid extracellular domain, a 28 amino acid transmembrane domain and a 72 amino acid cytoplasmic tail. MUC1-C is involved in intracellular signaling. MUC1-C functions as an oncoprotein, especially considering the findings that MUC1-C is involved in diverse signaling pathways that have been linked to tumorigenesis. In this context, overexpression of MUC1-C blocks induction of apoptosis in the response to DNA damage, oxidative stress, and hypoxia. Overexpression of MUC1-C has been shown to confer anchorage-independent growth and tumorigenicity. MUC1-C stabilizes β-catenin and the interaction between MUC1-C and β-catenin contributes in part to MUC1-induced transformation. MUC1-C also confers constitutive activation of the anti-apoptotic IKKD→NFκB pathway as found in diverse carcinomas and hematopoietic malignancies. Importantly, overexpression of the MUC1-C cytoplasmic domain is sufficient for inducing anchorage-independent growth and tumorigenicity, indicating that the shed MUC1-N mucin subunit is dispensable for transformation. See Kufe, Donald W. "Targeting the human MUC1 oncoprotein: a tale of two proteins." *Cancer biology & therapy* 7.1 (2008): 81-84.

MUC1 overexpression and aberrant glycosylation have been associated with many cancers, including human carcinomas and hematologic malignancies. See, for example, Sritama and Mukherjee. "*MUC1: a multifaceted oncoprotein with a key role in cancer progression.*" *Trends in molecular medicine* 20.6 (2014): 332-342. The ability of chemotherapeutic drugs to access the cancer cells is inhibited by the heavy glycosylation in the extracellular domain of MUC1. The glycosylation creates a highly hydrophilic region which prevents hydrophobic chemotherapeutic drugs from passing through. This prevents the drugs from reaching their targets which usually reside within the cell. Similarly, the glycosylation has been shown to bind to growth factors. This allows cancer cells which produce a large amount of MUC1 to concentrate growth factors near their receptors, increasing receptor activity and the growth of cancer cells. MUC1 also prevents the interaction of immune cells with receptors on the cancer cell surface through steric hindrance. This inhibits an anti-tumor immune response.

MUC1 is cleaved within the SEA domain soon after synthesis. The SEA domain is a highly conserved domain of 120 amino acids. Cleavage of MUC1 within the SEA domain yields 2 unequal chains: a large extracellular N terminal domain containing the tandem repeat array specifically bound in a strong noncovalent interaction to a smaller C terminal domain containing the transmembrane and cytoplasmic domains of the molecule. The occurrence of MUC1 cleavage can render the target problematic to some degree, as the shed component can sequester many anti-MUC1 antibodies. For example, the shed domain has been shown to sequester circulating antitandem repeat antibodies, limiting their ability to reach MUC1+ tumor cells. However, a region termed the SEA domain remains tethered to the cell surface after MUC1 cleavage. The MUC1 SEA domain is formed by the interaction of the N-terminal subunit with the extracellular portion of C-terminal subunit following cleavage, and thus remains fixed to the cell surface. Significantly, the SEA domain comprises a stable target structure for anti-cancer antibodies.

Aspects of the invention are directed towards the discovery of monoclonal antibodies and fragments thereof that recognize human MUC1-SEA. For example, embodiments can comprise fully human or humanized antibodies that recognize MUC1-SEA, but can also comprise antibody fragments, such as human single chain variable fragments (scFv). In the scFv-Fc format, for example, MUC1-SEA scFv T4E3 binds to MUC1+ cells with six-fold higher affinity than anti-MUC1-C antibody 3D1. The skilled artisan will recognize that the antibodies can be utilized in various forms and fashions, including in CAR T cells and CAR T factories, or as bispecific antibodies. When T4E3 is utilized as the targeting moiety of a CAR T cell, T4E3 CAR T cells preferentially kill MUC1+ tumor cells and do not kill MUC1− cells. Activated T cells from the same human white blood cell donor and CAR T cells that recognize CXCR4, do not kill either the MUC1+ or MUC1− tumor cell lines, which lack CXCR4.

Detailed descriptions of one or more preferred embodiments are provided herein. It is to be understood, however, that the present invention may be embodied in various forms. Therefore, specific details disclosed herein are not to be interpreted as limiting, but rather as a basis for the claims and as a representative basis for teaching one skilled in the art to employ the present invention in any appropriate manner.

Abbreviations and Definitions

The singular forms “a”, “an” and “the” include plural reference unless the context clearly dictates otherwise. The use of the word “a” or “an” when used in conjunction with the term “comprising” in the claims and/or the specification may mean “one,” but it is also consistent with the meaning of “one or more,” “at least one,” and “one or more than one.”

Wherever any of the phrases “for example,” “such as,” “including” and the like are used herein, the phrase “and without limitation” is understood to follow unless explicitly stated otherwise. Similarly, “an example,” “exemplary” and the like are understood to be nonlimiting.

The term “substantially” allows for deviations from the descriptor that do not negatively impact the intended purpose. Descriptive terms are understood to be modified by the term “substantially” even if the word “substantially” is not explicitly recited.

The terms “comprising” and “including” and “having” and “involving” (and similarly “comprises”, “includes,” “has,” and “involves”) and the like are used interchangeably and have the same meaning. Specifically, each of the terms is defined consistent with the common United States patent law definition of “comprising” and is therefore interpreted to be an open term meaning “at least the following,” and is also interpreted not to exclude additional features, limitations, aspects, etc. Thus, for example, “a process involving steps a, b, and c” means that the process includes at least steps a, b and c. Wherever the terms “a” or “an” are used, “one or more” is understood, unless such interpretation is nonsensical in context.

As used herein the term “about” is used herein to mean approximately, roughly, around, or in the region of. When the term “about” is used in conjunction with a numerical range, it modifies that range by extending the boundaries above and below the numerical values set forth. In general, the term “about” is used herein to modify a numerical value above and below the stated value by a variance of 20 percent up or down (higher or lower).

The MUC1 gene encodes a single polypeptide chain which, due to conformational stress, is autoproteolytically cleaved immediately after translation at the GSVVV motif (SEQ ID NO: 34) (see underline and bold below), located within the Sea urchin sperm protein enterokinase and agrin (SEA) domain, into two peptide fragments: the longer N-terminal subunit (MUC1-N) and the shorter C-terminal subunit (MUC1-C). Extracellularly, the two subunits remain associated through stable hydrogen bonds.

```
MUC1-SEA amino acid sequence
                                        (SEQ ID NO: 1)
MGSSHHHHHHSSGLVPRGSHMASMTGGQQMGRDPLSTGVSFFFLSFHISN

LQFNSSLEDPSTDYYQELQRDISEMFLQIYKQGGFLGLSNIKFRPGGGGG

SVVVQLTLAFREGTINVHDVETQFNQYKTEAASRYNLTISDVSVSDVPFP

FSAQSGAG

MUC1-SEA Nucleotide sequence
                                        (SEQ ID NO: 22)
ATGGGCAGCAGCCATCATCATCATCATCACAGCAGCGGCCTGGTGCCGCG

CGGCAGCCATATGGCTAGCATGACTGGTGGACAGCAAATGGGTCGGGATC

CGTTGTCTACTGGGGTCTCTTTCTTTTTCCTGTCTTTTNACATTTCAAAC

CTCCAGTTTAATTCCTCTCTGGAAGATCCCAGCACCGACTACTACCAAGA

GCTGCAGAGAGACATTTCTGAAATGTTTTTGCAGATTTATAAACAAGGGG

GTTTTCTGGGCCTCTCCAATATTAAGTTCAGGCCAGGAGGAGGAGGAGGA

TCTGTGGTGGTACAATTGACTCTGGCCTTCCGAGAAGGTACCATCAATGT

CCACGACGTGGAGACACAGTTCAATCAGTATAAAACGGAAGCAGCCTCTC

GATATAACCTGACGATCTCAGACGTCAGCGTGAGTGATGTGCCATTTCCT

TTCTCTGCCCAGTCTGGGGCTGGGTAA
```

Figure 8:
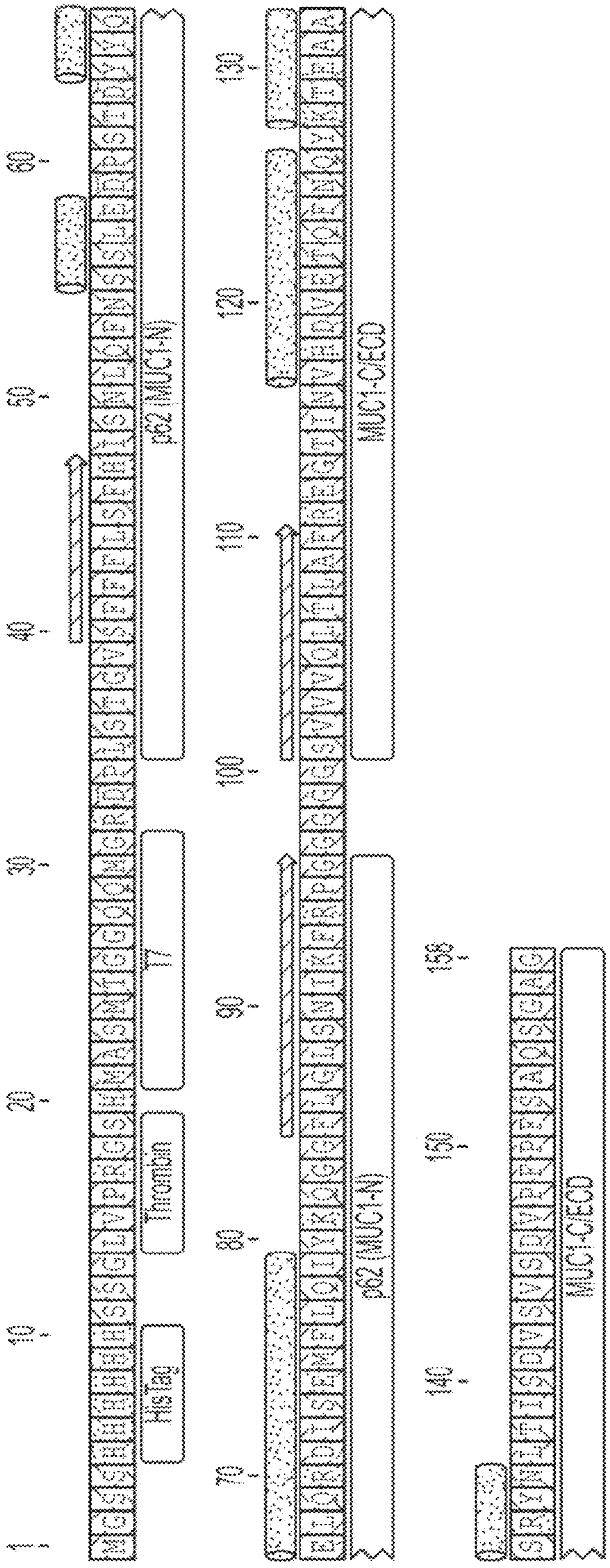
FIG. 8 shows annotated structure of MUC1-SEA (SEQ ID NO: 1).
Figure 11:
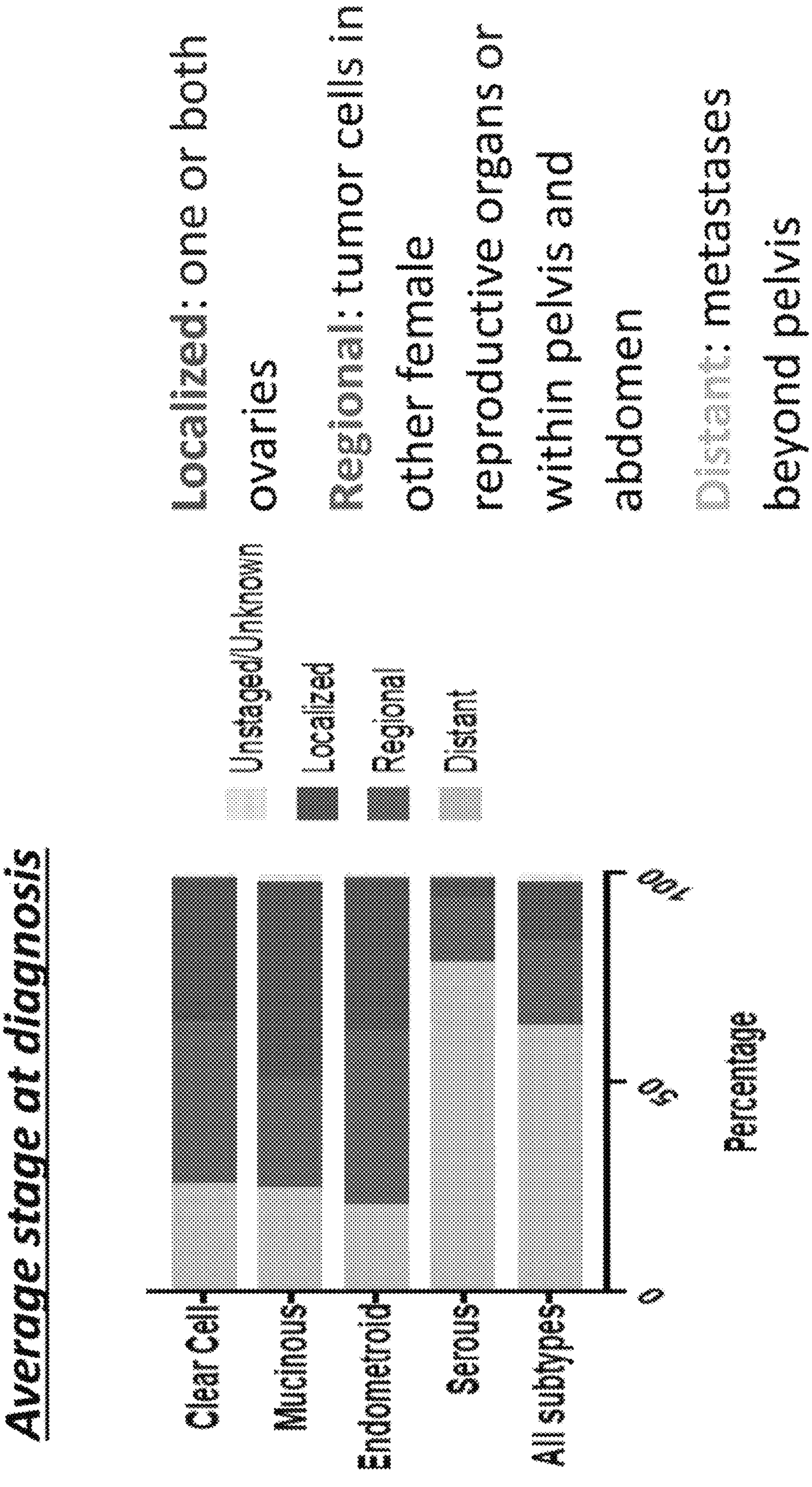
FIG. 11 shows epithelial ovarian cancer facts and figures.
Figure 13:
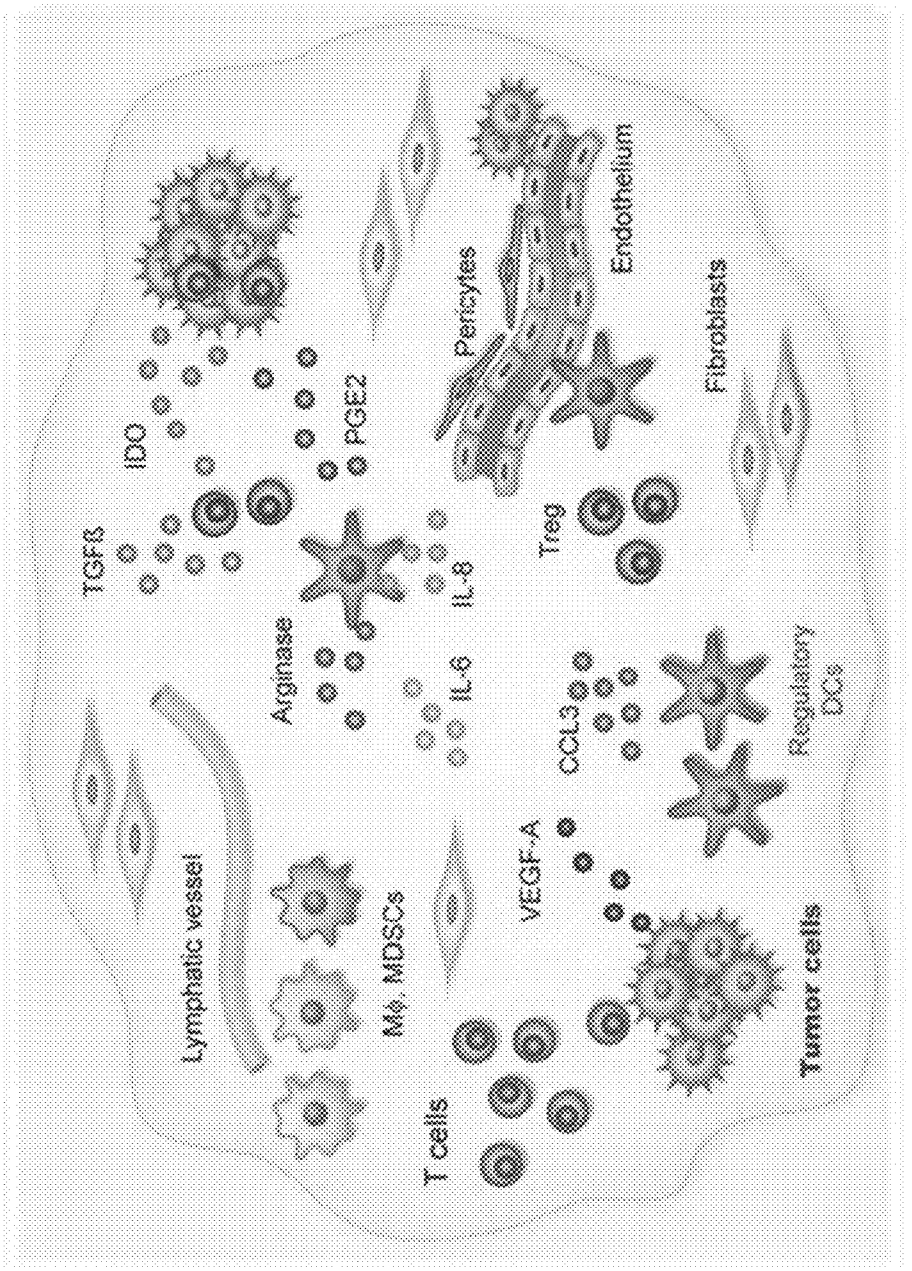
FIG. 13 shows the immunosuppressive microenvironment of ovarian cancer hinders CAR T cell effectiveness.
Figure 14:
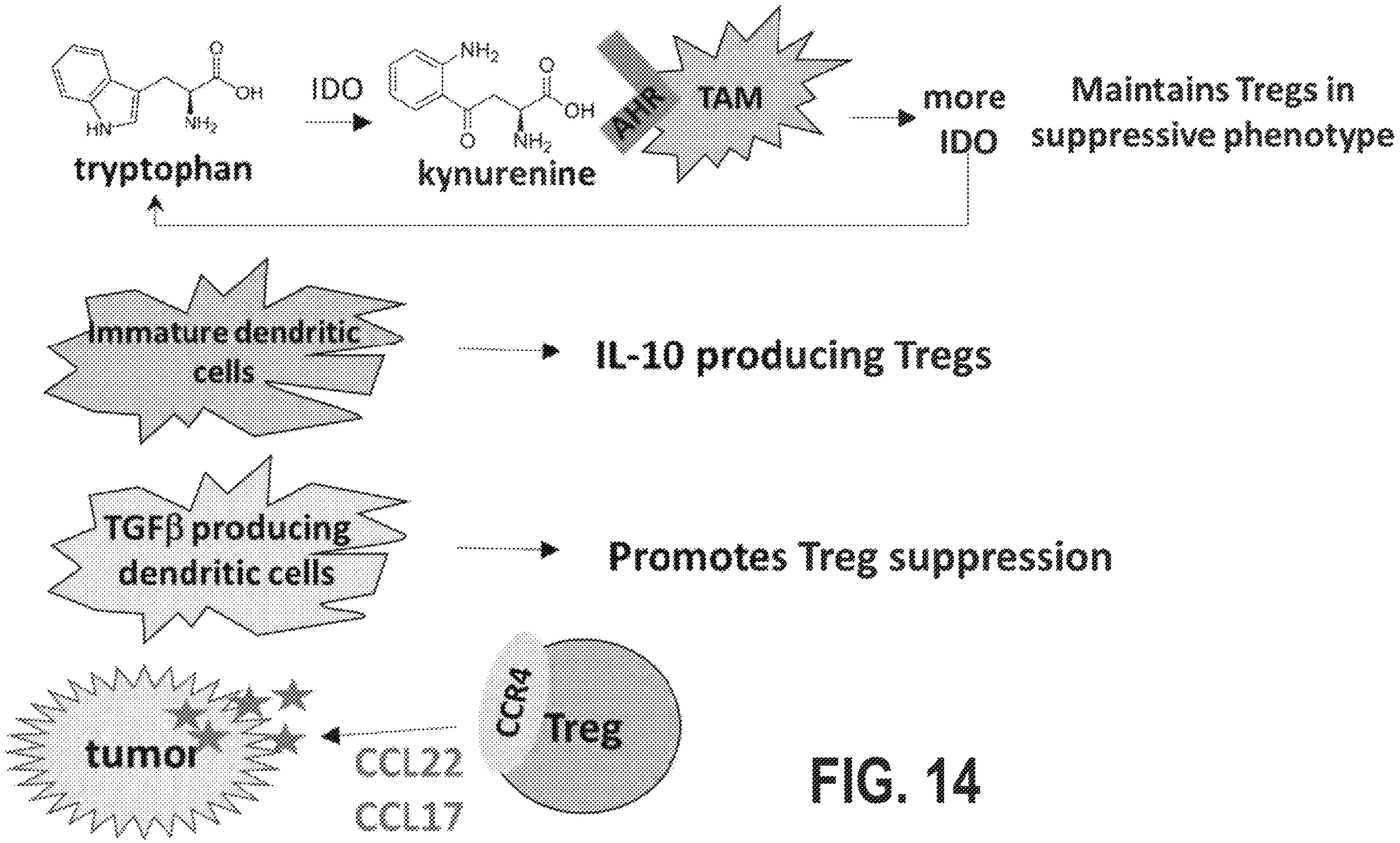
FIG. 14 shows Tregs in the ovarian cancer microenvironment hinder CAR T cell effectiveness. Tregs contribute to tumor progression in ovarian cancer by, for example, suppression of tumor-specific T cells and dendritic cells, blocking T cell proliferation by secretion of TGF-beta and IL-10, and high expression of CTLA-4 on Tregs, which leads to transmission of inhibitory signals to TILs.
Figure 15:
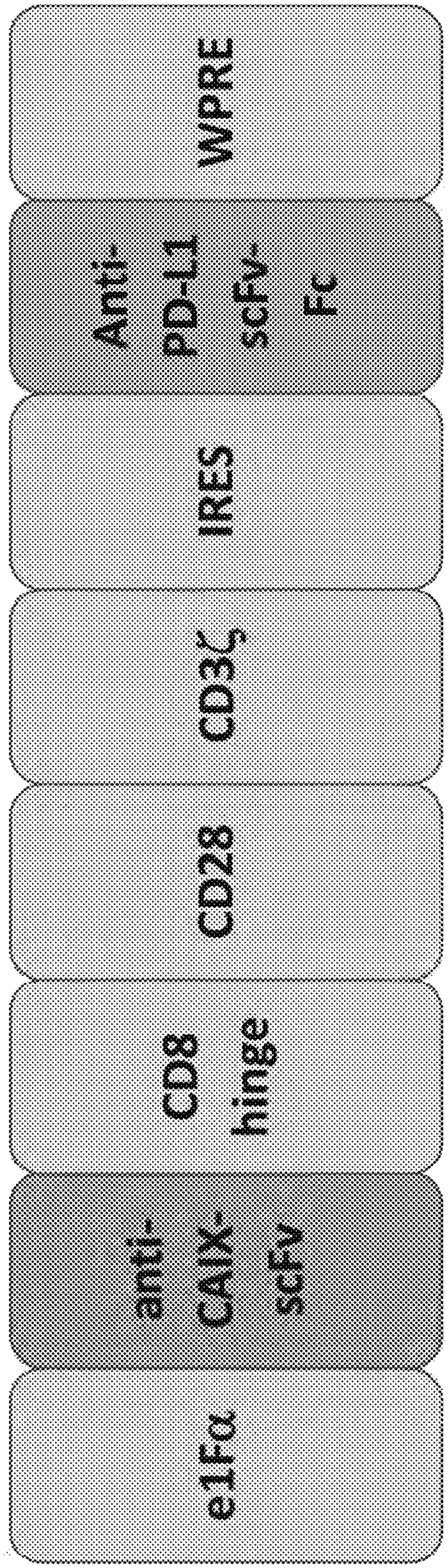
FIG. 15 shows CAR T cell factories for the treatment of solid tumors.
Figure 16:
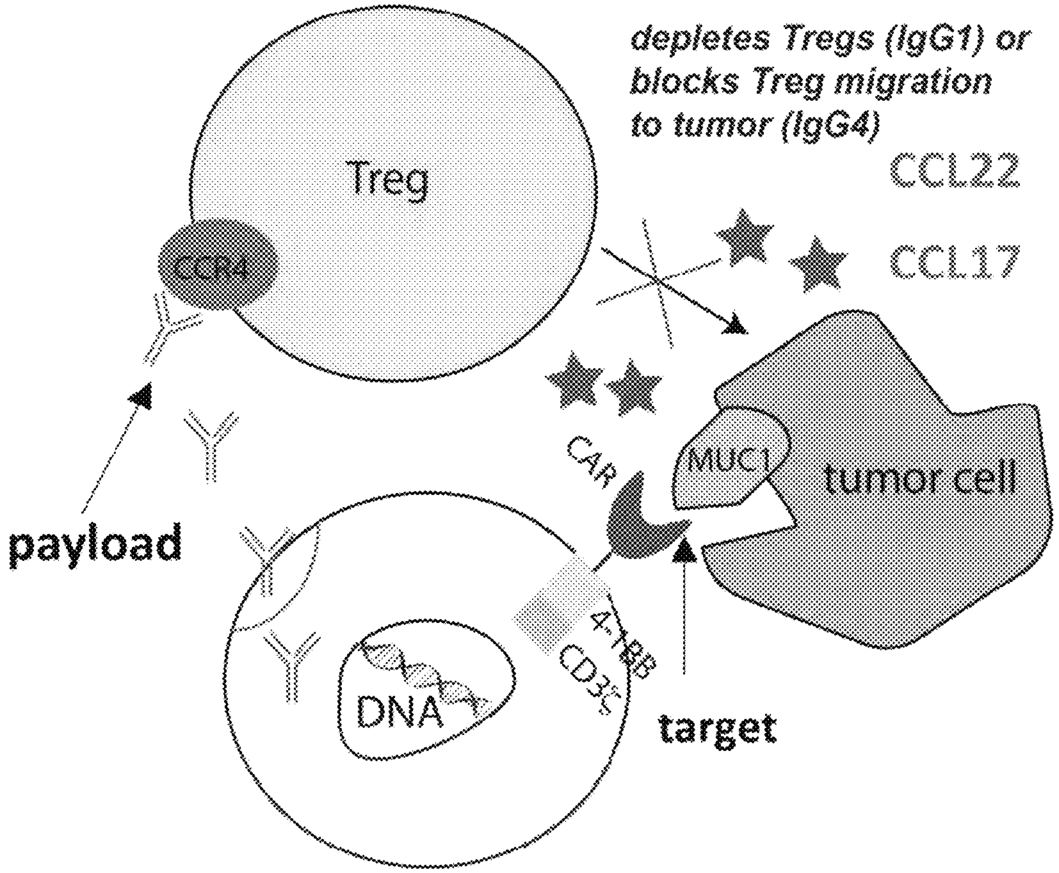
FIG. 16 shows selection of ovarian cancer CAR T cell factory components. In one embodiment, the targeting component comprises an anti-MUC1-C-CAR and the payload comprises an anti-CCR4 antibody. Without wishing to be bound by theory, MUC1-C CAR T cell factories will traffic to MUC1+ tumors, reverse the immunosuppressive ovarian cancer tumor microenvironment, and lead to tumor cell death
Figure 17:
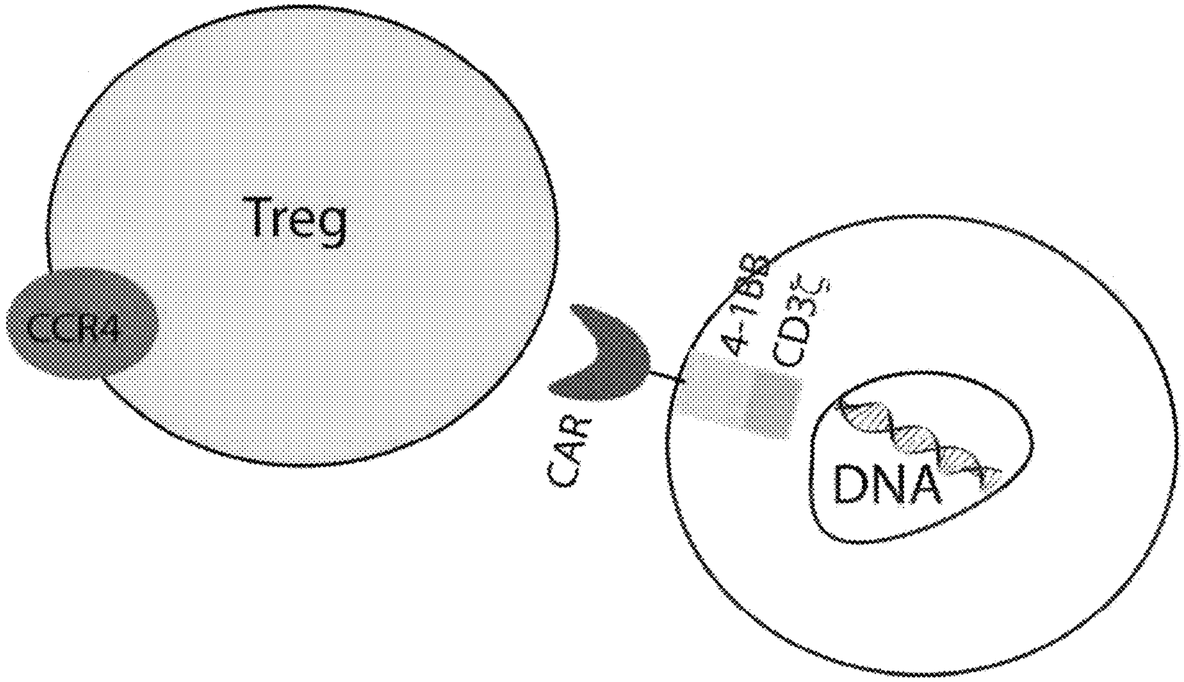
FIG. 17 shows the development of anti-CCR4 CAR T cells which can be used in conjunction with MUC1-C CAR T cell therapy.

MUC1-N is composed of the proline, threonine, and serine-rich (PTS) domain and the SEA domain. Aspects of the invention provide isolated monoclonal antibodies specific against MUC1, specifically against MUC1-SEA. Referring to FIG. 8, for example, see the annotated structure of MUC1-SEA.

The MUC1 antibodies were identified through the use of a 27 billion human single-chain antibody (scFv) phage display library, by using soluble human MUC1 as a library selection target. These antibodies represent a new class of monoclonal antibodies against MUC1.

For example, embodiments can comprise one or more nucleic acid and amino acid sequences as described herein:

Heavy Chain Nucleotide Sequences:

T4E3 $V_H$ (SEQ ID NO: 23)

caggtgcagctggtgcagtctgggggaggcttggtccagcctggggggtccctgagactctcctgtgcagcctctggattcacctttg atgattatgccatgcactgggtccggcaagctccagggaagggcctggagtgggtctcaggtattagttggaatagtggtagcatagg ctatgcggactctgtgaagggccgattcaccatctccagagacaacgccaagaactccctgtatctgcaaatgaacagtctgagagct gaggacacggccttgtattactgtgcaaaagatatcggttcagggagttattataactactactacggtatggacgtctggggccaggg gaccacggccaccatctcctca

G2-2-F8 $V_H$ (SEQ ID NO: 24)

caggtgcagctggtgcagtctgggggaggcttggtacagcctggcaggtccctgagactctcctgtgcagcctctggattcacctttga tgattatgccatgcactgggtccggcaagctccagggaagggcctggagtgggtctcaggtattagttggaatagtggtagcataggc tatgcggactctgtgaagggccgattcaccatctccagagacaacgccaagaactccctgtatctgcaaatgaacagtctgagagctg aggacacggccttgtattactgtgcaaaagatatgggaagtggctacgattggtactactacggtatggacgtctggggccaagggac cacggtcaccgtctcctca

G1-3-A3 $V_H$ (SEQ ID NO: 25)

caggtgcagctggtgcagtctgggggaggcttcgtacagcctggcaggtccctgagactctcctgtgcagcct ctggattcacctttgatgattatgccatgcactgggtccggcaagctccagggaagggcctggagtgggtctcaggtattagttggaata gtaataacataggctatgcggactctgtgaagggccgattcaccatctccagagagaacgcgaagaactccctgtatctgcaaatgaa cagcctgagagccgaggacacggctgtgtattactgtgcgagagttagtccgggttactatgatagtagtggccaagggactgatgctt ttgatatctggggccaagggaccacggtcaccgtctcctca

G1-2-B10 $V_H$ (SEQ ID NO: 26)

caggtgcagctggtgcagtctgggggaggcttggtacagcctggcaggtccctgagactctcctgtgcagcct ctggattcacctttgatgattatgccatgcactgggtccggcaagctccagggaagggcctggagtgggtctcaggtattagttggaata gtggtagcataggctatgcggactctgtgaagggccgattcaccatctccagagacaacgccaagaactccctgtatctgcaaatgaa cagtctgagagctgaggacacggccttgtattactgtgcaaaagatattagcagtggctggtaccctgatgclittgatatctggggcca aggcaccctggtcaccgtctcctca

G1-1-A1 $V_H$ (SEQ ID NO: 27)

caggtgcagctggtgcagtctggagctgaggtgaagaagcctggggcctcagtgaaggtctcctgcaaggctt ctggttacacctttaccagctatggtatcagctgggtgcgacaggcccctggacaagggcttgagtggatgggatggatcagcgctta caatggtaacacaaactatgcacagaaggtccagggcagagtcaccatgaccacagacacatccacgagcacagcctacatggagc tgaggagcctgagatctgacgacacggccgtgtattactgtgcgagagatccgcatcttagcagtggctggtacaagggaaacggtat ggacgtctggggccaaggaaccctggtcaccgtctcctca Muc1-R3-T4-D1

(SEQ ID NO: 35)

caggtgcagctggtgcagtctgggggaggcttggtccagcctggggggtccctgagactctcctgtgcagcct ctggattcacctttgatgattatgccatgcactgggtccggcaagctccagggaagggcctggagtgggtctcaggtattagttggaat.

agtggtagcataggctatgcggactctgtgaagggccgattcaccatctccagagacaacgccaagaactccctgtatctgcaaatga acagtctgagagctgaggacacggccttgtattactgtgcaaaagatatcggttcagggagttattataactactactacggtatggacgt ctggggccaggggaccacggtcaccgtctcctca Muc1-R3-T2-B1

(SEQ ID NO: 36)

caggtgcagctggtgcagtctgggggaggcttggtacagcctggcaggtccctgagactctcctgtgcagcct ctggattcacctttgatgattatgccatgcactgggtccggcaagctccagggaagggcctggagtgggtctcaggtattagttggaata -continued gtggtagcataggctatgcggactctgtgaagggccgattcaccatctccagagacaacgccaagaactccctgtatctgcaaatgaa cagtctgagagctgaggacacggccttgtattactgtgcaaaagatattagcagtggctggtaccctgatgcttttgatatctggggcca aggcaccctggtcaccgtctcctcag Muc1-R3-T4-B5

(SEQ ID NO: 24)

caggtgcagctggtgcagtctgggggaggcttggtacagcctggcaggtccctgagactctcctgtgcagcct ctggattcacctttgatgattatgccatgcactgggtccggcaagctccagggaagggcctggagtgggtctcaggtattagttggaata gtggtagcataggctatgcggactctgtgaagggccgattcaccatctccagagacaacgccaagaactccctgtatctgcaaatgaa cagtctgagagctgaggacacggccttgtattactgtgcaaaagatatgggaagtggctacgattggtactactacggtatggacgtct ggggccaagggaccacggtcaccgtctcctca Muc1-R3-E4-B12

(SEQ ID NO: 37)

caggtgcagctggtgcagtctggagccgaggtgaagaggcccggggcctcagtgaaggtctcctgcaaggct tctggttacacttttagcacctacgctatcaactgggtgcgacaggcccctggacaagggcctgagtggatgggatggatcagcggtta caatggtaacacaaaatatgcacagaaggtccagggtagagtcatcatgaccacagacacatccacgaccacagcctacatggagtt gaggagcctgacatctgacgacacggccgtgtattactgtgcgagagatggagtgggagctgcctttgactactggggccagggaac cctggtcaccgtctcctcag Muc1-R3-T3-H9

(SEQ ID NO: 38)

caggagcagctggtgcagtctggagctgaggtgaagaagcctggggcctcagtgaaggtctcctgcaaggct tctggttacacctttaccagctatggtatcagctgggtgcgacaggcccctggacaagggcttgagtggatgggatggatcagcgctta caatggtaacacaaattatgcacagaaggtccagggcagagtcaccatgcccacagacacattcacgagcacagcctacatggagct gaggagcctgagatctgacgacacggccgtgtattactgtgcgagagatccgcatcttagcagtggctggtgcaagggaaacggtat ggacgtctggggccaaggaaccctggtctccgtctcctca Muc1-R3-T3-H3

(SEQ ID NO: 39)

caggtgcagttggtgcagtttggaggtgaggtgaagaagcctggggcctcagtgaaggtctcctgcacagcttc tggttacacctataccagctatggtatcagctgggtgcgacaggcccctggacaagggcttgagtggatgggatggatcagcgcttac aatggtaacacaaactatgcacagaaggtccagggcagagtcaccatgaccacagacacatccacgagcacagcctacatggagct gaggagcctgagatctgacgacacggccgtgtattactgtgcgagagatccgcatgttagcagtggctggtacaagggaaacggtat ggacgtctggggccaaggaaccctggtcaccgtctcctca Muc1-R3-T4-D5

(SEQ ID NO: 40)

gaggtgcagctggtgcagtctggggctgaggtgaagaagcctgggtcctcagtgaaggtctcctgcaaggctt ctggatacaccttctccaattatgatatcaactgggtgcgacaggccactggacacgggcttgagtggatggggagaatgaatcctaac agtggaaacacaggctatgcagagaagttccagggcagagtcatcatgaccagtgacacctccatagacacagcctacatggacctg agcagccttagatctgaggacacggccgtctattattgtgcgagggaaatacgtggtgcttttgatatctggggccaagggacaatggt caccgtctcttcag Muc1-R3-T3-B9

(SEQ ID NO: 41)

gatgtgcagctggtgcagtctgggggtgaggcgaagaagcctgggtcctcagtgaaggtctcctgcaaggctt ctggatacaccttctgcaattatgatatcaactgggtgggacaggacactggacacgggcttgagtggatggggagaatgaatccttac agtggaaacacaggctatgcagagaagttccagggcagagtcatcatgaccagtgacacctccatagacacagcctacatggacctg agcagccttagatatgaggacacggccgtctattattgtgcgagggaaatacgtggtgcttttgatatgtggggccaagggccaatggt caccgtctcttcag -continued Muc1-R3-E4-G10

(SEQ ID NO: 42)

cagctgcagctggtgcagtatgggggaggattcgtacagcatggcaggtccttgaggctcttctgtgcagcatct ggattcacctctgatgattatgacatgcactgggtccggcaagctccagggaagagcctggagtgggtgtcaggtattagttggaatag taataacatagggtatgcggaatatgtgaagggccgattcaccatctccagagagaccgcgaagaactccctgtatatgcaaatgaac agcctgagagccgaggacacggctgtgtattactgtgcgagagttagtccgggttactatgatagtagtggccaagggagtgatgcttt tgatatctggggccaagggaccacggtcgccgtctcctcag Muc1-R3-T2-A3

(SEQ ID NO: 43)

caggtgcagctggtgcagtctgggggaggcgtggtccagcctgggaggtccctgagactctcctgtgcagcct ctggattcaccttcagtagctatggcatgcactgggtccgccaggctccaggcaaggggctggagtgggtggcagttatatcatatgat ggaagtaataaatactatgcagactccgtgaagggccgattcaccatctccagagacaattccaagaacacgctgtatctgcaaatgaa cagtctgagagtcgaggacacggctatgtattactgtgcaagtggtaacccatactactcttatgctatggacgtctggggccaaggga caatggtcaccgtctcttcag Muc1-R3-T3-B6

(SEQ ID NO: 44)

gaggtgcagctggtgcagtctggggggtgaggcgaagaagcctgggtcctcagtgaaggtctcctgcaaggctt ctggatacaccatctccaattatgatatcaactgggtgggacaggccactggacacgggcttgagtggatggagagaatgaatcctaa cagtggaaacacagggtatgcagagaagttgcagggcagagtcatcatgaccagtgcctcctccatagacacagcctacatgtacgt gagcagccttagatatgagggcgcggccgtttattattgtgggagggaaatgtgtggtggttttgatatgtgggtccaagggccaatggt caccgtctcttcag Muc1-R3-T4-E8

(SEQ ID NO: 45)

caggtgcagctgcaggagtcgggggggaggcttggtacagcctggggggtccctgagactctcctgtgcagcg tctggactcagttttagtaagcatgccatgaactgggtccgccaggctccagggaaggggctggagtgggtctcaactatcagtggca gtggtactagaacatactacgcagactccgtgaagggccggttcaccatctccagagacaataccagggacaccctctatctgcaaat gaacagactgagagccgaagacacggccatatattactgtgtaaaaggagaagagggaccttactactactactacggtttggacgtc tggggccaagggaccacggtcaccgtctcctca Muc1-R3-E4-E1

(SEQ ID NO: 46)

ccaggtgcgctggtgcaatctgggggaggcttggtccagcctggggggtccctgagactctcctgtgcagcct ctggattcacatttagtgacaattggatgagctgggtccgccaggctccagtgaaggggctggagtgggtggccaacataaagcaag atggaagtgagaaatactttgtggactctgtgaagggccgattcaccatttccagagacaacgccaagaagtcactgtatctgcagatg aacaacctgagagccgaagacacggccgtgtattactgtgtgcgcgagtttgtcggtgcttatgatatctggggccaagggacaatgg tcaccgtctcttcag Heavy Chain Amino AcidSequences (CDR1 indicated by bold, CDR2 indicated by underline, and CDR3 indicated by bold and underline)

T4E3 $V_H$ (SEQ ID NO: 12)

QVQLVQSGGGLVQPGGSLRLSCAASGFTFDDYAMHWVRQAPGKGLEWVSGISWNS

GSIGYADSVKGRFTISRDNAKNSLYLQMNSLRAEDTALYYC*AKDIGSGSYYNYYYGM*

*DV*WGQGTTATISS

G2-2-F8 $V_H$ (SEQ ID NO: 13)

QVQLVQSGGGLVQPGRSLRLSCAASGFTFDDYAMHWVRQAPGKGLEWVSGISWNS

GSIGYADSVKGRFTISRDNAKNSLYLQMNSLRAEDTALYYCAKDMGSGYDWYYY

GMDVWGQGTTVTVSS

-continued

G1-3-A3 $V_H$ (SEQ ID NO: 14)

QVQLVQSGGGFVQPGRSLRLSCAASGFTFDDYAMHWVRQAPGKGLEWVSGISWNS

NNIGYADSVKGRFTISRENAKNSLYLQMNSLRAEDTAVYYCARVSPGYYDSSGQGT

DAFDIWGQGTTVTVSS

G1-2-B10 $V_H$ (SEQ ID NO: 15)

QVQLVQSGGGLVQPGRSLRLSCAASGFTFDDYAMHWVRQAPGKGLEWVSGISWNS

GSIGYADSVKGRFTISRDNAKNSLYLQMNSLRAEDTALYYCAKDISSGWYPDAFDI

WGQGTLVTVSS

G1-1-A1 $V_H$ (SEQ ID NO: 16)

QVQLVQSGAEVKKPGASVKVSCKASGYTFTSYGISWVRQAPGQGLEWMGWISAY

NGNTNYAQKVQGRVTMTTDTSTSTAYMELRSLRSDDTAVYYCARDPHLSSGWYK

GNGMDVWGQGTLVTVSS

Muc1-R3-T4-D1 (SEQ ID NO: 47)

QVQLVQSGG.GLVQPGGSLRLSCAASGFTFDDYAMHWVRQAPGKGL

EWVSGISWNSGSIGYADSVK.GRFTISRDNAKNSLYLQMNSLRAEDTALYYCAKDIG

SGSYYNYYYGMDVWGQGTTVTVSS

Muc1-R3-T2-B1 (SEQ ID NO: 15)

QVQLVQSGG.GLVQPGRSLRLSCAASGFTFDDYAMHWVRQAPGKGL

EWVSGISWNSGSIGYADSVK.GRFTISRDNAKNSLYLQMNSLRAEDTALYYCAKDIS

SGWYPDAFDIWGQGTLVTVSS

Muc1-R3-T4-B5 (SEQ ID NO: 13)

QVQLVQSGG.GLVQPGRSLRLSCAASGFTFDDYAMHWVRQAPGKGL

EWVSGISWNSGSIGYADSVK.GRFTISRDNAKNSLYLQMNSLRAEDTALYYCAKDM

GSGYDWYYYGMDVWGQGTTVTVSS

Muc1-R3-E4-B12 (SEQ ID NO: 48)

QVQLVQSGA.EVKRPGASVKVSCKASGYTFSTYAINWVRQAPGQGPE

WMGWISGYNGNTKYAQKVQ.GRVIMTTDTSTTTAYMELRSLTSDDTAVYYCARDG

VGAAFDYWGQGTLVTVSS

Muc1-R3-T3-H9 (SEQ ID NO: 49)

QEQLVQSGA.EVKKPGASVKVSCKASGYTFTSYGISWVRQAPGQGLE

WMGWISAYNGNTNYAQKVQGRVTMPTDTFTSTAYMELRSLRSDDTAVYYCARDP

HLSSGWCKGNGMDVWGQGTLVSVSS

Muc1-R3-T3-H3 (SEQ ID NO: 50)

QVQLVQFGG.EVKKPGASVKVSCTASGYTYTSYGISWVRQAPGQGLE

WMGWISAYNGNTNYAQKVQGRVTMTTDTSTSTAYMELRSLRSDDTAVYYCARDP

HVSSGWYKGNGMDVWGQGTLVTVSS

Muc1-R3-T4-D5 (SEQ ID NO: 51)

EVQLVQSGA.EVKKPGSSVKVSCKASGYTFSNYDINWVRQATGHGLE

WMGRMNPNSGNTGYAEKFQ.GRVIMTSDTSIDTAYMDLSSLRSEDTAVYYCAREIR

GAFDIWGQGTMVTVSS

-continued

Muc1-R3-T3-B9 (SEQ ID NO: 52)

DVQLVQSGG.EAKKPGSSVKVSCKASGYTFCNYDINWVGQDTGHGLE

WMGRMNPYSGNTGYAEKFQ.GRVIMTSDTSIDTAYMDLSSLRYEDTAVYYCAREIR

GAFDMWGQGPMVTVSS

Muc1-R3-E4-G10 (SEQ ID NO: 53)

QLQLVQYGG.GFVQHGRSLRLFCAASGFTSDDYDMHWVRQAPGKSL

EWVSGISWNSNNIGYAEYVK.GRFTISRETAKNSLYMQMNSLRAEDTAVYYCARVS

PGYYDSSGGIGSDAFDIWGQ GTTVAVSS

Muc1-R3-T2-A3 (SEQ ID NO: 54)

QVQLVQSGG.GVVQPGRSLRLSCAASGFTFSSYGMHWVRQAPGKGLE

WVAVISYDGSNKYYADSVKGRFTISRDNSKNTLYLQMNSLRVEDTAMYYCASGNP

YYSYAMDVWGQGTMVTVSS

Muc1-R3-T3-B6 (SEQ ID NO: 55)

EVQLVQSGG.EAKKPGSSVKVSCKASGYTISNYDINWVGQATGHGLE

WMERMNPNSGNTGYAEKLQ.GRVIMTSASSIDTAYMYVSSLRYEGAAVYYCGREM

CGGFDMWVQGPMVTVSS

Muc1-R3-T4-E8 (SEQ ID NO: 56)

QVQLQESGG.GLVQPGGSLRLSCAASGLSFSKHAMNWVRQAPGKGLE

WVSTISGSGTRTYYADSVKGRFTISRDNTRDTLYLQMNRLRAEDTAIYYCVKGEEG

PYYYYYGLDVWGQGTTVTVSS

Muc1-R3-E4-E1 (SEQ ID NO: 57)

PGALVQSGG.GLVQPGGSLRLSCAASGFTFSDNWMSWVRQAPVKGLEWVANIKQD

GSEKYFVDSVKGRFTISRDNAKKSLYLQMNNLRAEDTAVYYCVREFVGAYDIWGQ

GTMVTVSS

Muc1-R3-E2-D12-PelB.ab1 (SEQ ID NO: 16)

QVQLVQSGA.EVKKPGASVKVSCKASGYTFTSYGISWVRQAPGQGLE

WMGWISAYNGNTNYAQKVQGRVTMTTDTSTSTAYMELRSLRSDDTAVYYCARDP

HLSSGWYKGNGMDVWGQGTLVTVSS

Muc1-R3-E2-F8-PelB.ab1 (SEQ ID NO: 58)

QVQLVQSGG.GLVQPGRSLRLSCAASGFTFDDYAMHWVRQAPGKGL

EWVSGIS*NSGSIGYADSVK.GRFTISRDNTKNLLYLQMNSLRVEDTAVYYCARDGG

YCDSTGCYDALDIWGQGTTVTVSS

Muc1-R3-E2-F11-PelB.ab1 (SEQ ID NO: 51)

EVQLVQSGA.EVKKPGSSVKVSCKASGYTFSNYDINWVRQATGHGLE

WMGRMNPNSGNTGYAEKFQGRVIMTSDTSIDTAYMDLSSLRSEDTAVYYCAREIR

GAFDIWGQGTMVTVSS

Muc1-R3-E2-B4-PelB.ab1 (SEQ ID NO: 14)

QVQLVQSGG.GFVQPGRSLRLSCAASGFTFDDYAMHWVRQAPGKGL

EWVSGISWNSNNIGYADSVKGRFTISRENAKNSLYLQMNSLRAEDTAVYYCARVSP

GYYDSSGQGTDAFDIWGQGTTVTVSS

-continued

Muc1-R3-E2-B2-PelB.ab1

(SEQ ID NO: 48)

QVQLVQSGA.EVKRPGASVKVSCKASGYTFSTYAINWVRQAPGQGPE

WMGWISGYNGNTKYAQKVQGRVIMTTDTSTTTAYMELRSLTSDDTAVYYCARDG

VGAAFDYWGQGTLVTVSS

Muc1-R3-T1-F11-PelB.ab 1

(SEQ ID NO: 177)

QVQLVQSGG.GFIQPGXSLXLSCAASGFTFDDYAMHWVRQAPGKGLE

WVSCISWNXNNIGYADSVKGQFTISRKNAKNSLYLQMNSLKAEDTAVYYCAKVSP

GYYDSSGQGTDAFDIWGQGTTVTVSS

Muc1-R3-T1-H8-PelB.ab1

(SEQ ID NO: 59)

QVQLVQSGA.EVKKPGASVKVSCKASGYTFTSYGISWVRQAPGQGLE

WMGWISTYNGNTKYAQKLQGRVTMTTDTSTSTAYMELRSLRSDDTAVYYCARDR

ATIDAFDIWGQGTTVTVSS

Light Chain Nucleotide Sequences

T4E3 $V_L$ (SEQ ID NO: 28)

tcttctgagctgactcaggaccctgctgtgtctgtggccttgggacagacagtcaggatcacatgccaaggagacagcctcagaagct attatgcaagctggtaccagcagaagccaggacaggcccctgtacttgtcatctatggtaaaaatagccggccctcggggatcccaga ccgattctctggctccaactcaggaagcacagcttccttgaccatcactggggctcaggcggaagatgaggctgactattactgtaact cccgggacaggtatggtaattcccttgtgatattcggcggagggaccaagctgaccgtccta

G2-2-F8 $V_L$ (SEQ ID NO: 29)

tcttctgagctgactcaggaccctgctgtgtctgtggccttgggacagacagtcaggatcacatgccgaggagacagcctcagaagct attatgcaagctggtaccagcagaagccaggacaggcccctgtacttgtcatttatggtaaaaacaaccggccctcagggatcccaga ccgattctctggctccagctcaggaaacacagcttccttgaccatcactggggctcaggcggaagatgaggctgactattactgtaact cccgggacagcagtggtaaccatctggtgttcggcggagggaccaagctgaccgtccta

G1-3-A3 $V_L$ (SEQ ID NO: 30)

gaaacgacactcacgcagtctccagccaccctgtctgtgtctccaggggaaagggccaccctctcctgcagggccagtcagagtgtt cgccgcaacgtagcctggtaccagcagaaacctggccaggctcccaggctcctcatctatggtgcatccttcagggccgctggcgtc ccagacaggttcagtggaagtgggtctgggacagacttcactctcaccatcaccagactggagcctgaagattttgcagtgtattactgt cagcagtatggtagctcacctcggacgttcggccaagggaccaaggtggaaatcaaa

G1-2-B10 $V_L$ (SEQ ID NO: 31)

tcttctgagctgactcaggaccctgctgtgtctgtggccttgggacagacagtcaggatcacatgccaaggagacagcctcagaagct attatgcaagctggtaccagcagaagccaggacaggcccctgtacttgtcatctatggtaaaaacaaccggccctcagggatcccaga ccgattctctggctccaactcaggaaacacagcttccttgaccatcactggggctcaggcggaagatgaggctgactattactgtaact cccgggacttcagtggtcttcagctggtattcggcggagggaccagactgaccgtcctg

G1-1-A1 $V_L$ (SEQ ID NO: 32)

tcttctgagctgactcaggaccctgctgtgtctgtggccttgggacagacagtcaggatcacatgccaaggagacagcctcagaaggt attatgcaagttggtaccagcagaagccaggacaggcccctgtacttgtcttctatgggaaaaacactcggccctcagggatcccaga ccgaatctctggctccagctctggaaacacagcttccttgaccatcactggggctcaggcggaagatgaggctgactattattgtaactc ccgggacagcagtggtaaccctgtggtattcggcggagggaccaagctgaccgtccta -continued

R3-T4-D1

(SEQ ID NO: 60)

tcttctgagctgactcaggaccctgctgtgtctgtggccttgggacagacagtcaggatcacatgccaaggaga cagcctcagaagctattatgcaagctggtaccagcagaagccaggacaggcccctgtacttgtcatctatggtaaaaatagccggccc tcggggatcccagaccgattctctggctccaactcaggaagcacagcttccttgaccatcactggggctcaggcggaagatgaggct gactattactgtaactcccgggacaggtatggtaatccccttgtgatattcggcggagggaccaagctgaccgtcctag

R3-T2-B1

(SEQ ID NO: 61)

tcttctgagctgactcaggaccctgctgtgtctgtggccttgggacagacagtcaggatcacatgccaaggaga cagcctcagaagctattatgcaagctggtaccagcagaagccaggacaggcccctgtacttgtcatctatggtaaaaacaaccggccc tcagggatcccagaccgattctctggctccaactcaggaaacacagcttccttgaccatcactggggctcaggcggaagatgaggctg actattactgtaactcccgggacttcagtggtcttcagctggtattcggcggagggaccagactgaccgtcctgg

R3-T4-B5

(SEQ ID NO: 62)

tcttctgagctgactcaggaccctgctgtgtctgtggccttgggacagacagtcaggatcacatgccgaggaga cagcctcagaagctattatgcaagctggtaccagcagaagccaggacaggcccctgtacttgtcatttatggtaaaaacaaccggccc tcagggatcccagaccgattctctggctccagctcaggaaacacagcttccttgaccatcactggggctcaggcggaagatgaggct gactattactgtaactcccgggacagcagtggtaaccatctggtgttcggcggagggaccaagctgaccgtcctag

R3-E4-B12

(SEQ ID NO: 63)

gaaacgacactcacgcagtctccagccaccctgtctgtgtctccaggggaaagagccaccctctcctgcaggg ccagtcagagtgttggcagcaacttagcctggtaccagcaaaaacctggccaggctcccaggctcctcatctacggtgcatccaccag ggccactggtatcccagccaggttcagtggcagtgggtctgggacagaattcactctcaccatcagcagcctagagcctgaagattttg cagtttattactgtcagcagcgtagcaactggcctccgacgttcggccaagggaccaaggtggagagcaaac

R3-T3-H9

(SEQ ID NO: 64)

tcttctgagctgactcaggaccctgct . . . gtgtctgtggccttgggacagacagtcaggatcacatgccaaggag acagcctcagaaggtattatgcaagttggtaccagcagaagccaggacaggcccctgtacttgtcttctatgggaaaaacagtcggcc ctcagggatcccagaccgaatctctggctccagctctggaaacacagcttccttgaccatcactgggggtcaggcggaagatgaggc tgactattattgtaactcccgggacagcagtggtaaccctgtggtattcggcggagggaccaagctgaccgtcctag

R3-T3-H3

(SEQ ID NO: 65)

tcttctgagctgactcaggaccctgctgtgtctgtggccttgggacagacagtcaggatcacatgccaaggaga cagcctcagaaggtattatgcaagttggtaccagcagaagccaggacaggcccctgtacttgtcttctatgggaaaaacactcggccct cagggatcccagaccgaatctttggctccagctctggaaacacagcttccttgaccatcactggggctcaggcggaagatgaggctg actattattgtaactcccgggacagcagtggtaaccctgtggtattcggcggagggaccaagctgaccgtcctag

R3-T4-D5

(SEQ ID NO: 66)

cagtctgccctgactcagcctccctccgtgtccgggtctcctggacagtcagtcaccatctcctgcactggaacc agcagtgacgttggtggttataaccgtgtctcctggtaccaacagcccccggcacagcccccaaactcatgattcatgacgtcagtag tcggccctcaggggtccctgatcgcttctctgggtccaagtctggcaacacggcctccctgaccatctctgggctccaggctgacgac gaggctgattattactgcagctcatatacaagcagcagccctcgggtgttcggcggagggaccaagctgaccgtcctag

R3-T3-B9

(SEQ ID NO: 67)

cagtctgccctgactcagcctccctccgtgtccgggtctcctggacagtcagtcaccatctcctgcactggaacc agcagtgacgttggtggttataaccgtgtctcctggtaccaacagcccccggcacagcccccaaactcatgattcatgacgtcagtag tcggccctcaggggtccctgatcgcttctctgggtccaagtctggcaacacggcctccctgaccatctgggggctccaggaagacga ggaggctgattattgttgcagctcatatacaagcagcagccctcgggtgttcggcggagggaccaagctgaccgtcctag -continued

R3-E4-G10

(SEQ ID NO: 68)

gaaacgacactcacgcagtcttcagccgcccagtgggtgtctccaggggaaagggccaccctctcctgcagg gccagtcagagtgttcgccgcaacgtagcctggtaccagcagaaacctggccaggctcccaggctcctcatttatggtgcatccttca gggcctctggcgtcccagacaggttcagtggaagtgggtctgggacagacttcactctcaccatcaccagcctggagcctgaagattt tgcagtgtattactgtcagcagtatggtagctcacctcggacgttcggccaagggaccaaggtggaaatcaaac

R3-T2-A3

(SEQ ID NO: 69)

aattttatgctgactcagccccactct . . . gtgtcggagtctccggggaagacggtaaccatctcctgcacccgca gcagtggcagcattgccaacaactatgtgcagtggtaccagcagcgcccgggcagttcccccaccactgtgatctatgaggataacc aaagaccctctggggtccctgatcggttctctggctccatcgacagctcctccaactctgcctccctcaccatctctggactgaagactg aggacgaggctgactactactgtcagtcttatgatagcatcaatcatcatgtggttttcggcggagggaccaagctgaccgtcctag

R3-T3-B6

(SEQ ID NO: 70)

cagtctgccctgactcagcctccctccgtgtccgggtctcctggacagtcagtcaccatctcctgcactggaacc agcagtgacgttggtggttataaccgtgtgtcctggtaccaacagcccccccggcacagcccccaaactcatgattcagaaagtcagta gtcggccctcaggggtccctgatcgcttctctgggtccaagtctggcaacacggcctccctgatcatctgggggctccaggaagacga ggaggctgattattgttgcagctcatacacaagcagcagccctcgggtgttcggcggagggaccaagctgaccgtcctag

R3-T4-E8

(SEQ ID NO: 71)

tcctatgagctgactcagccaccctcggtgtcagtggccccaggacagacggccaggattacctgtggggcaa acaacattggaagtaaaagtgtgcactggtaccagcagaagccaggccaggcccctgtgctggtcgtctatgatgatagcgaccggc cctcagggatccctgagcgattctctggctccaactctgggaacacggccaccctgaccatcagcagggtcgaagccggggatgag gccgactattactgtcaggtgtgggatagtagtactgatcatcaggttttcggcggagggaccaagctgaccgtcctag

R3-E4-E1

(SEQ ID NO: 72)

aattttatgctgactcagccccactctgtgtcggagtctccggggaagacggtaatcatctcctgcacccgcagc agcggcagcattgccaaccaccgtgtgcagtggctccagcagcgcccgggcagtgccccccctcactgtgatctatgaggaaaaccg aagaccctctggggtccctgatcggttctctggctccatcgacacgtcctccaactctgcctccctcaccatctctggactgaagcctga ggacgaggctgactactactgtcagtctttggatggcgtcactcattatgtcttcggaagtggggccaaggtcaccgtcctag Light Chains Amino Acid Sequences (CDR1 indicated by bold, CDR2 indicated by underline, and CDR3 indicated by bold and underline)

T4E3 $V_L$ (SEQ ID NO: 17)

SSELTQDPAVSVALGQTVRITCQGDSLRSYYASWYQQKPGQAPVLVIYGKNSRPSGI

PDRFSGSNSGSTASLTITGAQAEDEADYYCNSRDRYGNSLVIFGGGTKLTVL

G2-2-F8 $V_L$ (SEQ ID NO: 18)

SSELTQDPAVSVALGQTVRITCRGDSLRSYYASWYQQKPGQAPVLVIYGKNNRPSGI

PDRFSGSSSGNTASLTITGAQAEDEADYYCNSRDSSGNHLVFGGGTKLTVL

G1-3-A3 $V_L$ (SEQ ID NO: 19)

ETTLTQSPATLSVSPGERATLSCRASQSVRRNVAWYQQKPGQAPRLLIYGASFRAAG

VPDRFSGSGSGTDFTLTITRLEPEDFAVYYCQQYGSSPRTFGOGTKVEIK

G1-2-B10 $V_L$ (SEQ ID NO: 20)

SSELTQDPAVSVALGQTVRITCQGDSLRSYYASWYQQKPGQAPVLVIYGKNNRPSGI

PDRFSGSNSGNTASLTITGAQAEDEADYYCNSRDFSGLQLVFGGGTRLTVL

-continued

G1-1-A1 $V_L$
(SEQ ID NO: 21)
SSELTQDPAVSVALGQTVRITCQGDSLRRYYASWYQQKPGQAPVLVFYGKNTRPSG

IPDRISGSSSGNTASLTITGAQAEDEADYYCNSRDSSGNPVVFGGGTKLTVL

R3-T4-D1
(SEQ ID NO: 73)
SSELTQDPA.VSVALGQTVRITCQGDSLRSYYASWYQQKPGQAPVLVI

YGKNSRPSGIPDRFSGSNSGSTASLTITGAQAEDEADYYCNSRDRYGNPLVIFGGGT

KLTVL

R3-T2-B1
(SEQ ID NO: 20)
SSELTQDPA.VSVALGQTVRITCQGDSLRSYYASWYQQKPGQAPVLVI

YGKNNRPSGIP.DRFSGSNSGNTASLTITGAQAEDEADYYCNSRDFSGLQLVFGGGT

RLTVL

R3-T4-B5
(SEQ ID NO: 18)
SSELTQDPAVSVALGQTVRITCRGDSLRSYYASWYQQKPGQAPVLVI

YGKNNRPSGIP.DRFSGSSSGNTASLTITGAQAEDEADYYCNSRDSSGNHLVFGGGTK

LTVL

R3-E4-B12
(SEQ ID NO: 74)
ETTLTQSPATLSVSPGERATLSCRASQSVGSNLAWYQQKPGQAPRLLI

YGASTRATGIPARFSGSGSGTEFTLTISSLEPEDFAVYYCQQRSNWPPTFGQGTKVES

K

R3-T3-H9
(SEQ ID NO: 75)
SSELTQDPAVSVALGQTVRITCQGDSLRRYYASWYQQKPGQAPVLVF

YGKNSRPSGIPDRISGSSSGNTASLTITGGQAEDEADYYCNSRDSSGNPVVFGGGTKL

TVL

R3-T3-H3
(SEQ ID NO: 76)
SSELTQDPAVSVALGQTVRITCQGDSLRRYYASWYQQKPGQAPVLVF

YGKNTRPSGIPDRIFGSSSGNTASLTITGAQAEDEADYYCNSRDSSGNPVVFGGGTKL

TVL

R3-T4-D5
(SEQ ID NO: 77)
QSALTQPPS.VSGSPGQSVTISCTGTSSDVGGYNRVSWYQQPPGTAPKL

MIHDVSSRPSGVPDRFSGSKSGNTASLTISGLQADDEADYYCSSYTSSSPRVFGGGTK

LTVL

R3-T3-B9
(SEQ ID NO: 78)
QSALTQPPS.VSGSPGQSVTISCTGTSSDVGGYNRVSWYQQPPGTAPKL

MIHDVSSRPSGVPDRFSGSKSGNTASLTIWGLQEDEEADYCCSSYTSSSPRVFGGGTK

LTVL

R3-E4-G10
(SEQ ID NO: 79)
ETTLTQSSAAQWVSPGERATLSCRASQSVRRNVAWYQQKPGQAPRL

LIYGASFRASGVPDRFSGSGSGTDFTLTITSLEPEDFAVYYCQQYGSSPRTFGQGTKV

EIK

-continued

R3-T2-A3

(SEQ ID NO: 80)

NFMLTQPHS.VSESPGKTVTISCTRSSGSIANNYVQWYQQRPGSSPTTVI

Y<u>EDN</u>QRPSGVPDRFSGSIDSSSNSASLTISGLKTEDEADYYC<u>QSYDSINHHVV</u>FGGGT

KLTVL

R3-T3-B6

(SEQ ID NO: 81)

QSALTQPPS.VSGSPGQSVTISCTGTSSDVGGYNRVSWYQQPPGTAPKL

MIQ<u>KVS</u>SRPSGVPDRFSGSKSGNTASLIIWGLQEDEEADYCC<u>SSYTSSSPRV</u>FGGGTK

LTVL

R3-T4-E8

(SEQ ID NO: 82)

SYELTQPPS.VSVAPGQTARITCGANNIGSKSVHWYQQKPGQAPVLVV

Y<u>DDS</u>DRPSGIPERFSGSNSGNTATLTISRVEAGDEADYYC<u>QVWDSSTDHQV</u>FGGGT

KLTVL

R3-E4-E1

(SEQ ID NO: 83)

NFMLTQPHSVSESPGKTVHSCTRSSGSIANHRVQWLQQRPGSAPLTVI

Y<u>EEN</u>RRPSGVPDRFSGSIDTSSNSASLTISGLKPEDEADYYC<u>QSLDGVTHYV</u>FGSGAK

VTVL

R3-E2-D12-PelB.ab1

(SEQ ID NO: 21)

SSELTQDPA.VSVALGQTVRITCQGDSLRRYYASWYQQKPGQAPVLVF

Y<u>GKN</u>TRPSGIPDRISGSSSGNTASLTITGAQAEDEADYYC<u>NSRDSSGNPVV</u>FGGGTKL

TVL

R3-E2-F8-PelB.ab1

(SEQ ID NO: 84)

SYELTQPPSVSKGLRQTATLTCSGNSNNVGHEGAAWLQQHQGHPPKL

LSY<u>RNN</u>NRPSGISERFSASRSGNTASLTITGLQPEDEADYYC<u>ATWDGSLRGWV</u>FGG

GSKLTVL

R3-E2-F11-PelB.ab1

(SEQ ID NO: 85)

QSALTQPPS.VSGSPGQSVTISCTGTSSDVGGYNRVSWYQQPPGTAPKL

MIH<u>DVS</u>SRPSGVPDRFSGSKSGNTASLTISGLQADDEADYYC<u>SSYTSSSTRV</u>FGGGTK

LTVL

R3-E2-B4-PelB.ab1

(SEQ ID NO: 19)

ETTLTQSPATLSVSPGERATLSCRASQSVRRNVAWYQQKPGQAPRLLI

Y<u>GAS</u>FRAAGVP.DRFSGSGSGTDFTLTITRLEPEDFAVYYC<u>QQYGSSPRT</u>FGQGTKVE

IK

R3-E2-B2-PelB.ab1

(SEQ ID NO: 74)

ETTLTQSPATLSVSPGERATLSCRASQSVGSNLAWYQQKPGQAPRLLI

Y<u>GAS</u>TRATGIPARFSGSGSGTEFTLTISSLEPEDFAVYYC<u>QQRSNWPPT</u>FGQGTKVES

K

R3-T1-F11-PelB.ab1

(SEQ ID NO: 86)

KTTLTQSPATLSVSPGERATLSCXAXXIVRRNVX*YQXKPGQAPSLLI

Y<u>GAS</u>FXAAXVSHXXSXSGSGTYFSLTITXLXPXILQCITV<u>XSMVXHLX</u>FGXXTXVEI

X

-continued

R3-T1-H8-PelB.ab1

(SEQ ID NO: 87)

QSALTQPAS.VSGSPGQSITISCTGTSSDFGGYNYVSWYQQHPGKAPKL

MIYDVSNRPSGISNRFSGSKSGNTASLTITGLQSEDEADYYCSGWDRSLSAWVVGG

XTKLTVL

In sequences included herein, asterisks "*" can represent amber/stop codons. For example, the TG1 bacterial cells can be mutated such that the TAG stop codon is read as a Q (glutamine). When IMGT is used to break the DNA sequence down into FW and CDR regions, the TG1 bacterial cells do not know that there is an amber suppressor so the cells assume it is a stop codon while in the phage it reads as a Q. In embodiments, those sequences can be re-cloned such that the TAG is changed to the codons for Q.

Embodiments also feature antibodies that have a specified percentage identity or similarity to the amino acid or nucleotide sequences of the anti-MUC1 antibodies described herein. For example, the antibodies can have 60%, 70%, 75%, 80%, 85%, 90%, 91%, 92%, 93%, 94%, 95%, 96%, 97%, 98%, 99%, or higher identity when compared a specified region or the full length of any one of the anti-MUC1 antibodies described herein. Sequence identity or similarity to the nucleic acids and proteins of the present invention can be determined by sequence comparison and/or alignment by methods known in the art. For example, sequence comparison algorithms (i.e. BLAST or BLAST 2.0), manual alignment or visual inspection can be utilized to determine percent sequence identity or similarity for the nucleic acids and proteins of the present invention.

As to amino acid sequences, one of skill in the art will readily recognize that individual substitutions, deletions or additions to a nucleic acid, peptide, polypeptide, or protein sequence which alters, adds, deletes, or substitutes a single amino acid or a small percentage of amino acids in the encoded sequence is collectively referred to herein as a "conservatively modified variant". In some embodiments the alteration results in the substitution of an amino acid with a chemically similar amino acid. Conservative substitution tables providing functionally similar amino acids are well known in the art. Such conservatively modified variants of the anti-MUC1 antibodies disclosed herein can exhibit increased cross-reactivity to MUC1 in comparison to an unmodified MUC1 antibody.

As used herein, the term "antibody" can refer to an immunoglobulin molecule and immunologically active portions of an immunoglobulin (Ig) molecule, i.e., a molecule that contains an antigen binding site that specifically binds (immunoreacts with) an antigen. The term "antibody" herein is used in the broadest sense and encompasses various antibody structures, including but not limited to monoclonal antibodies, polyclonal antibodies, multispecific antibodies (e.g., bispecific antibodies), multivalent antibodies, monovalent antibodies, humanized antibodies, fully human antibodies, and antibody fragments so long as they exhibit the desired antigen-binding activity. By "specifically binds" or "immunoreacts with" is meant that the antibody reacts with one or more antigenic determinants of the desired antigen more readily than with other polypeptides. Antibodies include, but are not limited to, polyclonal, monoclonal, chimeric, dAb (domain antibody), single chain, $F_{ab}$, $F_{ab}'$ and $F_{(ab')2}$ fragments, scFvs, and $F_{ab}$ expression libraries.

The terms "antigen" or "antigen molecule" can be used interchangeable and can refer to all molecules that can be specifically bound by an antibody. The term "antigens" as used herein include e.g. proteins, different epitopes on proteins (as different antigens within the meaning of the invention), and polysaccharides. This mainly includes parts (coats, capsules, cell walls, flagella, fimbrae, and toxins) of bacteria, viruses, and other microorganisms. Lipids and nucleic acids are antigenic only when combined with proteins and polysaccharides. Non-microbial exogenous (non-self) antigens can include pollen, egg white, and proteins from transplanted tissues and organs or on the surface of transfused blood cells. Preferably the antigen is selected from the group consisting of cytokines, cell surface proteins, enzymes and receptors cytokines, cell surface proteins, enzymes and receptors.

The term "chimeric antibody" can refer to an antibody comprising a variable region, i.e., binding region, from one source or species and at least a portion of a constant region derived from a different source or species, usually prepared by recombinant DNA techniques. For example, chimeric antibodies can comprise a murine variable region and a human constant region. Other non-limiting forms of "chimeric antibodies" encompassed by the present invention are those in which the constant region has been modified or changed from that of the original antibody to generate specific properties, such as in regard to Fc receptor (FcR) binding. Such chimeric antibodies are also referred to as "class-switched antibodies." Chimeric antibodies are the product of expressed immunoglobulin genes comprising DNA segments encoding immunoglobulin variable regions and DNA segments encoding immunoglobulin constant regions. Methods for producing chimeric antibodies involve conventional recombinant DNA and gene transfection techniques are well known in the art. See, e.g., Morrison, S. L., et al., Proc. Natl. Acad. Sci. USA 81 (1984) 6851-6855; U.S. Pat. Nos. 5,202,238 and 5,204,244.

The term "humanized antibody" can refer to antibodies in which the framework or "complementarity determining regions" (CDR) have been modified to comprise the CDR of an immunoglobulin of different specificity as compared to that of the parent immunoglobulin. In one embodiment, a murine CDR is grafted into the framework region of a human antibody to prepare the "humanized antibody." See, e.g., Riechmann, L., et al., Nature 332 (1988) 323-327; and Neuberger, M. S., et al., Nature 314 (1985) 268-270. Particularly preferred CDRs correspond to those representing sequences recognizing the antigens noted herein. Other forms of "humanized antibodies" encompassed by the present invention are those in which the constant region has been additionally modified or changed from that of the original antibody to generate specific properties according to the invention, such as Fc receptor (FcR) binding.

The term "human antibody", as used herein, can include antibodies having variable and constant regions derived from human germ line immunoglobulin sequences. Human antibodies are well-known in the state of the art (van Dijk, M. A., and van de Winkel, J. G., Curr. Opin. Chem. Biol. 5 (2001) 368-374). Human antibodies can also be produced in transgenic animals (e.g., mice) that are capable, upon immunization, of producing a full repertoire or a selection of human antibodies in the absence of endogenous immunoglobulin production. Transfer of the human germ-line immunoglobulin gene array in such germ-line mutant mice will result in the production of human antibodies upon antigen challenge (see, e.g., Jakobovits, A., et al., Proc. Natl. Acad. Sci. USA 90 (1993) 2551-2555; Jakobovits, A., et al., Nature 362 (1993) 255-258; Bruggemann, M., et al., Year Immunol. 7 (1993) 33-40). Human antibodies can also be produced in phage display libraries (Hoogenboom, H. R., and Winter, G., J. Mol. Biol. 227 (1992) 381-388; Marks, J. D., et al., J. Mol. Biol. 222 (1991) 581-597). The techniques of Cole, et al., and Boerner, et al. are also available for the preparation of human monoclonal antibodies (Cole, et al., Monoclonal Antibodies and Cancer Therapy, Alan R. Liss, p. 77 (1985); and Boemer, P., et al., J. Immunol. 147 (1991) 86-95). As already mentioned for chimeric and humanized antibodies according to the invention the term "human antibody" as used herein also comprises such antibodies which are modified in the constant region to generate specific properties, such as in regard to FcR binding, e.g. by "class switching" i.e. change or mutation of Fc parts (e.g. from IgG1 to IgG4 and/or IgG1/IgG4 mutation.)

The term "recombinant human antibody", as used herein, can include all human antibodies that are prepared, expressed, created or isolated by recombinant means, such as antibodies isolated from a host cell such as a NS0 or CHO cell or from an animal (e.g. a mouse) that is transgenic for human immunoglobulin genes or antibodies expressed using a recombinant expression vector transfected into a host cell. Such recombinant human antibodies have variable and constant regions in a rearranged form. The recombinant human antibodies according to the invention have been subjected to in vivo somatic hypermutation. Thus, the amino acid sequences of the VH and VL regions of the recombinant antibodies are sequences that, while derived from and related to human germ line VH and VL sequences, may not naturally exist within the human antibody germ line repertoire in vivo.

A single chain Fv ("scFv") polypeptide molecule is a covalently linked $V_H$:$V_L$ heterodimer, which can be expressed from a gene fusion including $V_H$- and $V_L$-encoding genes linked by a peptide-encoding linker. (See Huston et al. (1988) Proc Nat Acad Sci USA 85(16):5879-5883). Referring to FIG. 9, for example, an embodiment can comprise the T4E3 $V_H$ (SEQ ID NO: 12) amino acid sequence described herein linked to the T4E3 $V_L$ (SEQ ID NO: 17) amino acid sequence.

A number of methods have been described to discern chemical structures for converting the naturally aggregated, but chemically separated, light and heavy polypeptide chains from an antibody V region into an scFv molecule, which will fold into a three-dimensional structure substantially similar to the structure of an antigen-binding site. See, e.g., U.S. Pat. Nos. 5,091,513; 5,132,405; and 4,946,778.

Very large naive human scFv libraries have been and can be created to offer a large source of rearranged antibody genes against a plethora of target molecules. Smaller libraries can be constructed from individuals with infectious diseases in order to isolate disease-specific antibodies. (See Barbas et al., Proc. Natl. Acad. Sci. USA 89:9339-43 (1992); Zebedee et al, Proc. Natl. Acad. Sci. USA 89:3 175-79 (1992)).

In general, antibody molecules obtained from humans relate to any of the classes IgG, IgM, IgA, IgE and IgD, which differ from one another by the nature of the heavy chain present in the molecule. Certain classes have subclasses as well, such as $IgG_1$, $IgG_2$, $IgG_3$ and IgG4 and others. Furthermore, in humans, the light chain can be a kappa chain or a lambda chain. Referring to FIG. 7, for example, the light chain of embodiments herein can be kappa chain or lamda chain. The "antibodies" according to the invention can be of any class (e.g. IgA, IgD, IgE, IgG, and IgM, preferably IgG or IgE), or subclass (e.g., IgG1, IgG2, IgG3, IgG4, IgA1 and IgA2, preferably IgG1), The term "antigen-binding site," or "binding portion" can refer to the part of the immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains, referred to as "hypervariable regions," are interposed between more conserved flanking stretches known as "framework regions," or "FRs". Thus, the term "FR" can refer to amino acid sequences which are naturally found between, and adjacent to, hypervariable regions in immunoglobulins. In an antibody molecule, the three hypervariable regions of a light chain and the three hypervariable regions of a heavy chain are disposed relative to each other in three-dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs." For example, $V_H$ and $V_L$ regions, which contain the CDRs, of exemplary antibodies are shown in FIG. 9.

TABLE 1

| | CDR1 | CDR2 | CDR3 | SEQ ID NOS, respectively, in order of appearance |
|---|---|---|---|---|
| VH | | | | |
| T4E3 | GFTFDDYA | ISWNSGSI | AKDIGSGSYYNYYYGMDV | 2, 96, 104 |
| G2-2-F8 | GFTFDDYA | ISWNSGSI | AKDMGSGYDWYYYGMDV | 2, 96, 105 |
| G1-3-A3 | GFTFDDYA | ISWNSNNI | ARVSPGYYDSSGQGTDA | 2, 97, 106 |
| G1-2-B10 | GFTFDDYA | ISWNSGSI | AKDISSGWYPDA | 2, 96, 107 |
| G1-1-A1 | GYTFTSYG | ISAYNGNT | ARDPHLSSGWYKGNGMDV | 6, 98, 108 |
| R3-T4-D1 | GFTFDDYA | ISWNSGSI | AKDIGSGSYYNYYYGMDV | 2, 96, 104 |
| R3-T2-B1 | GFTFDDYA | ISWNSGSI | AKDISSGWYPDAFDI | 2, 96, 109 |
| R3-T4-B5 | GFTFDDYA | ISWNSGSI | AKDMGSGYDWYYYGMDV | 2, 96, 105 |
| R3-E4-B12 | GYTFSTYA | ISGYNGNT | ARDGVGAAFDY | 88, 99, 110 |
| R3-T3-H9 | GYTFTSYG | ISAYNGNT | ARDPHLSSGWCKGNGMDV | 6, 98, 111 |
| R3-T3-H3 | GYTYTSYG | ISAYNGNT | ARDPHVSSGWYKGNGMDV | 89, 98, 112 |

TABLE 1-continued

| | | | | |
|---|---|---|---|---|
| R3-E2-D12-PelB.ab1 | GYTFTSYG | ISAYNGNT | ARDPHLSSGWYKGNGMDV | 6, 98, 108 |
| R3-E2-F8-PelB.ab1 | GFTFDDYA | IS*NSGSI | ARDGGYCDSTGCYDALDI | 2, 100, 113 |
| R3-E2-F11-PelB.ab1 | GYTFSNYD | MNPNSGNT | AREIRGAFDI | 90, 101, 114 |
| R3-E2-64-PelB.ab1 | GFTFDDYA | ISWNSNNI | ARVSPGYYDSSGQGTDAFDI | 2, 97, 115 |
| R3-E2-62-PelB.ab1 | GYTFSTYA | ISGYNGNT | ARDGVGAAFDY | 88, 99, 110 |
| R3-T1-F11-PelB.ab1 | GFTFDDYA | ISWNXNNI | AKVSPGYYDSSGQGTDAFDI | 2, 102, 116 |
| R3-T1-H8-PelB.ab1 | GYTFTSYG | ISTYNGNT | ARDRATIDAFDI | 6, 103, 117 |

| | CDR1 | CDR2 | CDR3 | SEQ ID NO: |
|---|---|---|---|---|
| VL | | | | |
| T4E3 | SLRSYY | GKN | NSRDRYGNSLVIFGGGTK | 7, 118 |
| G2-2-F8 | SLRSYY | GKN | NSRDSSGNHLVFGGGTK | 7, 119 |
| G1-3-A3 | QSVRRN | GAS | QQYGSSPRTFGQGTKVEIK | 9, 120 |
| G1-2-B10 | SLRSYY | GKN | NSRDFSGLQLVFGGGTR | 7, 121 |
| G1-1-A1 | SLRRYY | GKN | NSRDSSGNPVVFGGGTK | 11, 122 |
| R3-T4-D1 | SLRSYY | GKN | NSRDRYGNPLVI | 7, 123 |
| R3-T2-B1 | SLRSYY | GKN | NSRDFSGLQLV | 7, 124 |
| R3-T4-B5 | SLRSYY | GKN | NSRDSSGNHLV | 7, 125 |
| R3-E4-B12 | QSVGSN | GAS | QQRSNWPPT | 91, 126 |
| R3-T3-H9 | SLRRYY | GKN | NSRDSSGNPVV | 11, 127 |
| R3-E2-D12-PelB.ab1 | SLRRYY | GKN | NSRDSSGNPVV | 11, 127 |
| R3-E2-F8-PelB.ab1 | SNNVGHEG | RNN | ATWDGSLRGWV | 92, 128 |
| R3-E2-F11-PelB.ab1 | SSDVGGYNR | DVS | SSYTSSSTRV | 93, 129 |
| R3-E2-64-PelB.ab1 | QSVRRN | GAS | QQYGSSPRT | 9, 130 |
| R3-E2-62-PelB.ab1 | QSVGSN | GAS | QQRSNWPPT | 91, 126 |
| R3-T1-F11-PelB.ab1 | XIVRRN | GAS | XSMVXHLX | 94, 131 |
| R3-T1-H8-PelB.ab1 | SSDFGGYNY | DVS | SGWDRSLSAWV | 95, 132 |

As used herein, the term “epitope” can include any protein determinant capable of specific binding to an immunoglobulin, a scFv, or a T-cell receptor. The variable region allows the antibody to selectively recognize and specifically bind epitopes on antigens. For example, the VL domain and VH domain, or subset of the complementarity determining regions (CDRs), of an antibody combine to form the variable region that defines a three-dimensional antigen-binding site. This quaternary antibody structure forms the antigen-binding site present at the end of each arm of the Y. Epitopic determinants usually consist of chemically active surface groupings of molecules such as amino acids or sugar side chains and usually have specific three-dimensional structural characteristics, as well as specific charge characteristics. For example, antibodies can be raised against N-terminal or C-terminal peptides of a polypeptide. As another example, the epitope of the antibodies can be within the MUC1 of the panning antigen, as described herein. Further as described herein, anti-MUC1-antibodies can be directed towards the SEA domain of MUC1.

As used herein, the terms “immunological binding,” and “immunological binding properties” can refer to the non-covalent interactions of the type which occur between an immunoglobulin molecule and an antigen for which the immunoglobulin is specific. The strength, or affinity of immunological binding interactions can be expressed in terms of the dissociation constant ($K_D$) the interaction, wherein a smaller ($K_D$) presents a greater affinity. Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and geometric parameters that equally influence the rate in both directions. Thus, both the “on rate constant” ($K_{on}$) and the “off rate constant” ($K_{off}$) can be determined by calculation of the concentrations and the actual rates of association and dissociation. (See Nature 361: 186-87 (1993)). The ratio of $K_{off}/K_{on}$ enables the cancellation of all parameters not related to affinity, and is equal to the dissociation constant %. (See, generally, Davies et al. (1990) Annual Rev Biochem 59:439-473). An antibody of the present invention is said to specifically bind to a MUC1 epitope when the equilibrium binding constant sufficient to induce a therapeutic effect. In many instances, the equilibrium binding constant is ≤10 μM, preferably ≤10 nM, and most preferably ≤100 pM to about 1 pM, as measured by assays such as radioligand binding assays or similar assays known to those skilled in the art, such as a BIAcore. Alternatively, moderate affinity is sufficient to induce a therapeutic effect.

"Specifically binds" or "has specificity to," can refer to an antibody that binds to an epitope via its antigen-binding domain, and that the binding entails some complementarity between the antigen-binding domain and the epitope. For example, an antibody is said to "specifically bind" to an epitope when it binds to that epitope, via its antigen-binding domain more readily than it would bind to a random, unrelated epitope.

Functionally, the binding affinity of the anti-MUC1 antibody is within the range of $10^{-5}$M to $10^{-12}$ M. For example, the binding affinity of the anti-MUC1 antibody is from $10^{-6}$ M to $10^{-12}$ M, from $10^{-7}$ M to $10^{-12}$ M, from $10^{-8}$ M to $10^{-12}$ M, from $10^{-9}$ M to $10^{-12}$ M, from $10^{-5}$ M to $10^{-11}$ M, from $10^{-6}$ M to $10^{-11}$ M, from $10^{-7}$ M to $10^{-11}$ M, from $10^{-8}$ M to $10^{-11}$ M, from $10^{-9}$ M to $10^{-11}$ M, from $10^{-10}$ M to $10^{-11}$ M, from $10^{-5}$ M to $10^{-10}$ M, from $10^{-6}$ M to $10^{-10}$ M, from $10^{-7}$ M to $10^{-10}$ M, from $10^{-8}$ M to $10^{-10}$M, from $10^{-9}$ M to $10^{-10}$ M, from $10^{-5}$ M to $10^{-9}$ M, from $10^{-6}$ M to $10^{-9}$M, from $10^{-7}$ M to $10^{-9}$ M, from $10^{-8}$ M to $10^{-9}$ M, from $10^{-5}$ M to $10^{-8}$ M, from $10^{-6}$ M to $10^{-8}$ M, from $10^{-7}$ M to $10^{-8}$ M, from $10^{-5}$ M to $10^{-7}$ M, from $10^{-6}$ M to $10^{-7}$ M, or from $10^{-5}$ M to $10^{-6}$ M.

For example, the anti-MUC1 antibody 1 antibody can be monovalent or bivalent, and comprises a single or double chain. For example, a monovalent antibody has an affinity for one antigen and/or one epitope, such as the MUC1-SEA peptide or fragment thereof.

The term "bivalent" or "bispecific" antibody can refer to an antibody that is capable of specifically binding to two different antigens at the same time. For example, a bivalent antibody can comprise two pairs of heavy chain and light chain (HC/LC) specifically binding to a different antigen, i.e. the first heavy and the first light chain (originating from an antibody against a first antigen) are specifically binding together to a first antigen, and, the second heavy and the second light chain (originating from an antibody against a second antigen) are specifically binding together to a second antigen. Such bivalent, bispecific antibodies are capable of specifically binding to two different antigens at the same time, and not to more than two antigens, in contrary to, on the one hand a monospecific, monovalent antibody capable of binding only to one antigen, and on the other hand e.g. a tetravalent, tetraspecific antibody which can bind to four antigen molecules at the same time.

A MUC1 protein, MUC1-SEA peptide, or a derivative, fragment, analog, homolog or ortholog thereof, can be utilized as an immunogen in the generation of antibodies that immunospecifically bind these protein components. A MUC1 protein, MUC1-SEA peptide or a derivative, fragment, analog, homolog, or ortholog thereof, coupled to a proteoliposome can be utilized as an immunogen in the generation of antibodies that immunospecifically bind these protein components.

Those skilled in the art will recognize that it is possible to determine, without undue experimentation, if a human monoclonal antibody has the same specificity as a human monoclonal antibody of the invention by ascertaining whether the former prevents the latter from binding to MUC1. If the human monoclonal antibody being tested competes with the human monoclonal antibody of the invention, as shown by a decrease in binding by the human monoclonal antibody of the invention, then it is likely that the two monoclonal antibodies bind to the same, or to a closely related, epitope.

Another way to determine whether a human monoclonal antibody has the specificity of a human monoclonal antibody of the invention is to pre-incubate the human monoclonal antibody of the invention with the MUC1 protein or MUC1-SEA peptide, with which it is normally reactive, and then add the human monoclonal antibody being tested to determine if the human monoclonal antibody being tested is inhibited in its ability to bind MUC1. If the human monoclonal antibody being tested is inhibited then, in all likelihood, it has the same, or functionally equivalent, epitopic specificity as the monoclonal antibody of the invention. Screening of human monoclonal antibodies of the invention can be also carried out by utilizing MUC1 and/or MUC1-SEA and determining whether the test monoclonal antibody is able to neutralize MUC1 and/or MUC1-SEA.

Various procedures known within the art can be used for the production of polyclonal or monoclonal antibodies directed against a protein of the invention, or against derivatives, fragments, analogs homologs or orthologs thereof (see, for example, Antibodies: A Laboratory Manual, Harlow E, and Lane D, 1988, Cold Spring Harbor Laboratory Press, Cold Spring Harbor, NY, incorporated herein by reference).

Antibodies can be purified by well-known techniques, such as affinity chromatography using protein A or protein G, which provide primarily the IgG fraction of immune serum. Subsequently, or alternatively, the specific antigen which is the target of the immunoglobulin sought, or an epitope thereof, can be immobilized on a column to purify the immune specific antibody by immunoaffinity chromatography. Purification of immunoglobulins is discussed, for example, by D. Wilkinson (The Scientist, published by The Scientist, Inc., Philadelphia PA, Vol. 14, No. 8 (Apr. 17, 2000), pp. 25-28).

The term "monoclonal antibody" or "MAb" or "monoclonal antibody composition", as used herein, can refer to a population of antibody molecules that contain only one molecular species of antibody molecule consisting of a unique light chain gene product and a unique heavy chain gene product. In particular, the complementarity determining regions (CDRs) of the monoclonal antibody are identical in all the molecules of the population. MAbs contain an antigen binding site capable of immunoreacting with a particular epitope of the antigen characterized by a unique binding affinity for it.

Monoclonal antibodies can be prepared using hybridoma methods, such as those described by Kohler and Milstein, Nature, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes can be immunized in vitro.

The immunizing agent will typically include the protein antigen, a fragment thereof or a fusion protein thereof. Generally, either peripheral blood lymphocytes are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, Monoclonal Antibodies: Principles and Practice, Academic Press, (1986) pp. 59-103). Immortalized cell lines are usually transformed mammalian cells, particularly myeloma cells of rodent, bovine and human origin. Usually, rat or mouse myeloma cell lines are employed. The hybridoma cells can be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high-level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, California and the American Type Culture Collection, Manassas, Virginia. Human myeloma and mouse-human heteromyeloma cell lines also have been described for the production of human monoclonal antibodies. (See Kozbor, J. Immunol, 133:3001 (1984); Brodeur et al, Monoclonal Antibody Production Techniques and Applications, Marcel Dekker, Inc., New York, (1987) pp. 51-63)).

The culture medium in which the hybridoma cells are cultured can then be assayed for the presence of monoclonal antibodies directed against the antigen. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, Anal. Biochem., 107:220 (1980). Moreover, in therapeutic applications of monoclonal antibodies, it is important to identify antibodies having a high degree of specificity and a high binding affinity for the target antigen.

After the desired hybridoma cells are identified, the clones can be subcloned by limiting dilution procedures and grown by standard methods. (See Goding, Monoclonal Antibodies: Principles and Practice, Academic Press, (1986) pp. 59-103). Suitable culture media for this purpose include, for example, Dulbecco's Modified Eagle's Medium and RPMI-1640 medium. Alternatively, the hybridoma cells can be grown in vivo as ascites in a mammal.

The monoclonal antibodies secreted by the subclones can be isolated or purified from the culture medium or ascites fluid by conventional immunoglobulin purification procedures such as, for example, protein A-Sepharose, hydroxylapatite chromatography, gel electrophoresis, dialysis, or affinity chromatography.

Monoclonal antibodies can also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA can be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also can be modified, for example, by substituting the coding sequence for human heavy and light chain constant domains in place of the homologous murine sequences (see U.S. Pat. No. 4,816,567; Morrison, Nature 368, 812-13 (1994)) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

Fully human antibodies are antibody molecules in which the entire sequence of both the light chain and the heavy chain, including the CDRs, arise from human genes. Such antibodies are termed "humanized antibodies", "human antibodies", or "fully human antibodies" herein. Human monoclonal antibodies can be prepared by using trioma technique; the human B-cell hybridoma technique (see Kozbor, et al, 1983 Immunol Today 4: 72); and the EBV hybridoma technique to produce human monoclonal antibodies (see Cole, et al, 1985 In: MONOCLONAL ANTIBODIES AND CANCER THERAPY, Alan R. Liss, Inc., pp. 77-96). Human monoclonal antibodies can be utilized and can be produced by using human hybridomas (see Cote, et al, 1983. Proc Natl Acad Sci USA 80: 2026-2030) or by transforming human B-cells with Epstein Barr Virus in vitro (see Cole, et al., 1985 In: MONOCLONAL ANTIBODIES AND CANCER THERAPY, Alan R. Liss, Inc., pp. 77-96).

In addition, human antibodies can also be produced using other techniques, including phage display libraries. (See Hoogenboom and Winter, J. Mol. Biol, 227:381 (1991); Marks et al., J. Mol. Biol, 222:581 (1991)). Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in Marks et al, Bio/Technology 10, 779-783 (1992); Lonberg et al, Nature 368 856-859 (1994); Morrison, Nature 368, 812-13 (1994); Fishwild et al, Nature Biotechnology 14, 845-51 (1996); Neuberger, Nature Biotechnology 14, 826 (1996); and Lonberg and Huszar, Intern. Rev. Immunol. 13 65-93 (1995).

Human antibodies can additionally be produced using transgenic nonhuman animals which are modified so as to produce fully human antibodies rather than the animal's endogenous antibodies in response to challenge by an antigen. (See PCT publication WO94/02602). The endogenous genes encoding the heavy and light immunoglobulin chains in the nonhuman host have been incapacitated, and active loci encoding human heavy and light chain immunoglobulins are inserted into the host's genome. The human genes are incorporated, for example, using yeast artificial chromosomes containing the requisite human DNA segments. An animal which provides all the desired modifications is then obtained as progeny by crossbreeding intermediate transgenic animals containing fewer than the full complement of the modifications. The preferred embodiment of such a nonhuman animal is a mouse, and is termed the Xenomouse™ as disclosed in PCT publications WO 96/33735 and WO 96/34096. This animal produces B cells which secrete fully human immunoglobulins. The antibodies can be obtained directly from the animal after immunization with an immunogen of interest, as, for example, a preparation of a polyclonal antibody, or alternatively from immortalized B cells derived from the animal, such as hybridomas producing monoclonal antibodies. Additionally, the genes encoding the immunoglobulins with human variable regions can be recovered and expressed to obtain the antibodies directly, or can be further modified to obtain analogs of antibodies such as, for example, single chain Fv (scFv) molecules.

An example of a method of producing a nonhuman host, exemplified as a mouse, lacking expression of an endogenous immunoglobulin heavy chain is disclosed in U.S. Pat. No. 5,939,598. It can be obtained by a method, which includes deleting the J segment genes from at least one endogenous heavy chain locus in an embryonic stem cell to prevent rearrangement of the locus and to prevent formation of a transcript of a rearranged immunoglobulin heavy chain locus, the deletion being effected by a targeting vector containing a gene encoding a selectable marker; and producing from the embryonic stem cell a transgenic mouse whose somatic and germ cells contain the gene encoding the selectable marker.

One method for producing an antibody of interest, such as a human antibody, is disclosed in U.S. Pat. No. 5,916,771. This method includes introducing an expression vector that contains a nucleotide sequence encoding a heavy chain into one mammalian host cell in culture, introducing an expression vector containing a nucleotide sequence encoding a light chain into another mammalian host cell, and fusing the two cells to form a hybrid cell. The hybrid cell expresses an antibody containing the heavy chain and the light chain.

In a further improvement on this procedure, a method for identifying a clinically relevant epitope on an immunogen and a correlative method for selecting an antibody that binds immunospecifically to the relevant epitope with high affinity, are disclosed in PCT publication WO 99/53049.

The antibody can be expressed by a vector containing a DNA segment encoding the single chain antibody described above. For example, the vector can comprise one or more of SEQ ID NOs: 23-27, 35, 36, 24, or 37-46 (heavy chain sequences) or SEQ ID NOS 28-32 or 60-72 (light chain sequences).

In embodiments, the antibody or fragment thereof can be provided as a nucleic acid construct encoding the antibody or fragment. See, for example, U.S. application Ser. No. 15/537,779, which is incorporated by reference herein in its entirety.

These can include vectors, liposomes, naked DNA, adjuvant-assisted DNA, gene gun, catheters, etc. Vectors include chemical conjugates such as described in WO 93/64701, which has targeting moiety (e.g. a ligand to a cellular surface receptor), and a nucleic acid binding moiety (e.g. polylysine), viral vector (e.g. a DNA or RNA viral vector), fusion proteins such as described in PCT/US 95/02140 (WO 95/22618) which is a fusion protein containing a target moiety (e.g. an antibody specific for a target cell) and a nucleic acid binding moiety (e.g. a protamine), plasmids, phage, etc. The vectors can be chromosomal, non-chromosomal or synthetic.

Preferred vectors include viral vectors, fusion proteins and chemical conjugates. Retroviral vectors include moloney murine leukemia viruses. DNA viral vectors are preferred. These vectors include pox vectors such as orthopox or avipox vectors, herpesvirus vectors such as a herpes simplex I virus (HSV) vector (see Geller, A. I. et al, J. Neurochem, 64:487 (1995); Lim, F., et al, in DNA Cloning: Mammalian Systems, D. Glover, Ed. (Oxford Univ. Press, Oxford England) (1995); Geller, A. I. et al, Proc Natl. Acad. Sci.: U.S.A. 90:7603 (1993); Geller, A. I., et al, Proc Natl. Acad. Sci USA 87: 1149 (1990), Adenovirus Vectors (see LeGal LaSalle et al, Science, 259:988 (1993); Davidson, et al, Nat. Genet 3:219 (1993); Yang, et al, J. Virol. 69:2004 (1995) and Adeno-associated Virus Vectors (see Kaplitt, M. G. et al, Nat. Genet. 8: 148 (1994).

Pox viral vectors introduce the gene into the cell's cytoplasm. Avipox virus vectors result in only a short-term expression of the nucleic acid. Adenovirus vectors, adeno-associated virus vectors and herpes simplex virus (HSV) vectors are preferred for introducing the nucleic acid into neural cells. The adenovirus vector results in a shorter-term expression (about 2 months) than adeno-associated virus (about 4 months), which in turn is shorter than HSV vectors. The particular vector chosen will depend upon the target cell and the condition being treated. The introduction can be by standard techniques, e.g. infection, transfection, transduction or transformation. Examples of modes of gene transfer include e.g., naked DNA, $CaP0_4$ precipitation, DEAE dextran, electroporation, protoplast fusion, lipofection, cell microinjection, and viral vectors.

The vector can be employed to target essentially any desired target cell. For example, stereotaxic injection can be used to direct the vectors (e.g. adenovirus, HSV) to a desired location. Additionally, the particles can be delivered by intracerebroventricular (icv) infusion using a minipump infusion system, such as a SynchroMed Infusion System. A method based on bulk flow, termed convection, has also proven effective at delivering large molecules to extended areas of the brain and can be useful in delivering the vector to the target cell. (See Bobo et al, Proc. Natl. Acad. Sci. USA 91:2076-2080 (1994); Morrison et al, Am. J. Physiol. 266: 292-305 (1994)). Other methods that can be used include catheters, intravenous, parenteral, intraperitoneal and subcutaneous injection, and oral or other known routes of administration.

These vectors can be used to express large quantities of antibodies that can be used in a variety of ways. For example, to detect the presence of MUC1 in a sample. The antibody can also be used to try to bind to and disrupt a MUC1 activity.

Techniques can be adapted for the production of single-chain antibodies specific to an antigenic protein of the invention (see e.g., U.S. Pat. No. 4,946,778). In addition, methods can be adapted for the construction of $F_{ab}$ expression libraries (see e.g., Huse, et al, 1989 Science 246: 1275-1281) to allow rapid and effective identification of monoclonal $F_{ab}$ fragments with the desired specificity for a protein or derivatives, fragments, analogs or homologs thereof. Antibody fragments that contain the idiotypes to a protein antigen can be produced by techniques known in the art including, but not limited to: (i) an $F_{(ab')2}$ fragment produced by pepsin digestion of an antibody molecule; (ii) an $F_{ab}$ fragment generated by reducing the disulfide bridges of an $F_{(ab')2}$ fragment; (iii) an $F_{ab}$ fragment generated by the treatment of the antibody molecule with papain and a reducing agent and (iv) Fv fragments.

Heteroconjugate antibodies are also within the scope of the present invention. Heteroconjugate antibodies are composed of two covalently joined antibodies. Such antibodies have, for example, been proposed to target immune system cells to unwanted cells (see U.S. Pat. No. 4,676,980), and for treatment of HIV infection (see WO 91/00360; WO 92/200373; EP 03089). It is contemplated that the antibodies can be prepared in vitro using known methods in synthetic protein chemistry, including those involving crosslinking agents. For example, immunotoxins can be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

In certain embodiments, the antibody is engineered or modified with respect to alter the function of an antibody for clinical use. For example, the antibody's effector function can be the focus of such engineering efforts, so as to enhance the effectiveness of the antibody in treating cancer. The skilled artisan will recognize that whether or not such modifications are employed depends on the use of the antibody. The Fc domain in particular is critical to the functioning of an antibody and has been the focus of many engineering efforts. These efforts to alter the function of an antibody can generally be broken down into efforts to increase effector function, decrease effector function, and/or extending serum half-life of the antibody. If the antibody or fragments thereof are utilized for targeting CART cells, then the Fc is not involved and such Fc modifications are not utilized. On the other hand, for soluble antibodies, it can be desired to enhance Fc effector functions using mutations.

One of the key mechanisms of action for anti-cancer antibodies is the targeted killing of tumor cells through recruitment of components of the immune system. This activity is achieved through interaction of the Fc domain of the anti-cancer antibody with the complement component C1q or Fcγ receptors. However, many anti-cancer antibodies have failed in clinical trials due to insufficient efficacy. This has, therefore, lead to efforts to increase the potency of antibodies through enhancement of the antibody's ability to mediate cellular cytotoxicity functions such as antibody dependent cell mediated cytotoxicity (ADCC) and antibody dependent cell mediated phagocytosis (ADCP).

For example, such engineering efforts have focused on increasing the affinity of the Fc domain of the anticancer antibody for the low affinity receptor FcγIIIa. A number of mutations within the Fc domain have been identified that either directly or indirectly enhance binding of Fc receptors and through this significantly enhance cellular cytotoxicity (see, for example, Lazar, G. A., et al. (2006) PNAS 103, 4005-4010; Shields, R. L. et al. (2001) J. Biol. Chem. 276, 6591-6604; Stewart, R. et al. (2011) Protein Engineering, Design and Selection 24, 671-678; and Richards, J. O. et al. (2008) Mol Cancer Ther 7, 2517-2527). For example, such mutations include the mutations S239D/A330L/1332E (dubbed 3M), F243L and G236A.

An alternative approach has focused on glycosylation of the Fc domain. FcγRs interact with the carbohydrates on the CH2 domain and that the composition of these glycans has a substantial effect on effector function activity. One example of this is afucosylated (non-fucosylated) antibodies, which exhibit greatly enhanced ADCC activity through increased binding to FcγRIIIa.

In other embodiments, it is desirable to provide an antibody unable to activate effector functions. For these purposes IgG4 has commonly been used. Furthermore, Fc engineering approaches have been used to determine the key interaction sites for the Fc domain with Fcγ receptors and C1q and then mutate these positions to reduce or abolish binding. Through alanine scanning the binding site of C1q was isolated to a region covering the hinge and upper CH2 of the Fc domain. Mutations such as K322A, L234A and L235A in combination are sufficient to almost completely abolish FcγR and C1q binding. Similarly, a set of three mutations, L234F/L235E/P331S (dubbed TM), have a very similar effect.

An alternative approach is modification of the glycosylation on asparagine 297 of the Fc domain, which is known to be required for optimal FcR interaction. A loss of binding to FcRs has been observed in N297 point mutations, enzymatically degylcosylated Fc domains, recombinantly expressed antibodies in the presence of a glycosylation inhibitor and the expression of Fc domains in bacteria.

Embodiments of the invention can further comprise antibodies or fragments that have enhanced serum half-life of IgG through Fc engineering. IgG naturally persists for a prolonged period in the serum due to FcRn-mediated recycling, giving it a typical half-life of approximately 21 days. Despite this there have been a number of efforts to engineer the pH dependent interaction of the Fc domain with FcRn to increase affinity at pH 6.0 while retaining minimal binding at pH 7.4. For example, the mutations T250Q/M428L resulted in an approximate 2-fold increase in IgG half-life in rhesus monkeys, and the mutations M252Y/S254T/T256E (dubbed YTE) resulted in an approximate 4-fold increase in IgG half-life in cynomolgus monkeys.

As will be apparent to the skilled artisan, any number of such mutations can be made to provide an engineered antibody or fragment thereof with altered function and/or half-life. For example, cysteine residue(s) can be introduced into the Fc region, thereby allowing interchain disulfide bond formation in this region. The homodimeric antibody thus generated can have improved internalization capability and/or increased complement-mediated cell killing and antibody-dependent cellular cytotoxicity (ADCC). (See Caron et al, J. Exp Med., 176: 1 191-1 195 (1992) and Shopes, J. Immunol., 148: 2918-2922 (1992)). Alternatively, an antibody can be engineered that has dual Fc regions and can thereby have enhanced complement lysis and ADCC capabilities. (See Stevenson et al, Anti-Cancer Drug Design, 3. 219-230 (1989)).

In certain embodiments, an antibody of the invention can comprise an Fc variant comprising an amino acid substitution which alters the antigen-independent effector functions of the antibody, in particular the circulating half-life of the antibody. Such antibodies exhibit either increased or decreased binding to FcRn when compared to antibodies lacking these substitutions, therefore, have an increased or decreased half-life in serum, respectively. Fc variants with improved affinity for FcRn are anticipated to have longer serum half-lives, and such molecules have useful applications in methods of treating mammals where long half-life of the administered antibody is desired, e.g., to treat a chronic disease or disorder. In contrast, Fc variants with decreased FcRn binding affinity are expected to have shorter half-lives, and such molecules are also useful, for example, for administration to a mammal where a shortened circulation time can be advantageous, e.g. for in vivo diagnostic imaging or in situations where the starting antibody has toxic side effects when present in the circulation for prolonged periods. Fc variants with decreased FcRn binding affinity are also less likely to cross the placenta and, thus, are also useful in the treatment of diseases or disorders in pregnant women. In addition, other applications in which reduced FcRn binding affinity can be desired include those applications in which localization to the brain, kidney, and/or liver is desired. In one exemplary embodiment, the altered antibodies of the invention exhibit reduced transport across the epithelium of kidney glomeruli from the vasculature. In another embodiment, the altered antibodies of the invention exhibit reduced transport across the blood brain barrier (BBB) from the brain, into the vascular space. In one embodiment, an antibody with altered FcRn binding comprises an Fc domain having one or more amino acid substitutions within the "FcRn binding loop" of an Fc domain. The FcRn binding loop is comprised of amino acid residues 280-299 (according to EU numbering). Exemplary amino acid substitutions which altered FcRn binding activity are disclosed in International PCT Publication No. WG05/047327 which is incorporated by reference herein. In certain exemplary embodiments, the antibodies, or fragments thereof, of the invention comprise an Fc domain having one or more of the following substitutions: V284E, H285E, N286D, K290E and S304D (EU numbering).

In some embodiments, mutations are introduced to the constant regions of the mAb such that the antibody dependent cell-mediated cytotoxicity (ADCC) activity of the mAb is altered. For example, the mutation is an LALA mutation in the CH2 domain. In one aspect, the bsAb contains mutations on one scFv unit of the heterodimeric mAb, which reduces the ADCC activity. In another aspect, the mAb contains mutations on both chains of the heterodimeric mAb, which completely ablates the ADCC activity. For example, the mutations introduced one or both scFv units of the mAb are LALA mutations in the CH2 domain. These mAbs with variable ADCC activity can be optimized such that the mAbs exhibits maximal selective killing towards cells that express one antigen that is recognized by the mAb, however exhibits minimal killing towards the second antigen that is recognized by the mAb.

In other embodiments, antibodies, for use in the diagnostic and treatment methods described herein have a constant region, e.g., an IgG1 or IgG4 heavy chain constant region, which is altered to reduce or eliminate glycosylation. For example, an antibody of the invention can also comprise an Fc variant comprising an amino acid substitution which alters the glycosylation of the antibody. For example, said Fc variant can have reduced glycosylation (e.g., N- or O-linked glycosylation).

Exemplary amino acid substitutions which confer reduced or altered glycosylation are disclosed in International PCT Publication No, WO05/018572, which is incorporated by reference herein. In preferred embodiments, the antibodies, or fragments thereof of the invention are modified to eliminate glycosylation. Such antibodies, or fragments thereof, can be referred to as "agly" antibodies, or fragments thereof, (e.g. "agly" antibodies). While not being bound by theory, it is believed that "agly" antibodies, or fragments thereof, can have an improved safety and stability profile in vivo. Exemplary agly antibodies, or fragments thereof, comprise an aglycosylated Fc region of an IgG4 antibody which is devoid of Fc-effector function thereby eliminating the potential for Fc mediated toxicity to the normal vital organs that express MUC1. In yet other embodiments, antibodies, or fragments thereof, of the invention comprise an altered glycan. For example, the antibody can have a reduced number of fucose residues on an N-glycan at Asn297 of the Fc region, i.e., is afucosylated. In another embodiment, the antibody can have an altered number of sialic acid residues on the N-glycan at Asn297 of the Fc region.

The invention also pertains to immunoconjugates comprising an antibody conjugated to a cytotoxic agent such as a toxin (e.g., an enzymatically active toxin of bacterial, fungal, plant, or animal origin, or fragments thereof), or a radioactive isotope (i.e., a radioconjugate).

Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes. A variety of radionuclides are available for the production of radioconjugated antibodies. Examples include $^{212}$Bi, $^{131}$I, $^{131}$In, $^{90}$Y, and $^{186}$Re.

Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al, Science 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. (See WO94/11026).

Those of ordinary skill in the art will recognize that a large variety of possible moieties can be coupled to the resultant antibodies or to other molecules of the invention. (See, for example, "Conjugate Vaccines", Contributions to Microbiology and Immunology, J. M. Cruse and R. E. Lewis, Jr (eds), Carger Press, New York, (1989), the entire contents of which are incorporated herein by reference).

Coupling can be accomplished by any chemical reaction that will bind the two molecules so long as the antibody and the other moiety retain their respective activities. This linkage can include many chemical mechanisms, for instance covalent binding, affinity binding, intercalation, coordinate binding and complexation. The preferred binding is, however, covalent binding. Covalent binding can be achieved either by direct condensation of existing side chains or by the incorporation of external bridging molecules. Many bivalent or polyvalent linking agents are useful in coupling protein molecules, such as the antibodies of the present invention, to other molecules. For example, representative coupling agents can include organic compounds such as thioesters, carbodiimides, succinimide esters, diisocyanates, glutaraldehyde, diazobenzenes and hexamethylene diamines. This listing is not intended to be exhaustive of the various classes of coupling agents known in the art but, rather, is exemplary of the more common coupling agents. (See Killen and Lindstrom, Jour. Immun. 133: 1335-2549 (1984); Jansen et al., Immunological Reviews 62: 185-216 (1982); and Vitetta et al, Science 238: 1098 (1987)). Preferred linkers are described in the literature. (See, for example, Ramakrishnan, S. et al., Cancer Res. 44:201-208 (1984) describing use of MBS (M-maleimidobenzoyl-N-hydroxysuccinimide ester). See also, U.S. Pat. No. 5,030,719, describing use of halogenated acetyl hydrazide derivative coupled to an antibody by way of an oligopeptide linker. Particularly preferred linkers include: (i) EDC (1-ethyl-3-(3-dimethylamino-propyl) carbodiimide hydrochloride; (ii) SMPT (4-succinimidyloxycarbonyl-alpha-methyl-alpha-(2-pridyl-dithio)-toluene (Pierce Chem. Co., Cat. (21558G); (iii) SPDP (succinimidyl-6 [3-(2-pyridyldithio) propionamido]hexanoate (Pierce Chem. Co., Cat #21651G); (iv) Sulfo-LC-SPDP (sulfosuccinimidyl 6 [3-(2-pyridyldithio)-propianamide]hexanoate (Pierce Chem. Co. Cat. #2165-G); and (v) sulfo-NHS (-hydroxysulfo-succinimide: Pierce Chem. Co., Cat. #24510) conjugated to EDC.

The linkers described above contain components that have different attributes, thus leading to conjugates with differing physio-chemical properties. For example, sulfo-NHS esters of alkyl carboxylates are more stable than sulfo-NHS esters of aromatic carboxylates. NHS-ester containing linkers are less soluble than sulfo-NHS esters. Further, the linker SMPT contains a sterically hindered disulfide bond, and can form conjugates with increased stability. Disulfide linkages, are in general, less stable than other linkages because the disulfide linkage is cleaved in vitro, resulting in less conjugate available. Sulfo-NHS, in particular, can enhance the stability of carbodimide couplings. Carbodimide couplings (such as EDC) when used in conjunction with sulfo-NHS, forms esters that are more resistant to hydrolysis than the carbodimide coupling reaction alone.

The antibodies disclosed herein can also be formulated as immunoliposomes.

Liposomes containing the antibody are prepared by methods known in the art, such as described in Epstein et al, Proc. Natl. Acad. Sci. USA, 82: 3688 (1985); Hwang et al, Proc. Natl Acad. Sci. USA, 77: 4030 (1980); and U.S. Pat. Nos. 4,485,045 and 4,544,545.

Liposomes with enhanced circulation time are disclosed in U.S. Pat. No. 5,013,556.

Particularly useful liposomes can be generated by the reverse-phase evaporation method with a lipid composition comprising phosphatidylcholine, cholesterol, and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al, J. Biol. Chem., 257: 286-288 (1982) via a disulfide-interchange reaction.

Bi-Specific Antibodies

A bi-specific antibody (bsAb) is an antibody comprising two variable domains or scFv units such that the resulting antibody recognizes two different antigens. The present invention provides for bi-specific antibodies that recognize MUC1-SEA and a second antigen. Exemplary second antigens include tumor associated antigens (e.g., Mesothelin, LINGO1), cytokines (e.g., IL-12, IL-15) and cell surface receptors. Different format of bispecific antibodies are also provided herein. In some embodiments, each of the anti-MUC1 fragment and the second fragment is each independently selected from a $F_{ab}$ fragment, a single-chain variable fragment (scFv), or a single-domain antibody. In some embodiments, the bispecific antibody further includes a Fc fragment. A bi-specific antibody of the present invention comprises a heavy chain and a light chain combination or scFv of the MUC1 antibodies disclosed herein. See, for example, SEQ ID NO: 23-27, 35, 36, 24, or 37-46 (heavy chain sequences) or SEQ ID NOS 28-32 or 60-72 (light chain sequences).

In some embodiments, the second antigen of the bispecific antibody is mesothelin. Mesothelin is so named because of its expression in mesothelial cells. Mesothelin is a glycophosphatidylinositol (GPI)-linked cell-surface glycoprotein synthesized as a 71-kD precursor protein. After synthesis, the precursor protein is then cleaved by the endoprotease furin to release the secreted N-terminal region, called megakaryocyte potentiating factor (MPF), whereas the 41-kD mature MSLN remains attached to the membrane.

Mesothelin expression is normally limited to mesothelial cells lining the pleura, peritoneum, and pericardium, but is also highly expressed in many cancers and solid tumors, including malignant mesothelioma, pancreatic cancer, ovarian cancer, lung adenocarcinoma, endometrial cancer, biliary cancer, gastric cancer, and pediatric acute myeloid leukemia. Higher expression of MSLN has been correlated with poorer prognosis for patients with ovarian cancer, cholangiocarcinoma, lung adenocarcinoma, triple-negative breast cancer, and resectable pancreatic adenocarcinoma. See Hassan, Raffit, et al. "Mesothelin immunotherapy for cancer: ready for prime time?." *Journal of Clinical Oncology* 34.34 (2016): 4171. Thus, the bispecific antibody can comprise a first antibody targeted to MUC1, and a second antibody targeted to mesothelin.

In other embodiments, the second antigen of the bispecific antibody is CCR4. Chemokines are a family of secreted proteins known primarily for their roles in leukocyte activation and chemotaxis. Their specific interaction with chemokine receptors on target cells trigger signaling cascades that result in inflammatory mediator release, changes in cell shape, and cellular migration. The CC chemokine receptor 4 (CCR4) is the cognate receptor for the CC chemokines CCL17 and CCL22, and is expressed on functionally distinct subsets of T cells, including T helper type 2 cells (Th2), and the majority of regulatory T cells (Tregs) (Iellem et al, 2001; and Imai et al, 1999). Growing evidence indicate that CCL 17/22 secretion promotes increased numbers of tumor-infiltrating Tregs by malignant entities such as colorectal, ovarian, Hodgkin's lymphoma and glioblastoma (Curiel et al, 2004; Wagsater et al, 2008; Niens et al, 2008; Jacobs et al, 2010; Hiraoka et al, 2006). Increased levels of Treg in tumors hinder efficient antitumor immune responses (Wood et al, 2003; and Levings et al, 2001) and are often associated with poor clinical outcome and tumor progression (Hiraoka et al, 2006; and Woo et al, 2001). Accordingly, one major obstacle of successful cancer therapies might be caused by migration of Treg into tumors and their suppression of antitumor immune responses in the tumor microenvironment (Zou et al, 2006; and Yu et al, 2005).

Thus, the bispecific antibody can comprise a first antibody targeted to MUC1, and a second antibody targeted to CCR4. The skilled artisan will recognize that any second antibody targeted to CCR4 or fragment thereof can be utilized in the invention, including those included in PCT/US2008/088435, PCT/US2013/039744, PCT/US2015/054202, and PCT/US2016/026232, which are incorporated herein by reference in their entireties.

Aspects of the invention comprise multi-valent antibody and antigen-binding fragments that bind MUC1 and one or more additional antigens For example, the multivalent antibody or antigen-binding fragment can be specific for MUC1 and Mesothelin. A multivalent antigen-binding protein has more than one antigen-binding site. For the purposes of this application, "valent" can refer to the numerosity of antigen binding sites. Thus, a bivalent antibody can refer to an antibody with two binding sites; a trivalent antibody can refer to an antibody with three binding sites, and so on. The term "multivalent" can refer to any assemblage, covalently or non-covalently joined, of two or more antigen-binding proteins, the assemblage having more than one antigen-binding site. The term "multivalent" encompasses bivalent, trivalent, tetravalent, etc.

Bi-specific antibodies of the present invention can be constructed using methods known art. In some embodiments, the bi-specific antibody is a single polypeptide wherein the two scFv fragments are joined by a long linker polypeptide, of sufficient length to allow intramolecular association between the two scFv units to form an antibody. In other embodiments, the bi-specific antibody is more than one polypeptide linked by covalent or non-covalent bonds.

In another embodiment, the bi-specific antibody is constructed using the "knob into hole" method (Ridgway et al, Protein Eng 7:617-621 (1996)). In this method, the Ig heavy chains of the two different variable domains are reduced to selectively break the heavy chain pairing while retaining the heavy-light chain pairing. The two heavy-light chain heterodimers that recognize two different antigens are mixed to promote heteroligation pairing, which is mediated through the engineered "knob into holes" of the CH3 domains.

In another embodiment, the bi-specific antibody can be constructed through exchange of heavy-light chain dimers from two or more different antibodies to generate a hybrid antibody where the first heavy-light chain dimer recognizes MUC1 and the second heavy-light chain dimer recognizes a second antigen. The mechanism for heavy-light chain dimer is similar to the formation of human IgG4, which also functions as a bispecific molecule. Dimerization of IgG heavy chains is driven by intramolecular force, such as the pairing the CH3 domain of each heavy chain and disulfide bridges. Presence of a specific amino acid in the CH3 domain (R409) has been shown to promote dimer exchange and construction of the IgG4 molecules. Heavy chain pairing is also stabilized further by interheavy chain disulfide bridges in the hinge region of the antibody. Specifically, in IgG4, the hinge region contains the amino acid sequence Cys-Pro-Ser-Cys (SEQ ID NO: 133) (in comparison to the stable IgG1 hinge region which contains the sequence Cys-Pro-Pro-Cys (SEQ ID NO: 134) at amino acids 226-230. This sequence difference of Serine at position 229 has been linked to the tendency of IgG4 to form novel intrachain disulfides in the hinge region (Van der Neut Kolfschoten, M. et al, 2007, Science 317: 1554-1557 and Labrijn, A. F. et al, 2011, Journal of Immunol 187:3238-3246).

Therefore, bi-specific antibodies of the present invention can be created through introduction of the R409 residue in the CH3 domain and the Cys-Pro-Ser-Cys sequence (SEQ ID NO: 133) in the hinge region of antibodies that recognize MUC1 or a second antigen, so that the heavy-light chain dimers exchange to produce an antibody molecule with one heavy-light chain dimer recognizing MUC1 and the second heavy-light chain dimer recognizing a second antigen, wherein the second antigen is any antigen disclosed herein. Known IgG4 molecules can also be altered such that the heavy and light chains recognize MUC1 or a second antigen, as disclosed herein. Use of this method for constructing the bi-specific antibodies of the present invention can be beneficial due to the intrinsic characteristic of IgG4 molecules wherein the Fc region differs from other IgG subtypes in that it interacts poorly with effector systems of the immune response, such as complement and Fc receptors expressed by certain white blood cells. This specific property makes these IgG4-based bi-specific antibodies attractive for therapeutic applications, in which the antibody is required to bind the target(s) and functionally alter the signaling pathways associated with the target(s), however not trigger effector activities.

In some embodiments, mutations are introduced to the constant regions of the bsAb such that the antibody dependent cell-mediated cytotoxicity (ADCC) activity of the bsAb is altered. For example, the mutation is an LALA mutation in the CH2 domain. In one aspect, the bsAb contains mutations on one scFv unit of the heterodimeric bsAb, which reduces the ADCC activity. In another aspect, the bsAb contains mutations on both chains of the heterodimeric bsAb, which completely ablates the ADCC activity. For example, the mutations introduced one or both scFv units of the bsAb are LALA mutations in the CH2 domain. These bsAbs with variable ADCC activity can be optimized such that the bsAbs exhibits maximal selective killing towards cells that express one antigen that is recognized by the bsAb, however exhibits minimal killing towards the second antigen that is recognized by the bsAb.

The bi-specific antibodies disclosed herein can be useful in treatment of diseases or medical conditions, for example, cancer.

Chimeric Antigen Receptor (CAR) T-Cell Therapies

Cellular therapies, such as chimeric antigen receptor (CAR) T-cell therapies, are also provided herein. CAR T-cell therapies redirect a patient's T-cells to kill tumor cells by the exogenous expression of a CAR. A CAR can be a membrane spanning fusion protein that links the antigen recognition domain of an antibody to the intracellular signaling domains of the T-cell receptor and co-receptor. A suitable cell can be used, that is put in contact with an anti-MUC1 antibody of the present invention (or alternatively engineered to express an anti-MUC1 antibody as described herein). Solid tumors offer unique challenges for CAR-T therapies. Unlike blood cancers, tumor-associated target proteins are overexpressed between the tumor and healthy tissue resulting in on-target/off-tumor T-cell killing of healthy tissues. Furthermore, immune repression in the tumor microenvironment (TME) limits the activation of CAR-T cells towards killing the tumor. Upon such contact or engineering, the cell can then be introduced to a cancer patient in need of a treatment. The cancer patient may have a cancer of any of the types as disclosed herein. The cell (e.g., a T cell) can be, for instance, a tumor-infiltrating T lymphocyte, a CD4+ T cell, a CD8+ T cell, or the combination thereof, without limitation. Exemplary CARS useful in aspects of the invention include those disclosed in, for example, PCT/US2015/067225 and PCT/US2019/022272, each of which are hereby incorporated by reference in their entireties.

In particular cases, the lymphocytes include a receptor that is chimeric, non-natural and engineered at least in part by the hand of man. In particular cases, the engineered chimeric antigen receptor (CAR) has one, two, three, four, or more components, and in some embodiments the one or more components facilitate targeting or binding of the lymphocyte to one or more tumor antigen-comprising cancer cells.

The CAR according to the invention generally comprises at least one transmembrane polypeptide comprising at least one extracellular ligand-biding domain and; one transmembrane polypeptide comprising at least one intracellular signaling domain; such that the polypeptides assemble together to form a Chimeric Antigen Receptor.

The term "extracellular ligand-binding domain" as used herein is defined as an oligo- or polypeptide that is capable of binding a ligand. Preferably, the domain will be capable of interacting with a cell surface molecule. For example, the extracellular ligand-binding domain may be chosen to recognize a ligand that acts as a cell surface marker on target cells associated with a particular disease state.

In particular, the extracellular ligand-binding domain can comprise an antigen binding domain derived from an antibody against an antigen of the target.

In a preferred embodiment, said extracellular ligand-binding domain is a single chain antibody fragment (scFv) comprising the light (VL) and the heavy (VH) variable fragment of a target antigen specific monoclonal antibody joined by a flexible linker.

Other binding domain than scFv can also be used for predefined targeting of lymphocytes, such as camelid single-domain antibody fragments or receptor ligands, antibody binding domains, antibody hypervariable loops or CDRs as non-limiting examples.

In a preferred embodiment said transmembrane domain further comprises a stalk region between said extracellular ligand-binding domain and said transmembrane domain. The term "stalk region" used herein generally means any oligo- or polypeptide that functions to link the transmembrane domain to the extracellular ligand-binding domain. In particular, stalk region are used to provide more flexibility and accessibility for the extracellular ligand-binding domain. A stalk region may comprise up to 300 amino acids, preferably 10 to 100 amino acids and most preferably 25 to 50 amino acids. Stalk region may be derived from all or part of naturally occurring molecules, such as from all or part of the extracellular region of CD8, CD4 or CD28, or from all or part of an antibody constant region. Alternatively the stalk region may be a synthetic sequence that corresponds to a naturally occurring stalk sequence, or may be an entirely synthetic stalk sequence. In a preferred embodiment said stalk region is a part of human CD8 alpha chain.

The signal transducing domain or intracellular signaling domain of the CAR of the invention is responsible for intracellular signaling following the binding of extracellular ligand binding domain to the target resulting in the activation of the immune cell and immune response. In other words, the signal transducing domain is responsible for the activation of at least one of the normal effector functions of the immune cell in which the CAR is expressed. For example, the effector function of a T cell can be a cytolytic activity or helper activity including the secretion of cytokines. Thus, the term "signal transducing domain" refers to the portion of a protein which transduces the effector signal function signal and directs the cell to perform a specialized function.

Signal transduction domain comprises two distinct classes of cytoplasmic signaling sequence, those that initiate antigen-dependent primary activation, and those that act in an antigen-independent manner to provide a secondary or co-stimulatory signal. Primary cytoplasmic signaling sequence can comprise signaling motifs which are known as immunoreceptor tyrosine-based activation motifs of ITAMs. ITAMs are well defined signaling motifs found in the intracytoplasmic tail of a variety of receptors that serve as binding sites for syk/zap70 class tyrosine kinases. Examples of ITAM used in the invention can include as non-limiting examples those derived from TCR zeta, FcR gamma, FcR beta, FcR epsilon, CD3 gamma, CD3 delta, CD3 epsilon, CD5, CD22, CD79a, CD79b and CD66d. In a preferred embodiment, the signaling transducing domain of the CAR can comprise the CD3 zeta signaling domain, or the intracytoplasmic domain of the Fc epsilon RI beta or gamma chains. In another preferred embodiment, the signaling is provided by CD3 zeta together with co-stimulation provided by CD28 and a tumor necrosis factor receptor (TNFr), such as 4-1BB or OX40), for example.

In particular embodiment the intracellular signaling domain of the CAR of the present invention comprises a co-stimulatory signal molecule. In some embodiments the intracellular signaling domain contains 2, 3, 4 or more co-stimulatory molecules in tandem. A co-stimulatory molecule is a cell surface molecule other than an antigen receptor or their ligands that is required for an efficient immune response.

"Co-stimulatory ligand" refers to a molecule on an antigen presenting cell that specifically binds a cognate co-stimulatory molecule on a T-cell, thereby providing a signal which, in addition to the primary signal provided by, for instance, binding of a TCR/CD3 complex with an MHC molecule loaded with peptide, mediates a T cell response, including, but not limited to, proliferation activation, differentiation and the like. A co-stimulatory ligand can include but is not limited to CD7, B7-1 (CD80), B7-2 (CD86), PD-L1, PD-L2, 4-1BBL, OX40L, inducible costimulatory ligand (ICOS-L), intercellular adhesion molecule (ICAM, CD30L, CD40, CD70, CD83, HLA-G, MICA, M1CB, HVEM, lymphotoxin beta receptor, 3/TR6, ILT3, ILT4, an agonist or antibody that binds Toll ligand receptor and a ligand that specifically binds with B7-H3. A co-stimulatory ligand also encompasses, inter alia, an antibody that specifically binds with a co-stimulatory molecule present on a T cell, such as but not limited to, CD27, CD28, 4-IBB, OX40, CD30, CD40, PD-1, ICOS, lymphocyte function-associated antigen-1 (LFA-1), CD2, CD7, LTGHT, NKG2C, B7-H3, a ligand that specifically binds with CD83.

A "co-stimulatory molecule" refers to the cognate binding partner on a T-cell that specifically binds with a co-stimulatory ligand, thereby mediating a co-stimulatory response by the cell, such as, but not limited to proliferation. Co-stimulatory molecules include, but are not limited to an MHC class 1 molecule, BTLA and Toll ligand receptor. Examples of costimulatory molecules include CD27, CD28, CD8, 4-1BB (CD137), OX40, CD30, CD40, PD-1, ICOS, lymphocyte function-associated antigen-1 (LFA-1), CD2, CD7, LIGHT, NKG2C, B7-H3 and a ligand that specifically binds with CD83 and the like.

In another particular embodiment, said signal transducing domain is a TNFR-associated Factor 2 (TRAF2) binding motifs, intracytoplasmic tail of costimulatory TNFR member family. Cytoplasmic tail of costimulatory TNFR family member contains TRAF2 binding motifs consisting of the major conserved motif (P/S/A)X(Q/E)E) or the minor motif (PXQXXD), wherein X is any amino acid. TRAF proteins are recruited to the intracellular tails of many TNFRs in response to receptor trimerization.

The distinguishing features of appropriate transmembrane polypeptides comprise the ability to be expressed at the surface of an immune cell, in particular lymphocyte cells or Natural killer (NK) cells, and to interact together for directing cellular response of immune cell against a predefined target cell. The different transmembrane polypeptides of the CAR of the present invention comprising an extracellular ligand-biding domain and/or a signal transducing domain interact together to take part in signal transduction following the binding with a target ligand and induce an immune response. The transmembrane domain can be derived either from a natural or from a synthetic source. The transmembrane domain can be derived from any membrane-bound or transmembrane protein.

The term "a part of" used herein refers to any subset of the molecule, that is a shorter peptide. Alternatively, amino acid sequence functional variants of the polypeptide can be prepared by mutations in the DNA which encodes the polypeptide. Such variants or functional variants include, for example, deletions from, or insertions or substitutions of, residues within the amino acid sequence. Any combination of deletion, insertion, and substitution may also be made to arrive at the final construct, provided that the final construct possesses the desired activity, especially to exhibit a specific anti-target cellular immune activity. The functionality of the CAR of the invention within a host cell is detectable in an assay suitable for demonstrating the signaling potential of said CAR upon binding of a particular target. Such assays are available to the skilled person in the art. For example, this assay allows the detection of a signaling pathway, triggered upon binding of the target, such as an assay involving measurement of the increase of calcium ion release, intracellular tyrosine phosphorylation, inositol phosphate turnover, or interleukin (IL) 2, interferon .gamma., GM-CSF, IL-3, IL-4 production thus effected.

Aspects of the invention are also directed towards methods and embodiments that comprise CAR T cells which target more than one antigen. This can be accomplished by different approaches: (a) generate 2 or more cell populations expressing different CARs and administer them to a subject together or sequentially (coadministration); (b) use a bicistronic vector that encodes 2 different CARs on the same cell; (c) simultaneously engineer T cells with 2 different CAR constructs (cotransduction), which may generate three CAR-T subsets consisting of dual and single CAR-expressing cells; or (d) encode 2 CARs on the same chimeric protein using a single vector (i.e., bi-specific or tandem CARs).

In embodiments, the dual targeted CAR T cells can target MUC1 and one or more additional antigens. In embodiments, the one or more additional antigens can comprise targets on a tumor cell, such as Mesothelin, or targets on a non-tumor cell, such as a Treg. For example, the dual targeted CAR T cell can target MUC1 on a tumor cell and CCR4 on Tregs that have been recruited to the tumor microenvironment. Such dual-targeted CAR T cell can be referred to as a "dual target cell bispecific CAR".

The antigen recognition domain of the CAR can be an antibody as described herein, including an antibody fragment. An "antibody fragment" can be a molecule other than an intact antibody that comprises a portion of an intact antibody that binds the antigen to which the intact antibody binds. Examples of antibody fragments include but are not limited to Fv, Fab, Fab', Fab'-SH, F(ab')2; diabodies; linear antibodies; single-chain antibody molecules (e.g. scFv); and multispecific antibodies formed from antibody fragments.

The antigen recognition domain can be directed towards any antigen target of interest. In embodiments, the antigen target of interest is on the surface of a cell, such as the surface of a cancer cell. Non-limiting examples of antigen targets comprise Muc1 and/or Mesothelin.

The antigen recognition domain useful in constructing the CAR-Ts, for example scFVs directed toward Muc1 and/or mesothelin, can be synthesized, engineered, and/or produced using nucleic acids (e.g., DNA). The DNA encoding the antigen recognition domain can be cloned in frame to DNA encoding necessary CAR-T elements such as, but not limited to, CD8 hinge regions, transmembrane domains, co-stimulatory domains of molecules of immunological interest such as, but not limited to, CD28 and 41BB and CD3-zeta intracellular signaling domains.

Chimeric antigen receptors fuse antigen-recognition domains to signaling domains (also referred to as stimulatory domains) that modulate (i.e., stimulate) cell signaling. Non-limiting examples of such stimulatory domains comprise those of CD28, 41BB, and/or CD3-zeta intracellular signaling domains.

DNA constructs, which can also be referred to as "DNA vectors", as described herein can be cloned into a vector which will be used to transduce and produce chimeric-antigen receptor T-cells, including those that secrete polypeptides and/or fragments thereof. In one embodiment, DNA constructs can be cloned into a lentiviral vector for production of lentivirus, which will be used to transduce and produce chimeric-antigen receptor T-cells, including those that secrete a mono, bi- or tri-specific immune-modulating antibody/minibody and/or antibody-fusion protein at the tumor site.

As used herein, the term "engineered" or "recombinant" cell can refer to a cell into which a recombinant gene, such as a gene encoding a chimeric antigen receptor, has been introduced. Therefore, engineered cells are distinguishable from naturally occurring cells which do not contain a recombinantly introduced gene. Engineered cells are thus cells having a gene or genes introduced through the hand of man. Recombinantly introduced genes will either be in the form of a cDNA gene (i.e., they will not contain introns), a copy of a genomic gene, or will include genes positioned adjacent to a promoter not naturally associated with the particular introduced gene.

In embodiments, it will be more convenient to employ as the recombinant gene a cDNA version of the gene as the use of a cDNA version will provide advantages in that the size of the gene will generally be much smaller and more readily employed to transfect the targeted cell than will a genomic gene, which will typically be up to an order of magnitude larger than the cDNA gene. However, the possibility of employing a genomic version of a particular gene where desired is not excluded.

In embodiments, the antigen recognition domain can be linked to signaling domains to form a CAR on the surface of a cell of any kind, including immune cells capable of expressing the antibody fragment for cancer therapy or a cell, such as a bacterial cell, that harbors an expression vector that encodes the CAR. As used herein, the terms "cell," "cell line," and "cell culture" may be used interchangeably. All of these terms also include their progeny, which is any and all subsequent generations. Without being bound by theory, all progeny may not be identical due to deliberate or inadvertent mutations. In the context of expressing a heterologous nucleic acid sequence, "host cell" refers to a eukaryotic cell that is capable of replicating a vector and/or expressing a heterologous gene encoded by a vector. A host cell can, and has been, used as a recipient for vectors. A host cell may be "transfected" or "transformed," which refers to a process by which exogenous nucleic acid is transferred or introduced into the host cell. A transformed cell includes the primary subject cell and its progeny. As used herein, the terms "engineered" and "recombinant" cells or host cells can refer to a cell into which an exogenous nucleic acid sequence, such as, for example, a vector, has been introduced. Therefore, recombinant cells are distinguishable from naturally occurring cells which do not contain a recombinantly introduced nucleic acid.

The cells can be autologous cells, syngeneic cells, allogenic cells and even in some cases, xenogeneic cells.

In embodiments of the invention, a host cell is a T cell, including (but not limited to) a cytotoxic T cell (also known as TC, Cytotoxic T Lymphocyte, CTL, T-Killer cell, cytolytic T cell, CD8+ T-cells or killer T cell); CD4+ T cells; NK cells; and NKT cells.

For example, chimeric-antigen receptor (CAR) T-cell therapies redirect a patient's T-cells to kill tumor cells by the exogenous expression of a CAR. A CAR is a membrane spanning fusion protein that links the antigen recognition domain of an antibody or fragment to the intracellular signaling domains of the T-cell receptor and co-receptor. For example, chimeric antigen receptors fuse antigen-specific antibody fragments to T-cell co-stimulatory domains and the CD3 zeta intracellular signaling domain, allowing for the re-direction of T-cells towards an antigen presented on a cell of interest, for example, onto tumor cells.

An emerging mechanism associated with the progression of tumors is the immune checkpoint pathway, which consists in cellular interactions that prevent excessive activation of T cells under normal conditions, allowing T cell function in a self-limited manner. As an evasion mechanism, many tumors are able to stimulate the expression of immune checkpoint molecules, resulting in an anergic phenotype of T cells that cannot restrain tumor progression. Emerging clinical data highlight the importance of one inhibitory ligand and receptor pair as an immune checkpoint: the programmed death-ligand 1 (PD-L1; B7-H1 and CD274) and programmed death receptor-1 (PD-1; CD279), in preventing killing of cancer cells by cytotoxic T-lymphocytes. PD1 receptor is expressed by many cell types like T cells, B cells, Natural Killer cells (NK) and host tissues. Tumors and Antigen-presenting cells (APC) expressing PD-L1 can block T cell receptor (TCR) signaling of cytotoxic T-lymphocytes through binding to receptor PD-1, decreasing the production of cytokines and T cell proliferation. PD-L1 overexpression can be found in many tumor types and may also mediate an immunosuppressive function through its interaction with other proteins, including CD80 (B7.1), blocking its ability to activate T cells through binding to CD28.

Genetic engineering of human lymphocytes to express tumor-directed chimeric antigen receptors (CAR) can produce antitumor effector cells that bypass tumor immune escape mechanisms that are due to abnormalities in protein-antigen processing and presentation. Moreover, these transgenic receptors can be directed to tumor-associated antigens that are not protein-derived. In certain embodiments of the invention there are lymphocytes (CARTS) that are modified to comprise at least a CAR, and in particular embodiments of the invention a single CAR targets two or more antigens. In preferred embodiments, the CARTS are further modified to express and secrete one or more polypeptides, such as for example an antibody or a cytokine. Such CARTS are referred to herein as armed CARTS. Armed CARTS allow for simultaneous secretion of the polypeptide locally at the targeted site (i.e., tumor site). For example, an anti-MUC1 antibody can be the targeting moiety of an engineered CART cell, and an anti-CCR4 antibody can be the payload of the engineered CAR T cell. This exemplary embodiment is not to be limiting, however, as the skilled artisan will recognize that any of a number of antibodies can be utilized as the payload.

The polypeptide can be, for example, an antibody or fragment thereof as described herein. For example, a second expression construct, which can be in the same DNA vector as that which encodes the CAR (e.g. the antigen-recognition domain) or in a second separate vector, can be used to encode a mini body (scFv-Fc) or antibody, or a fragment thereof, that is directed against a single or multiple antigens of interest, and can be cloned after an internal ribosomal entry site (IRES). For example, the second expression cassette comprises either a fluorescent molecule or an immune-modulating minibody.

In embodiments, the engineered cell can secrete mono, bi-, or tri-specific minibody, antibody or minibody/antibody fusion protein at the tumor site so to provide additional benefit by altering (i.e., modulating) the immune-repressive tumor microenvironment. For example, the secreted antibody can be an anti-CCR4 antibody.

In cancer, the normal intercellular interactions in tissues are disrupted, and the tumor microenvironment evolves to accommodate the growing tumor. The tumor microenvironment (TME) refers to the cellular environment in which a tumor exists, including components such as surrounding blood vessels, immune cells, fibroblasts, bone marrow-derived inflammatory cells, lymphocytes, signaling molecules and the extracellular matrix (ECM). Tumor microenvironment is complex and is heavily influenced by immune system.

Figure 18:
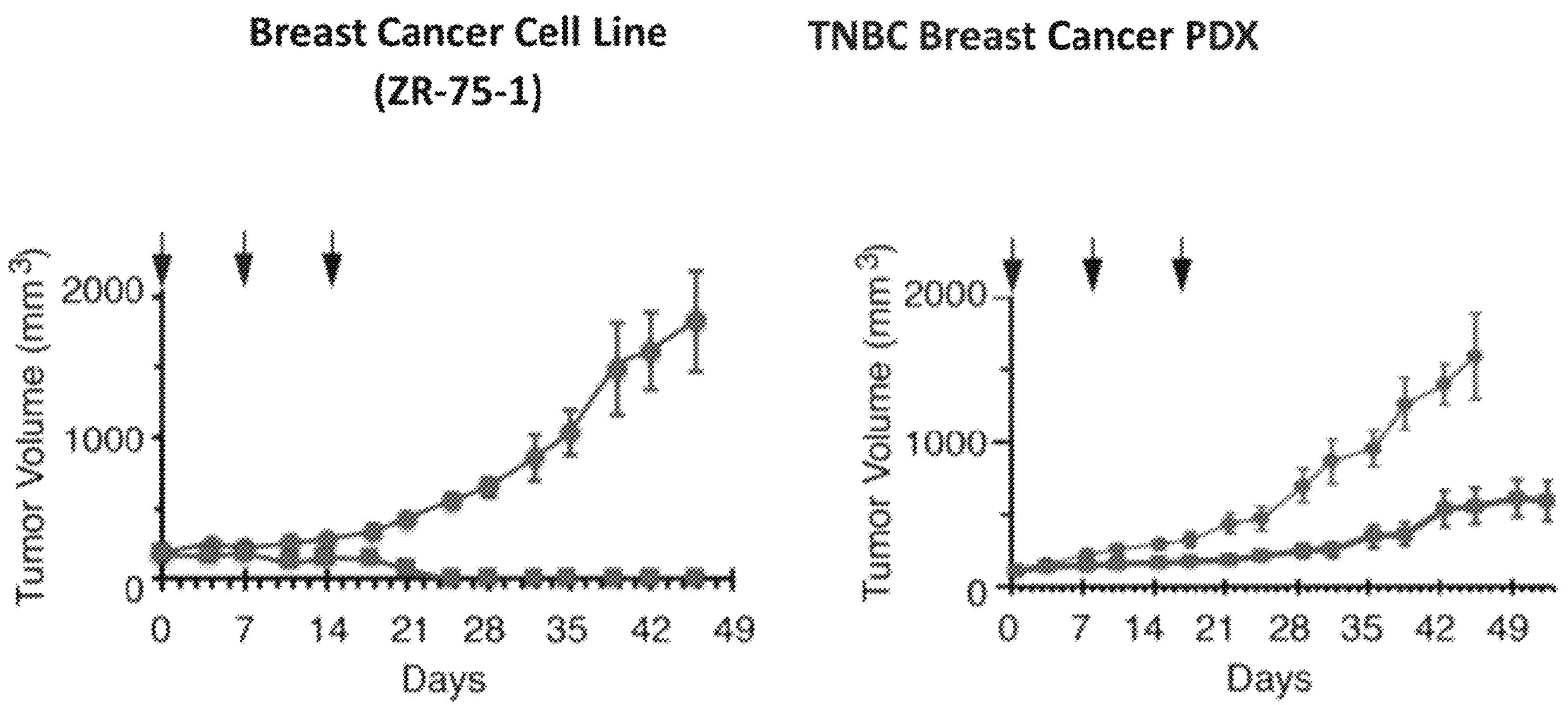
FIG. 18 shows a schematic of the MUC1-C terminal domain and binding epitope of anti-MUC1-C antibody h3D1 IgG (kindly provided by Kufe laboratory).
Figure 19:
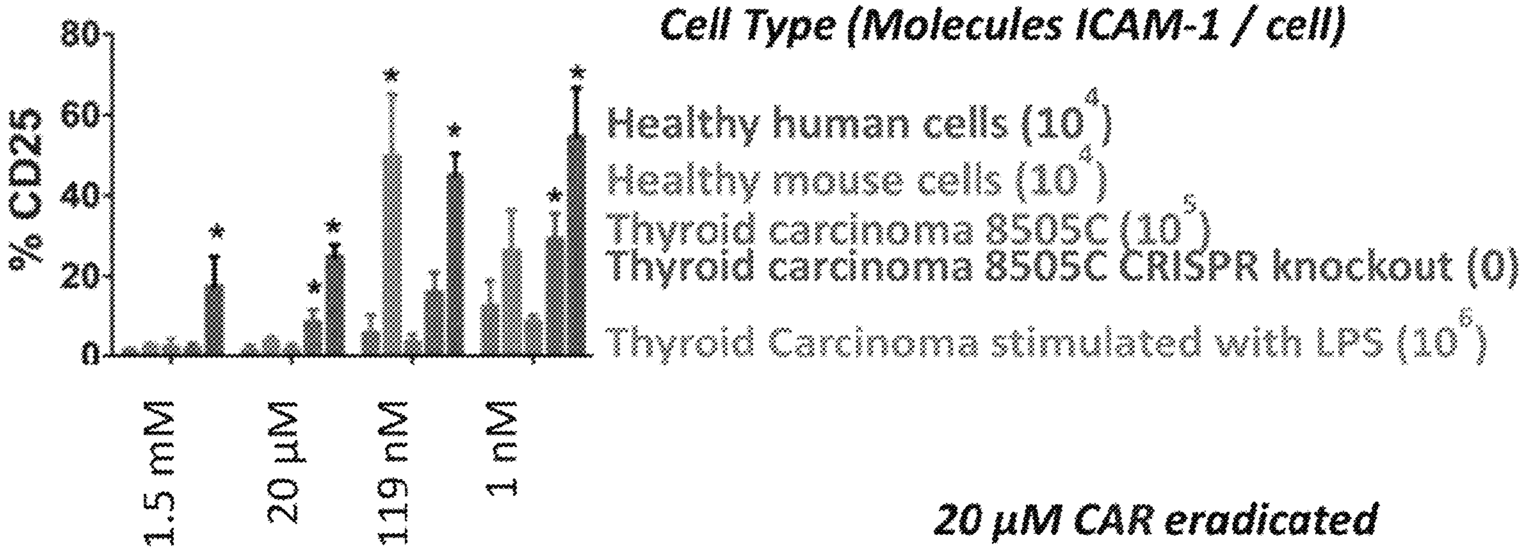
FIG. 19 shows the effect of CAR affinity and the effect of the CAR epitope. For example, the affinity of CAR influences T cell activation, rate of killing, and CAR's ability to distinguish between healthy and cancerous tissues. Further, more efficient T cell activation occurs when CAR recognizes a membrane proximal epitope on the antigen even if membrane proximal CAR has lower binding efficiency.
Figure 20:
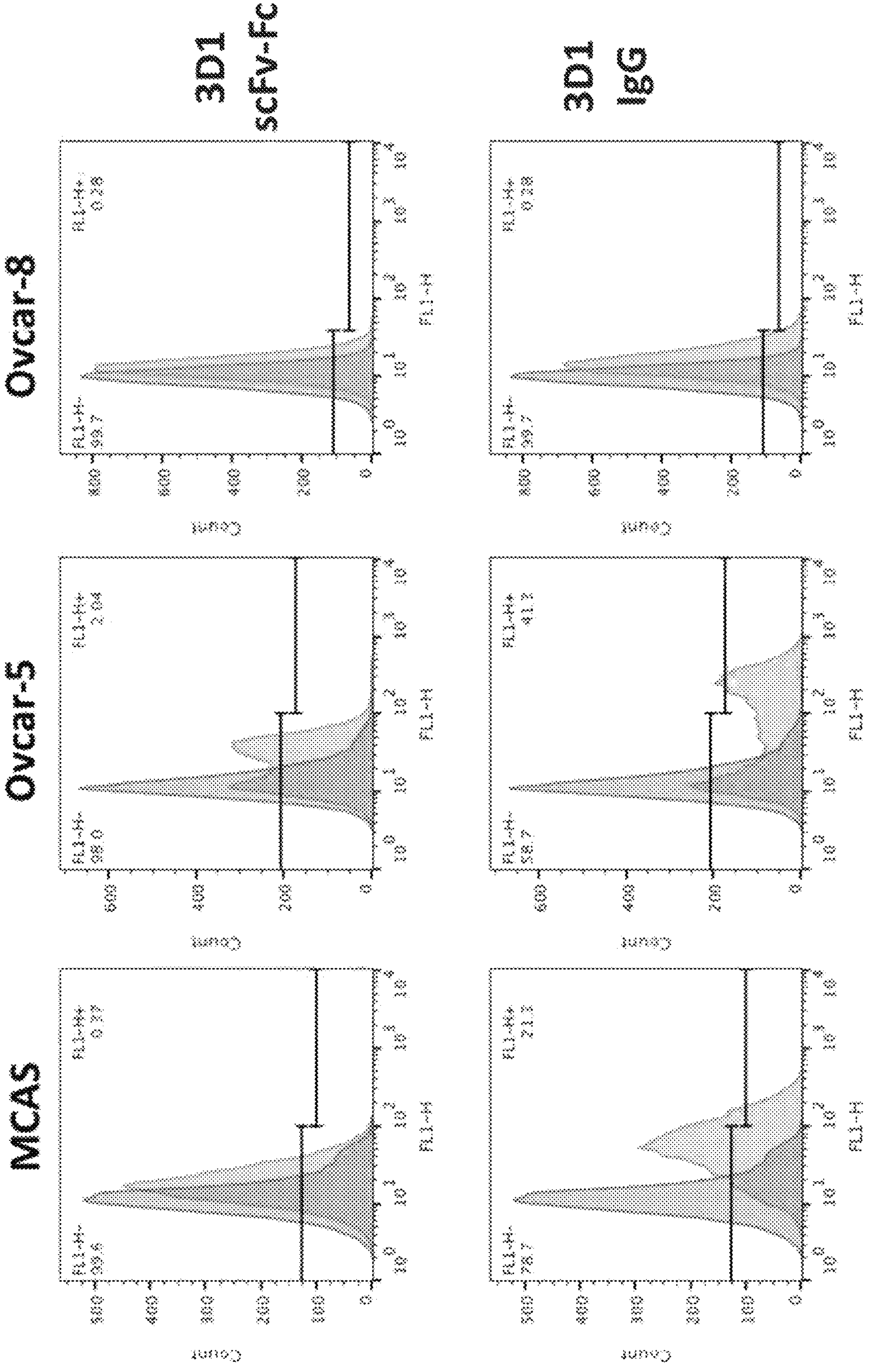
FIG. 20 shows reduction in affinity upon conversion of h3D1 IgG to scFv. Loss of affinity of scFv-Fc upon binding to cell lines hindered initial MUC-1C CAR T cell efforts. Quantification of affinities of 3D1 scFv-Fc and 3D1 IgG. Figure discloses SEQ ID NO: 159.
Figure 21:
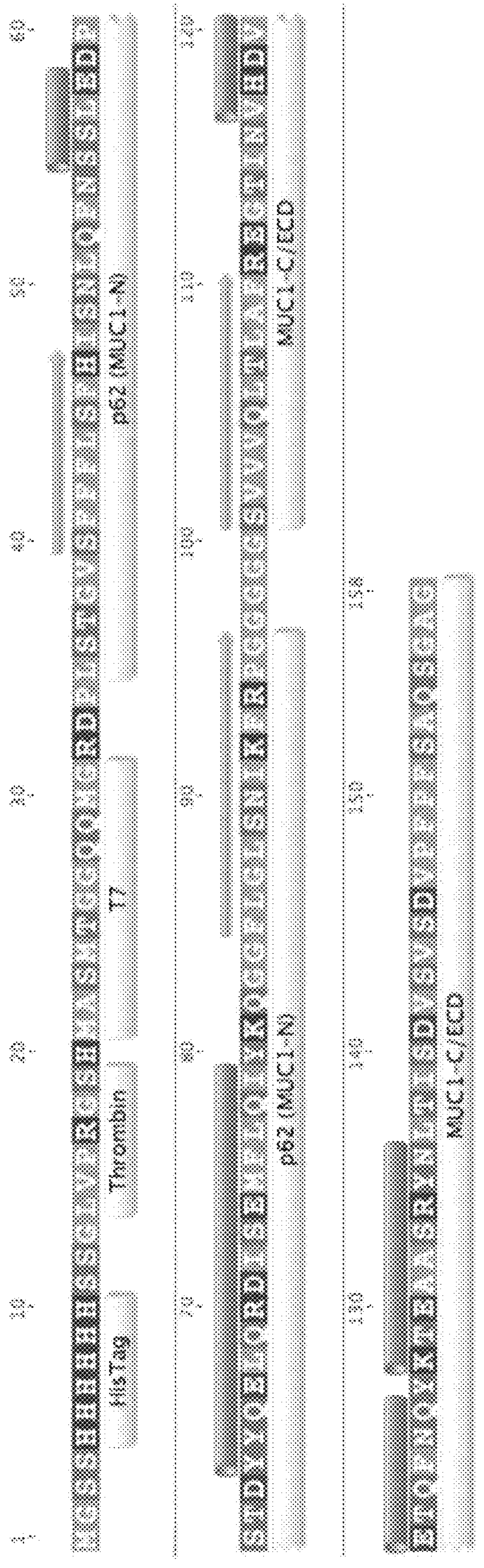
FIG. 21 shows amino acid sequence of construct comprising MUC1-SEA (SEQ ID NO: 1).
Figure 22:
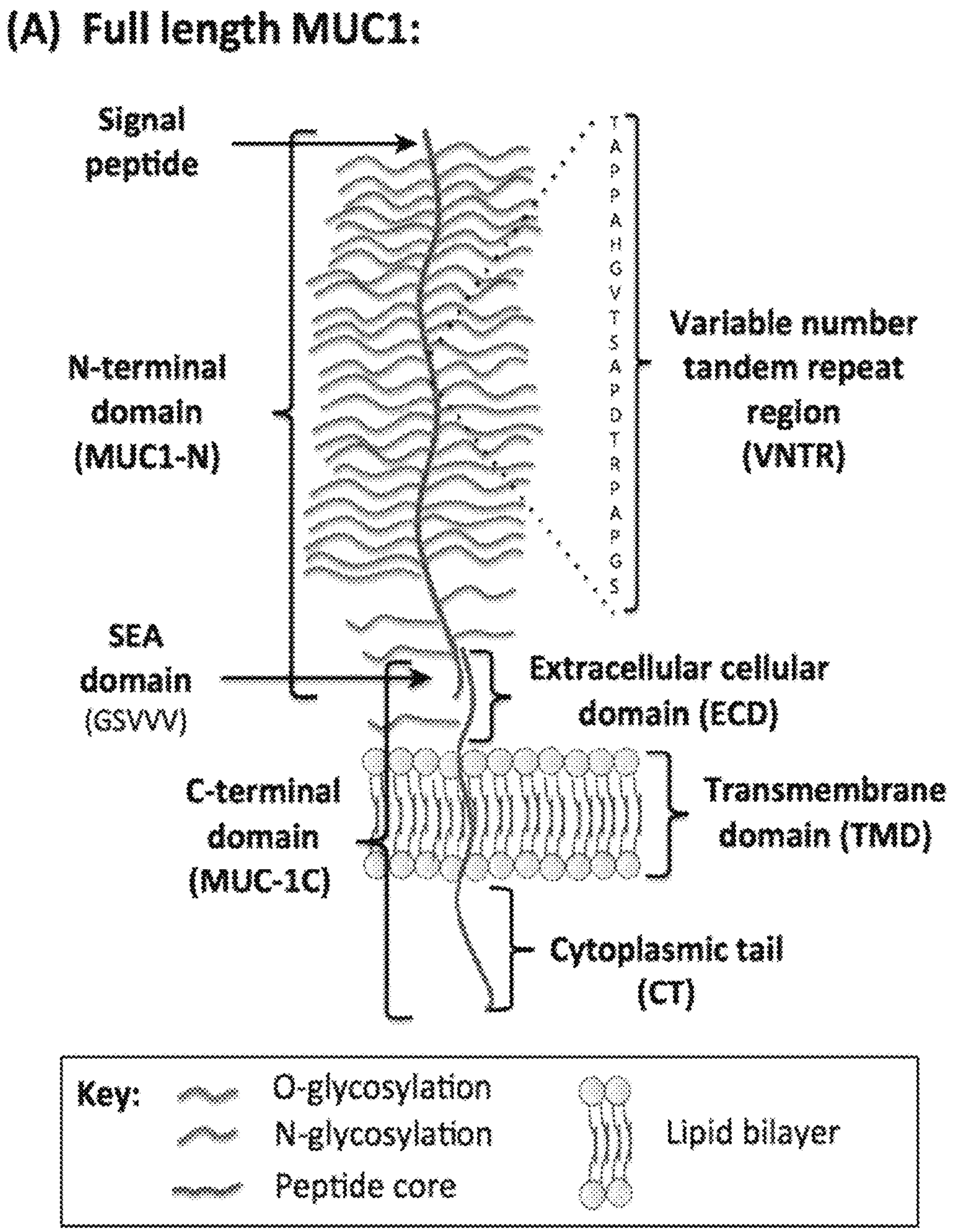
FIG. 22 shows full length MUC1, including MUC1-SEA domain. MUC1-SEA domain undergoes autoproteolytic self-cleavage at the conserved GVVS sequence (SEQ ID NO: 33). Cleavage occurs after the G and before the V, as indicated by the arrow. Figure discloses SEQ ID NOS 160, 34, and 161, respectively, in order of appearance.
Figure 23:
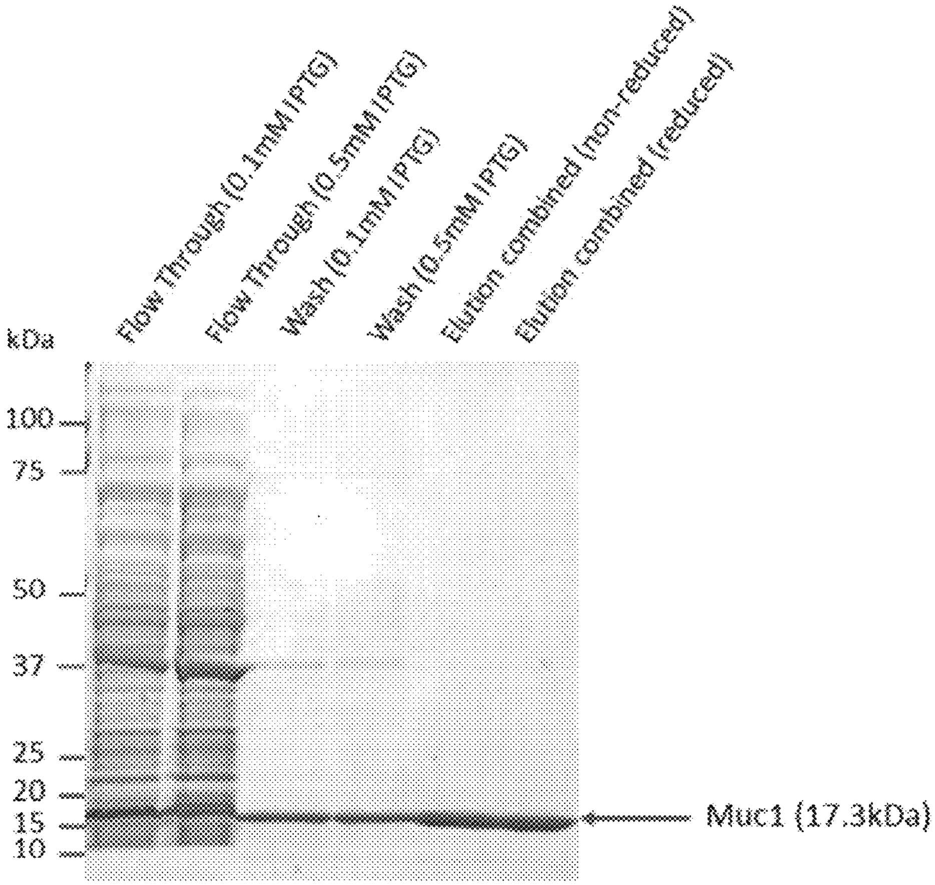
FIG. 23 shows Muc1-SEA purification. Muc1-SEA was expressed from a pET28a vector in BL21 (DE3) cells. The protein was purified via the N terminal His Tag (Ni-NTA resin). 125 ml of BL21(DE3) with pET28a-MUC1(sea) were subculture to OD 0.6 and induced with either 0.1 or 0.5 mM IPTG. Cultures were grown overnight at 30° C. and pelleted at 9000 rpm. The pellet was resuspended in 4 mL B-PER before sonicating for 15 min (30/59 sec on/off cycle). Lysed cells were spun down and the supernatant was diluted 50:50 with Ni-NTA binding buffer (20 mM imidazole) before incubating with Ni-NTA resin for 1 hour. Resin was collected and washed with binding buffer (20 mM imidazole) before eluting with 250 mM imidazole. Collected protein was buffer exchanged into PBS for long term storage. For visualization, all samples were prepared with 4×LDS loading dye. Samples 1-5 are not reduced; sample 6 is reduced with 10% BME.
Figure 24:
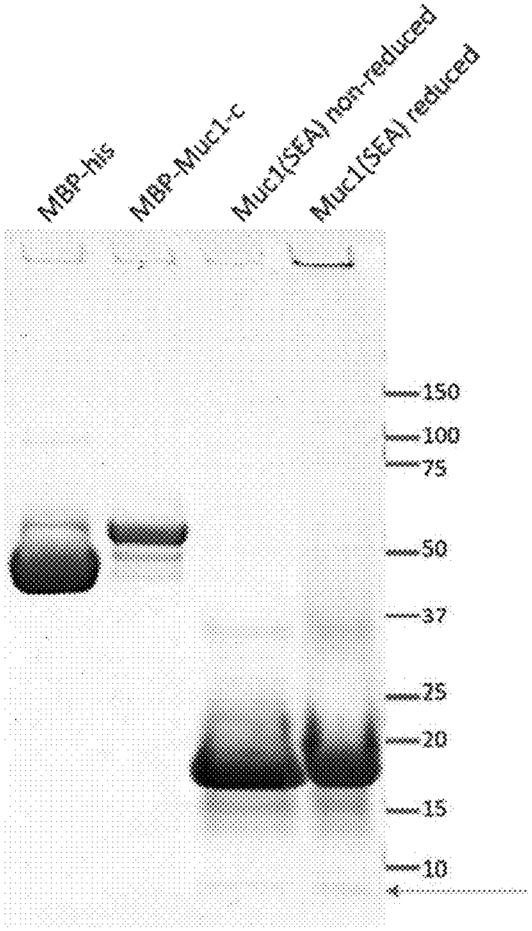
FIG. 24 shows Muc1-SEA autocleavage. 4-12% Bolt Gel ran in MES buffer. Samples are non-reduced unless specified (10% BME). Approximately 5 ug was loaded into each well, except MBP-Muc1 (~4 ug). Very faint band at approximately 6 kDa may be cleavage product.
Figure 25:
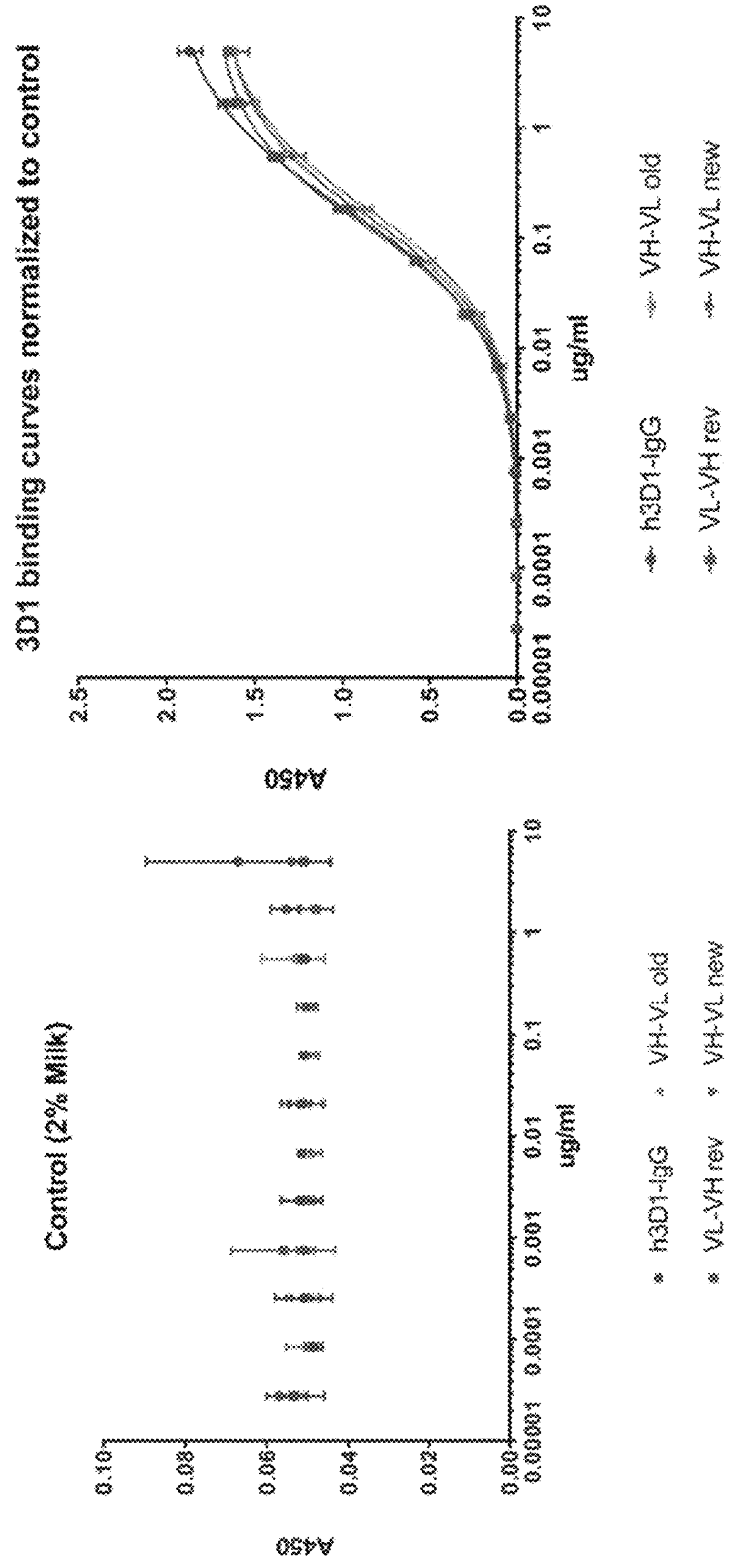
FIG. 25 shows h3D1 binding. Nunc maxisorb plates were coated with 1 μg/ml Muc1-SEA in PBS overnight at 4° C. The next day the plates were blocked with 4% milk-PBS for 2 hours at 37° C. The blocking solution was then dumped out and replaced with the appropriate antibody dilutions in 2% milk-PBST. The antibody solutions were incubated for 1 hour at 37° C. before being washed 6× with PBST. Anti-human Fc-HRP secondary was used to detect 3D1 binding (1:100 k dilution in 2% milk-PBST). After 1 hour incubation at 37° C., the plate was washed 6× with PBST and the TMB substrate was added. The reaction was quenched by the addition of stop buffer and read at 450 nm.
Figure 27:
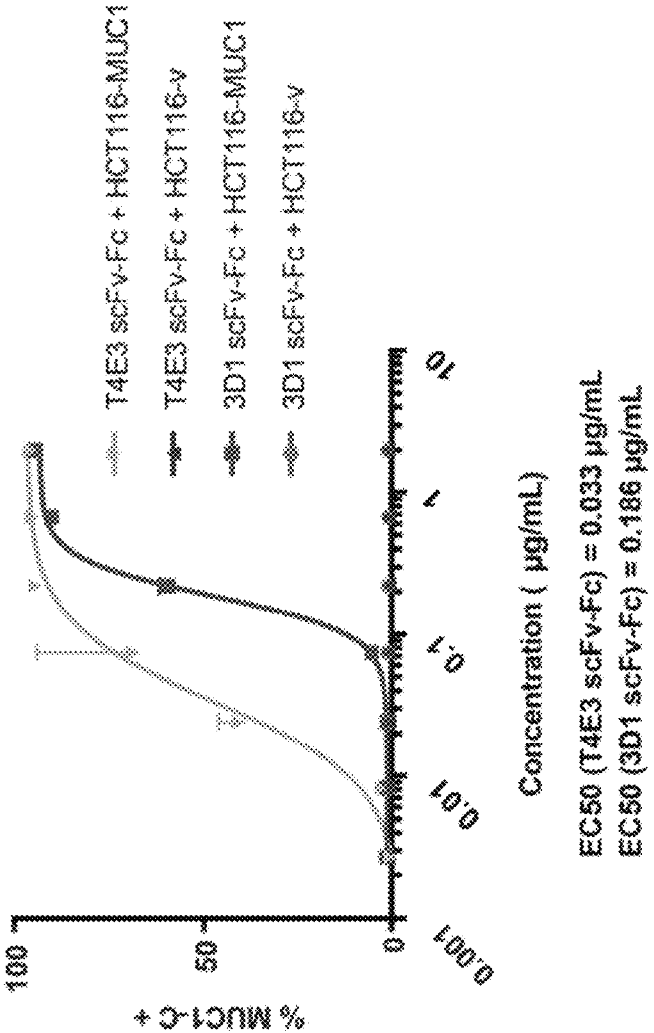
FIG. 27 shows dose response curves of two anti-MUC1-C scFv-Fcs. T4E3 scFv-Fc exhibits a 6-fold lower EC50 than 3D1 scFv-Fc. Dose response curves were generated by incubating serial dilutions of scFv-Fcs with HCT116-MUC1 (MUC1-C+) or HCT116-v (MUC1−) colon carcinoma cell lines followed by incubation with a secondary anti-human Fc-FITC antibody, and detecting binding by flow cytometry
Figure 28:
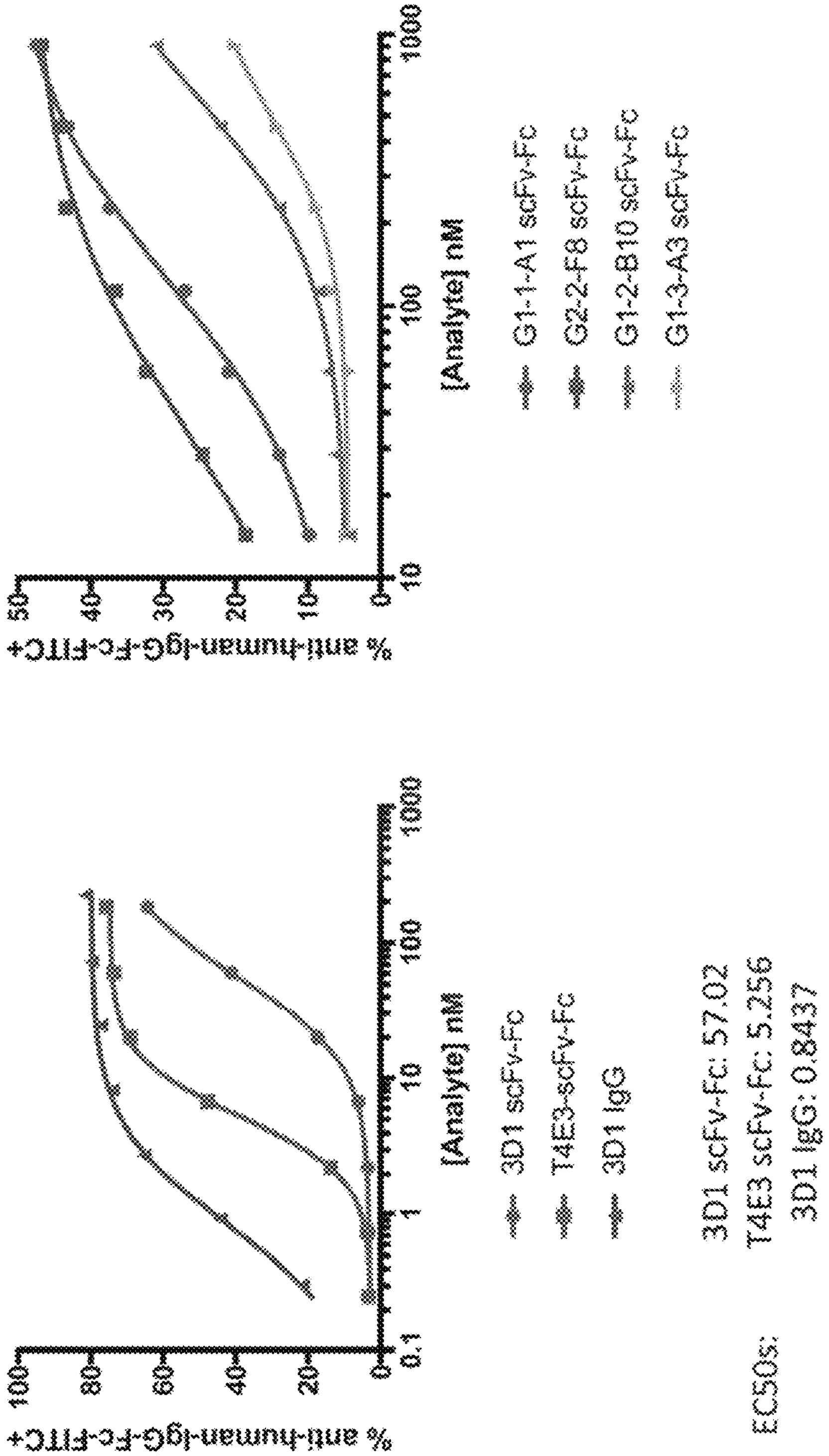
FIG. 28 shows binding characteristics of anti-MUC1-SEA scFvs.
Figure 31:
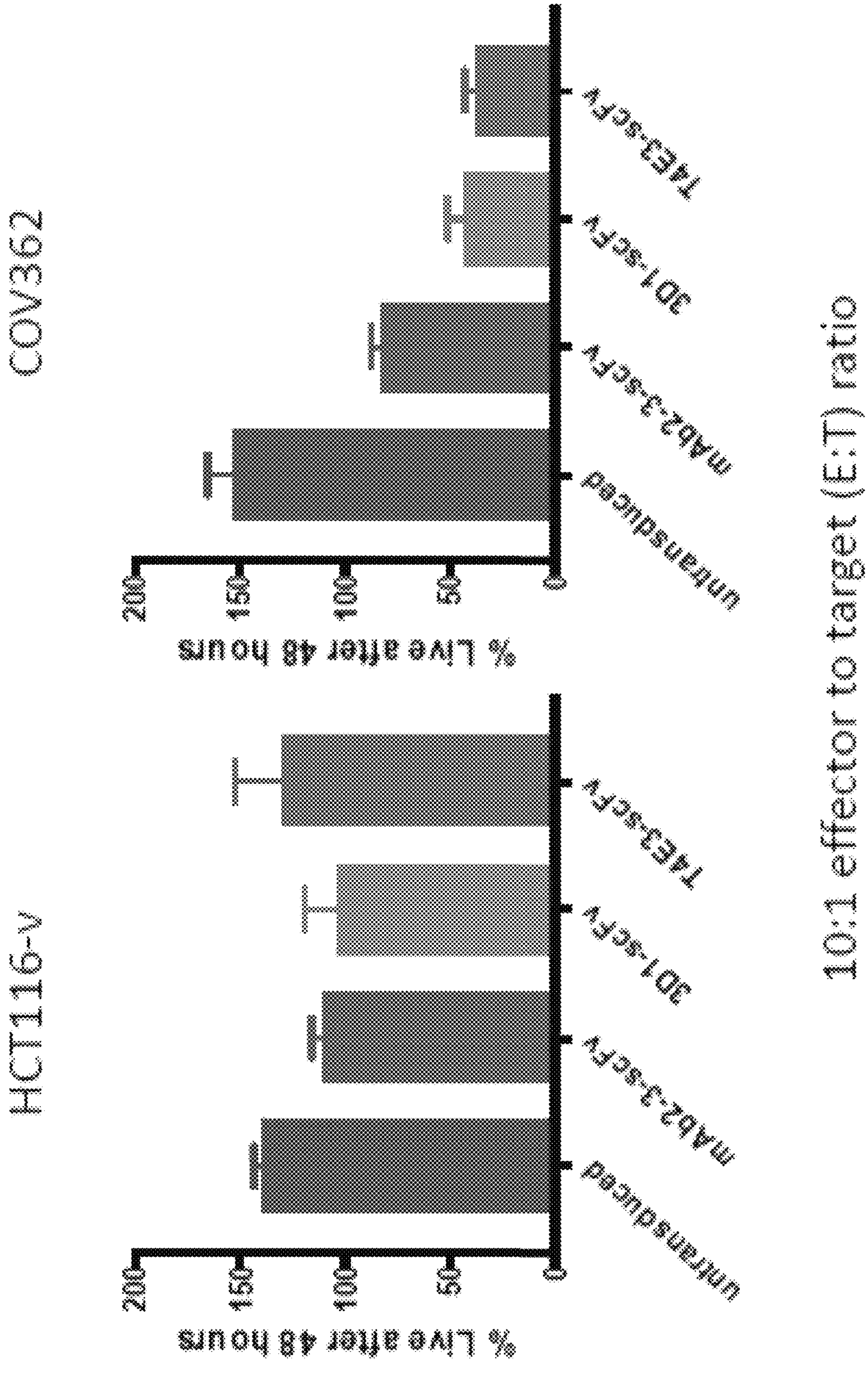
FIG. 31 shows T4E3 scFv CAR T vs 3D1 scFv CAR T killing. Colon carcinoma cell line HCT116-v is the control, MUC1− cell line. COV362 is MUC1+ cell line. mAb2-3 is a control, anti-CCR4 antibody.
Figure 32:
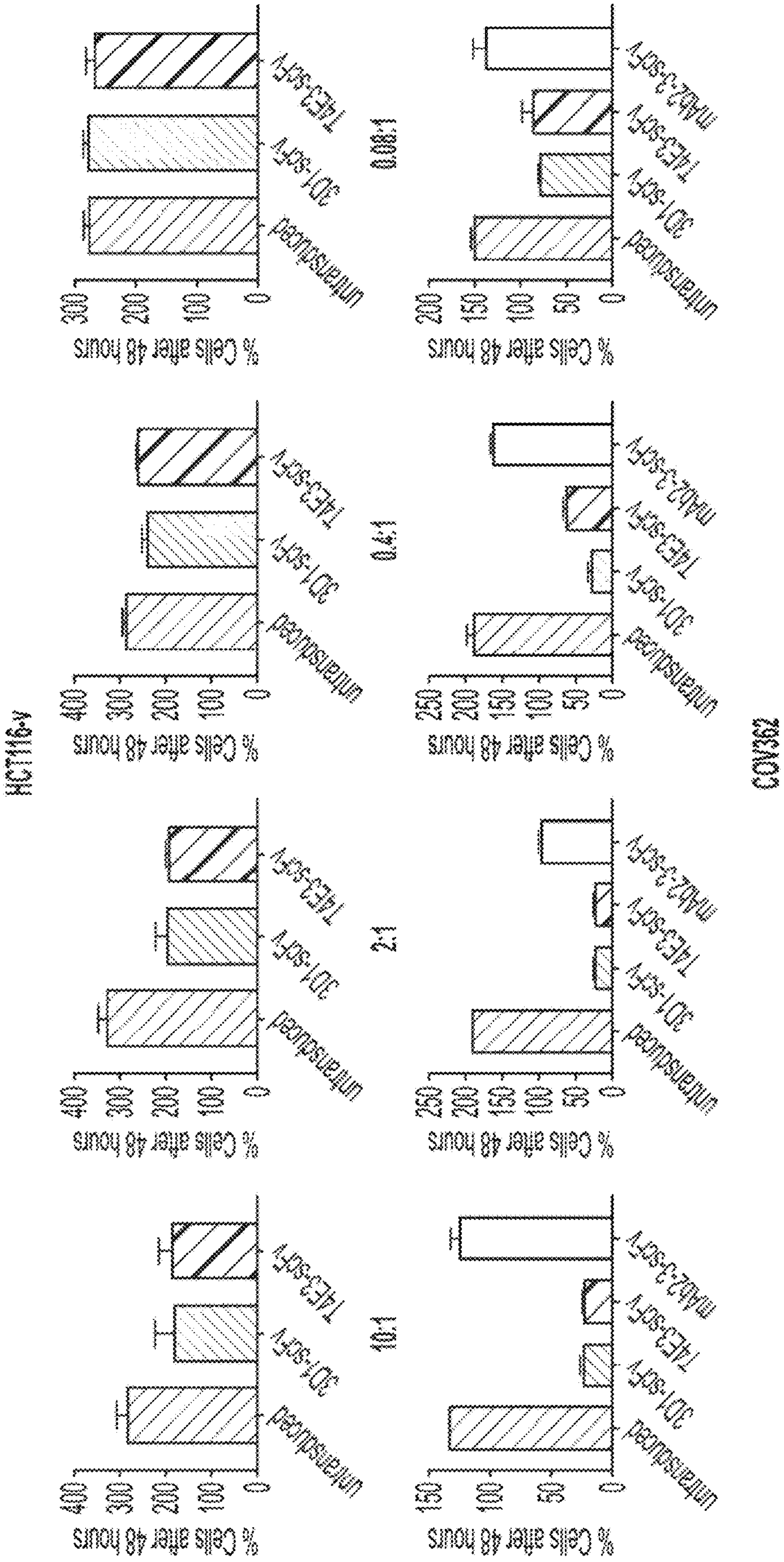
FIG. 32 shows dose dependent killing. HCT116-v is the control, MUC1− cell line. COV362 is MUC1+ cell line. mAb2-3 is a control, anti-CCR4 antibody.
Figure 33:
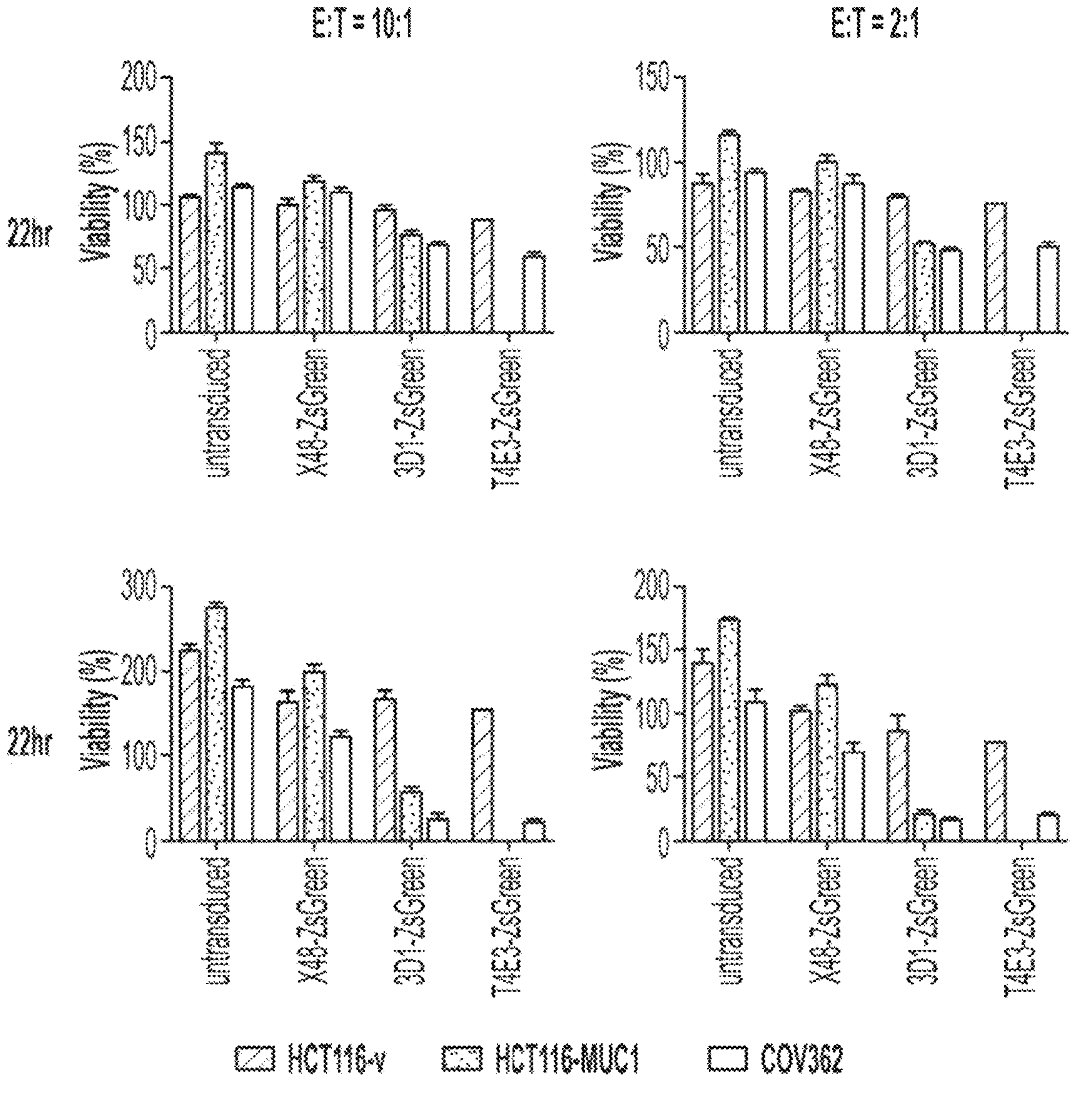
FIG. 33 shows tumor cell killing by anti-MUC1-C CAR T cells 3D1-ZsGreen and T4E3-ZsGreen. The cell killing assay utilizes a Celigo imaging cytometer to visualize cell killing. The cancer cell lines expressing the fluorescent protein: HCT116-v, HCT116-MUC1, and COV362 are plated in a 96 well plate (3000 cells/well) and incubated with T cells in effector to target (E:T) ratios of 10:1 or 2:1. The plates are imaged after 22 hours and 42 hours. Cell viability can be calculated by counting mCardinal+ cells. A loss of mCardinal signal suggests cancer cell death. The colon carcinoma cell line HCT116-v does not express MUC1-C, whereas HCT116-MUC1 and COV362 are 100% MUC1-C positive. X48-ZsGreen is a CAR T cell which targets CXCR4 which is not found on any of the cancer cell lines utilized.
Figure 34:
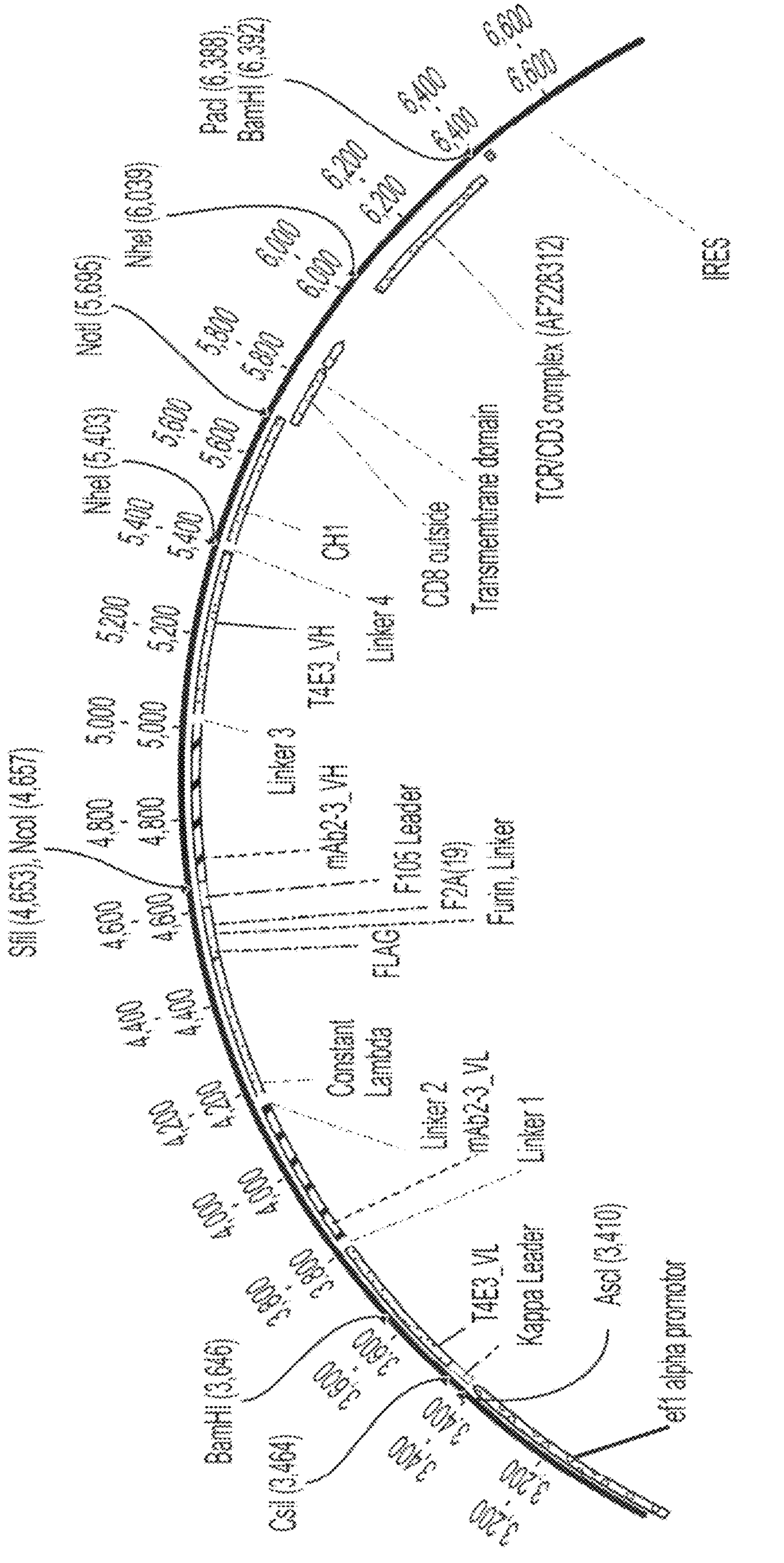
FIG. 34 shows CAR insert map of MUC1-CCR4 dual target CAR to kill Tregs and tumor cells alike.
Figure 35:
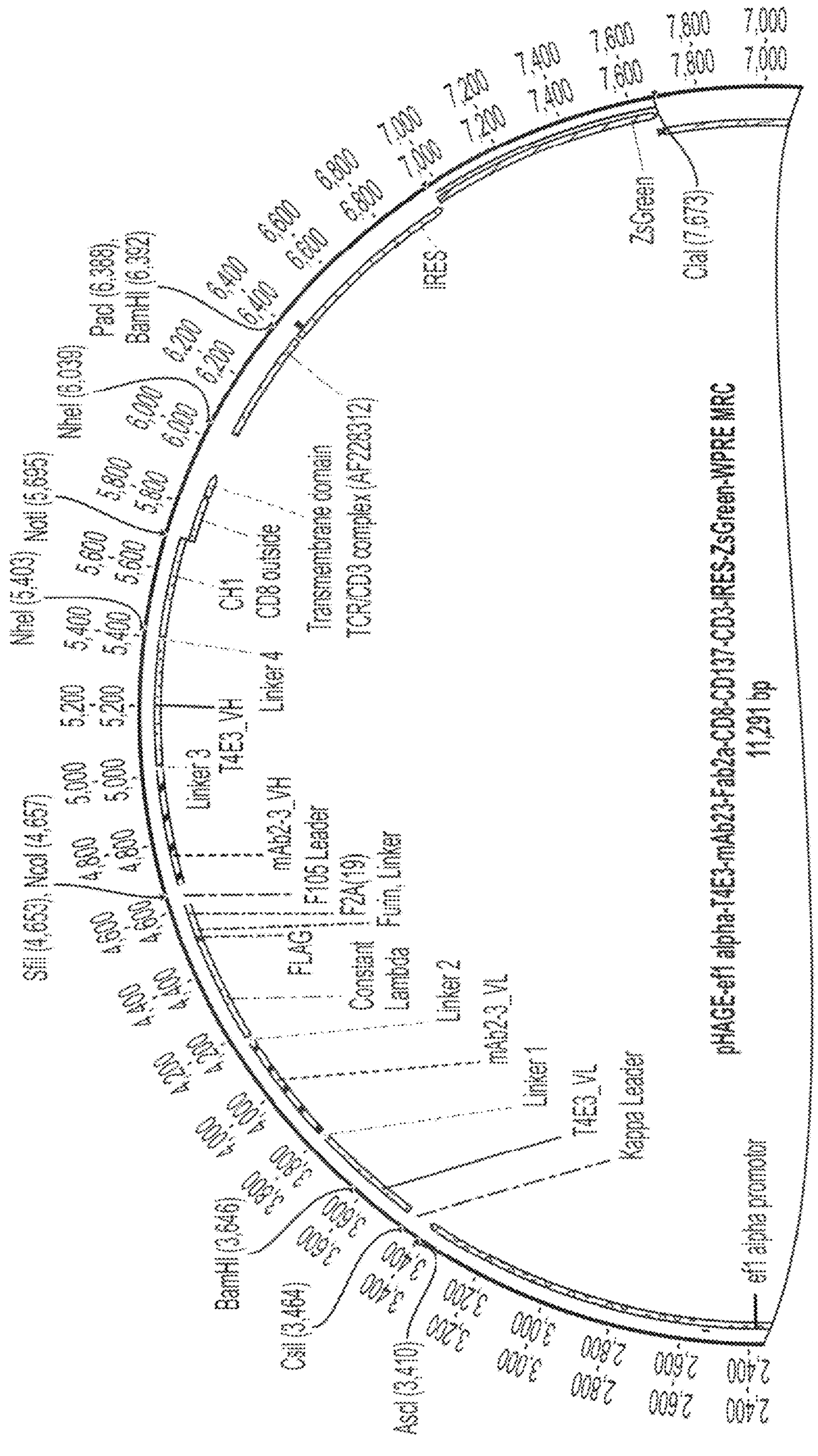
FIG. 35 shows vector map of MUC1-CCR4 dual target CAR to kill Tregs and tumor cells alike.
Figure 36:
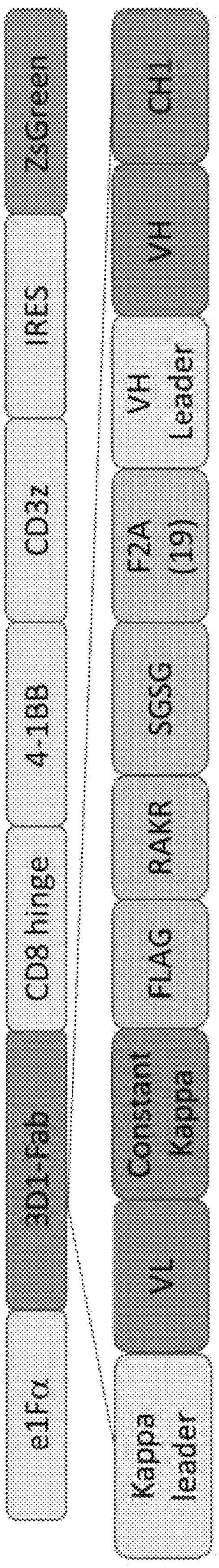
FIG. 36 shows utilization of F2A to generate Fab constructs. Figure discloses alignment sequences as SEQ ID NOS 163-174, respectively, in order of appearance, and "RAKRSGSG" as SEQ ID NO: 162.
Figure 37:
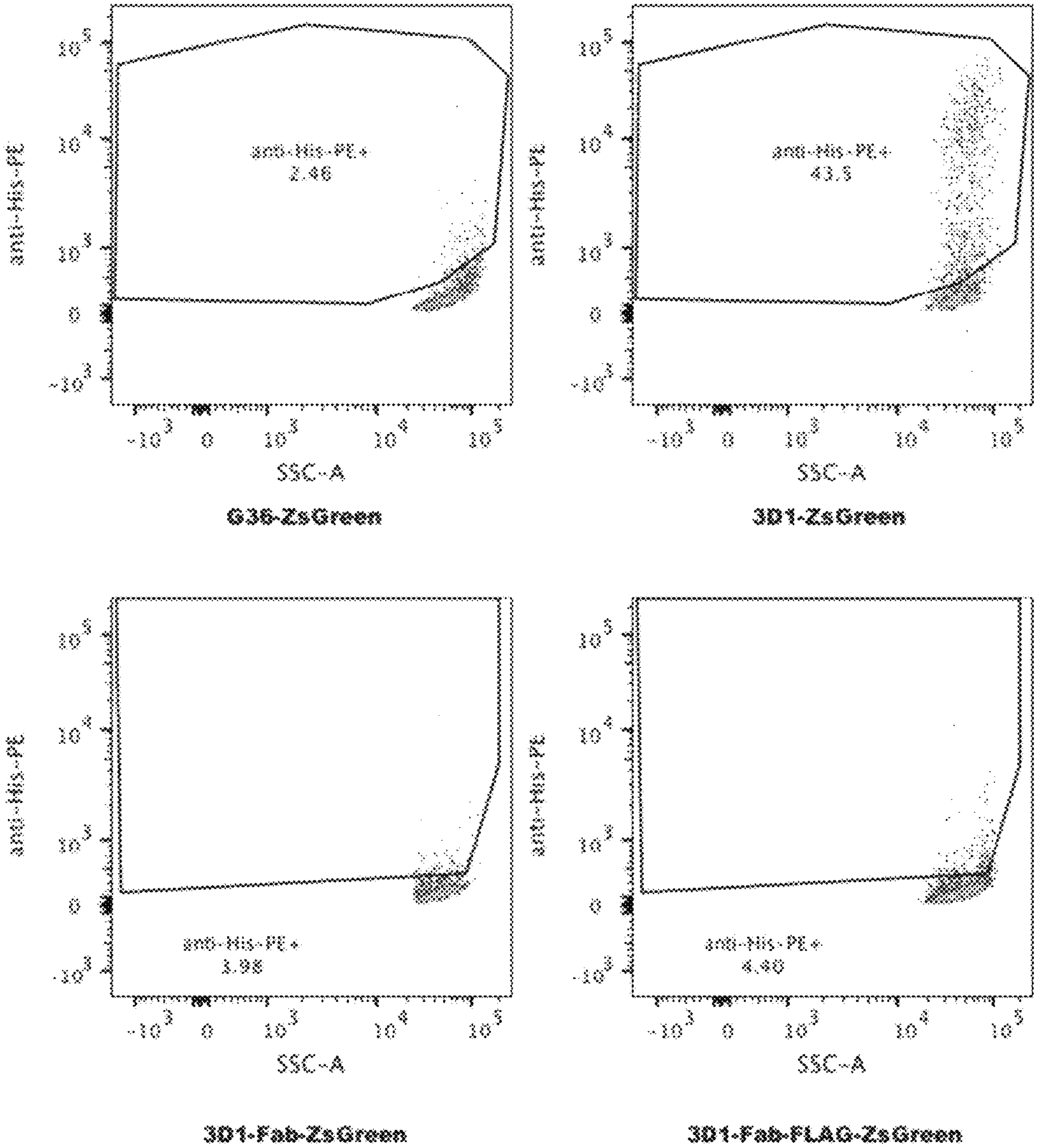
FIG. 37 shows analysis of initial design construct design.
Figure 38:
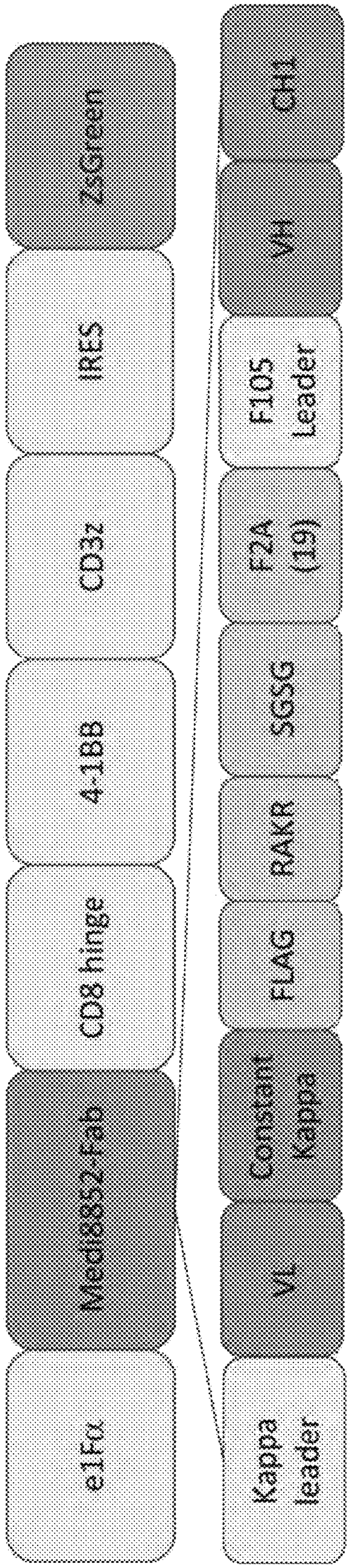
FIG. 38 shows strategy for Fab design using F105 leader. The leader sequence was changed in the construct based on the observation that the initial B cell receptor design used the F105 leader which is in the pHAGE vector instead of the VH leader for expression of the heavy chain. Additionally, the identity of the Fab was changed to the commercially available anti-hemagglutinin antibody Medi8852, which binds to the HA stem. Figure discloses "RAKRSGSG" as SEQ ID NO: 162.
Figure 39:
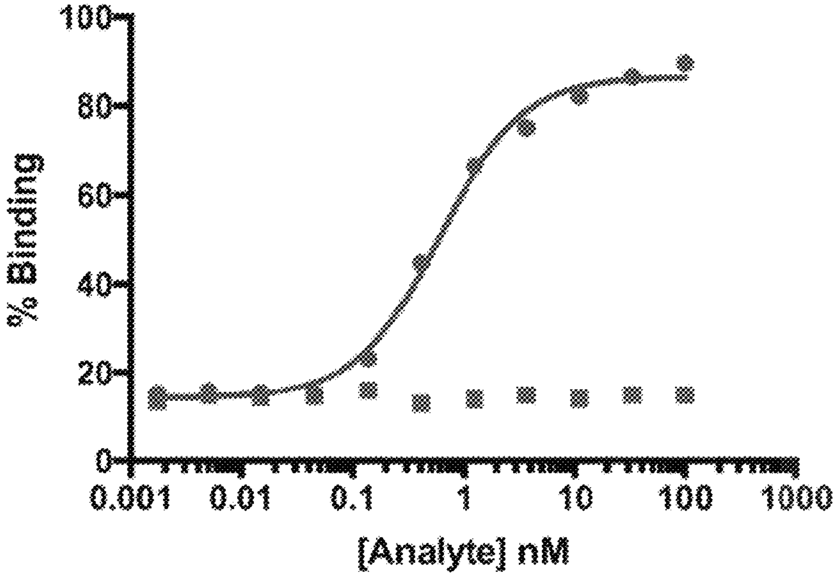
FIG. 39 shows Medi8852 binds to HA-stem but not to MUC1-SEA.
Figure 40:
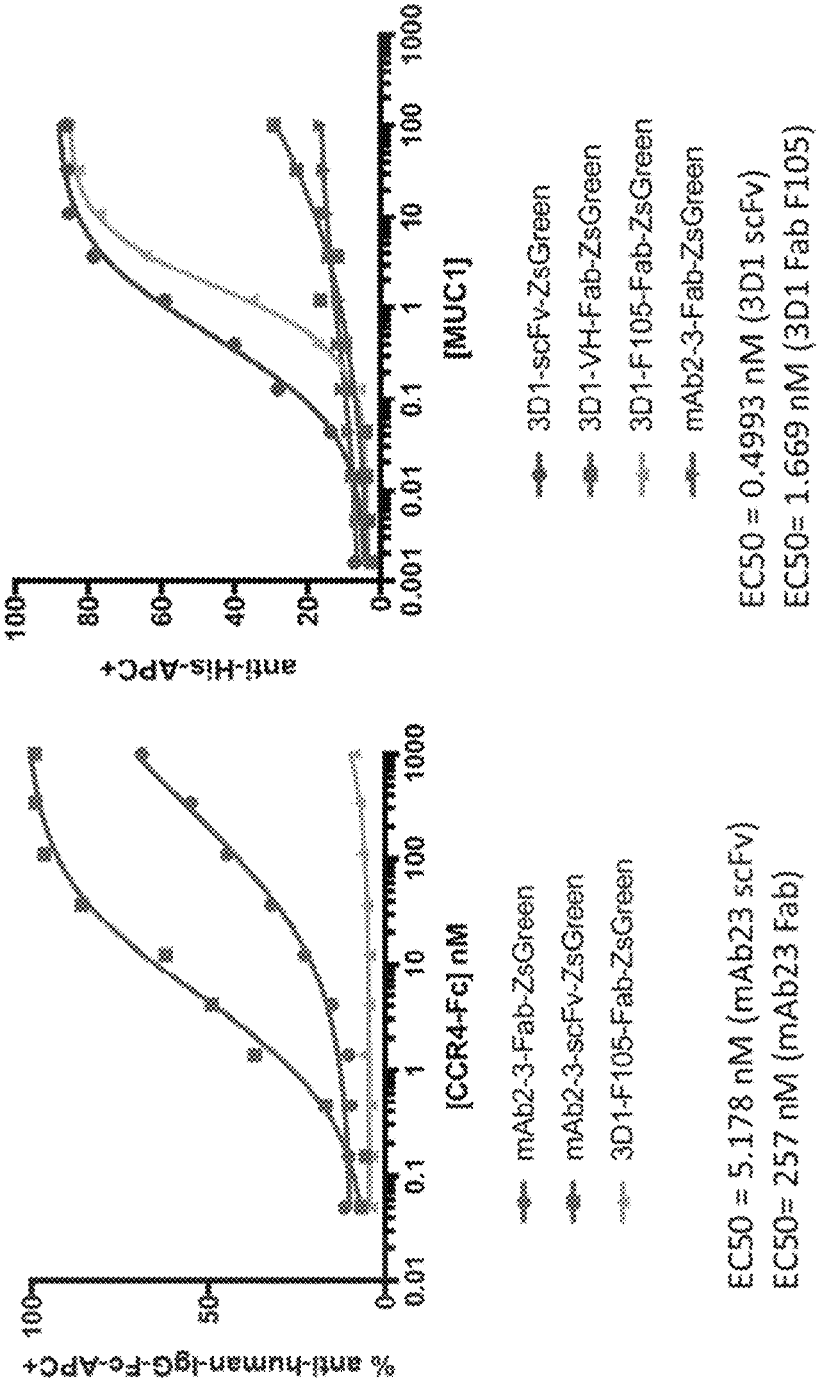
FIG. 40 shows mAb2-3 Fab and 3D1 Fabs cloned into Medi8852 Fab F105 construct and evaluated for binding and expression. It was observed that both mAb2-3 and 3D1 Fab have higher EC50s that their respective scFvs.
Figure 42:
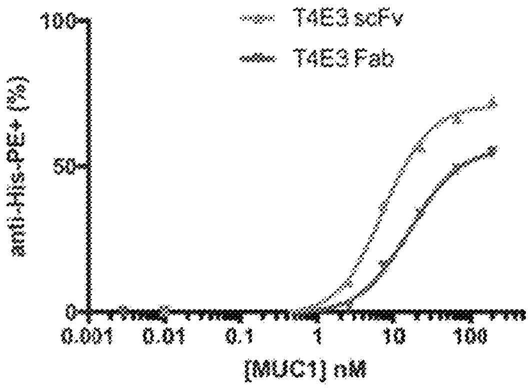
FIG. 42 shows Media8852 construct extended to generate a Fab with a lambda light chain (anti-Muc1 T4E3 Fab). Results show an example of Fab with less affinity than scFv.
Figure 43:
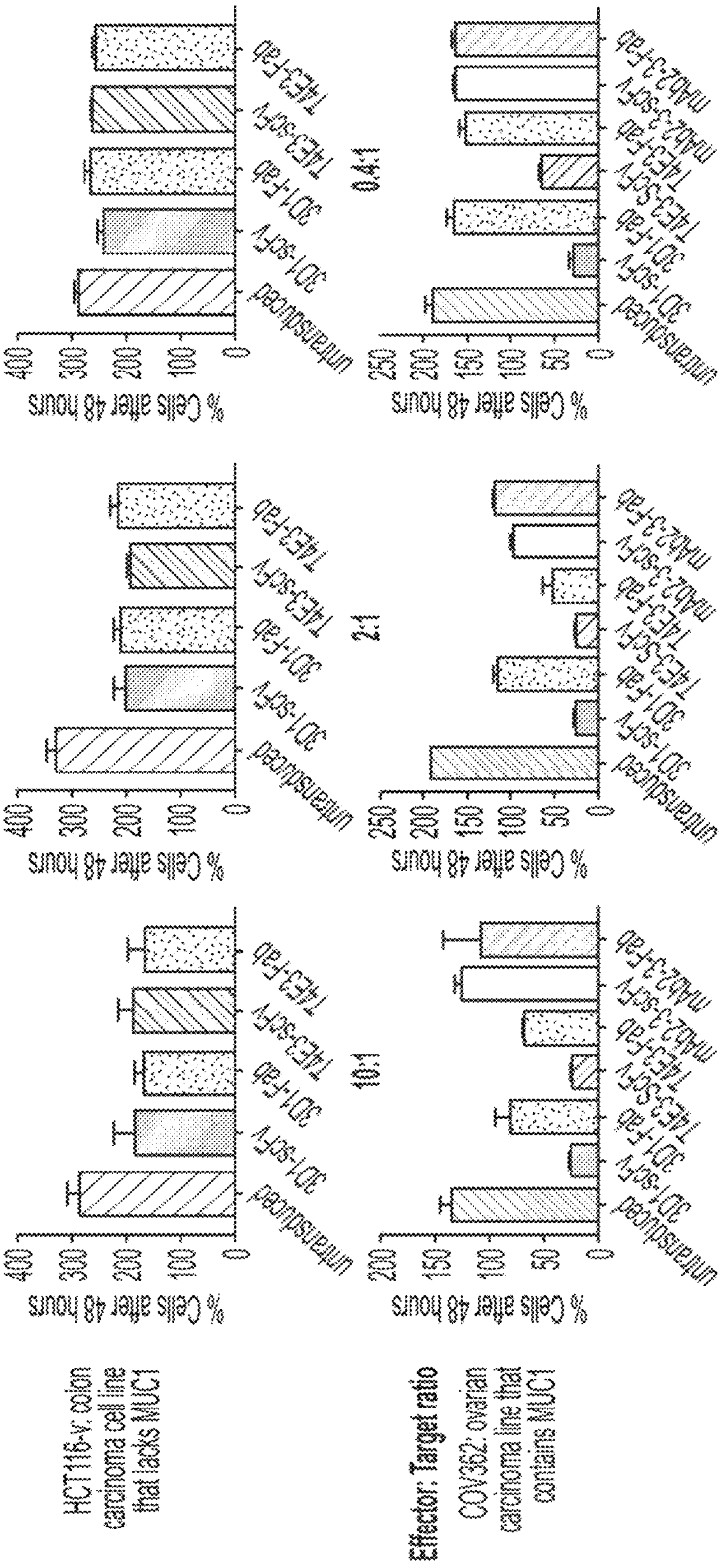
FIG. 43 shows Fab CAR T cell killing. Fab CAR T cells kill MUC1+ tumor cells less efficiently than scFv CAR T cells.
Figure 44:
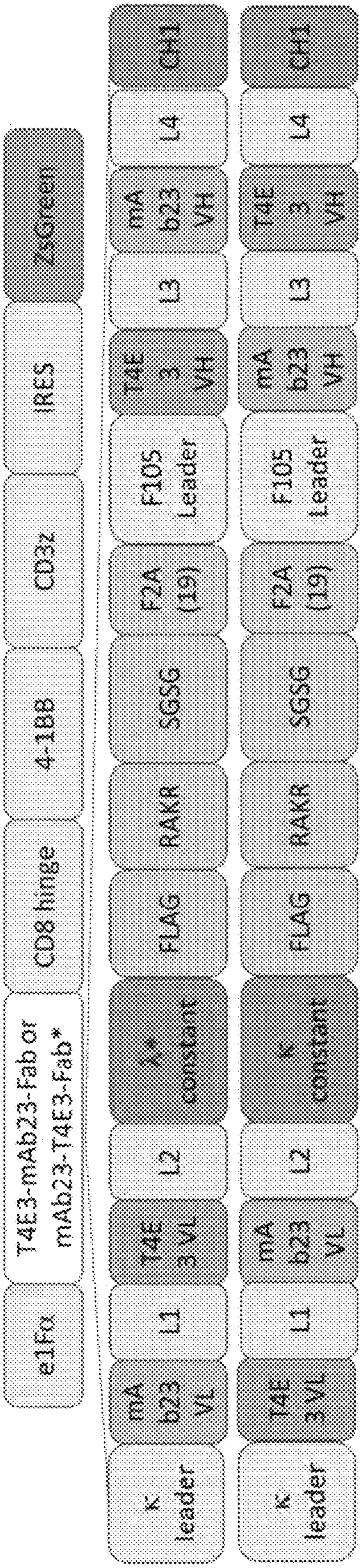
FIG. 44 shows embodiment(s) of a bispecific crossover Fab. L1, L2, L3 and L4 refer to non-limiting examples of linkers. Figure discloses "RAKRSGSG" as SEQ ID NO: 162, "$(Gly)_7$" as SEQ ID NO: 175, and "$(Gly)_5$" as SEQ ID NO: 176.
Figure 45:
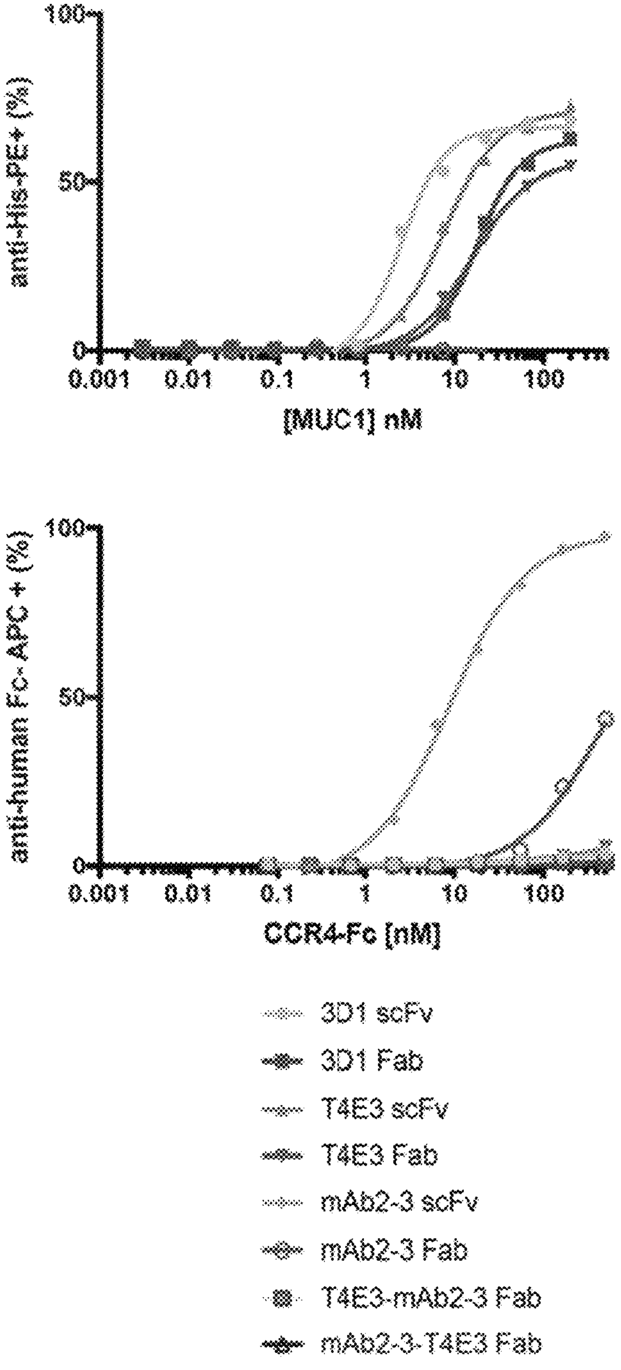
FIG. 45 shows embodiment(s) of a bispecific crossover Fab. All values are average of three replicates.
Figure 46:
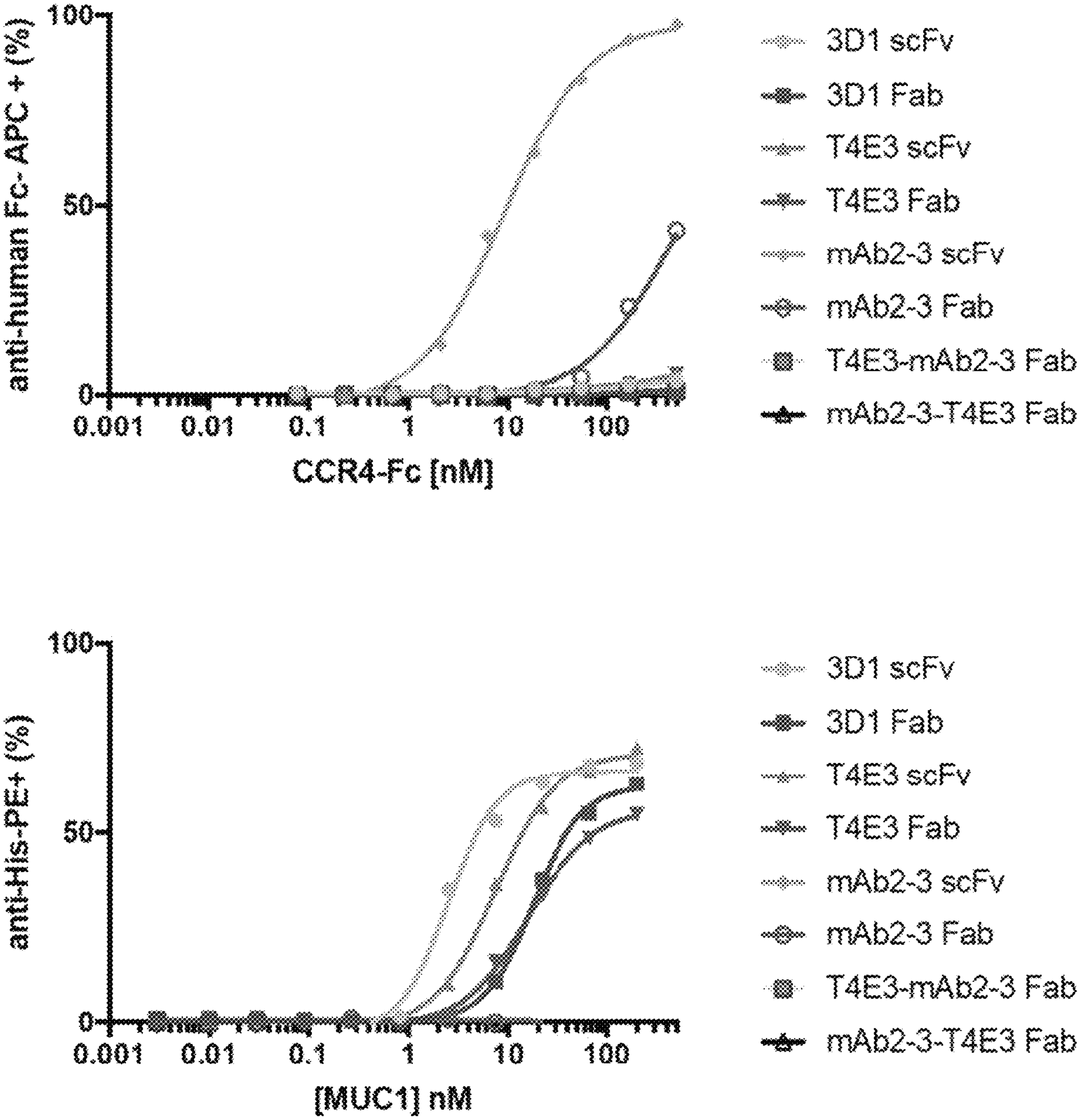
FIG. 46 shows dose response curves for binding.
Figure 47:
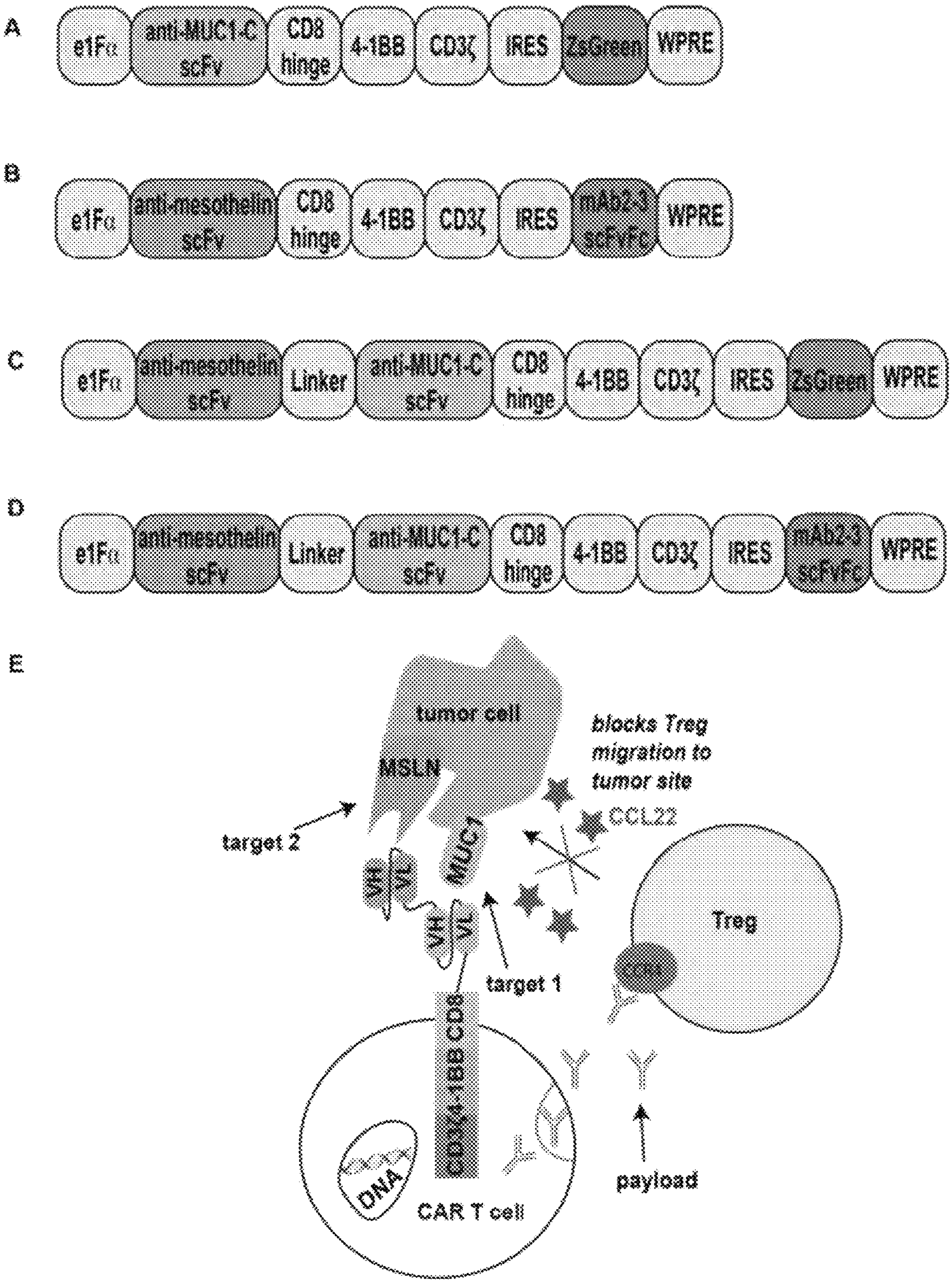
FIG. 47 shows (A) lentiviral construct of monospecific anti-MUC1-C and (B) anti-mesothelin CAR T cell. (C) Lentiviral construct of bispecific anti-MUC1-C/mesothelin CAR T cell. (D) Lentiviral construct of bispecific anti-MUC1-C/mesothelin CAR T cell factory (E) Cartoon representation of anti-MUC1-C/mesothelin CAR T factory mechanism of action
Figure 48:
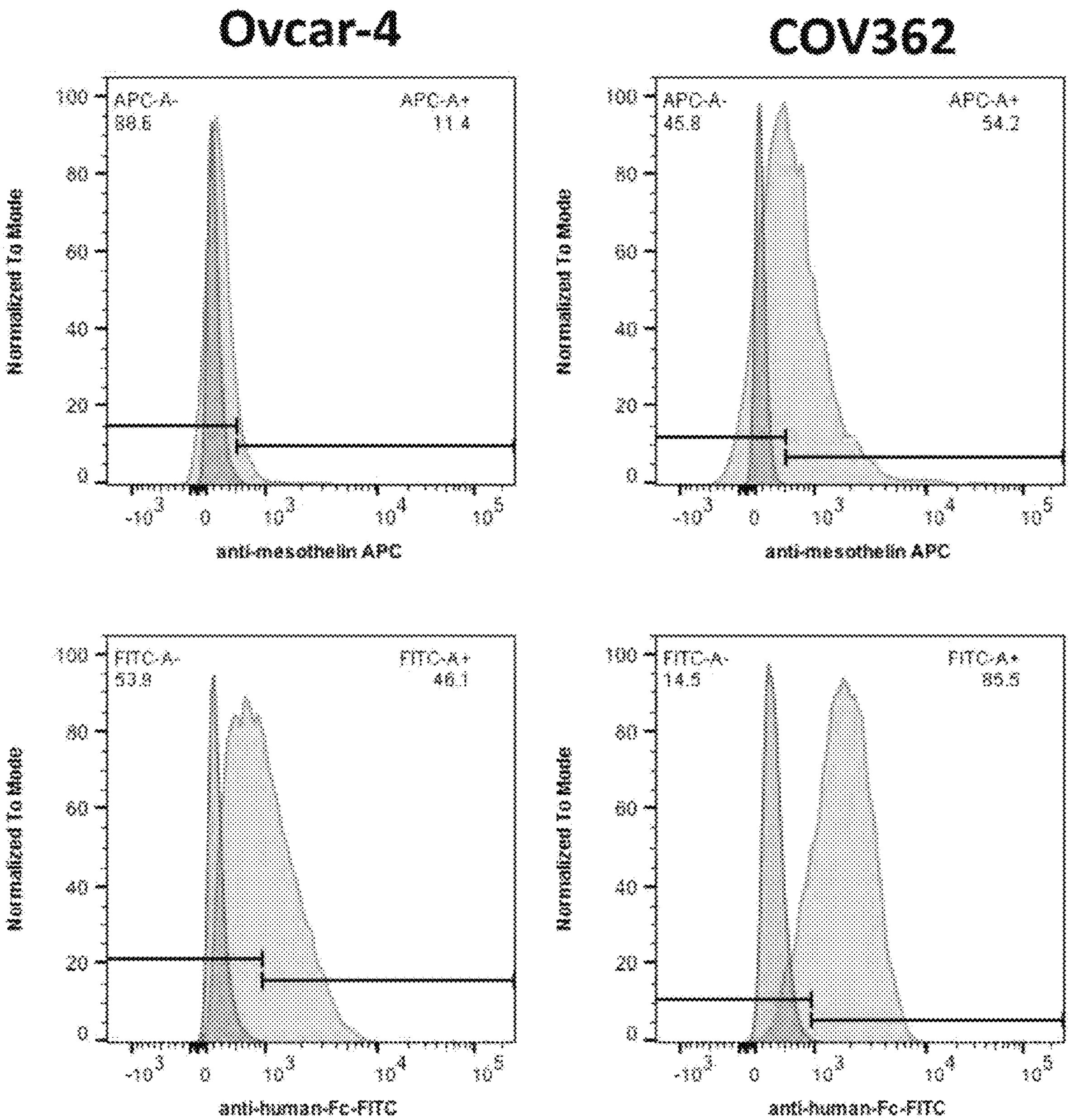
FIG. 48 shows (Top panel) flow cytometry histograms of Ovcar-4 and COV362 stained with anti-mesothelin APC (blue) compared to unstained controls (red) revealing that Ovcar-4 is 11.4% mesothelin+ and COV362 is 54.2% mesothelin+ (Bottom panel) Flow cytometry histograms of Ovcar-4 and COV362 stained with 233 nM anti-MUC1-C h3D1 IgG followed by staining with anti-human-Fc-FITC secondary revealing that Ovcar-4 is 46.1% MUC1-C+ and COV362 is 85.5% MUC1-C+
Figure 49:
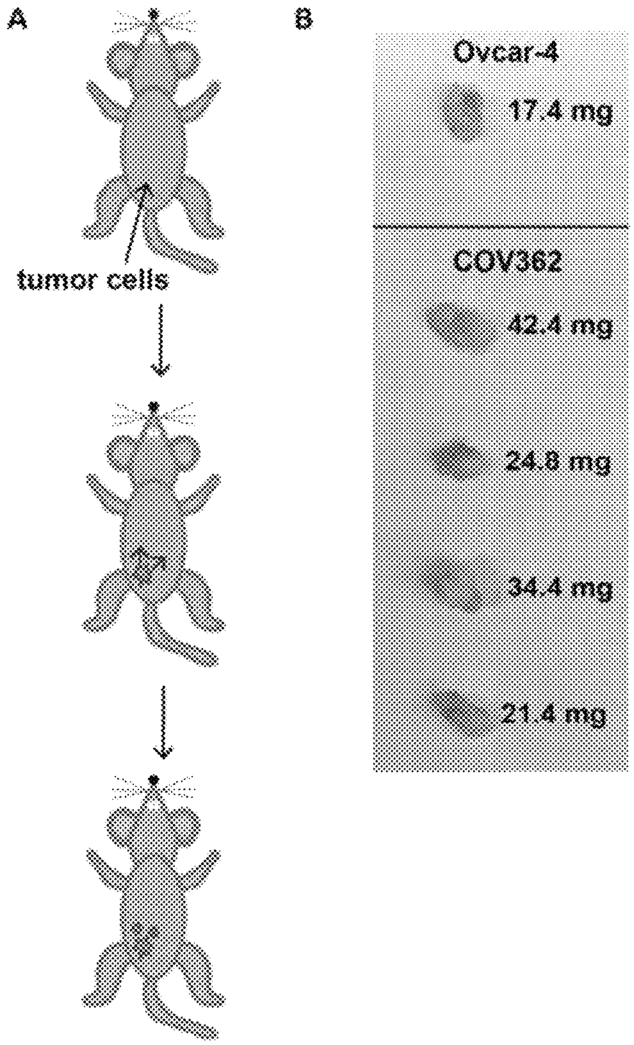
FIG. 49 shows (A) cartoon representation of orthotopic mouse model of ovarian cancer, emphasizing its utility in showing ovarian cancer metastasis. (B) Tumors and ovaries obtained from five mice with orthotopic ovarian tumors. The tumor of the top mouse was generated from the high grade serous ovarian cancer (HGSC) cell line Ovcar-4 (350,000 cells/mouse), and the bottom four ovaries and tumors were generated from the HGSC cell line COV362 (500,000 cells/mouse).
Figure 50:
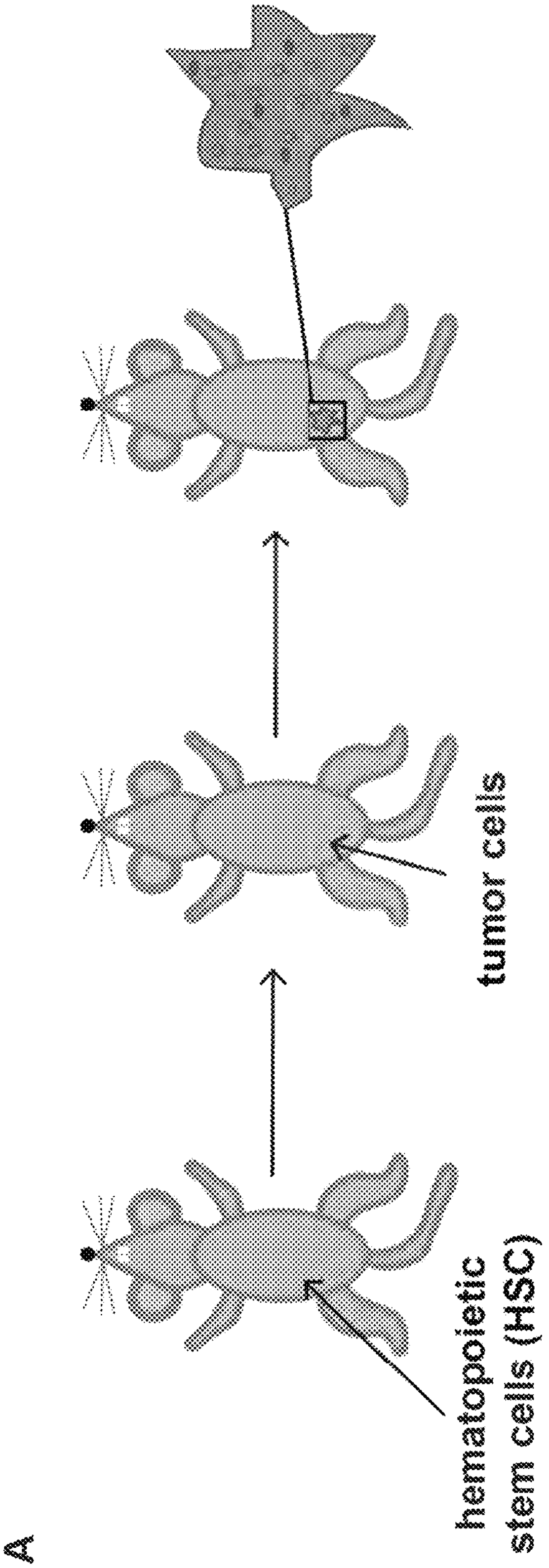
FIG. 50 shows (A) cartoon representation of orthotopic, humanized mouse model, which enables study of metastasis and the tumor microenvironment (B) t-SNE 2D scatter plot shows mapping of CD45+ leukocytes in a humanized NSG-SGM3 mouse model of renal cell carcinoma (C) Violin plot showing the presence of CCR4 within clusters 1 and 2, suggesting the presence of Tregs and Th2 cells.

Aspects of the invention are further drawn to antibody-drug conjugates (or ADCs). ADCs, which can also be referred to as immunoconjugates, combine the targeting capabilities of antibodies or antigen-binding fragments, such as those described herein, with the cancer-killing ability of cytotoxic drugs. Thus, ADCs are a targeted therapy for the treatment of people with cancer. Unlike chemotherapy, ADCs are intended to target and kill only the cancer cells and spare healthy cells. For example, Referring to FIG. 18, for example, 3D1-MMAE antibody conjugates regress tumor growth of MUC1-C+ tumors but not MUC1-C- tumors. Monomethyl auristatin E (or MMAE) is a potent and highly toxic antimicrotubule agent. Because of its high toxicity MMAE, which inhibits cell division by blocking the polymerization of tubulin, cannot be used as a single-agent chemotherapeutic drug. The skilled artisan will recognize that MMAE can be replaced with one or more of various chemicals known to kill tumor cells, such as MUC1+ tumor cells. For example, the antibody-drug conjugates of the invention can comprise various chemicals (i.e., chemotherapies) known to the skilled artisan to kill MUC1+ tumor cells, in addition to MMAE.

ADCs are complex molecules composed of an antibody linked to a biologically active cytotoxic (anticancer) payload or drug. Antibody-drug conjugates can also be referred to as bioconjugates or immunoconjugates. In developing antibody-drug conjugates, an anticancer drug is coupled to an antibody that specifically targets a certain tumor marker (e.g. a protein that, ideally, is only to be found in or on tumor cells). In embodiments, the tumor marker comprises, for example, MUC1. As desired, the tumor marker can further comprise mesothelin. Antibodies track these proteins down in the body and attach themselves to the surface of cancer cells. The biochemical reaction between the antibody and the target protein triggers a signal in the tumor cell, which then absorbs or internalizes the antibody together with the cytotoxin. After the ADC is internalized, the cytotoxic drug is released and kills the cancer. Due to this targeting, ideally the drug has lower side effects and gives a wider therapeutic window than other chemotherapeutic agents.

A stable link between the antibody and cytotoxic (anti-cancer) agent is a crucial aspect of an ADC. A highly stable ADC linker will ensure that less of the cytotoxic payload falls off in circulation, driving an improved safety profile, and will also ensure that more of the payload arrives at the cancer cell, driving enhanced efficacy. In embodiments, linkers utilized herein can comprise those based on chemical motifs including disulfides, hydrazones or peptides (cleavable), or thioethers (noncleavable) and control the distribution and delivery of the cytotoxic agent to the target cell. Cleavable and noncleavable types of linkers have been proven to be safe in preclinical and clinical trials.

The availability of better and more stable linkers has changed the function of the chemical bond. The type of linker, cleavable or noncleavable, lends specific properties to the cytotoxic (anti-cancer) drug. For example, a non-cleavable linker keeps the drug within the cell. As a result, the entire antibody, linker and cytotoxic (anti-cancer) agent enter the targeted cancer cell where the antibody is degraded to the level of an amino acid. The resulting complex—amino acid, linker and cytotoxic agent—now becomes the active drug. In contrast, cleavable linkers are catalyzed by enzymes in the cancer cell where it releases the cytotoxic agent. The difference is that the cytotoxic payload delivered via a cleavable linker can escape from the targeted cell and, in a process called "bystander killing", attack neighboring cancer cells.

Other linkers, such as those that add an extra molecule between the cytotoxic drug and the cleavage site, allows for the development of ADCs with more flexibility without worrying about changing cleavage kinetics.

Non-limiting examples of linkers are described in the literature. (See, for example, Ramakrishnan, S. et al., Cancer Res. 44:201-208 (1984) describing use of MBS (M-maleimidobenzoyl-N-hydroxysuccinimide ester). See also, U.S. Pat. No. 5,030,719, describing use of halogenated acetyl hydrazide derivative coupled to an antibody by way of an oligopeptide linker. Non-limiting examples of useful linkers that can be used with the antibodies of the invention include: (i) EDC (1-ethyl-3-(3-dimethylamino-propyl) carbodiimide hydrochloride; (ii) SMPT (4-succinimidyloxycarbonyl-alpha-methyl-alpha-(2-pridyl-dithio)-toluene (Pierce Chem. Co., Cat. (21558G); (iii) SPDP (succinimidyl-6 [3-(2-pyridyldithio) propionamido]hexanoate (Pierce Chem. Co., Cat #21651G); (iv) Sulfo-LC-SPDP (sulfosuccinimidyl 6 [3-(2-pyridyldithio)-propianamide]hexanoate (Pierce Chem. Co. Cat. #2165-G); and (v) sulfo-NHS (-hydroxysulfo-succinimide: Pierce Chem. Co., Cat. #24510) conjugated to EDC.

The linkers described herein contain components that have different attributes, thus leading to conjugates with differing physio-chemical properties. For example, sulfo-NHS esters of alkyl carboxylates are more stable than sulfo-NHS esters of aromatic carboxylates. NHS-ester containing linkers are less soluble than sulfo-NHS esters. Further, the linker SMPT contains a sterically hindered disulfide bond, and can form conjugates with increased stability. Disulfide linkages, are in general, less stable than other linkages because the disulfide linkage is cleaved in vitro, resulting in less conjugate available. Sulfo-NHS, in particular, can enhance the stability of carbodimide couplings. Carbodimide couplings (such as EDC) when used in conjunction with sulfo-NHS, forms esters that are more resistant to hydrolysis than the carbodimide coupling reaction alone.

Pharmaceutical Compositions

Antibodies specifically binding a MUC1 protein or fragment thereof of the invention can be administered for the treatment of a cancer in the form of pharmaceutical compositions. Principles and considerations involved in preparing therapeutic compositions comprising the antibody, as well as guidance in the choice of components are provided, for example, in Remington: The Science And Practice Of Pharmacy 19th ed. (Alfonso R. Gennaro, et al, editors) Mack Pub. Co., Easton, Pa., 1995; Drug Absorption Enhancement: Concepts, Possibilities, Limitations, And Trends, Harwood Academic Publishers, Langhorne, Pa., 1994; and Peptide And Protein Drug Delivery (Advances In Parenteral Sciences, Vol. 4), 1991, M. Dekker, New York.

A therapeutically effective amount of an antibody of the invention can relate to generally to the amount needed to achieve a therapeutic objective. As noted above, this can be a binding interaction between the antibody and its target antigen that, in certain cases, interferes with the functioning of the target. The amount required to be administered will furthermore depend on the binding affinity of the antibody for its specific antigen, and will also depend on the rate at which an administered antibody is depleted from the free volume other subject to which it is administered. Common ranges for therapeutically effective dosing of an antibody or antibody fragment of the invention can be, by way of nonlimiting example, from about 0.1 mg/kg body weight to about 50 mg/kg body weight. Common dosing frequencies can range, for example, from twice daily to once a week.

Where antibody fragments are used, the smallest inhibitory fragment that specifically binds to the binding domain of the target protein is preferred. For example, based upon the variable-region sequences of an antibody, peptide molecules can be designed that retain the ability to bind the target protein sequence. Such peptides can be synthesized chemically and/or produced by recombinant DNA technology. (See, e.g., Marasco et al, Proc. Natl. Acad. Sci. USA, 90: 7889-7893 (1993)). The formulation can also contain more than one active compound as necessary for the particular indication being treated, preferably those with complementary activities that do not adversely affect each other. Alternatively, or in addition, the composition can comprise an agent that enhances its function, such as, for example, a cytotoxic agent, cytokine (e.g. IL-15), chemotherapeutic agent, or growth-inhibitory agent. Such molecules are suitably present in combination in amounts that are effective for the purpose intended.

The active ingredients can also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles, and nanocapsules) or in macroemulsions.

The formulations to be used for in vivo administration must be sterile. This is readily accomplished by filtration through sterile filtration membranes.

Sustained-release preparations can be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods.

The antibodies or agents of the invention (also referred to herein as "active compounds"), and derivatives, fragments, analogs and homologs thereof, can be incorporated into pharmaceutical compositions suitable for administration. Such compositions typically comprise the antibody or agent and a pharmaceutically acceptable carrier. As used herein, the term "pharmaceutically acceptable carrier" can include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, ringer's solutions, dextrose solution, and 5% human serum albumin. Liposomes and non-aqueous vehicles such as fixed oils can also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (i.e., topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use can include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In embodiments, the composition is sterile and is fluid to the extent that easy syringeability exists. It can be stable under the conditions of manufacture and storage and can be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means.

For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, or dispenser together with instructions for administration.

Methods of Treatment

Antibodies or fragments specifically binding a MUC1 protein or a fragment thereof, such as MUC1-SEA, can be administered for the treatment of a MUC1-associated disease or disorder. A "MUC1-associated disease or disorder" includes disease states and/or symptoms associated with a disease state where increased levels of MUC1 gene expression or protein levels, such as on the surface of a cancer cell, and/or activation of cellular signaling pathways involving MUC1 are found. MUC1-associated diseases and disorders may also be characterized by diseases wherein MUC1 is aberrantly glycosylated. See, for example, Nath, S., & Mukherjee, P. (2014). MUC1: a multifaceted oncoprotein with a key role in cancer progression. *Trends in molecular medicine,* 20(6), 332-342, and Horm, T. M., & Schroeder, J. A. (2013). MUC1 and metastatic cancer: expression, function and therapeutic targeting. *Cell adhesion & migration,* 7(2), 187-198, each of which are incorporated by reference herein in their entireties. Exemplary MUC1-associated disease or disorder include, but are not limited to, cancer, such as epithelial cancer.

MUC1 overexpression and aberrant glycosylation have been associated with many cancers, including most human epithelial cancers. As used herein, "epithelial cancer" can refer to any cancer that arise from epithelial cells which include, but are not limited to, breast cancer, basal cell carcinoma, adenocarcinoma, gastrointestinal cancer, lip cancer, mouth cancer, esophageal cancer, small bowel cancer and stomach cancer, colon cancer, liver cancer, bladder cancer, pancreas cancer, ovary cancer, cervical cancer, lung cancer, breast cancer and skin cancer, such as squamous cell and basal cell cancers, prostate cancer, renal cell carcinoma, and other known cancers that effect epithelial cells throughout the body.

Known risk factors for epithelial cancers include, but are not limited to, family history, genetic predisposition (i.e., mutations in BRCA1 and BRCA2, BRIP1, MSH6, RAD15C), personal history of an epithelial cancer, physical inactivity or obesity.

Epithelial cancers can be diagnosed by methods known in the art, including testing for tumor markers (such as CA125), imaging via CT scan, MRI, or TVU, or fine needle biopsy.

Epithelial cancers may be treated by debulking surgery (such as, removal of both ovaries and fallopian tubes), the uterus, the omentum, biopsies of the peritoneum (lining of abdominal cavity), chemotherapy (such as platinum and taxane based chemotherapy).

Referring to the Examples, aspects of the invention are particularly useful for the treatment of ovarian cancer and colon cancer.

Ovarian cancer is responsible for significant morbidity and mortality in populations around the world. Ovarian cancer is a type of cancer that begins in the ovaries. The female reproductive system contains two ovaries, one on each side of the uterus. The ovaries—each about the size of an almond—produce eggs (ova) as well as the hormones estrogen and progesterone. Ovarian cancer often goes undetected until it has spread within the pelvis and abdomen. At this late stage, ovarian cancer is more difficult to treat. Early-stage ovarian cancer, in which the disease is confined to the ovary, is more likely to be treated successfully. Surgery and chemotherapy are generally used to treat ovarian cancer.

Early-stage ovarian cancer rarely causes any symptoms. Advanced-stage ovarian cancer may cause few and nonspecific symptoms that are often mistaken for more common benign conditions. Signs and symptoms of ovarian cancer may include abdominal bloating or swelling; quickly feeling full when eating; weight loss; discomfort in the pelvis area; changes in bowel habits, such as constipation; and a frequent need to urinate.

Tests and procedures used to diagnose ovarian cancer include pelvic exam, imaging tests (such as ultrasound or CT scans), blood tests (such as for organ function and/or for tumor markers), surgery and/or biopsy.

Once ovarian cancer is diagnosed, the doctor will use information from such tests and procedures to assign the cancer a stage. The stages of ovarian cancer are indicated using Roman numerals ranging from I to IV, with the lowest stage indicating that the cancer is confined to the ovaries. By stage IV, the cancer has spread to distant areas of the body.

Current treatment of ovarian cancer usually involves a combination of surgery and chemotherapy.

Surgical operations to remove ovarian cancer include surgery to remove one ovary, surgery to remove both ovaries and/or fallopian tubes, surgery to remove both ovaries and the uterus, or, if cancer is advanced, chemotherapy followed by surgery to remove as much of the cancer as possible.

Chemotherapy can refer to a drug treatment that uses chemicals to kill fast-growing cells in the body, including cancer cells. Chemotherapy drugs can be injected into a vein or taken by mouth. Sometimes the drugs are injected directly into the abdomen (intraperitoneal chemotherapy). Chemotherapy is often used after surgery to kill any cancer cells that might remain. It can also be used before surgery.

Colon cancer is a type of cancer that begins in the large intestine (colon). The colon is the final part of the digestive tract. Colon cancer typically affects older adults, though it can happen at any age. It usually begins as small, noncancerous (benign) clumps of cells called polyps that form on the inside of the colon. Over time some of these polyps can become colon cancers. Polyps may be small and produce few, if any, symptoms. For this reason, doctors recommend regular screening tests to help prevent colon cancer by identifying and removing polyps before they turn into cancer. If colon cancer develops, many treatments are available to help control it, including surgery, radiation therapy and drug treatments, such as chemotherapy, targeted therapy and immunotherapy. Colon cancer can be referred to as colorectal cancer, which is a term that combines colon cancer and rectal cancer, which begins in the rectum.

Signs and symptoms of colon cancer include a persistent change in your bowel habits, including diarrhea or constipation or a change in the consistency of your stool; rectal bleeding or blood in your stool; persistent abdominal discomfort, such as cramps, gas or pain; a feeling that your bowel doesn't empty completely; weakness or fatigue; unexplained weight loss.

Many people with colon cancer experience no symptoms in the early stages of the disease. When symptoms appear, they'll likely vary, depending on the cancer's size and location in your large intestine. Doctors recommend certain screening tests for healthy people with no signs or symptoms in order to look for signs of colon cancer or noncancerous colon polyps. Finding colon cancer at its earliest stage provides the greatest chance for a cure. Screening has been shown to reduce your risk of dying of colon cancer.

Several screening options exist, such as blood tests or colonoscopy.

The stages of colon cancer are indicated by Roman numerals that range from 0 to IV, with the lowest stages indicating cancer that is limited to the lining of the inside of the colon. By stage IV, the cancer is considered advanced and has spread (metastasized) to other areas of the body.

Treatment for colon cancer usually involves surgery to remove the cancer. Other treatments, such as radiation therapy and chemotherapy, might also be recommended.

Aspects of the invention are directed towards methods of treating cancer, including epithelial cancer, such as colon cancer or ovarian cancer, by administering compositions as described herein to a subject afflicted with a cancer. Antibodies of the invention, including fragments, bi-specific, polyclonal, monoclonal, humanized and fully human antibodies, and CAR-T cells, can be used as therapeutic agents. Such agents will generally be employed to treat or prevent cancer in a subject, increase vaccine efficiency or augment a natural immune response. An antibody preparation, preferably one having high specificity and high affinity for its target antigen, is administered to the subject and will generally have an effect due to its binding with the target. Administration of the antibody can abrogate or inhibit or interfere with an activity of the MUC1 protein. Administration of the antibody may also be used to target a therapeutic to a specific cell, such as a cancer cell, and/or sensitize a cancer cell to an anti-cancer treatment.

The invention provides for both prophylactic and therapeutic methods of treating a subject at risk of (or susceptible to) a cancer, or other cell proliferation-related diseases or disorders. Such diseases or disorders include but are not limited to, e.g., those diseases or disorders associated with aberrant expression of MUC1 and/or aberrant glycosylation of MUC1. For example, the methods are used to treat, prevent or alleviate a symptom cancer. Non-limiting examples of cancers that can be treated by embodiments herein comprise lung cancer, ovarian cancer, prostate cancer, colon cancer, cervical cancer, brain cancer, skin cancer, liver cancer, pancreatic cancer or stomach cancer. Additionally, the methods of the invention can be used to treat hematologic cancers such as leukemia and lymphoma. Alternatively, the methods can be used to treat, prevent or alleviate a symptom of a cancer that has metastasized.

Accordingly, in one aspect, the invention provides methods for preventing, treating or alleviating a symptom cancer or a cell proliferative disease or disorder in a subject by administering to the subject a monoclonal antibody, scFv antibody of the invention or bi-specific antibody of the invention. For example, an anti-MUC1 antibody can be administered in therapeutically effective amounts.

Subjects at risk for cancer or cell proliferation-related diseases or disorders can include patients who have a family history of cancer or a subject exposed to a known or suspected cancer-causing agent. Administration of a prophylactic agent can occur prior to the manifestation of cancer such that the disease is prevented or, alternatively, delayed in its progression.

Figure 2:
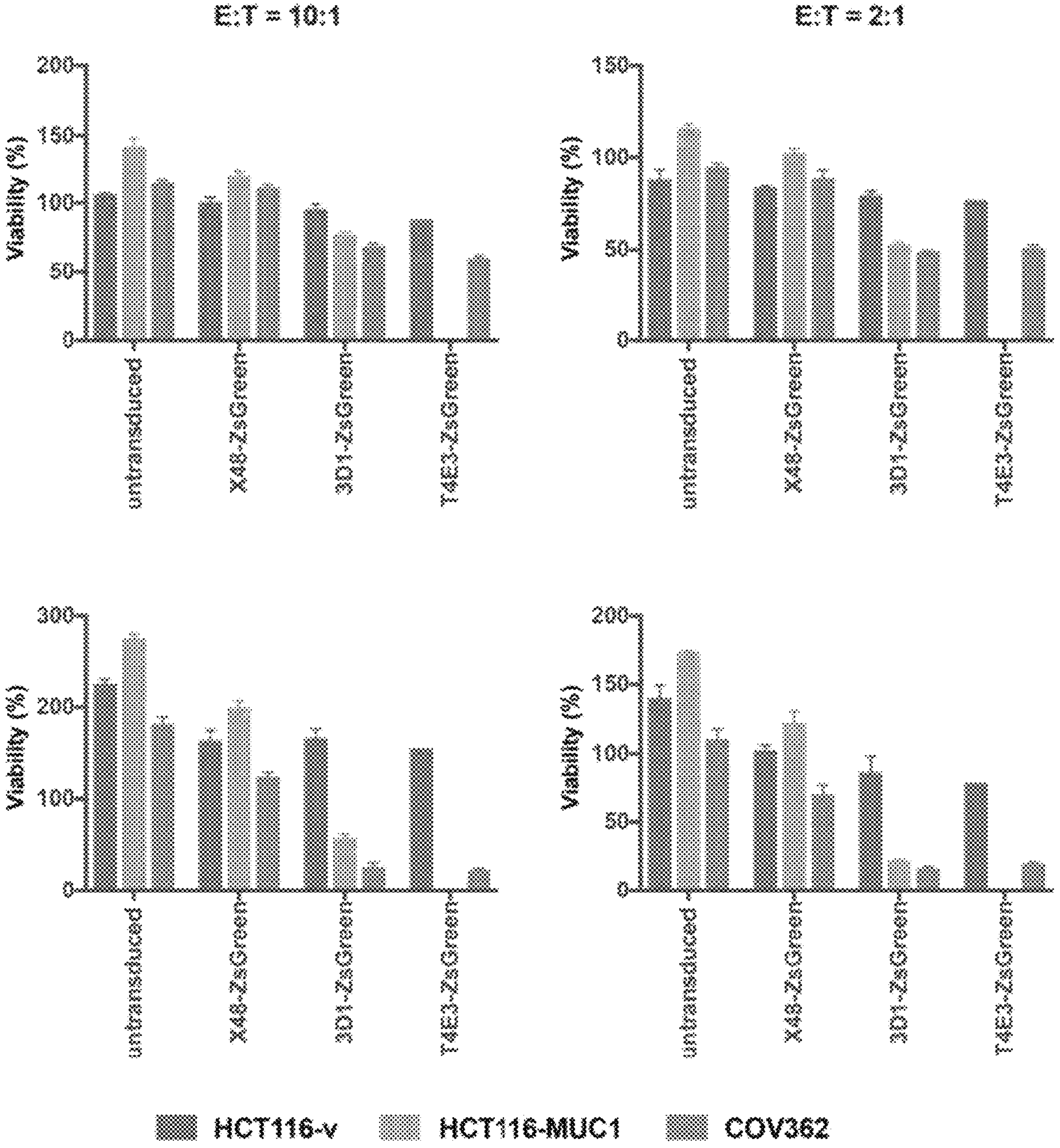
FIG. 2 shows tumor cell killing by anti-MUC1-C CAR T cells 3D1-ZsGreen and T4E3-ZsGreen. The cell killing assay utilizes a Celigo imaging cytometer to visualize cell killing. The cancer cell lines expressing the fluorescent protein: HCT116-v, HCT116-MUC1, and COV362 are plated in a 96 well plate (3000 cells/well) and incubated with T cells in effector to target (E:T) ratios of 10:1 or 2:1. The plates are imaged after 22 hours and 42 hours. Cell viability can be calculated by counting mCardinal+ cells. A loss of mCardinal signal suggests cancer cell death. The colon carcinoma cell line HCT116-v does not express MUC1-C, whereas HCT116-MUC1 and COV362 are 100% MUC1-C positive. X48-ZsGreen is a CAR T cell which targets CXCR4 which is not found on any of the cancer cell lines utilized. Note-T4E3-ZsGreen CAR T cells were not incubated with HCT116-MUC1 cancer cells due to availability of T cells.
Figure 4:
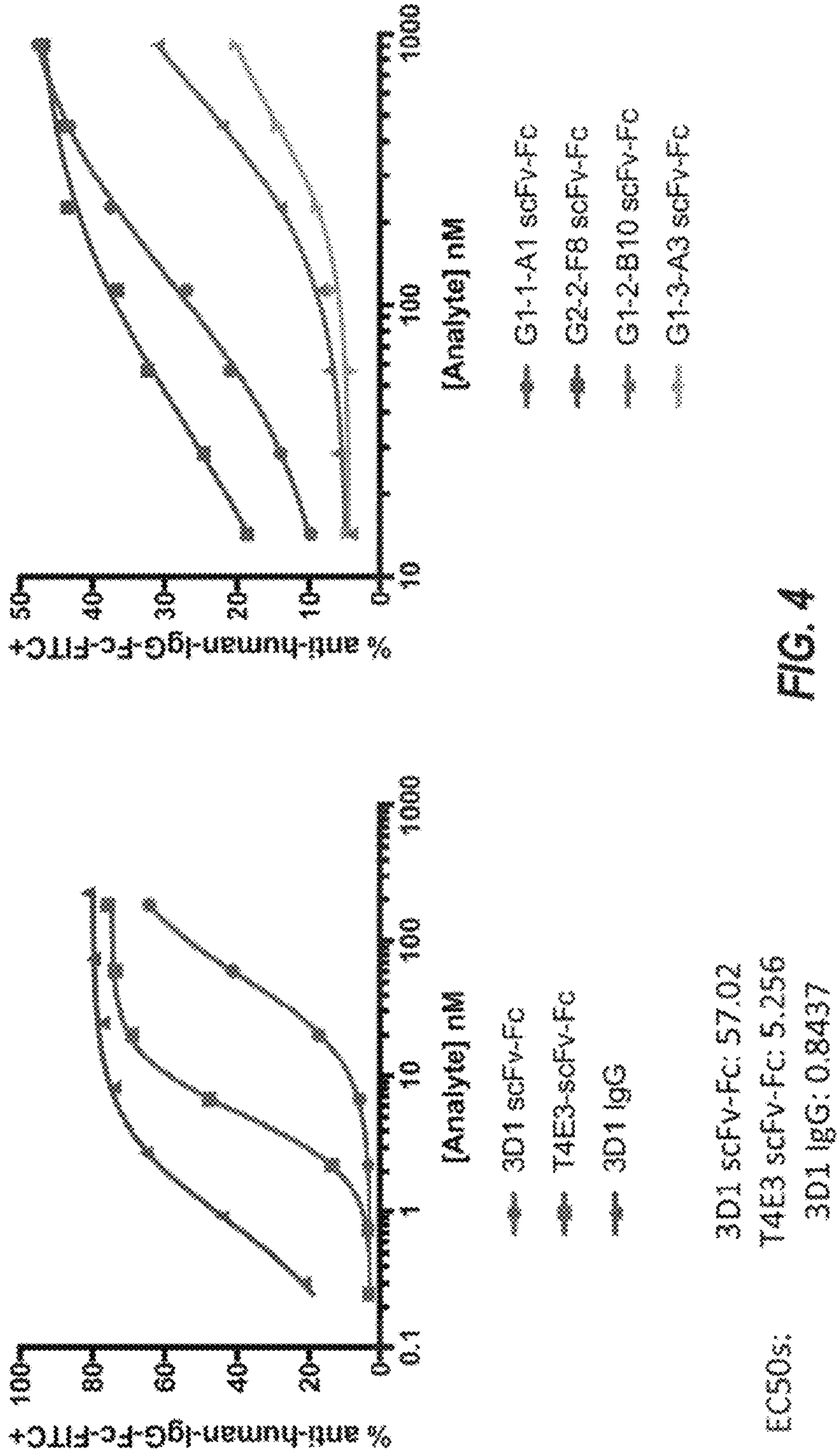
FIG. 4 shows discovery of anti-MUC-1-SEA scFvs.
Figure 5:
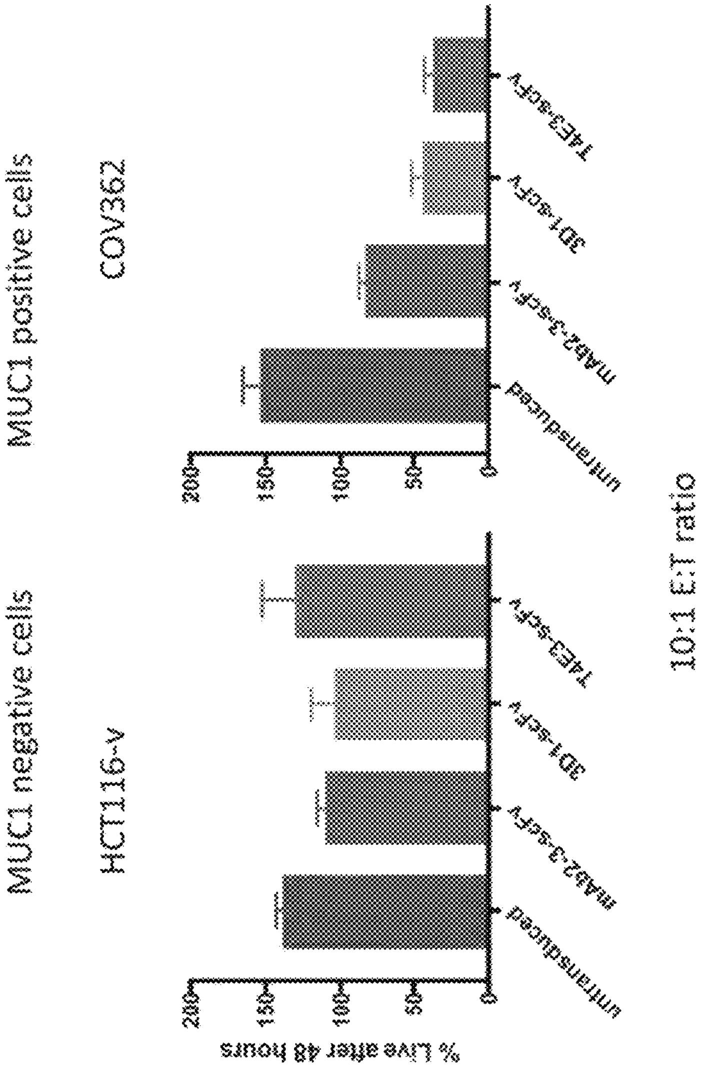
FIG. 5 shows T4E3 scFv CAR T vs 3D1 scFv CAR T killing.
Figure 6:
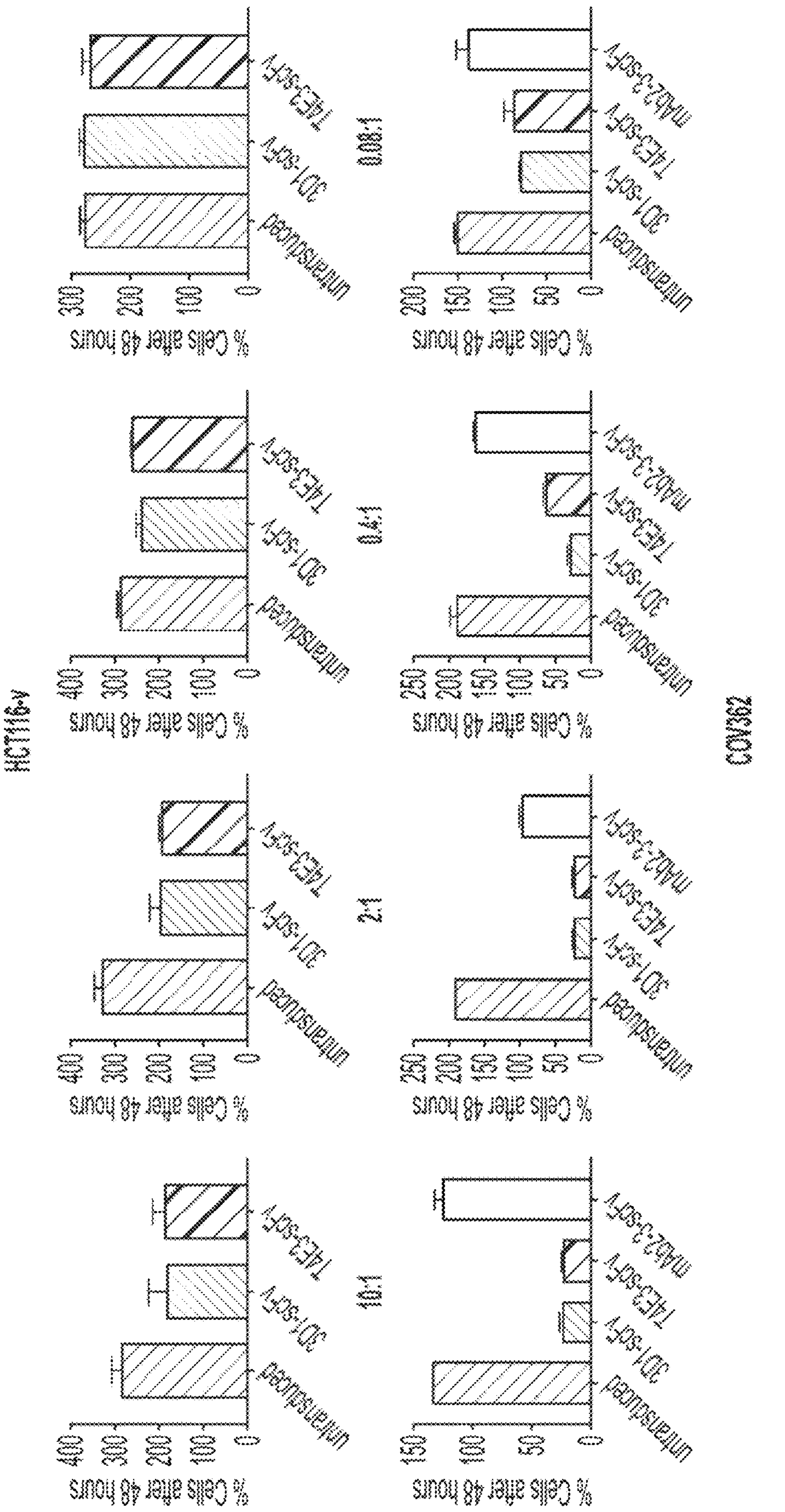
FIG. 6 shows dose dependent killing.

In one aspect, tumor cell viability can be inhibited by contacting a cell with an anti-MUC1 antibody of the invention. Referring to FIG. 2, for example, colon carcinoma cell lines expressing MUC1 show reduced viability (or increased cell killing) by anti-MUC1 CAR T cells. Further, FIG. 5 and FIG. 6 further demonstrate tumor cell killing activity of anti-MUC1 scFv CAR T cells.

In another aspect, tumor cell growth can be inhibited by contacting a cell with an anti-MUC1 antibody of the invention. The cell can be any cell that expresses MUC1.

Also included in the invention are methods of increasing or enhancing an immune response to an antigen. An immune response is increased or enhanced by administering to the subject a monoclonal antibody, scFv antibody, or bi-specific antibody of the invention. The immune response is augmented for example by augmenting antigen specific T effector function. The antigen is a viral (e.g. HIV), bacterial, parasitic or tumor antigen. The immune response is a natural immune response. By natural immune response is meant an immune response that is a result of an infection. The infection is a chronic infection. Increasing or enhancing an immune response to an antigen can be measured by a number of methods known in the art. For example, an immune response can be measured by measuring any one of the following: T cell activity, T cell proliferation, T cell activation, production of effector cytokines, and T cell transcriptional profile.

Alternatively, the immune response is a response induced due to a vaccination.

Accordingly, in another aspect the invention provides a method of increasing vaccine efficiency by administering to the subject a monoclonal antibody or scFv antibody of the invention and a vaccine. The antibody and the vaccine are administered sequentially or concurrently. The vaccine is a tumor vaccine a bacterial vaccine or a viral vaccine.

In another aspect, the invention provides treating cancer in a patient by administering two antibodies that bind to the same epitope of the MUC1 protein or, alternatively, two different epitopes of the MUC1 protein. Alternatively, the cancer is treated by administering a first antibody that binds to MUC1 and a second antibody that binds to a protein other than MUC1. For example, the other protein other than MUC1 can include, but is not limited to, LIGO1 and/or mesothelin. For example, the other protein other than MUC1 is a tumor-associated antigen.

In some embodiments, the invention provides administration of an anti-MUC1 antibody alone or with an additional antibody that recognizes another protein other than MUC1, with cells that are capable of effecting or augmenting an immune response. For example, these cells can be peripheral blood mononuclear cells (PBMC), or any cell type that is found in PBMC, e.g., cytotoxic T cells, macrophages, and natural killer (NK) cells.

Additionally, the invention provides administration of an antibody that binds to the MUC1 protein and an antineoplastic agent, such a small molecule, a growth factor, a cytokine or other therapeutics including biomolecules such as peptides, peptidomimetics, peptoids, polynucleotides, lipid-derived mediators, small biogenic amines, hormones, neuropeptides, and proteases. Small molecules include, but are not limited to, inorganic molecules and small organic molecules. Suitable growth factors or cytokines include an IL-2, GM-CSF, IL-12, and TNF-alpha. Small molecule libraries are known in the art. (See, Lam, Anticancer Drug Des., 12: 145, 1997.)

Diagnostic Assays

The anti-MUC1 antibodies can be used diagnostically to, for example, monitor the development or progression of cancer as part of a clinical testing procedure to, e.g., determine the efficacy of a given treatment and/or prevention regimen.

In some aspects, for diagnostic purposes the anti-MUC1 antibody of the invention is linked to a detectable moiety, for example, so as to provide a method for detecting a cancer cell in a subject at risk of or suffering from a cancer.

The detectable moieties can be conjugated directly to the antibodies or fragments, or indirectly by using, for example, a fluorescent secondary antibody. Direct conjugation can be accomplished by standard chemical coupling of, for example, a fluorophore to the antibody or antibody fragment, or through genetic engineering. Chimeras, or fusion proteins can be constructed which contain an antibody or antibody fragment coupled to a fluorescent or bioluminescent protein. For example, Casadei, et al, describe a method of making a vector construct capable of expressing a fusion protein of aequorin and an antibody gene in mammalian cells.

As used herein, the term "labeled", with regard to the probe or antibody, can encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently-labeled secondary antibody and end-labeling of a DNA probe with biotin such that it can be detected with fluorescently-labeled streptavidin. The term "biological sample" is intended to include tissues, cells and biological fluids isolated from a subject (such as a biopsy), as well as tissues, cells and fluids present within a subject. That is, the detection method of the invention can be used to detect cells that express MUC1 in a biological sample in vitro as well as in vivo. For example, in vitro techniques for detection of MUC1 include enzyme linked immunosorbent assays (ELISAs), Western blots, immunoprecipitations, and immunofluorescence. Furthermore, in vivo techniques for detection of MUC1 include introducing into a subject a labeled anti-MUC1 antibody. For example, the antibody can be labeled with a radioactive marker whose presence and location in a subject can be detected by standard imaging techniques. In the case of "targeted" conjugates, that is, conjugates which contain a targeting moiety—a molecule or feature designed to localize the conjugate within a subject or animal at a particular site or sites, localization can refer to a state when an equilibrium between bound, "localized", and unbound, "free" entities within a subject has been essentially achieved. The rate at which such equilibrium is achieved depends upon the route of administration. For example, a conjugate administered by intravenous injection can achieve localization within minutes of injection. On the other hand, a conjugate administered orally can take hours to achieve localization. Alternatively, localization can simply refer to the location of the entity within the subject or animal at selected time periods after the entity is administered. By way of another example, localization is achieved when an moiety becomes distributed following administration.

It is understood that a reasonable estimate of the time to achieve localization can be made by one skilled in the art. Furthermore, the state of localization as a function of time can be followed by imaging the detectable moiety (e.g., a light-emitting conjugate) according to the methods of the invention, such as with a photodetector device. The "photodetector device" used should have a high enough sensitivity to enable the imaging of faint light from within a mammal in a reasonable amount of time, and to use the signal from such a device to construct an image.

In cases where it is possible to use light-generating moieties which are extremely bright, and/or to detect light-generating fusion proteins localized near the surface of the subject or animal being imaged, a pair of "night-vision" goggles or a standard high-sensitivity video camera, such as a Silicon Intensified Tube (SIT) camera (e.g., from Hammamatsu Photonic Systems, Bridgewater, N.J.), can be used. More typically, however, a more sensitive method of light detection is required.

In extremely low light levels the photon flux per unit area becomes so low that the scene being imaged no longer appears continuous. Instead, it is represented by individual photons which are both temporally and spatially distinct form one another. Viewed on a monitor, such an image appears as scintillating points of light, each representing a single detected photon. By accumulating these detected photons in a digital image processor over time, an image can be acquired and constructed. In contrast to conventional cameras where the signal at each image point is assigned an intensity value, in photon counting imaging the amplitude of the signal carries no significance. The objective is to simply detect the presence of a signal (photon) and to count the occurrence of the signal with respect to its position over time.

At least two types of photodetector devices, described below, can detect individual photons and generate a signal which can be analyzed by an image processor. Reduced-Noise Photodetection devices achieve sensitivity by reducing the background noise in the photon detector, as opposed to amplifying the photon signal. Noise is reduced primarily by cooling the detector array. The devices include charge coupled device (CCD) cameras referred to as "backthinned", cooled CCD cameras. In the more sensitive instruments, the cooling is achieved using, for example, liquid nitrogen, which brings the temperature of the CCD array to approximately −120° C. "Backthinned" refers to an ultra-thin backplate that reduces the path length that a photon follows to be detected, thereby increasing the quantum efficiency. A particularly sensitive backthinned cryogenic CCD camera is the "TECH 512", a series 200 camera available from Photometries, Ltd. (Tucson, Ariz.). [00120]"Photon amplification devices" amplify photons before they hit the detection screen. This class includes CCD cameras with intensifiers, such as microchannel intensifiers. A microchannel intensifier typically contains a metal array of channels perpendicular to and co-extensive with the detection screen of the camera. The microchannel array is placed between the sample, subject, or animal to be imaged, and the camera. Most of the photons entering the channels of the array contact a side of a channel before exiting. A voltage applied across the array results in the release of many electrons from each photon collision. The electrons from such a collision exit their channel of origin in a "shotgun" pattern, and are detected by the camera.

Even greater sensitivity can be achieved by placing intensifying microchannel arrays in series, so that electrons generated in the first stage in turn result in an amplified signal of electrons at the second stage. Increases in sensitivity, however, are achieved at the expense of spatial resolution, which decreases with each additional stage of amplification. An exemplary microchannel intensifier-based single-photon detection device is the C2400 series, available from Hamamatsu.

Image processors process signals generated by photodetector devices which count photons in order to construct an image which can be, for example, displayed on a monitor or printed on a video printer. Such image processors are typically sold as part of systems which include the sensitive photon-counting cameras described above, and accordingly, are available from the same sources. The image processors are usually connected to a personal computer, such as an IBM-compatible PC or an Apple Macintosh (Apple Computer, Cupertino, Calif), which may or may not be included as part of a purchased imaging system. Once the images are in the form of digital files, they can be manipulated by a variety of image processing programs (such as "ADOBE PHOTOSHOP", Adobe Systems, Adobe Systems, Mt. View, Calif) and printed.

In an embodiment, the biological sample contains protein molecules from the test subject. Exemplary biological samples comprise a peripheral blood leukocyte sample isolated by conventional means from a subject, or a sample comprising one of more cancer cells isolated by conventional means from a subject. The skilled artisan will recognize that any biological sample can be utilized in such embodiments, non-limiting examples of which include ascites, pleural effusions, urine, saliva, bronchial alveolar lavages, and the like.

The invention also encompasses kits for detecting the presence of MUC1 or a MUC1-expressing cell in a biological sample. For example, the kit can comprise: a labeled compound or agent capable of detecting a cancer or tumor cell (e.g., an anti-MUC1 scFv or monoclonal antibody) in a biological sample; means for determining the amount of MUC1 in the sample; and means for comparing the amount of MUC1 in the sample with a standard. The standard is, in some embodiments, a non-cancer cell or cell extract thereof. The compound or agent can be packaged in a suitable container. The kit can further comprise instructions for using the kit to detect cancer in a sample.

An antibody according to the invention can be used as an agent for detecting the presence of MUC1 (or a protein or a protein fragment thereof) in a sample. Preferably, the antibody contains a detectable label. Antibodies can be polyclonal or monoclonal. An intact antibody, or a fragment thereof (e.g., $F_ab$, scFv, or F(ab)2) can be used. The term "labeled", with regard to the probe or antibody, can encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently-labeled secondary antibody and end-labeling of a DNA probe with biotin such that it can be detected with fluorescently-labeled streptavidin. The term "biological sample" can include tissues, cells and biological fluids isolated from a subject, as well as tissues, cells and fluids present within a subject. Included within the usage of the term "biological sample", therefore, is blood and a fraction or component of blood including blood serum, blood plasma, or lymph. That is, the detection method of the invention can be used to detect an analyte mRNA, protein, or genomic DNA in a biological sample in vitro as well as in vivo. For example, in vitro techniques for detection of an analyte mRNA includes Northern hybridizations and in situ hybridizations. In vitro techniques for detection of an analyte protein include enzyme linked immunosorbent assays (ELISAs), Western blots, immunoprecipitations, and immunofluorescence. In vitro techniques for detection of an analyte genomic DNA include Southern hybridizations.

Procedures for conducting immunoassays are described, for example in "ELISA: Theory and Practice: Methods in Molecular Biology", Vol. 42, J. R. Crowther (Ed.) Human Press, Totowa, NJ, 1995; "Immunoassay", E. Diamandis and T. Christopoulus, Academic Press, Inc., San Diego, CA, 1996; and "Practice and Theory of Enzyme Immunoassays", P. Tijssen, Elsevier Science Publishers, Amsterdam, 1985. Furthermore, in vivo techniques for detection of an analyte protein include introducing into a subject a labeled anti-analyte protein antibody. For example, the antibody can be labeled with a radioactive marker whose presence and location in a subject can be detected by standard imaging techniques.

Antibodies directed against a MUC1 protein (or a fragment thereof) can be used in methods known within the art relating to the localization and/or quantitation of a MUC1 protein (e.g., for use in measuring levels of the MUC1 protein within appropriate physiological samples, for use in diagnostic methods, for use in imaging the protein, and the like). In a given embodiment, antibodies specific to a MUC1 protein, or derivative, fragment, analog or homolog thereof, that contain the antibody derived antigen binding domain, are utilized as pharmacologically active compounds (referred to hereinafter as "Therapeutics").

An antibody specific for a MUC1 protein of the invention can be used to isolate a MUC1 polypeptide by standard techniques, such as immunoaffinity, chromatography or immunoprecipitation. Antibodies directed against a MUC1 protein (or a fragment thereof) can be used diagnostically to monitor protein levels in tissue as part of a clinical testing procedure, e.g., to, for example, determine the efficacy of a given treatment regimen.

Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The invention will be further described in the following examples, which do not limit the scope of the invention described in the claims.

EXAMPLES

Examples are provided below to facilitate a more complete understanding of the invention. The following examples illustrate the exemplary modes of making and practicing the invention. However, the scope of the invention is not limited to specific embodiments disclosed in these Examples, which are for purposes of illustration only, since alternative methods can be utilized to obtain similar results.

Example 1

Discovery of Human Anti-MUC1 Antibody that Targets MUC-SEA Domain

We report here the discovery of a human single chain variable fragment (scFv), called T4E3, that recognizes human MUC1-SEA. In the scFv-Fc format, T4E3 binds to MUC1+ cells with six fold higher affinity than the anti-MUC1-C antibody 3D1 (FIG. 1). When T4E3 is utilized as the targeting moiety of a CAR T cell, T4E3 CAR T cells preferentially kill MUC1+ tumor cells and do not kill MUC1− cells. Activated T cells from the same human white blood cell donor and CAR T cells that recognize CXCR4, do not kill either the MUC1+ or MUC1− tumor cell lines, which lack CXCR4 (FIG. 2).

Example 2

Observations from CDR3 Analysis

- G1-1-A1 $V_H$ has more similarities to T4E3 and G2-2-F8 in $V_H$ than G1-3-A3 and G1-2-B10 even though it has a different VGene assignment.
- G1-3-A3 has a completely different $V_L$ gene and has such a different $V_H$ gene from T4E3 it abrogates binding.
- The GMDV at the end of the $V_H$-CDR3 appears to be critical for binding to MUC1 (T4E3, G2-2-F8, and G1-1-A1, the highest affinity binders share this motif).
- 17-18 amino acids are the lengths of the $V_H$ CDR3s that have highest binding. G1-3-A3 and G1-2-B10 have 20 and 15, respectively.
- The T4E3 $V_L$ CDR3 has an insertion at the 3' that none of the low affinity hits have. Additionally, two consecutive serines are mutated from germline to arginine and tyrosine, respectively, within the interior of CDR3-$V_L$, and histidine at the 3' in germline is mutated to serine. None of the low affinity hits maintain these mutations.

EQUIVALENTS

Those skilled in the art will recognize, or be able to ascertain, using no more than routine experimentation, numerous equivalents to the specific substances and procedures described herein. Such equivalents are considered to be within the scope of this invention, and are covered by the following claims.

What is claimed is:

1. An isolated monoclonal antibody or antigen-binding fragment thereof that binds to a peptide corresponding to the MUC1-SEA domain (SEQ ID NO: 1) or an epitope thereon, wherein the antibody or antigen-binding fragment thereof comprises three heavy chain complementarity determining regions (HCDR1, HCDR2 and HCDR3) and three light chain complementarity determining regions (LCDR1, LCDR2 and LCDR3), wherein HCDRs 1-3 and LCDRs 1-3 comprise:

a) SEQ ID NO: 2, SEQ ID NO: 96, SEQ ID NO: 104, SEQ ID NO: 7, GKN, and SEQ ID NO: 118;
b) SEQ ID NO: 2, SEQ ID NO: 96, SEQ ID NO: 105, SEQ ID NO: 7, GKN, and SEQ ID NO: 119;
c) SEQ ID NO: 2, SEQ ID NO: 97, SEQ ID NO: 106, SEQ ID NO: 9, GAS, and SEQ ID NO: 120;
d) SEQ ID NO: 2, SEQ ID NO: 96, SEQ ID NO: 107, SEQ ID NO: 7, GKN, and SEQ ID NO: 121;
e) SEQ ID NO: 6, SEQ ID NO: 98, SEQ ID NO: 108, SEQ ID NO: 11, GKN, and SEQ ID NO: 122;
f) SEQ ID NO: 2, SEQ ID NO: 96, SEQ ID NO: 104, SEQ ID NO: 7, GKN, and SEQ ID NO: 123;
g) SEQ ID NO: 2, SEQ ID NO: 96, SEQ ID NO: 109, SEQ ID NO: 7, GKN, and SEQ ID NO: 124;
h) SEQ ID NO: 2, SEQ ID NO: 96, SEQ ID NO: 105, SEQ ID NO: 7, GKN, and SEQ ID NO: 125;
i) SEQ ID NO: 88, SEQ ID NO: 99, SEQ ID NO: 110, SEQ ID NO: 91, GAS, and SEQ ID NO: 126;
j) SEQ ID NO: 6, SEQ ID NO: 98, SEQ ID NO: 111, SEQ ID NO: 11, GKN, and SEQ ID NO: 127;
k) SEQ ID NO: 89, SEQ ID NO: 98, SEQ ID NO: 112, SEQ ID NO: 11, GKN, and SEQ ID NO: 127;
l) SEQ ID NO: 6, SEQ ID NO: 98, SEQ ID NO: 108, SEQ ID NO: 11, GKN, and SEQ ID NO: 127;
m) SEQ ID NO: 2, SEQ ID NO: 100, SEQ ID NO: 113, SEQ ID NO: 92, RNN, and SEQ ID NO: 128;
n) SEQ ID NO: 90, SEQ ID NO: 101, SEQ ID NO: 114, SEQ ID NO: 93, DVS, and SEQ ID NO: 129;
o) SEQ ID NO: 2, SEQ ID NO: 97, SEQ ID NO: 115, SEQ ID NO: 9, GAS, and SEQ ID NO: 130;
p) SEQ ID NO: 2, SEQ ID NO: 102, SEQ ID NO: 116, SEQ ID NO: 94, GAS, and SEQ ID NO: 131; or
q) SEQ ID NO: 6, SEQ ID NO: 103, SEQ ID NO: 117, SEQ ID NO: 95, DVS, and SEQ ID NO: 132; respectively.

2. The antibody or antigen-binding fragment thereof of claim 1, wherein the antibody comprises a $V_H$ corresponding to one or more amino acid sequences of SEQ ID NO: 12, 13, 14, 15, 16, 47, 48, 49, 50, 51, 52, 53, 54, 55, 56, 57, 58, 59, 177, or a portion thereof;
a $V_L$ corresponding to one or more amino acid sequence of SEQ ID NO: 17, 18, 19, 20, 21, 73, 74, 75, 76, 77, 78, 79, 80, 81, 82, 83, 84, 85, 86, 87, or a portion thereof;

or any combination thereof and a VL corresponding to:

a) SEQ ID NOs: 12 and 17;
b) SEQ ID NOs: 13 and 18;
c) SEQ ID NOs: 14 and 19;
d) SEQ ID NOs: 15 and 20;
e) SEQ ID NOs: 16 and 21;
f) SEQ ID NOs: 47 and 73;
g) SEQ ID NOs: 48 and 74;
h) SEQ ID NOs: 49 and 75;
i) SEQ ID NOs: 50 and 76;
j) SEQ ID NOs: 51 and 77;
k) SEQ ID NOs: 52 and 78;
l) SEQ ID NOs: 53 and 79;
m) SEQ ID NOs: 54 and 80;
n) SEQ ID NOs: 55 and 81;
o) SEQ ID NOs: 56 and 82;
p) SEQ ID NOs: 57 and 83;
q) SEQ ID NOs: 58 and 84;
r) SEQ ID NOs: 51 and 85; or
s) SEQ ID NOs: 59 and 87; respectively.

3. The antibody or antigen-binding fragment thereof of claim 1, wherein said antibody or antigen-binding fragment thereof is a single chain antibody.

4. The antibody or antigen-binding fragment thereof of claim 1, wherein said antibody or antigen-binding fragment thereof comprises a $F_{ab}$ fragment antibody.

5. The antibody or antigen-binding fragment thereof of claim 1, wherein said antibody or antigen-binding fragment thereof has a binding affinity within the range of 1 pM to 1 μM.

6. The antibody or antigen-binding fragment thereof of claim 1 linked to a therapeutic agent.

7. The antibody or antigen-binding fragment thereof of claim 6 wherein said therapeutic agent is a toxin, a radiolabel, a siRNA a small molecule or a cytokine.

8. The antibody or antigen-binding fragment thereof of claim 6, wherein the therapeutic agent is MMAE.

9. A cell producing the antibody or antigen-binding fragment thereof of claim 1.

10. A pharmaceutical composition comprising the antibody or antigen-binding fragment thereof according to claim 1 and a pharmaceutically acceptable excipient.

11. A nucleic acid encoding the antibody or antigen-binding fragment thereof according to claim 1.

12. The nucleic acid of claim 11, wherein the nucleic acid comprises one or more nucleotide sequences according to SEQ ID NO: 23-32, 35-46, and/or 60-72, a portion thereof, or any combination thereof nucleotide sequences according to:

a. SEQ ID NOs: 23 and 28;
b. SEQ ID NOs: 24 and 29;
c. SEQ ID NOs: 25 and 30;
d. SEQ ID NOs: 26 and 31;
e. SEQ ID NOs: 27 and 32;
f. SEQ ID NOs: 35 and 60;
g. SEQ ID NOs: 36 and 61;
h. SEQ ID NOs: 24 and 62;
i. SEQ ID NOs: 37 and 63;
j. SEQ ID NOs: 38 and 64;
k. SEQ ID NOs: 39 and 65;
l. SEQ ID NOs: 40 and 66;
m. SEQ ID NOs: 41 and 67;
n. SEQ ID NOs: 42 and 68;
o. SEQ ID NOs: 43 and 69;
p. SEQ ID NOs: 44 and 70;
q. SEQ ID NOs: 45 and 71; or
r. SEQ ID NOs: 46 and 72.

13. A vector comprising the nucleic acid of claim 11.

14. A cell comprising the vector of claim 13.

15. A pharmaceutical composition comprising the cell of claim 14.

16. A chimeric antigen receptor (CAR) comprising the antibody or antigen-binding fragment thereof of claim 1 or an antigen-binding fragment thereof.

17. The CAR of claim 16, wherein the antigen-binding fragment comprises an scFv or a $F_{ab}$.

18. A cell comprising the CAR of claim 16.

19. The cell of claim 18, wherein the cell is a T cell.

20. A pharmaceutical composition comprising the cell of claim 18 and a pharmaceutically acceptable excipient.

21. A nucleic acid encoding the CAR according to claim 16.

* * * * *